US011890285B2

(12) United States Patent
Briere et al.

(10) Patent No.: US 11,890,285 B2
(45) Date of Patent: Feb. 6, 2024

(54) COMBINATION THERAPIES

(71) Applicant: Mirati Therapeutics, Inc., San Diego, CA (US)

(72) Inventors: David Briere, San Diego, CA (US); James Gail Christensen, San Diego, CA (US); Peter Olson, San Diego, CA (US)

(73) Assignee: Mirati Therapeutics, Inc., San Diego, CA (US)

( * ) Notice: Subject to any disclaimer, the term of this patent is extended or adjusted under 35 U.S.C. 154(b) by 327 days.

(21) Appl. No.: 17/029,654

(22) Filed: Sep. 23, 2020

(65) Prior Publication Data

US 2021/0085683 A1    Mar. 25, 2021

Related U.S. Application Data

(60) Provisional application No. 62/905,107, filed on Sep. 24, 2019.

(51) Int. Cl.
*A61K 31/519* (2006.01)
*A61P 35/04* (2006.01)
*C07K 16/28* (2006.01)

(52) U.S. Cl.
CPC ............ *A61K 31/519* (2013.01); *A61P 35/04* (2018.01); *C07K 16/2818* (2013.01); *C07K 16/2827* (2013.01)

(58) Field of Classification Search
CPC ......... A61K 31/519; A61P 35/00; A61P 35/04
See application file for complete search history.

(56) References Cited

U.S. PATENT DOCUMENTS

| | | | |
|---|---|---|---|
| 8,163,763 B2 | 4/2012 | Bergeron et al. |
| 8,426,401 B2 | 4/2013 | Bian et al. |
| 9,562,019 B2 | 2/2017 | Djaballah et al. |
| 9,840,516 B2 | 12/2017 | Li et al. |
| 10,125,134 B2 | 11/2018 | Blake et al. |
| 2003/0191143 A1 | 10/2003 | Pitts et al. |
| 2010/0081654 A1 | 4/2010 | Stockwell et al. |
| 2011/0269244 A1 | 11/2011 | Petter et al. |
| 2013/0029978 A1 | 1/2013 | Kamino et al. |
| 2014/0288045 A1 | 9/2014 | Ren et al. |
| 2015/0175558 A1 | 6/2015 | Stockwell et al. |
| 2015/0239900 A1 | 8/2015 | Li et al. |
| 2016/0031898 A1 | 2/2016 | Ren et al. |
| 2016/0108019 A1 | 4/2016 | Li et al. |
| 2016/0166571 A1 | 6/2016 | Janes et al. |
| 2016/0229836 A1 | 8/2016 | Stockwell et al. |
| 2016/0264627 A1 | 9/2016 | Henning et al. |
| 2016/0297774 A1 | 10/2016 | Li et al. |
| 2017/0022184 A1 | 1/2017 | Li et al. |
| 2017/0115303 A1 | 4/2017 | Cravatt et al. |
| 2017/0190672 A1 | 7/2017 | Mani et al. |
| 2017/0197945 A1 | 7/2017 | Li et al. |
| 2018/0015087 A1 | 1/2018 | Liu et al. |
| 2018/0118757 A1 | 5/2018 | Li et al. |
| 2018/0118761 A1 | 5/2018 | Sebti et al. |
| 2018/0127396 A1 | 5/2018 | Li et al. |
| 2018/0141927 A1 | 5/2018 | Li et al. |
| 2018/0155348 A1 | 6/2018 | Li et al. |
| 2018/0162812 A1 | 6/2018 | Ren et al. |
| 2018/0177767 A1 | 6/2018 | Lanman et al. |
| 2018/0194748 A1 | 7/2018 | Li et al. |
| 2018/0201610 A1 | 7/2018 | Tao et al. |
| 2018/0273515 A1 | 9/2018 | Li et al. |
| 2018/0273523 A1 | 9/2018 | Li et al. |
| 2018/0273577 A1 | 9/2018 | Revenko et al. |
| 2018/0282307 A1 | 10/2018 | Li et al. |
| 2018/0282308 A1 | 10/2018 | Li et al. |
| 2018/0289683 A1 | 10/2018 | McCormick et al. |
| 2019/0144444 A1* | 5/2019 | Blake ................... C07D 471/04 |
| | | | 514/210.21 |
| 2019/0270743 A1* | 9/2019 | Marx ................... C07D 519/00 |
| 2020/0262837 A1 | 8/2020 | Marx et al. |
| 2020/0399297 A1 | 12/2020 | Campbell et al. |

FOREIGN PATENT DOCUMENTS

| | | |
|---|---|---|
| WO | 02/053558 A1 | 7/2002 |
| WO | 02/087513 A2 | 11/2002 |
| WO | 2006121168 A1 | 11/2006 |
| WO | 2007/146122 A2 | 12/2007 |
| WO | 2008/009078 A2 | 1/2008 |
| WO | 2009/047255 A1 | 4/2009 |

(Continued)

OTHER PUBLICATIONS

Sundar. Therapeutic Advances in Medical Oncology, 2015, 7(2), 85-96 (Year: 2015).*
Horita. Scientific Reports, 2016, 6: 35297), 1-8 (Year: 2016).*
Migden. The New England Journal of Medicine, 2018, 379:4, 341-351 (Year: 2018).*
Sundhu. Annals of Oncology, 2018, supplement 10, x28 (Year: 2018).*
Krishnamurthy. Drugs of Today, 2017, 53(4), 217 (Year: 2017).*
Gulley. Journal of Clinical Oncology, 2015, 33(15), supplement 8034 (Year: 2015).*
Munoz-Unceta. Therapeutic Advances in Medical Oncology, 2018, 10, 1-15 (Year: 2018).*
International Search Report and the Written Opinion for corresponding PCT Application No. PCT/US20/52185 dated Dec. 17, 2020.
Figueras, A. et al., "The impact of KRAS mutations on VEGF-A production and tumour vascular network", BMC Cancer 2013, 13:125.

(Continued)

*Primary Examiner* — Noble E Jarrell
(74) *Attorney, Agent, or Firm* — Wood, Phillips, Katz, Clark & Mortimer

(57) ABSTRACT

The present invention relates to combination therapies for treating KRas G12C cancers. In particular, the present invention relates to methods of treating cancer in a subject in need thereof, comprising administering to the subject a therapeutically effective amount of a combination of a an agent that blocks Programmed Death-1 receptor (PD-1) and Programmed Death Ligand-1 (PD-L1) signaling and a KRAS G12C inhibitor of Formula (I), Formula I-A or Formula I-B, kits comprising the compositions and methods of use therefor.

43 Claims, No Drawings

(56) References Cited

FOREIGN PATENT DOCUMENTS

| | | |
|---|---|---|
| WO | 2010/014939 A1 | 2/2010 |
| WO | 2010/120996 A1 | 10/2010 |
| WO | 2013/155223 A1 | 10/2013 |
| WO | 2014/143659 A1 | 9/2014 |
| WO | 2014/152588 A1 | 9/2014 |
| WO | 2016/049568 A1 | 3/2015 |
| WO | 2015/054572 A1 | 4/2015 |
| WO | 2016/025650 A1 | 2/2016 |
| WO | 2016/044772 A1 | 3/2016 |
| WO | 2016/049565 A1 | 3/2016 |
| WO | 2016/164675 A1 | 10/2016 |
| WO | 2016/168540 A1 | 10/2016 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |
| WO | 2017/079864 A1 | 5/2017 |
| WO | 2017/080980 A1 | 5/2017 |
| WO | 2017/087528 A1 | 5/2017 |
| WO | 2017/100546 A1 | 6/2017 |
| WO | 2018/064510 A1 | 4/2018 |
| WO | 2018/068017 A1 | 4/2018 |
| WO | 2018098352 A2 | 5/2018 |
| WO | 2018/102452 A2 | 6/2018 |
| WO | 2018/102453 A1 | 6/2018 |
| WO | 2018/112420 A1 | 6/2018 |
| WO | 2018/115380 A1 | 6/2018 |
| WO | 2018/119183 A2 | 6/2018 |
| WO | 2018119183 A2 | 6/2018 |
| WO | 2018/140512 A1 | 8/2018 |
| WO | 2018/140513 A1 | 8/2018 |
| WO | 2018/140514 A1 | 8/2018 |
| WO | 2018/140598 A1 | 8/2018 |
| WO | 2018/140599 A1 | 8/2018 |
| WO | 2018/140600 A1 | 8/2018 |
| WO | 2018/143315 A1 | 8/2018 |
| WO | 2018/195439 A2 | 10/2018 |
| WO | 2018217651 A1 | 11/2018 |
| WO | 2019/051291 A1 | 3/2019 |
| WO | 2019051291 A1 | 3/2019 |
| WO | 202063594 | 4/2020 |
| WO | 202098488 | 5/2020 |
| WO | 202027202 | 8/2020 |
| WO | 2020163598 | 8/2020 |
| WO | 2020165670 | 8/2020 |
| WO | 2020169838 | 8/2020 |
| WO | 2020171499 | 8/2020 |
| WO | 2020172332 | 8/2020 |
| WO | 2020176693 | 9/2020 |
| WO | 2020176963 | 9/2020 |
| WO | 2020177629 | 9/2020 |
| WO | 2020178282 | 9/2020 |
| WO | 2020181142 | 9/2020 |
| WO | 2020198125 | 10/2020 |
| WO | 2020204359 | 10/2020 |
| WO | 2020205473 | 10/2020 |
| WO | 2020205486 | 10/2020 |
| WO | 2020212895 | 10/2020 |
| WO | 2020214537 | 10/2020 |
| WO | 2020221239 | 11/2020 |
| WO | 2020230028 | 11/2020 |
| WO | 2020230091 | 11/2020 |
| WO | 2020231806 | 11/2020 |
| WO | 2020231808 | 11/2020 |
| WO | 2020232130 | 11/2020 |
| WO | 2020233592 | 11/2020 |
| WO | 2020234103 | 11/2020 |
| WO | 2020236940 | 11/2020 |
| WO | 2020236947 | 11/2020 |
| WO | 2020236948 | 11/2020 |
| WO | 2020247914 | 12/2020 |
| WO | 2020252336 | 12/2020 |
| WO | 2020252353 | 12/2020 |
| WO | 2021000885 | 1/2021 |
| WO | 2021023154 | 2/2021 |
| WO | 2021023247 | 2/2021 |
| WO | 2021027911 | 2/2021 |
| WO | 2021027943 | 2/2021 |
| WO | 2021031952 | 2/2021 |
| WO | 2021034992 | 2/2021 |
| WO | 2021037018 | 3/2021 |
| WO | 2021041671 | 3/2021 |
| WO | 2021043322 | 3/2021 |
| WO | 2021045279 | 3/2021 |
| WO | 2021050732 | 3/2021 |
| WO | 2021051034 | 3/2021 |
| WO | 2021052499 | 3/2021 |
| WO | 2021055728 | 3/2021 |
| WO | 2021057832 | 4/2021 |
| WO | 2021058018 | 4/2021 |
| WO | 2021061515 | 4/2021 |
| WO | 2021061749 | 4/2021 |
| WO | 2021063346 | 4/2021 |
| WO | 2021068898 | 4/2021 |
| WO | 2021075147 | 4/2021 |
| WO | 2021076655 | 4/2021 |
| WO | 2021078285 | 4/2021 |
| WO | 2021078312 | 4/2021 |
| WO | 2021080359 | 4/2021 |
| WO | 2021081212 | 4/2021 |
| WO | 2021083167 | 5/2021 |
| WO | 2021084765 | 5/2021 |
| WO | 2021085653 | 5/2021 |
| WO | 2021086833 | 5/2021 |
| WO | 2021088458 | 5/2021 |
| WO | 2021088938 | 5/2021 |
| WO | 2021091956 | 5/2021 |
| WO | 2021091967 | 5/2021 |
| WO | 2021091982 | 5/2021 |
| WO | 2021093758 A1 | 5/2021 |
| WO | 2021104431 A1 | 6/2021 |
| WO | 2021106230 A1 | 6/2021 |
| WO | 2021106231 A1 | 6/2021 |
| WO | 2021107160 A1 | 6/2021 |
| WO | 2021108683 A1 | 6/2021 |
| WO | 2021109737 A1 | 6/2021 |
| WO | 2021113595 A1 | 6/2021 |
| WO | 2021120045 A1 | 6/2021 |
| WO | 2021121330 A1 | 6/2021 |
| WO | 2021121367 A1 | 6/2021 |
| WO | 2021121371 A1 | 6/2021 |
| WO | 2021121397 A1 | 6/2021 |
| WO | 2021126120 A1 | 6/2021 |
| WO | 2021126799 A1 | 6/2021 |
| WO | 2021127404 A1 | 6/2021 |
| WO | 2021129820 A1 | 7/2021 |
| WO | 2021129824 A1 | 7/2021 |
| WO | 2021139678 A1 | 7/2021 |
| WO | 2021139748 A1 | 7/2021 |
| WO | 2021141628 A1 | 7/2021 |
| WO | 2021142252 A1 | 7/2021 |
| WO | 2021143693 A1 | 7/2021 |
| WO | 2021145520 A1 | 7/2021 |
| WO | 2021145521 A1 | 7/2021 |
| WO | 2021147965 A1 | 7/2021 |
| WO | 2021147967 A1 | 7/2021 |
| WO | 2021150613 A1 | 7/2021 |
| WO | 2021152149 A1 | 8/2021 |
| WO | 2021168193 A1 | 8/2021 |
| WO | 2021169963 A1 | 9/2021 |
| WO | 2021169990 A1 | 9/2021 |
| WO | 2021173923 A1 | 9/2021 |
| WO | 2021175199 A1 | 9/2021 |
| WO | 2021177721 A1 | 9/2021 |
| WO | 2021178740 A2 | 9/2021 |
| WO | 2021178741 A1 | 9/2021 |
| WO | 2021180181 A1 | 9/2021 |
| WO | 2021185233 A1 | 9/2021 |
| WO | 2021190467 A2 | 9/2021 |

(56) References Cited

FOREIGN PATENT DOCUMENTS

| | | | |
|---|---|---|---|
| WO | 2021197499 A1 | 10/2021 | |
| WO | 2021203768 A1 | 10/2021 | |
| WO | 2021207172 A1 | 10/2021 | |
| WO | 2021211864 A1 | 10/2021 | |
| WO | 2021215544 A1 | 10/2021 | |
| WO | 2021216770 A1 | 10/2021 | |
| WO | 2021217019 A1 | 10/2021 | |
| WO | 2021090855 A1 | 11/2021 | |
| WO | 2021218110 A1 | 11/2021 | |
| WO | 2021219072 A1 | 11/2021 | |
| WO | 2021219090 A2 | 11/2021 | |
| WO | 2021219091 A1 | 11/2021 | |
| WO | 2021228161 A1 | 11/2021 | |
| WO | 2021231526 A1 | 11/2021 | |
| WO | 2021236475 A1 | 11/2021 | |
| WO | 2021239058 A1 | 12/2021 | |
| WO | 2021243280 A1 | 12/2021 | |
| WO | 2021244603 A1 | 12/2021 | |
| WO | 2021245051 A1 | 12/2021 | |
| WO | 2021245055 A1 | 12/2021 | |
| WO | 2021245499 A1 | 12/2021 | |
| WO | 2021248079 A1 | 12/2021 | |
| WO | 2021248082 A1 | 12/2021 | |
| WO | 2021248083 A1 | 12/2021 | |
| WO | 2021248090 A1 | 12/2021 | |
| WO | 2021248095 A1 | 12/2021 | |
| WO | 2021249563 A1 | 12/2021 | |
| WO | 2021252339 A1 | 12/2021 | |
| WO | 2021257828 A1 | 12/2021 | |
| WO | 2021259331 A1 | 12/2021 | |
| WO | 2022002102 A1 | 1/2022 | |
| WO | 2022015375 A1 | 1/2022 | |
| WO | 2022017339 A1 | 1/2022 | |
| WO | 2022028346 A1 | 2/2022 | |
| WO | 2022028492 A1 | 2/2022 | |
| WO | 2022031678 A1 | 2/2022 | |
| WO | 2022036176 A1 | 2/2022 | |

OTHER PUBLICATIONS

Janes, M. et al., "Targeting KRAS Mutant Cancers with a Covalent G12C-Specific Inhibitor", 2018, Cell 172, 578-589, Jan. 25, 2018, Elsevier Inc.
Matikas, A. et al., "Targeting KRAS mutated non-small cell lung cancer: A history of failures and a future of hope for a diverse entity", Cretical Reviews in Oncology/Hematology 110 (2017) 1-12, Elsevier Ireland Ltd.
McCormick, F., "Targeting KRAS Directly", Annual Review of Cancer Biology, 2018, 2:81, 81-90.
Misalee, S. et al., KRAS G12C NSCLC models are sensitive to direct targeting of KRAS in combination with PI3K inhibition, Downloaded from clincancerres.aacrjournals.org on Oct. 22, 2018. © 2018 American Association for Cancer Research.
Nabet, B. et al., "It Takes Two to Target: A Study in KRAS Dimerization", pubs.acs.org/biochemistry, DOI: 10.1021, 2018, 57, 16, 2289-2290. https://doi.org/10.1021/acs.biochem.8b00376.
O'Bryan, J., "Pharmacological Targeting of RAS: Recent Success with Direct Inhibitors", Pharmacological Research (2018), https://doi.org/10.1016/j.phrs.2018.10.021.
Ross, S. et al., "Targeting KRAS-dependent tumors with AZD4785, a high-affinity therapeutic antisense oligonucleotide inhibitor of KRAS", Sci. Transl. Med. 9, eaal5253 (2017) Jun. 14, 2017.
Ruess, D. et al., "Mutant KRAS-driven cancers depend on PTPN11/SHP2 phosphatase", Nature Medicine, Letters, https://doi.org/10.1038/s41591-018-0024-8, 2018, 24(7), 954-960.
Simanshu, D. et al., "RAS Proteins and Their Regulators in Human Disease", Cell 170, 17-33, Jun. 29, 2017.
Suzawa, K., et al., "Activation of KRAS mediates resistance to targeted therapy in MET exon 14 mutant non-small cell lung cancer", Author Manuscript Published OnlineFirst on Oct. 23, 2018; DOI: 10.1158/1078-0432. CCR-18-1640, Downloaded from clincancer-res.aacrjournals.org on Oct. 29, 2018. © 2018 American Association for Cancer Research.
Wijeratne, A. et al., "Chemical Proteomic Characterization of a covalent KRASG12C inhibitor", ACS Med. Chem. Ltter., DOI: 10.1021/acsmedchemlett.8b00110, May 21, 2018.
Wood, K. et al., "Prognostic and Predictive Value in KRAS in Non-Small-Cell Lung Cancer a Review", JAMA Oncol. 2016:2(6), 805-812, Apr. 21, 2016.
Yen, I. et al., "Pharmacological Induction of RAS-GTP Confers RAF Inhibitor Sensitivity in KRAS Mutant Tumors", Cancer Cell 34, 611-625, Oct. 8, 2018, Elsevier Inc.
Ziemke, E. et al., "Sensitivity of KRAS-Mutant Colorectal Cancers to Combination Therapy That Cotargets MEK and CDK4/6", Clin Cancer Res; 22(2) Jan. 15, 2016.
Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.
Hansen, R. et al., "An Internally Controlled Quantitative Target Occupancy Assay for Covalent Inhibitors", Scientific Reports, 8:14312 (2018), DOI: 10.1038/s41598-018-32683-w.
Pantar, T. et al., "Assessment of mutation probabilities of KRAS G12 missense mutants and their long-timescale dynamics by atomistic molecular simulations and Markov state modeling", PLOS Computational Biology, Sep. 10, 2018.
Skoulidis, F. et al., "STK11/LKB1 Mutations and PD-1 Inhibitor Resistance in KRAS-Mutant Lung Adenocarcinoma", Downloaded from cancerdiscovery.aacrjournals.org on May 21, 2018. © 2018 American Association for Cancer Research.
Yuan, T. et al., "Differential Effector Engagement by Oncogenic KRAS", Cell Reports 22, 1889-1902, Feb. 13, 2018, Cell Press.
Calles, et al., "Immunohistochemical Loss of LKB1 Is a Biomarker for More Aggressive Biology in KRAS-Mutant Lung Adenocarcinoma", Clin Cancer Res. 2015. 21(12).
Torralvo et al., "The Activity of Immune Checkpoint Inhibition in KRAS Mutated Non-small Cell Lung Cancer: A Single Centre Experience", Cancer Genomics & Proteomics, 2019. 16: 577-582.
International Search Report and Written Opinion for PCT Application No. PCT/US2020/0052185 dated Dec. 17, 2020.
Blake et al., "Discovery of 5,6,7,8-tetrahydropyrido[3,4-d]pyrimidine inhibitors of Erk2" Bioorganic & Medicinal Chemistry Letters, Jun. 15, 2014, vol. 24, p. 2635-2639; p. 2635, Figure 1, p. 2637, right col, Para 2.
Ambrogio, C. et al., "Combined inhibition of DDR1 and Notch signaling is a therapeutic strategy for KRAS-driven lung adenocarcinoma", Nature Medicine, vol. 22, No. 3, pp. 270-279, Mar. 2016.
Araki, M. et al., "Solution Structure of the State 1 Conformer of GTP-bound H-Ras Protein and Distinct Dynamic Properties between the State 1 and State 2 Conformers" The Journal of Biological Chemistry vol. 286, No. 45, pp. 39644-39653, Nov. 11, 2011.
Broutin, S. et al., "Insights into significance of combined inhibition of MEK and m-TOR signalling output in KRAS mutant non-small-cell lung cancer", British Journal of Cancer (2016), 1-4 | doi: 10.1038/bjc.2016.220.
Burgess, M. et al., "KRAS Allelic Imbalance Enhances Fitness and Modulates MAP Kinase Dependence in Cancer", Cell 168, 817-829, Feb. 23, 2017, Elsevier Inc.
Cammarata, M. et al., "Impact of G12 Mutations on the Structure of K-Ras Probed by Ultraviolet Photodissociation Mass Spectrometry", . Am. Chem. Soc., 2016, 138 (40), pp. 13187-13196.
Costa-Cabral, S. et al., "CDK1 Is a Synthetic Lethal Target for KRAS Mutant Tumours", PLOS One | DOI:10.1371/journal.pone.0149099 Feb. 16, 2016.
Cully, "Closing the door on KRAS-mutant lung cancer", Nature Reviews Drug Discovery | Published online Nov. 3, 2016; doi:10.1038/nrd.2016.216, MacMillan Publishers.
Dharmaiah, S. et al., "Structural basis of recognition of farnesylated and methylated KRAS4b by PDEδ", E6766-E6775, PNAS, Published online Oct. 17, 2016.
Fiala, O. et al., "The dominant role of G12C over other KRAS mutation types in the negative prediction of efficacy of epidermal

(56) References Cited

OTHER PUBLICATIONS growth factor receptor tyrosine kinase inhibitors in nonesmall cell lung cancer", Cancer Genetics 206 (2013) 26-31.
Ford, B. et al., "Structure of the G60A Mutant of Ras Implications for the Dominant Negative Effect", J. Biol. Chem., vol. 280, No. 27, Issue of Jul. 8, pp. 25697-25705, 2005.
Hall, B. et al., "The structural basis for the transition from Ras-GTP to Ras-GDP", PNAS, vol. 99, No. 19, pp. 12138-12142, Sep. 17, 2002.
Hunter, J. et al., "In situ selectivity profiling and crystal structure of SML-8-73-1, an active site inhibitor of oncogenic K-Ras G12C", PNAS, vol. 111, No. 24, pp. 8895-8900, Jun. 17, 2014.
Ihle, N. et al., "Effect of KRAS Oncogene Substitutions on Protein Behavior: Implications for Signaling and Clinical Outcome", JNCI, Oxford Journals, vol. 104, Issue 3, Feb. 8, 2012.
Jarvis, L., "Have drug hunters finally cracked KRas?", c&en, vol. 94, Issue 23, pp. 28-33, Jun. 6, 2016.
Kamerkar, S. et al., "Exosomes facilitate therapeutic targeting of oncogenic KRAS in pancreatic cancer", Nature 546, 498-503 (Jun. 22, 2017) doi:10.1038/nature22341.
Kaufman, J. et al., "Treatment of KRAS-Mutant Non-Small Cell Lung Cancer the End of the Beginning for Targeted Therapies", JAMA May 9, 2017 vol. 317, No. 18.
Kerr, E. et al., "Mutant Kras copy number defines metabolic reprogramming and therapeutic susceptibilities", Nature 531, 110-113, (Mar. 3, 2016) doi:10.1038/nature16967.
Kim, J. et al., "CPS1 maintains pyrimidine pools and DNA synthesis in KRAS/LKB1-mutant lung cancer cells", Nature 546, 168-172, (Jun. 1, 2017) doi:10.1038/nature22359.
Kim, J. et al., "XPO1-dependent nuclear export is a druggable vulnerability in KRAS-mutant lung cancer", Nature 538, 114-117 (Oct. 6, 2016) doi:10.1038/nature19771.
Kitai, H. et al., "Key roles of EMT for adaptive resistance to MEK inhibitor in KRAS mutant lung cancer", SSN: 2154-1248 (Print) 2154-1256 (Online) Journal homepage: http://www.tandfonline.com/loi/ksgt20, 2017, 8(3).
Kosloff, M. et al., "GTPase Catalysis by Ras and Other G-proteins: Insights from Substrate Directed SuperImposition", J. Mol. Biol. (2003) 331, 1157-1170, doi:10.1016/S0022-2836(03)00847-7.
Ledford, H., "Thirty years of pursuit have failed to yield a drug to take on one of the deadliest families of cancer-causing proteins. Now some researchers are taking another shot." The RAS Renaissance, Nature, vol. 520, 278-280, Apr. 16, 2015.
Lim, S. et all., "Therapeutic Targeting of Oncogenic K-Ras by a Covalent Catalytic Site Inhibitor", Angew. Chem. Int. Ed. 2014, 53, 199-204.
Loncle, C. et al., "The pancreatitis-associated protein VMP1, a key regulator of inducible autophagy, promotes KrasG12D-mediated pancreatic cancer initiation", Cell Death and Disease (2016) 7, e2295; doi:10.1038/cddis.2016.202 Official journal of the Cell Death Differentiation Association.
Manchado, E. et al., "A combinatorial strategy for treating KRAS-mutant lung cancer", Nature 534, 647-651 (Jun. 30, 2016) doi:10.1038/nature18600.
Maurer, T. et al., "Small-molecule ligands bind to a distinct pocket in Ras and inhibit SOS-mediated nucleotide exchange activity", PNAS, Apr. 3, 2012, vol. 109, No. 14, pp. 5299-5304.
Muller, M. et al., "Nucleotide based covalent inhibitors of KRas can only be efficient in vivo if they bind reversibly with GTP-like affinity", Scientific Reports, 7: 3687 | DOI:10.1038/s41598-017-03973-6, 2017, 7: 3687, 1-11.
Nadal, E. et al., "Abstract C141: KRAS G12C mutation is prognostic of poor outcome in resected lung adenocarcinomas and predictive of poor response to MEK inhibition in vitro", Mol Cancer Ther Nov. 2013 12; C141, doi: 10.1158/1535-7163.TARG-13-C141.
Nussinov, R. et al., "Independent and core pathways in oncogenic KRAS signaling", Journal: Expert Review of Proteomics, DOI: 10.1080/14789450.2016.1209417, Published by Taylor & Francis.

Ostrem, J. et al., "Direct small-molecule inhibitors of KRAS: from structural insights to mechanism-based design", Nature Reviews Drug Discovery 15, 771-785 (2016) doi:10.1038/nrd.2016.139.
Ostrem, J. et al., "K-Ras(G12C) inhibitors allosterically control GTP affinity and effector interactions", Nature, vol. 503: 548, Nov. 28, 2013.
Papke, B. et al., "Drugging RAS: Know the enemy", Science 355, 1158-1163 (2017) Mar. 17, 2017.
Park, K. et al., "The HSP90 inhibitor, NVP-AUY922, sensitizes KRAS-mutant non-small cell lung cancer with intrinsic resistance to MEK inhibitor, trametinib", Cancer Letters 372 (2016) 75-81.
Patricelli, M. et al., "Selective Inhibition of Oncogenic KRAS Output with Small Molecules Targeting the Inactive State", OnlineFirst on Jan. 6, 2016; DOI: 10.1158/2159-8290.CD-15-1105.
Perara, D. et al., "Oncogenic KRAS triggers MAPK-dependent errors in mitosis and MYC-dependent sensitivity to anti-mitotic agents", Scientific Reports, 6:29741, DOI: 10.1038/srep29741, 2016, 1-15.
Renaud, S. et al., "KRAS in Non-Small-Cell Lung Cancer: Oncogenic Addiction and Epidermal Growth Factor Receptor Tyrosine Kinase Inhibitors", JAMA Oncology Published online Jul. 21, 2016.
Riquelme, E. et al., "Modulation of EZH2 expression by MEK-ERK or PI3K-AKT signaling in lung cancer is dictated by different KRAS oncogene mutations", Author Manuscript Published OnlineFirst on Dec. 16, 2015; DOI: 10.1158/0008-5472.CAN-15-1141, American Association for Cancer Research.
Rudoni, S. et al., "Role of guanine nucleotides in the regulation of the Ras/cAMP pathway in *Saccharomyces cerevisiae*", Biochimica et Biophysica Acta 1538 (2001) 181ˆ 189.
Samatar, A. et al., "Targeting RAS-ERK signalling in cancer: promises and challenges", Nature Reviews Drug Discovery, vol. 13, pp. 928-942, Dec. 2014.
Sautier, B. et al., "Latest advances towards Ras inhibition—A medicinal chemistry perspective", Angewandte Chemie International Edition, 10.1002/anie.201608270, 2016, 55, 15982-15988.
Serresi, M. et al., "Polycomb Repressive Complex 2 Is a Barrier to KRAS-Driven Inflammation and Epithelial-Mesenchymal Transition in Non-Small-Cell Lung Cancer", Cancer Cell 29, 17-31, Jan. 11, 2016, 2016 Elsevier Inc. 17.
Shima, F. et al., "Structural Basis for Conformational Dynamics of GTP-bound Ras Protein", The Journal of Biological Chemistry, vol. 285, No. 29, pp. 22696-22705, Jul. 16, 2010.
Shipman, L., "Putting the brakes on KRAS-G12C nucleotide cycling", Nature Reviews Cancer, Published online Feb. 19, 2016; doi:10.1038/nrc.2016.13.
Spoerner, M. et al., "Dynamic properties of the Ras switch I region and its importance for binding to effectors", PNAS, vol. 98, No. 9, pp. 4944-4949, Apr. 24, 2001.
Sun, Q. et al., "Discovery of Small Molecules that Bind to K-Ras and Inhibit Sos-Mediated Activation**", Angew. Chem. Int. Ed. 2012, 51, 1-5, 2012 Wiley-VCH Verlag GmbH & Co. KGaA, Weinheim.
Sun, Q., et al., "A method for the second-site screening of K-Ras in the presence of a covalently attached first-site ligand", J Biomol NMR (2014) 60:11-14 DOI 10.1007/s10858-014-9849-8.
Sunaga, N. et al., "Oncogenic KRAS-induced epiregulin overexpression contributes to aggressive phenotype and is a promising therapeutic target in non-small-cell lung cancer", Oncogene (2013) 32, 4034-4042& 2013 Macmillan Publishers Limited.
Sung, Y. et al., "Mutagenesis of the H-ras p21 at Glycine-60 Residue Disrupts GTP-Induced Conformational Change", Biochemistry 1995, 34, 3470-3477, American Chemical Society.
Tape, C. et al., "Oncogenic KRAS Regulates Tumor Cell Signaling via Stromal Reciprocation", Cell 165, 1-11May 5, 2016.
Thierry, A. et al., "Clinical validation of the detection of KRAS and BRAF mutations from circulating tumor DNA", Nature Medicine, vol. 20, No. 4, pp. 430-436 , Apr. 2014.
Tran, E. et al., "T-Cell Transfer Therapy Targeting Mutant KRAS in Cancer", N Engl J Med 2016;375:2255-62., Dec. 8, 2016; DOI: 10.1056/NEJMoa1609279.
Wang, Y. et al., "Targeting Mutant KRAS for Anticancer Therapeutics: A Review of Novel Small Molecule Modulators", J. Med.

(56) References Cited

OTHER PUBLICATIONS

Chem. 2013, 56, 5219-5230, dx.doi.org/10.1021/jm3017706; 2013 American Chemical Society, ACS Publications.
Wang, Y. et al., "Ezh2 Acts as a Tumor Suppressor in Kras-driven Lung Adenocarcinoma", International Journal of Biological Sciences 2017; 13(5): 652-659. doi: 10.7150/ijbs.19108.
Welsch, M. et al., "Multivalent Small-Molecule Pan-RAS Inhibitors", Welsch et al., 2017, Cell 168, 878-889 Feb. 23, 2017; 2017 Elsevier Inc. http://dx.doi.org/10.1016/j.cell.2017.02.006.
Winter, J. et al., "Small Molecule Binding Sites on the Ras:SOS Complex Can Be Exploited for Inhibition of Ras Activation", J. Med. Chem. 2015, 58, 2265-2274; DOI: 10.1021/jm501660t; 2015 American Chemical Society, ACS Publications.
Wood, K. et al., "Reply" Comments & Response, Letters JAMA Oncology Published online Jul. 21, 2016, American Medical Association.
Xiong, Y. et al., "Development of covalent guanosine mimetic inhibitors of G12C KRAS", ACS Med. Chem. Lett., Just Accepted Manuscript • DOI: 10.1021/acsmedchemlett.6b00373 • Publication Date (Web): Nov. 30, 2016 Downloaded from http://pubs.acs.org on Dec. 1, 2016.
Xiong, Y. et al., "Covalent Guanosine Mimetic Inhibitors of G12C KRAS" ACS Med. Chem. Lett. 2017, 8, 61-66, DOI: 10.1021/acsmedchemlett.6b00373; 2016 American Chemical Society, ACS Publications.
Janes et al., "Targeting KRAS Mutant Cancers with a Covalent G12C-Specific Inhibitor", Cell 172, 578-589, Jan. 25, 2018.
Singh et al., "A Gene Expression Signature Associated with K-Ras Addiction" Reveals Regulators of EMT and Tumor Cell Survival, Cancer Cell 15, p. 489-500, Jun. 2, 2009.
Stephen et al., "Dragging Ras Back in the Ring", Cancer Cell 25, p. 272, Mar. 17, 2014.
Zhu et al., "Inhibition of KRAS-driven tumorigenicity by interruption of an autocrine cytokine circuit", doi:10.1158/2159-8290.CD-13-0646; Cancer Discovery Published OnlineFirst Jan. 20, 2014.
Simanshu et al., "RAS Proteins and Their Regulators in Human Disease", Cell 170, p. 17, Jun. 29, 2017.
Pacold et al., "Crystal Structure and Functional Analysis of Ras Binding to Its Effector Phosphoinositide 3-Kinase gamma", Cell, vol. 103, p. 931-943, Dec. 8, 2000.
Lech-Gustav et al., "The Renaissance of Ras", ACS Chem. Biol., 2014, 9, 2447-2458.
Karachaliou et al., "KRAS Mutations in Lung Cancer", Clinical Lung Cancer, vol. 14, No. 3, p. 2015-14, 2013.
Schwartz et al., "Covalent EGFR inhibitor analysis reveals importance of reversible interactions to potency and mechanisms of drug resistance", PNAS, vol. 111, No. 1, p. 173-178, Jan. 7, 2014.
Sun et al., "A method for the second-site screening of K-Ras in the presence of a covalently attached first-site ligand", J. Biomol. NMR (2014) vol. 60 p. 11-14.
Kyriakis, J., "Thinking Outside the Box about Ras", J. Biol. Chem. 2009, 284:10993-10994, published online Dec. 17, 2008.
Sunaga et al., "Knockdown of Oncogenic KRAS in Non-Small Cell Lung Cancers Suppresses Tumor Growth and Sensitizes Tumor Cells to Targeted Therapy", Mol. Cancer Ther. 2011; 10:336-346.
Serafimova et al., "Reversible targeting of noncatalytic cysteines with chemically tuned electrophiles", Nat Chem Biol.; 8(5):471-476. doi:10.1038/nchembio.925, 2012, 8(5), 471-476.
Walker et al., "Structural insights into phosphoinositide 3-kinase catalysis and signalling", Nature vol. 402, p. 18 Nov. 1999; www.nature.com.
Barbie et al., "Systematic RNA interference reveals that oncogenic KRAS-driven cancers require TBK1", Nature, vol. 462, p. 108, Nov. 5, 2009; doi:10.1038/nature08460.
Zimmermann et al., "Small molecule inhibition of the KRAS-PDEdelta interaction impairs oncogenic KRAS signalling", Nature, vol. 497, p. 638, May 30, 2013.
Karnoub et al., "Ras oncogenes: split personalities", Nature Reviews, molecular Cell Biology, vol. 9, Jul. 2008 p. 517.
Nassar et al., "Ras/Rap effector specificity determined by charge reversal", Nature Structural Biology, vol. 3, No. 8, Aug. 1996.
De Rooij et al., "Minimal Ras-binding domain of Raf1 can be used as an activation-specific probe for Ras", Oncogene (1997) 14, 623-625, 1997 Stockton Press.
Cox et al., "The dark side of RAs: regulation of apoptosis", Oncogene (2003) 22, 8999-9006, 2003 Nature Publishing Group.
Tanaka et al., "Interfering with RAS-effector protein interactions prevent RAS-dependent tumour initiation and causes stop-start control of cancer growth", Oncogene (2010) 29, 6064-6070, 2010 Macmillan Publishers Limited.
Grant et al., "Novel Allosteric Sites on Ras for Lead Generation", PLOS One, vol. 6, Issue 10, Oct. 2011.
Maegley et al., "Ras-catalyzed hydrolysis of GTP: A new perspective from model studies", Proc. Natl. Acad. Sci. USA, vol. 93, pp. 8160-8166, Aug. 1996.
Ahmadian et al., "Guanosine triphosphatase stimulation of oncogenic Ras mutants", Proc. Natl. Acad. Sci. USA, vol. 96, pp. 7065-7070, Jun. 1999.
Kiel et al., "Electrostatically optimized Ras-binding Ral guanine dissociation stimulator mutants increase the rate of association by stabilizing the encounter complex", PNAS, vol. 101, No. 25, p. 9223-9228, Jun. 22, 2004.
Kotting et al., "The GAP arginine finger movement into the catalytic site of Ras increases the activation entropy", PNAS, vol. 105, No. 17, p. 6260-6265, Apr. 29, 2008.
Shaw et al., "Selective killing of K-ras mutant cancer cells by small molecule inducers of oxidative stress", PNAS, vol. 108, No. 21, p. 8773-8778, May 24, 2011.
Ischenko et al., "Direct reprogramming by oncogenic Ras and Myc", PNAS early edition 1, 2013.
Smith et al., "NMR-based functional profiling of RASopathies and oncogenic RAS mutations", PNAS, vol. 110, No. 12, p. 4574-4579, Mar. 19, 2013.
Shima, et al., "In silico discovery of small-molecule Ras inhibitors that display antitumor activity by blocking the Ras-effector interaction", PNAS, vol. 110, No. 20, p. 8182-8187, May 14, 2013.
Burns et al., "Approach for targeting Ras with small molecules that activate SOS-mediated nucleotide exchange", PNAS, vol. 111, No. 9, p. 3401-3406, Mar. 4, 2014.
Zeng et al., "Design of inhibitors of Ras-Raf interaction using a computational combinatorial algorithm", Protein Engineering, vol. 14, No. 1, p. 39-45, 2001.
Scheffzek et al., "The Ras-RasGAP Complex: Structural Basis for GTPAse Activation and Its Loss in Oncogenic Ras Mutants", Science, vol. 277, Jul. 18, 1997.
Taylor et al., "Protein Kinases: Evolution of Synamic Regulatory Proteins", Trends Biochem Sci. Feb. 2011; 36 (2): 65-77. doi:10.1016/j.tibs.2010.09.006.
Fell et al. 'Discovery of Tetrahydropyridopyrimidines as Irreversible Covalent Inhibitors of KRAS-G12C with In Vivo Activity', ACS Medicinal Chemistry Letters, Nov. 7, 2018 (Nov. 7, 2018), vol. 9, pp. 1230-1234.
International Search Report and Written Opinion for corresponding PCT application No. PCT/US18/61060 dated Feb. 7, 2019.
Martin, James S. et al., "Characterising covalent warhead reactivity", Bioorganic & Medicinal Chemistry, 27 (2019) 2066-2074.
Palkowitz, Maximilian D. et al., "Synthesis of Diverse N-Acryloyl Azetidines and Evaluation of Their Enhanced Thiol Reactivities", ACS Publications Mar. 16, 2017, 9, 9, 2270-2273.

* cited by examiner

COMBINATION THERAPIES

FIELD OF THE INVENTION

The present invention relates to combination therapies useful for treating cancer. In particular, the present invention relates to therapeutically effective combinations of an agent that disrupts Programmed cell death protein 1 (PD-1) and Programmed death-ligand 1 (PD-L1) axis signaling (a "PD-1/PD-L1 inhibitor") and a KRas G12C inhibitor, kits comprising the compositions and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors regulating a wide variety of processes, including cellular proliferation (e.g., see Alamgeer et al., (2013) Current Opin Pharmcol. 13:394-401).

The role of activated KRas in malignancy was observed over thirty years ago (e.g., see Der et al., (1982) Proc. Natl Acad. Sci. USA 79(11):3637-3640). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas (e.g., see Samatar and Poulikakos (2014) Nat Rev Drug Disc 13(12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma, with a G12C transversion being the most common activating mutation (e.g., see Dogan et al., (2012) Clin Cancer Res. 18(22):6169-6177, published online 2012 Sep. 26. doi: 10.1158/1078-0432.CCR-11-3265).

Oncogenic KRas mutations create an immunosuppressive microenvironment which results in resistance to immune checkpoint blockade (ICB) therapy, including anti-PD-1 and anti-PD-L1 inhibitors. Activated KRas has been demonstrated to repress the expression of interferon regulatory factor 2 (IRF2), which directly represses CXCL3 expression. This KRas-mediated repression of IRF2 leads to increased expression of CXCL3, which binds to CXCR2 on myeloid-derived suppressor cells (MDSC) promoting migration of these cells to the tumor microenvironment. A role for KRAS in modulating the immune microenvironment and primary ICB resistance in advanced colorectal cancer has been established. In colorectal cancer, anti-PD-1 resistance of KRAS-expressing tumors can be overcome by enforced IRF2 expression or by inhibition of CXCR2. (e.g., see Liao et al., (2019) Cancer Cell 35:559-572).

In addition, oncogenic KRas signaling has been shown to promote tumor immunoresistance to ICB therapy by stabilizing PD-L1 mRNA via repression of the AU-rich element-binding protein tristetraprolin (TTP), which negatively regulates PD-L1 expression through AU-rich elements in the 3' UTR of PD-L1 mRNA (e.g., see Coelho et al., (2017) Immunity 47(6):1083-1099).

Oncogenic KRas also has been demonstrated to impair antigen presentation by repressing MHC I expression thereby allowing tumor cells to evade cytotoxic T-lymphocytes (e.g., see El-Jawhari et al., (2014) Molecular Immunology 58(2):160-168), and KRas activating mutations upregulate IL-8 expression in NSCLC, and IL-8 plays a role in cell growth and migration in KRas-associated NSCLC (e.g., see Sunaga et al., (2012) Int. J. Cancer 130(8):1733-1744).

Thus, activated KRas G12C expression modulates many aspects of the immune system and is responsible for the immunosuppressive tumor microenvironment in KRas G12C-associated tumors. As such, the direct inhibition of KRas G12C-mediated cell activity should reverse this reported immunosuppressive tumor microenvironment thereby improving the clinical activity of immune checkpoint blockade therapy, including the PD-1/PD-L1 pathway.

For all the foregoing reasons, there is a need to develop combination therapies using KRas G12C inhibitors and ICB therapy, including anti-PD-1 and anti-PD-L1 inhibitors, for treating KRas G12C-associated cancers that are resistant to ICB therapy.

SUMMARY OF THE INVENTION

In one aspect of the invention, provided herein are methods of treating cancer in a subject in need thereof, comprising administering to the subject a therapeutically effective amount of a combination of an agent that disrupts Programmed cell death protein 1 (PD-1) and Programmed death-ligand 1 (PD-L1) axis signaling (a "PD-1/PD-L1 inhibitor) and a KRAS G12C inhibitor of Formula (I):

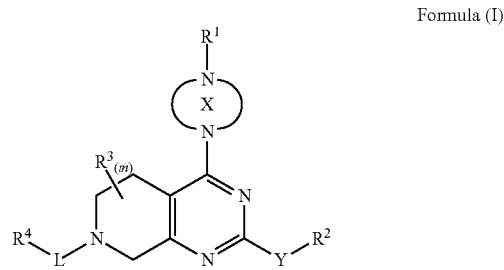

Formula (I)

or a pharmaceutically acceptable salt thereof, wherein:

X is a 4-12 membered saturated or partially saturated monocyclic, bridged or spirocyclic ring, wherein the saturated or partially saturated monocyclic ring is optionally substituted with one or more $R^8$;

Y is a bond, O, S or $NR^5$;

$R^1$ is $-C(O)C(R^A)\!=\!\!=\!\!=C(R^B)_p$ or $SO_2C(R^A)\!=\!\!=\!\!=C(R^B)_p$;

$R^2$ is hydrogen, alkyl, hydroxyalkyl, dihydroxyalkyl, alkylaminylalkyl, dialkylaminylalkyl, $-Z-NR^5R^{10}$, heterocyclyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;

Z is C1-C4 alkylene;

each $R^3$ is independently C1-C3 alkyl, oxo, or haloalkyl;

L is a bond, $-C(O)-$, or C1-C3 alkylene;

$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$ or $R^7$;

each $R^5$ is independently hydrogen or C1-C3 alkyl;

$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;

each $R^7$ is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;

$R^8$ is oxo, C1-C3 alkyl, C2-C4 alkynyl, heteroalkyl, cyano, —C(O)OR$^5$, —C(O)N(R$^5$)$_2$, —N(R$^5$)$_2$, wherein the C1-C3 alkyl may be optionally substituted with cyano, halogen, —OR$^5$, —N(R$^5$)$_2$, or heteroaryl each $R^9$ is independently hydrogen, oxo, acyl, hydroxyl, hydroxyalkyl, cyano, halogen, C1-C6 alkyl, aralkyl, haloalkyl, heteroalkyl, cycloalkyl, heterocyclylalkyl, alkoxy, dialkylaminyl, dialkylamidoalkyl, or dialkylaminylalkyl, wherein the C1-C6 alkyl may be optionally substituted with cycloalkyl;

each $R^{10}$ is independently hydrogen, acyl, C1-C3 alkyl, heteroalkyl or hydroxyalkyl;

$R^{11}$ is haloalkyl;

$R^A$ is absent, hydrogen, deuterium, cyano, halogen, C1-C-3 alkyl, haloalkyl, heteroalkyl, —C(O)N(R$^5$)$_2$, or hydroxyalkyl;

each $R^B$ is independently hydrogen, deuterium, cyano, C1-C3 alkyl, hydroxyalkyl, heteroalkyl, C1-C3 alkoxy, halogen, haloalkyl, —ZNR$^5$R$^{11}$, —C(O)N(R$^5$)$_2$, —NHC(O)C1-C3 alkyl, —CH$_2$NHC(O)C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more R$^7$;

m is zero or an integer between 1 and 2;

p is one or two; and wherein, when ══ is a triple bond then $R^A$ is absent, $R^B$ is present and p equals one, or when ══ is a double bond then $R^A$ is present, $R^B$ is present and p equals two, or $R^A$, $R^B$ and the carbon atoms to which they are attached form a 5-8 membered partially saturated cycloalkyl optionally substituted with one or more R$^7$.

Also included for use in the methods provided herein are KRas G12C inhibitor compounds of Formula I having the Formula I-A:

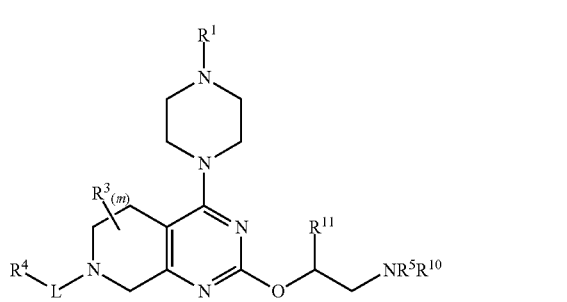

Formula I-A or a pharmaceutically acceptable salt thereof, wherein R$^1$, R$^3$, R$^4$, R$^5$, R$^{10}$, R$^{11}$, L and m are as defined for Formula I, and the piperazinyl ring is optionally substituted with R$^8$ wherein R$^8$ is as defined for Formula I.

Also included for use in the methods provided herein are KRas G12C inhibitor compounds of Formula I having the Formula I-B:

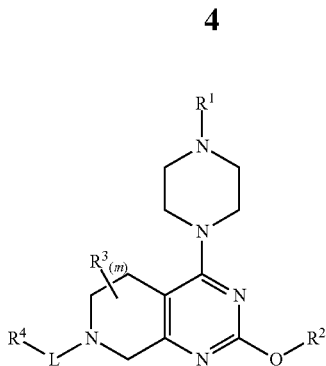

Formula I-B or a pharmaceutically acceptable salt thereof, wherein R$^1$, R$^3$, R$^4$, L and m are as defined for Formula I, R$^2$ is heterocyclylalkyl optionally substituted with one or more R$^9$ where R$^9$ is as defined for Formula I, and the piperazinyl ring is optionally substituted with R$^8$, where R$^8$ is as defined for Formula I.

In another aspect of the invention, pharmaceutical combinations are provided for use in the methods comprising a therapeutically effective amount of a combination of a PD-1/PD-L1 inhibitor, or a pharmaceutical composition thereof and a KRas G12C inhibitor compound Formula I, Formula I-A, or Formula 1-B or a pharmaceutically acceptable salt thereof, and a pharmaceutically acceptable excipient. In one embodiment, the PD-1/PD-L1 inhibitor binds to and/or inhibits the activity of the PD-1 receptor. In one embodiment, the PD-1/PD-L1 inhibitor binds to and/or inhibits the signaling of the PD-L1 ligand.

In one aspect of the invention, provided herein are methods of treating cancer in a subject in need thereof, comprising administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof. In one embodiment, the cancer is a KRas G12C-associated cancer. In one embodiment, the KRas G12C-associated cancer is lung cancer. In one embodiment, the PD-1/PD-L1 inhibitor binds to and/or inhibits the activity of the PD-1 receptor. In one embodiment, the PD-1/PD-L1 inhibitor binds to and/or inhibits the signaling of the PD-L1 ligand.

Also provided are methods of treating a KRas G12C-associated cancer in a subject in need thereof, wherein the KRas G12C-associated cancer is resistant to treatment with a PD-1/PD-L1 inhibitor, comprising administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof.

Also provided are methods of treating a subject identified or diagnosed as having a KRas G12C-associated cancer and determined to have previously developed resistance to treatment with a PD-1/PD-L1 inhibitor that include administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof.

Also provided are methods of suppressing resistance to treatment with a PD-1/PD-L1 inhibitor in a subject having a KRas G12C-associated cancer that include administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof.

Also provided herein are methods of treating a subject identified or diagnosed as having a KRAS G12C-associated cancer that include (a) detecting resistance of the KRas G12C-associated cancer in the subject to treatment with a PD-1/PD-L1 inhibitor that was previously administered to the patient; and (b) after (a), administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof.

Also provided herein are methods of treating a subject identified or diagnosed as having a KRas G12C-associated cancer and determined to have previously developed resistance to treatment with a KRAS G12C inhibitor that include administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof.

Also provided here a methods of treating a subject identified or diagnosed as having a KRas G12C-associated cancer, comprising (a) administering a KRAS G12C inhibitor as monotherapy until disease progression, and (b) after (a), administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof.

In some aspects of the invention, KRas G12C inhibitor compounds and PD-1/PD-L1 inhibitors are the only active agents in the provided combinations and methods.

Examples of PD-1/PD-L1 inhibitors that bind to and/or inhibit the activity of PD-1 receptor suitable for the provided combinations and methods include nivolumab (Opdivo®), pembrolizumab (Keytruda®), cemiplimab (Libtayo®) and tislelizumab, and biosimilars thereof. Examples of PD-1/PD-L1 inhibitors that bind to and/or inhibit the activity of PD-L1 ligand suitable for the provided combinations and methods include atezolizumab (Tecentriq®), avelumab (Bavencio®) and durvalumab (Imfinzi®), and biosimilars thereof.

Also provided herein are methods for treating cancer in a subject in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of a combination of a PD-1/PD-L1 inhibitor, or a pharmaceutical composition thereof, and a KRas G12C inhibitor compound of Formula I, Formula I-A, Formula 1-B or a pharmaceutically acceptable salt or a pharmaceutical composition thereof, wherein the combination induces a durable complete response in the patient compared to either the PD-1/PD-L1 inhibitor or KRas G12C inhibitor alone.

In one embodiment of the method, the PD-1/PD-L1 inhibitor or a pharmaceutical composition thereof and a KRas G12C inhibitor, or a pharmaceutically acceptable salt or a pharmaceutical composition thereof, are administered concurrently. In one embodiment of the method, the PD-1/PD-L1 inhibitor or a pharmaceutical composition thereof is administered weekly for three weeks and a KRas G12C inhibitor, or a pharmaceutically acceptable salt or a pharmaceutical composition thereof, is administered daily for about 28 days.

Also provided herein are kits comprising a PD-1/PD-L1 inhibitor or a pharmaceutical composition thereof and a KRas G12C inhibitor compound of Formula (I), Formula I-A or Formula I-B or a pharmaceutically acceptable salt or a pharmaceutical composition thereof. Also provided is a kit comprising a PD-1/PD-L1 inhibitor or a pharmaceutical composition thereof and a KRas G12C inhibitor compound of Formula (I), Formula I-A or Formula I-B or a pharmaceutically acceptable salt or a pharmaceutical composition thereof, for use in treating a KRas G12C cancer.

In a related aspect, the invention provides a kit containing a dose of a PD-1/PD-L1 inhibitor, or a pharmaceutical composition thereof and a KRas G12C inhibitor compound of Formula (I), Formula I-A or Formula I-B or a pharmaceutically acceptable salt or a pharmaceutical composition thereof in an amount effective to inhibit proliferation of cancer cells in a subject. The kit in some cases includes an insert with instructions for administration of a PD-1/PD-L1 inhibitor or a pharmaceutical composition thereof and a KRas G12C inhibitor compound of Formula (I), Formula I-A or Formula I-B, or a pharmaceutically acceptable salt or a pharmaceutical composition thereof. The insert may provide a user with one set of instructions for using the PD-1/PD-L1 inhibitor or a pharmaceutical composition thereof in combination with the KRas G12C inhibitor compound of Formula (I), Formula I-A or Formula I-B, or a pharmaceutically acceptable salt or a pharmaceutical composition thereof.

In some embodiments of any of the methods described herein, before treatment with the compositions or methods of the invention, the patient was treated with one or more of a chemotherapy, a targeted anticancer agent, radiation therapy, and surgery, and optionally, the prior treatment was unsuccessful; and/or the patient has been administered surgery and optionally, the surgery was unsuccessful; and/or the patient has been treated with a platinum-based chemotherapeutic agent, and optionally, the patient has been previously determined to be non-responsive to treatment with the platinum-based chemotherapeutic agent; and/or the patient has been treated with a kinase inhibitor, and optionally, the prior treatment with the kinase inhibitor was unsuccessful; and/or the patient was treated with one or more other therapeutic agent(s).

DETAILED DESCRIPTION OF THE INVENTION

The present invention relates to combination therapies for treating KRas G12C cancers. In particular, the present invention relates to methods of treating cancer in a subject in need thereof, comprising administering to the subject a therapeutically effective amount of a combination of a PD-1/PD-L1 inhibitor or a pharmaceutical composition thereof and a KRAS G12C inhibitor of Formula (I), Formula I-A or Formula I-B, or a pharmaceutically acceptable salt thereof or a pharmaceutical composition thereof, kits comprising the compositions and methods of use therefor.

In one embodiment, the combination of a PD-1/PD-L1 inhibitor or a pharmaceutical composition thereof and a KRas G12C inhibitor compound of Formula (I), Formula I-A or Formula I-B, or a pharmaceutically acceptable salt or a pharmaceutical composition thereof, induces a durable complete response in animals harboring KRas G12C-associated cancer compared to the KRas G12C inhibitor compound of Formula (I), Formula I-A or Formula I-B, or a pharmaceutically acceptable salt or a pharmaceutical composition thereof, administered as a single agent.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variant p.Gly12Cys.

As used herein, a "KRas G12C inhibitor" refers to compounds of the present invention that are represented by Formula (I), Formula I-A and Formula I-B as described herein. These compounds are capable of negatively modulating or inhibiting all or a portion of the enzymatic activity of KRas G12C. The KRas G12C inhibitors of the present invention interact with and irreversibly bind to KRas G12C by forming a covalent adduct with the sulfhydryl side chain of the cysteine residue at position 12 resulting in the inhibition of the enzymatic activity of KRas G12C. In one embodiment, the KRas G12C inhibitor is a compound selected from compound Nos 1-678 (as numbered in WO2019099524), or pharmaceutically acceptable salts thereof (e.g., Example Nos 234, 359, 478 or 507, or a pharmaceutically acceptable salt thereof).

A "KRas G12C-associated disease or disorder" as used herein refers to diseases or disorders associated with or mediated by or having a KRas G12C mutation. A non-limiting example of a KRas G12C-associated disease or disorder is a KRas G12C-associated cancer.

As used herein, Programmed cell death protein 1 (PD-1) is a 55 kDa type I transmembrane protein that is part of the Ig gene superfamily that delivers negative cellular signals upon interaction with its two ligands, PD-L1 or PD-L2, to suppress the immune response.

As used herein, a "PD-1/PD-L1 inhibitor" refers to an agent that is capable of negatively modulating or inhibiting all or a portion of the PD-1/PD-L1 axis signaling activity and include agents that block PD-1 or PD-L1 Examples include PD-1 and PD-L1 binding antagonists such as anti-PD-1 antibodies, antigen binding fragments thereof, immunoadhesins, aptamers, fusion proteins, and oligopeptides. In some embodiments, the PD-1 binding antagonist is an anti-PD-1 antibody. In some embodiments, the PD-L1 binding antagonist is an anti-PD-L1 antibody.

The term "PD-1 binding antagonist" as used herein refers to a PD-1 inhibitor, i.e., a molecule that decreases, blocks, inhibits, abrogates or interferes with signal transduction resulting from the interaction of PD-1 with one or more of its binding partners, such as PD-L1 and/or PD-L2. In some embodiments, the PD-1 inhibitor is a molecule that inhibits the binding of PD-1 to its binding partners. In a specific aspect, the PD-1 inhibitor inhibits the binding of PD-1 to PD-L1 and/or PD-L2. For example, PD-1 inhibitors include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 inhibitor reduces the negative co-stimulatory signal mediated by or through cell surface proteins expressed on T lymphocytes mediated signaling through PD-1 so as render a dysfunctional T-cell less non-dysfunctional. In some embodiments, the PD-1 inhibitor is an anti-PD-1 antibody. In one embodiment, the PD-1 antibody is pembrolizumab, or a biosimilar thereof. In one embodiment, the PD-1 antibody is cemiplimab, or a biosimilar thereof. In one embodiment, the PD-1 antibody is tislelizumab, or a biosimilar thereof.

The term "PD-L1 binding antagonist" as used herein refers to a PD-L1 inhibitor, i.e., a molecule that decreases, blocks, inhibits, abrogates or interferes with signal transduction resulting from the interaction of PD-L1 with either one or more of its binding partners, such as PD-1 and/or B7-1. In some embodiments, a PD-L1 inhibitor is a molecule that inhibits the binding of PD-L1 to its binding partners. In a specific aspect, the PD-L1 inhibitor inhibits binding of PD-L1 to PD-1 and/or B7-1. In some embodiments, the PD-L1 inhibitors include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1 and/or B7-1. In one embodiment, a PD-L1 inhibitor reduces the negative co-stimulatory signal mediated by or through cell surface proteins expressed on T lymphocytes mediated signaling through PD-L1 so as render a dysfunctional T-cell less non-dysfunctional. In some embodiments, a PD-L1 inhibitor is an anti-PD-L1 antibody. In a specific aspect, an anti-PD-L1 antibody is avelumab or a biosimilar thereof. In another specific aspect, an anti-PD-L1 antibody is atezolizumab or a biosimilar thereof. In another specific aspect, an anti-PD-L1 antibody is durvalumab or a biosimilar thereof. In another specific aspect, an anti-PD-L1 antibody is BMS-936559 (MDX-1105) or a biosimilar thereof.

A "biosimilar" means an antibody or antigen-binding fragment that has the same primary amino acid sequence as compared to a reference antibody (e.g., nivolumab or pembrolizumab) and optionally, may have detectable differences in post-translation modifications (e.g., glycosylation and/or phosphorylation) as compared to the reference antibody (e.g., a different glycoform).

As used herein a "complete response" refers to a subject having a KRas G12C-associated cancer that has been treated with the combination of a PD-1/PD-L1 inhibitor and a KRas G12C inhibitor of the present invention in which the treated tumor at some stage of treatment is no longer detectable by palpation, by calibration or by standard-of-care methodologies for detecting such tumors that eventually relapse. The duration of a complete response is typically measured in days.

As used herein a "durable complete response" refers to a subject having a KRas G12C-associated cancer that has been treated with the combination of a PD-1/PD-L1 inhibitor and a KRas G12C inhibitor of the present invention in which the treated tumor is no longer detectable by palpation, by calibration or by standard-of-care methodologies for detecting such tumors and the tumor fails to relapse due to an induced anti-tumor immunological memory in the subject, remaining undetectable after treatment and/or in patient-derived animal models (PDX) is recalcitrant to re-challenge using the same tumor cells of the initial tumor type. The duration of a durable complete response is typically measured in weeks, months or years.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12C mutation (e.g., as determined using a regulatory agency-approved, e.g., FDA-approved, assay or kit). In some embodiments, the subject has a tumor that is positive for a KRas G12C mutation (e.g., as determined using a regulatory agency-approved assay or kit). The subject can be a subject with a tumor(s) that is positive for a KRas G12C mutation (e.g., identified as positive using a regulatory agency-approved, e.g., FDA-approved, assay or kit). The subject can be a subject whose tumors have a KRas G12C mutation (e.g., where the tumor is identified as such using a regulatory agency-approved, e.g., FDA-approved, kit or assay). In some embodiments, the subject is suspected of having a KRas G12C gene-associated cancer. In some embodiments, the subject has a clinical record indicating that the subject has a tumor that has a KRas G12C mutation (and optionally the clinical record indicates that the subject should be treated with any of the compositions provided herein).

The term "pediatric patient" as used herein refers to a patient under the age of 16 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery MD, First LR. Pediatric Medicine, 2nd Ed. Baltimore: Williams & Wilkins; 1994.

In some embodiments of any of the methods or uses described herein, an assay is used to determine whether the patient has KRas G12C mutation using a sample (e.g., a biological sample or a biopsy sample such as a paraffin-embedded biopsy sample) from a patient (e.g., a patient suspected of having a KRas G12C-associated cancer, a patient having one or more symptoms of a KRas G12C-associated cancer, and/or a patient that has an increased risk of developing a KRas G12C-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR, quantitative real-time RT-PCR, allele-specific genotyping or ddPCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The term "amino" refers to —NH$_2$;
The term "acyl" refers to —C(O)CH$_3$.

The term "alkyl" as employed herein refers to straight and branched chain aliphatic groups having from 1 to 12 carbon atoms, 1-8 carbon atoms 1-6 carbon atoms, or 1-3 carbon atoms which is optionally substituted with one, two or three substituents. Examples of alkyl groups include, without limitation, methyl, ethyl, propyl, isopropyl, butyl, isobutyl, sec-butyl, tert-butyl, pentyl, and hexyl.

The term "haloalkyl" refers to an alkyl chain in which one or more hydrogen has been replaced by a halogen. Examples of haloalkyls are trifluoromethyl, difluoromethyl and fluoromethyl.

The term "haloalkyloxy" refers to —O-haloalkyl.

An "alkylene," group is an alkyl group, as defined hereinabove, that is positioned between and serves to connect two other chemical groups. Exemplary alkylene groups include, without limitation, methylene, ethylene, propylene, and butylene.

The term "alkoxy" refers to —OC1-C6 alkyl.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted. Examples of cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteroatom selected from the group consisting of O, S, and N.

As used herein, the term "hydroxyalkyl" refers to -alkyl-OH.

The term "dihydroxyalkyl" refers to an alkyl group as defined herein wherein two carbon atoms are each substituted with a hydroxyl group.

The term "alkylaminyl" refers to —NR$^x$-alkyl, wherein R$^x$ is hydrogen. In one embodiment, R$^x$ is hydrogen.

The term "dialkylaminyl" refers to —N(R$^y$)$_2$, wherein each R$^y$ is C1-C3 alkyl.

The term "alkylaminylalkyl" refers to -alkyl-NR$^x$-alkyl, wherein R$^x$ is hydrogen. In one embodiment, R$^x$ is hydrogen.

The term "dialkylaminylalkyl" refers to -alkyl-N(R$^y$)$_2$, wherein each R$^y$ is C1-C4 alkyl, wherein the alkyl of the -alkyl-N(R$^y$)$_2$ may be optionally substituted with hydroxy or hydroxyalkyl.

An "aryl" group is a C$_6$-C$_{14}$ aromatic moiety comprising one to three aromatic rings, which is optionally substituted. As one embodiment, the aryl group is a C$_6$-C$_{10}$ aryl group. Examples of aryl groups include, without limitation, phenyl, naphthyl, anthracenyl, fluorenyl, and dihydrobenzofuranyl.

An "aralkyl" or "arylalkyl" group comprises an aryl group covalently linked to an alkyl group, either of which may independently be optionally substituted or unsubstituted. An example of an aralkyl group is (C$_1$-C$_6$)alkyl(C$_6$-C$_{10}$)aryl, including, without limitation, benzyl, phenethyl, and naphthylmethyl. An example of a substituted aralkyl is wherein the alkyl group is substituted with hydroxyalkyl.

A "heterocyclyl" or "heterocyclic" group is a ring structure having from about 3 to about 12 atoms, for example 4 to 8 atoms, wherein one or more atoms are selected from the group consisting of N, O, and S, the remainder of the ring atoms being carbon. The heterocyclyl may be a monocyclic, a bicyclic, a spirocyclic or a bridged ring system. The heterocyclic group is optionally substituted with R$^7$ on carbon or nitrogen at one or more positions, wherein R$^7$ is as defined for Formula I. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, thiazolidinyl, dithianyl, trithianyl, dioxolanyl, oxazolidinyl, oxazolidinonyl, decahydroquinolinyl, piperidonyl, 4-piperidinonyl, thiomorpholinyl, thiomorpholinyl 1,1 dioxide, morpholinyl, oxazepanyl, azabicyclohexanes, azabicycloheptanes and oxa azabiocycloheptanes. Specifically excluded from the scope of this term are compounds having adjacent annular O and/or S atoms.

The term "heterocyclylalkyl" refers to a heterocyclyl group as defined herein linked to the remaining portion of the molecule via an alkyl linker, wherein the alkyl linker of the heterocyclylalkyl may be optionally substituted with hydroxy or hydroxyalkyl.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "heteroarylalkyl" group comprises a heteroaryl group covalently linked to an alkyl group, wherein the radical is on the alkyl group, either of which is independently optionally substituted or unsubstituted. Examples of heteroarylalkyl groups include a heteroaryl group having 5, 6, 9, or 10 ring atoms bonded to a C1-C6 alkyl group. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent annular O and/or S atoms.

As used herein, "an effective amount" of a compound is an amount that is sufficient to negatively modulate or inhibit the activity of the desired target, i.e., a PD-1/PD-L1 or KRas G12C. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of PD-1/PD-L1 or KRas G12C. Such amount may be administered as a single dosage or may be administered according to a regimen, whereby it is effective.

As used herein, a "therapeutically effective amount of a combination" of two compounds is an amount that together synergistically increases the activity of the combination in comparison to the therapeutically effective amount of each compound in the combination. For example, in vivo, the therapeutically effective amount of the combination of a PD-1/PD-L1 inhibitor or a pharmaceutical composition thereof and a KRas G12C inhibitor compound of Formula (I), Formula I-A, or Formula I-B or a pharmaceutically acceptable salt or a pharmaceutical composition thereof, results in a complete durable response in subjects relative to treatment with only the KRas G12C inhibitor. In one embodiment, the therapeutically effective amount of the combination of a PD-1/PD-L1 inhibitor or a pharmaceutical composition thereof and a KRas G12C inhibitor compound of Formula (I), Formula I-A, or Formula I-B or a pharmaceutically acceptable salt or a pharmaceutical composition thereof, results in an increased duration of overall survival ("OS") in subjects relative to treatment with only the KRas G12C inhibitor. In one embodiment, the therapeutically effective amount of the combination of a PD-1/PD-L1 inhibitor or a pharmaceutical composition thereof and a KRas G12C inhibitor compound of Formula (I), Formula I-A, or Formula I-B or a pharmaceutically acceptable salt or a pharmaceutical composition thereof, results in an increased duration of progression-free survival ("PFS") in subjects relative to treatment with only the KRas G12C inhibitor. In one embodiment, the therapeutically effective amount of the combination of a PD-1/PD-L1 inhibitor or a pharmaceutical composition thereof and a KRas G12C inhibitor compound of Formula (I), Formula I-A, or Formula I-B, or a pharmaceutically acceptable salt or a pharmaceutical composition thereof, results in increased tumor regression in subjects relative to treatment with only the KRas G12C inhibitor. In one embodiment, the therapeutically effective amount of the combination of a PD-1/PD-L1 inhibitor or a pharmaceutical composition thereof and a KRas G12C inhibitor compound of Formula (I), Formula I-A, or Formula I-B, or a pharmaceutically acceptable salt or a pharmaceutical composition thereof, results in increased tumor growth inhibition in subjects relative to treatment with only the KRas G12C inhibitor. In one embodiment, the therapeutically effective amount of the combination of a PD-1/PD-L1 inhibitor or a pharmaceutical composition thereof and a KRas G12C inhibitor compound of Formula (I), Formula I-A, or Formula I-B, or a pharmaceutically acceptable salt or a pharmaceutical composition thereof, results in an improvement in the duration of stable disease in subjects compared to treatment with only the KRas G12C inhibitor. The amount of each compound in the combination may be the same or different than the therapeutically effective amount of each compound when administered alone as a monotherapy as long as the combination is synergistic. Such amounts may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical combination refers to any lessening, whether permanent or temporary, lasting or transient that can be attributed to or associated with administration of the combination.

As used herein, the term "about" when used to modify a numerically defined parameter (e.g., the dose of a KRAS inhibitor or a PD-1/PD-L1 inhibitor or a pharmaceutically acceptable salt thereof, or the length of treatment time with a combination therapy described herein) means that the parameter may vary by as much as 10% below or above the stated numerical value for that parameter. For example, a dose of about 5 mg/kg may vary between 4.5 mg/kg and 5.5 mg/kg. "About" when used at the beginning of a listing of parameters is meant to modify each parameter. For example, about 0.5 mg, 0.75 mg or 1.0 mg means about 0.5 mg, about 0.75 mg or about 1.0 mg. Likewise, about 5% or more, 10% or more, 15% or more, 20% or more, and 25% or more means about 5% or more, about 10% or more, about 15% or more, about 20% or more, and about 25% or more.

Inhibitor Compounds

In one aspect of the invention, provided herein are methods of treating cancer in a subject in need thereof, comprising administering to the subject a therapeutically effective amount of a combination of a PD-1/PD-L1 inhibitor or a pharmaceutical composition thereof and a KRAS G12C inhibitor of Formula (I), Formula I-A or Formula I-B, or a pharmaceutically acceptable salt or a pharmaceutical composition thereof.

1. PD-1/PD-L1 Inhibitors

Programmed death protein 1 (PD-1) is an immunoinhibitory receptor that is primarily expressed on activated T and B cells. PD-1 is a 55 kDa type I transmembrane protein that is part of the Ig gene superfamily (Agata et al. (1996) Int Immunol 8:765-72). PD-1 contains a membrane proximal immunoreceptor tyrosine inhibitory motif (ITIM) and a membrane distal tyrosine-based switch motif (ITSM). Two ligands that bind to PD-1 have been identified, PD-L1 and PD-L2, that have been shown to downregulate T cell activation upon binding to PD-1 (Freeman et al. (2000) J Exp Med 192:1027-34). PD-L1 is a ligand for PD-1 and is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7).

Immune suppression can be reversed by inhibiting the local interaction of PD-1 with PD-L1, and the effect is additive when the interaction of PD-1 with PD-L2 is blocked as well. For instance, disruption of the PD-1/PD-L1 interaction has been shown to increase T cell proliferation and cytokine production and block progression of the cell cycle.

Given PD-L1 is upregulated in many cancers and contributes to evasion of the host immune system, blocking the interaction between PD-1 and PD-L1 has garnered the attention of the pharmaceutical industry leading to a new break-through class of immune checkpoint therapies for a wide range of cancers. The PD-1/PD-L1 pathway is a well-validated target for the development of antibody therapeutics for cancer treatment and several anti-PD-1 and anti-PD-L1 antibodies have undergone human clinical trials for a wide-variety of cancers including NSCLC, renal cell carcinoma, melanoma, head and neck squamous cancer, ureothelial cancer, hepatocellular carcinoma, and other cancers. Exemplary anti-PD-1 antibodies include nivolumab (Opdivo®), pembrolizumab (Keytruda®), cemiplimab (Libtayo®) and tislelizumab, and biosimilars thereof. Exemplary anti-PD-L1 antibodies include atezolizumab (Tecentriq®), avelumab (Bavencio®), and durvalumab (Imfinzi®), and biosimilars thereof.

Methods for manufacturing agents that disrupt PD-1/PD-L1 signalling axis, including the antibodies described herein, are well known to those skilled in the art and agents that disrupt PD-1/PD-L1 signalling axis may be obtained from a wide-variety of commercial suppliers, in forms suitable for both research or approved human clinical use. In addition, suitable agents that disrupt PD-1/PD-L1 signalling for use in the compositions and methods disclosed herein and methods for preparing such agents, and diagnostic and efficacy markers useful for monitoring treatment are disclosed in US Patent Application Publication Nos: 20180327848; 20180237524; 20180148790; 20180111996; 20160305947; 20160304969; 20160304606; 20150232555; 20150079109; 20140348743; 20140294852; 20140271684; 20140234296; 20130133091; 20110123550; and 20090217401.

2. KRas G12C Inhibitors

In one embodiment, the KRas G12C inhibitors used in the methods are compounds of Formula (I), Formula I-A or Formula I-B:

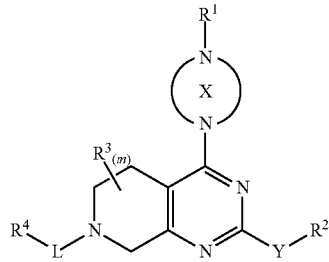

Formula (I)

or a pharmaceutically acceptable salt thereof, wherein:

X is a 4-12 membered saturated or partially saturated monocyclic, bridged or spirocyclic ring, wherein the saturated or partially saturated monocyclic ring is optionally substituted with one or more $R^8$;

Y is a bond, O, S or $NR^5$;

$R^1$ is $-C(O)C(R^A)=C(R^B)_p$ or $-SO_2C(R^A)=C(R^B)_p$;

$R^2$ is hydrogen, alkyl, hydroxyalkyl, dihydroxyalkyl, alkylaminylalkyl, dialkylaminylalkyl, $-Z-NR^5R^{10}$, heterocyclyl, heterocyclylalkyl, aryl, heteroaryl, or heteroarylalkyl, wherein each of the Z, heterocyclyl, heterocyclylalkyl, aryl, heteroaryl, and heteroarylalkyl may be optionally substituted with one or more $R^9$;

Z is C1-C4 alkylene;

each $R^3$ is independently C1-C3 alkyl, oxo, or haloalkyl;

L is a bond, $-C(O)-$, or C1-C3 alkylene;

$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more $R^6$ or $R^7$;

each $R^5$ is independently hydrogen or C1-C3 alkyl;

R[6] is cycloalkyl, heterocyclyl, heterocyclylalkyl, aryl, or heteroaryl, wherein each of the cycloalkyl, heterocyclyl, aryl, or heteroaryl may be optionally substituted with one or more R[7];

each R[7] is independently halogen, hydroxyl, C1-C6 alkyl, cycloalkyl, alkoxy, haloalkyl, amino, cyano, heteroalkyl, hydroxyalkyl or Q-haloalkyl, wherein Q is O or S;

R[8] is oxo, C1-C3 alkyl, C2-C4 alkynyl, heteroalkyl, cyano, —C(O)OR[5], —C(O)N(R[5])$_2$, —N(R[5])$_2$, wherein the C1-C3 alkyl may be optionally substituted with cyano, halogen, —OR[5], —N(R[5])$_2$, or heteroaryl;

each R[9] is independently hydrogen, oxo, acyl, hydroxyl, hydroxyalkyl, cyano, halogen, C1-C6 alkyl, aralkyl, haloalkyl, heteroalkyl, cycloalkyl, heterocyclylalkyl, alkoxy, dialkylaminyl, dialkylamidoalkyl, or dialkylaminylalkyl, wherein the C1-C6 alkyl may be optionally substituted with cycloalkyl;

each R[10] is independently hydrogen, acyl, C1-C3 alkyl, heteroalkyl or hydroxyalkyl;

R[11] is haloalkyl;

R[A] is absent, hydrogen, deuterium, cyano, halogen, C1-C3 alkyl, haloalkyl, heteroalkyl, —C(O)N(R[5])$_2$, or hydroxyalkyl;

each R[B] is independently hydrogen, deuterium, cyano, C1-C3 alkyl, hydroxyalkyl, heteroalkyl, C1-C3 alkoxy, halogen, haloalkyl, —ZNR[5]R[11], —C(O)N(R[5])$_2$, —NHC(O)C1-C3 alkyl, —CH$_2$NHC(O)C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more R[7];

m is zero or an integer between 1 and 2;
p is one or two; and wherein, when ≡≡≡ is a triple bond then R[A] is absent, R[B] is present and p equals one;

or when ═══ is a double bond then R[A] is present, R[B] is present and p equals two, or R[A], R[B] and the carbon atoms to which they are attached form a 5-8 membered partially saturated cycloalkyl optionally substituted with one or more R[7].

In one embodiment, KRas G12C inhibitors used in the methods herein includes compounds having the Formula I-A:

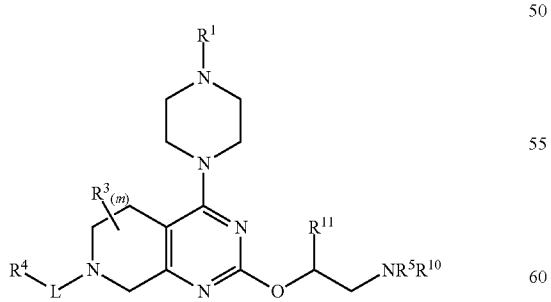

or a pharmaceutically acceptable salt thereof, wherein R[1], R[3], R[4], R[5], R[10], L and m are as defined for Formula I, R[11] is hydrogen, methyl or hydroxyalkyl, and the piperidinyl ring is optionally substituted with R[8] wherein R[8] is as defined for Formula I.

In one embodiment, KRas G12C inhibitors used in the methods herein include compounds having the Formula I-B:

Formula I-B

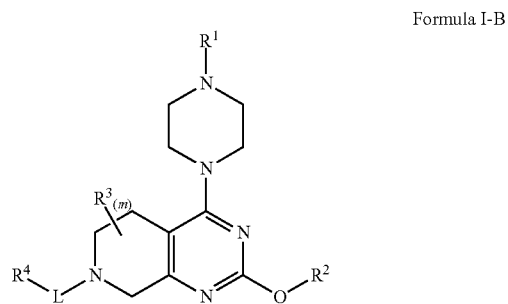

or a pharmaceutically acceptable salt thereof, wherein R[1], R[3], R[4], R[9], R[11], L and m are as defined for Formula I.

Nonlimiting examples of KRas G12C inhibitor compounds of Formula (I), Formula I-A and Formula I-B useful in the methods disclosed herein are selected from the group consisting of Example Nos 1-678 (as numbered in international patent publication No WO2019099524) including the following structures:

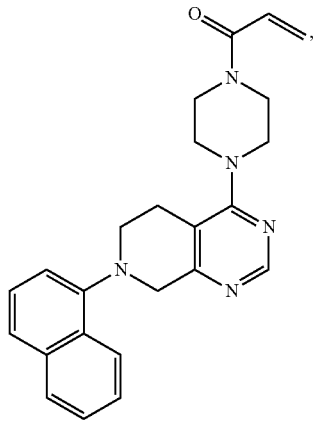

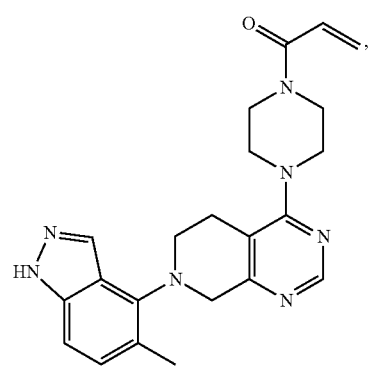

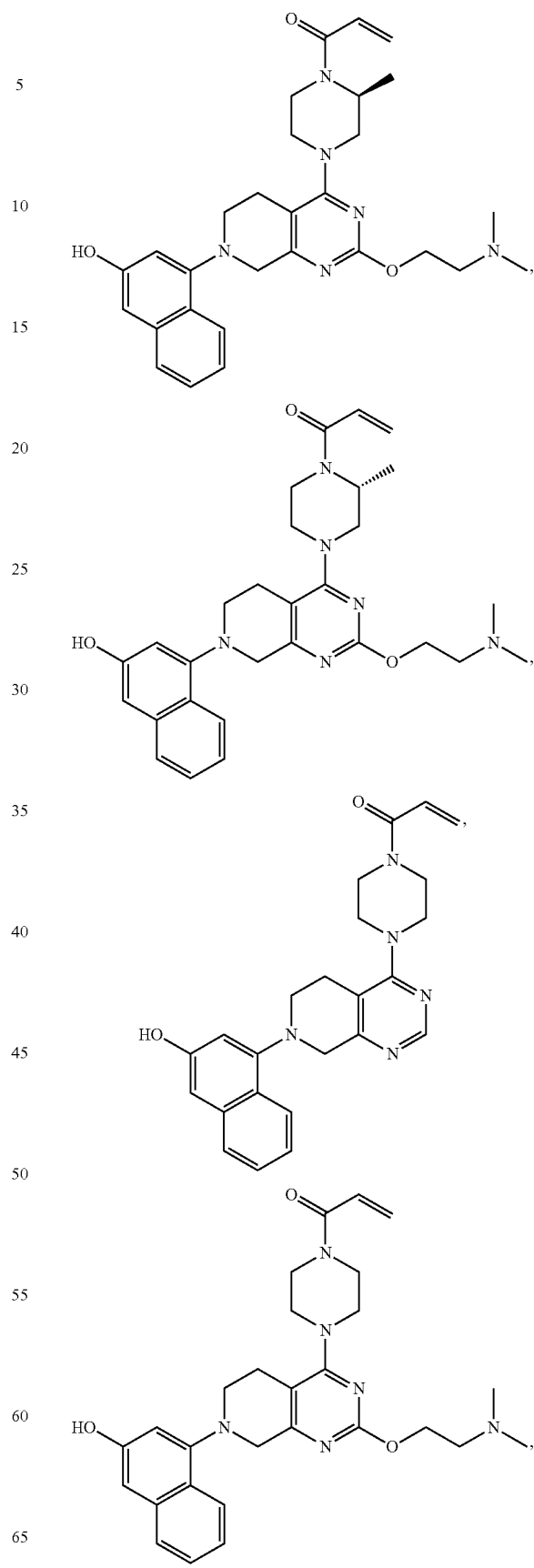
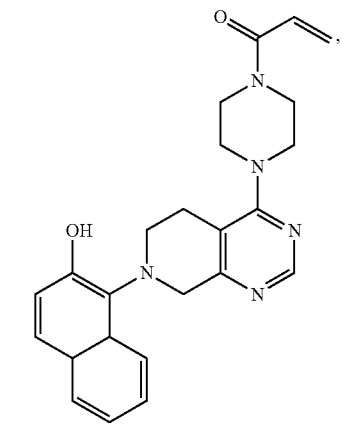

19
-continued
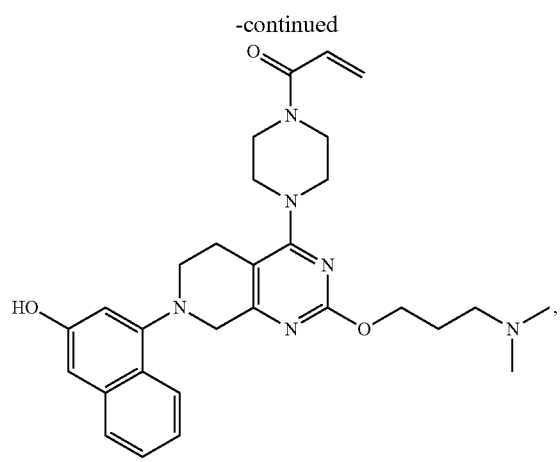
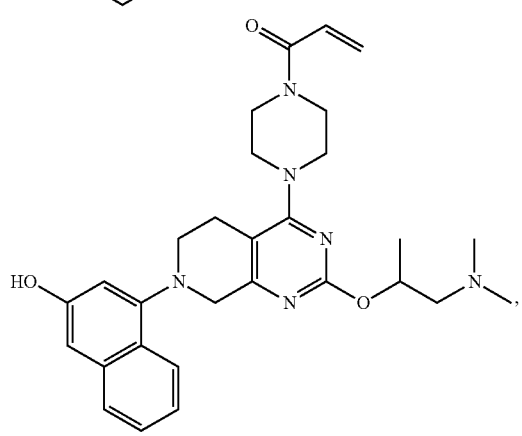
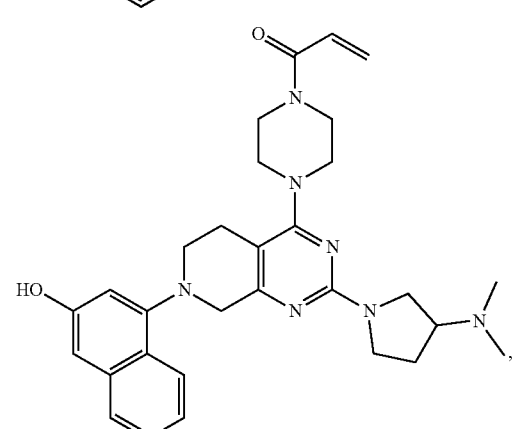
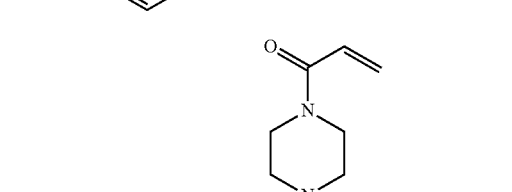
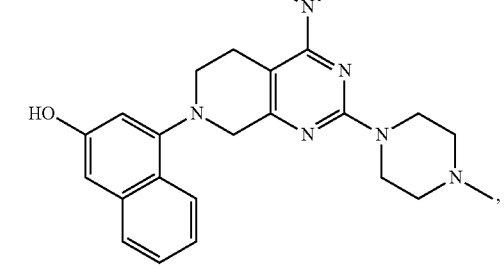
20
-continued
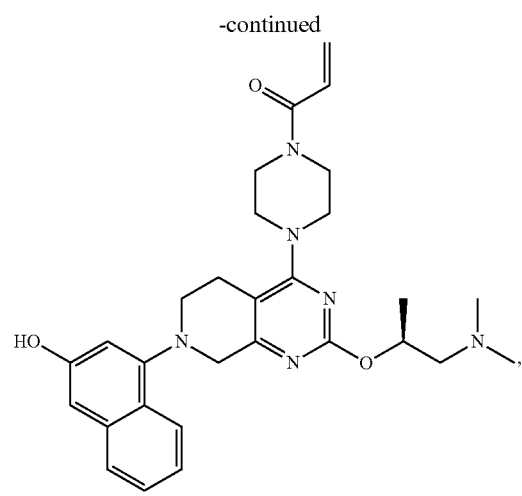
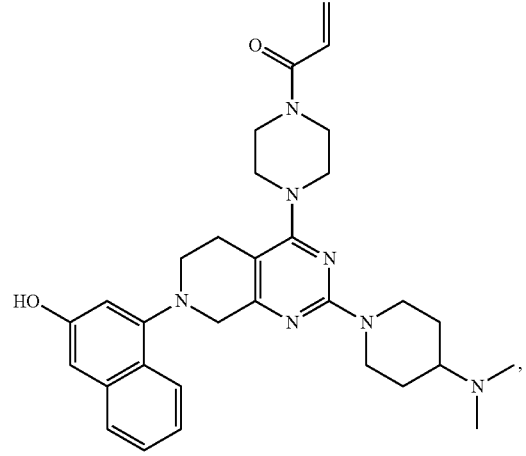
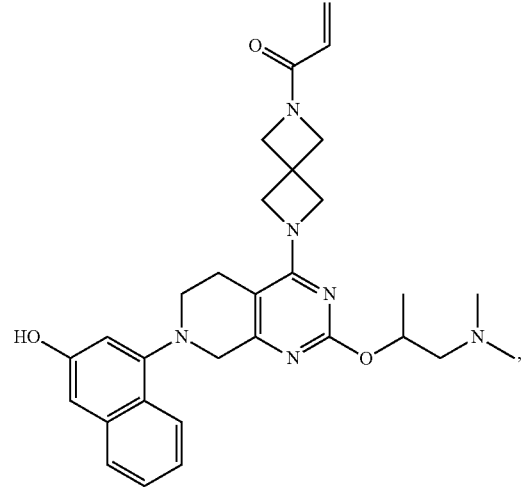

21
-continued
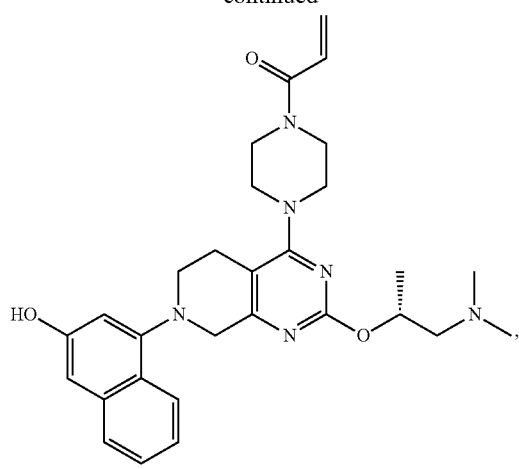
22
-continued
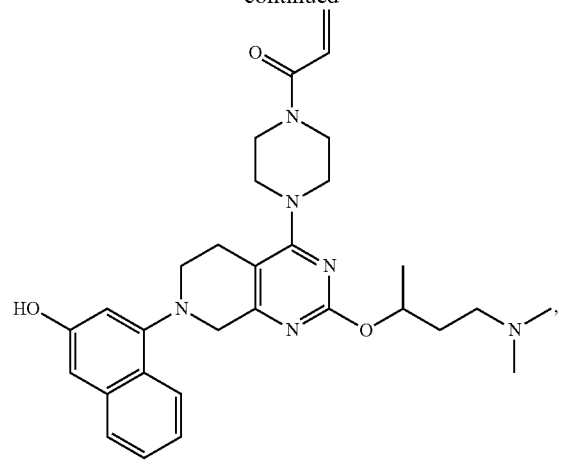
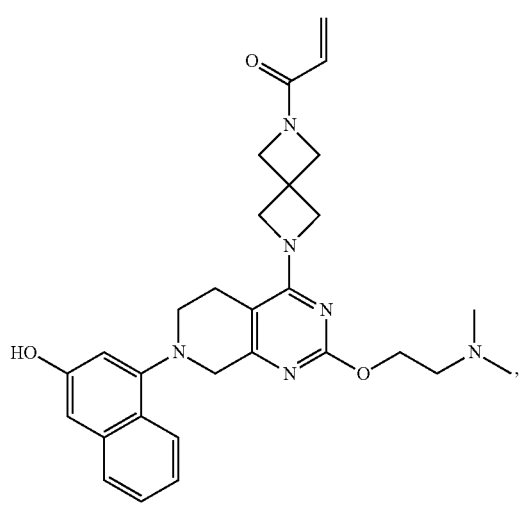
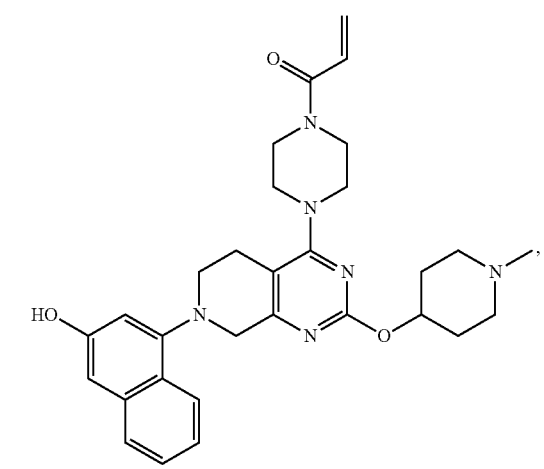
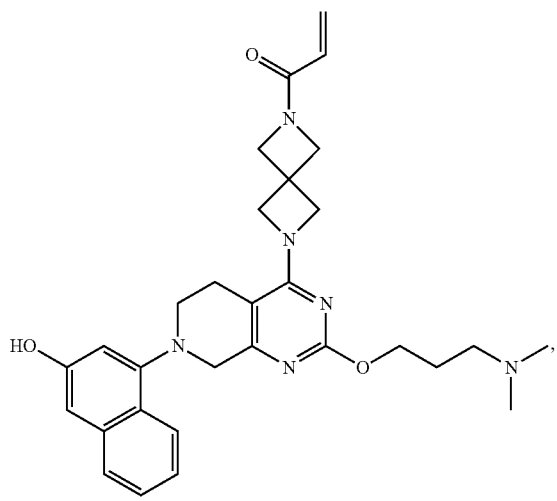
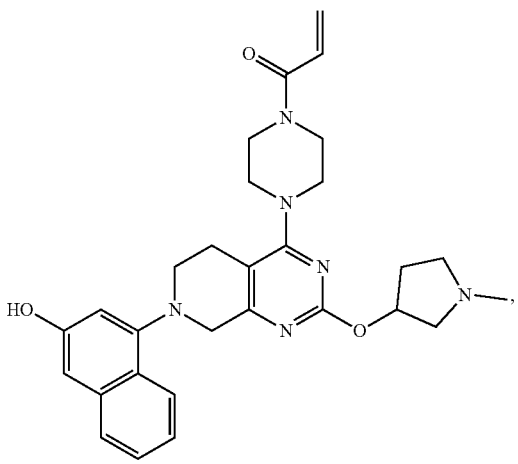

-continued
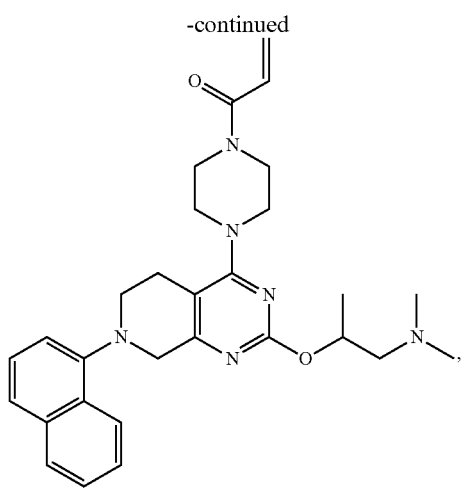
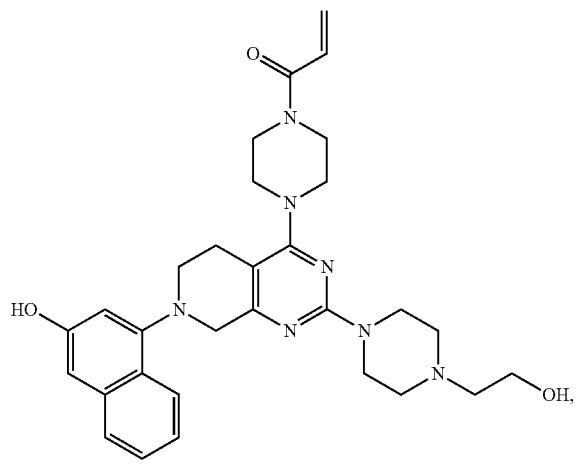
-continued
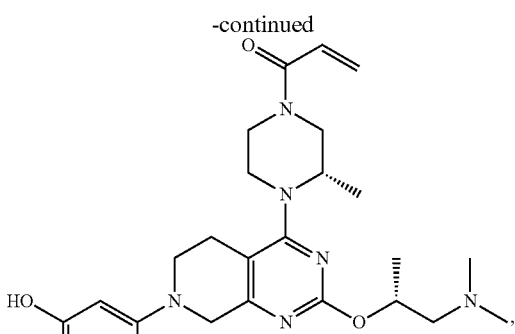
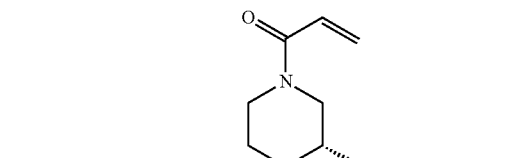
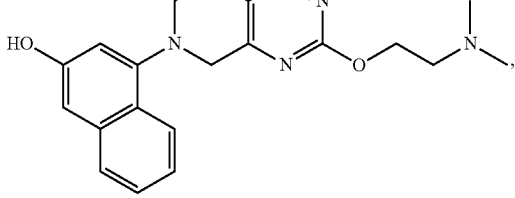
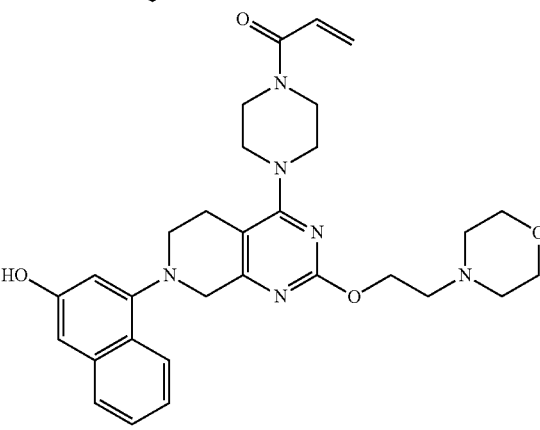
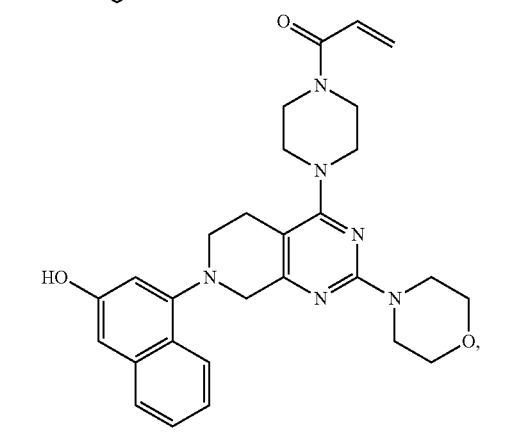

25
-continued
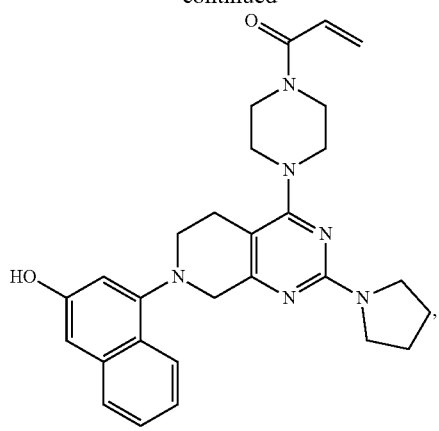
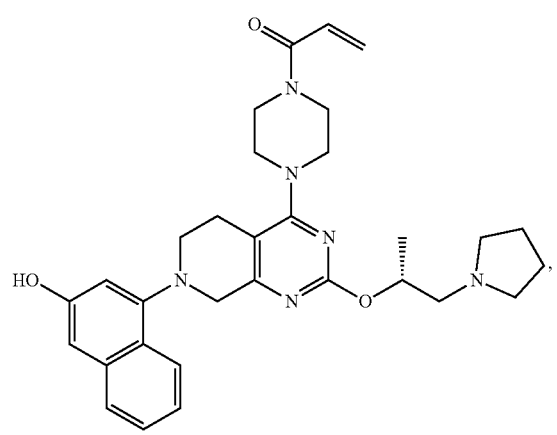
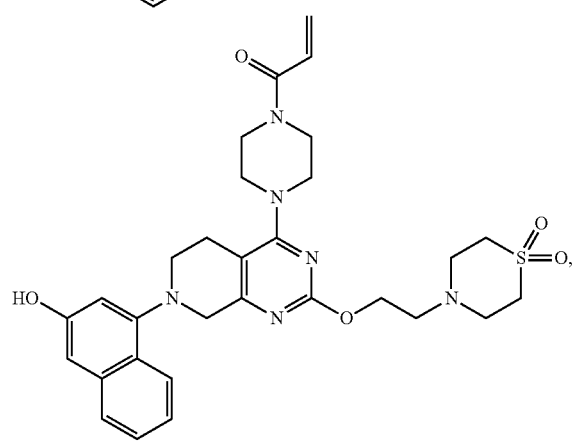
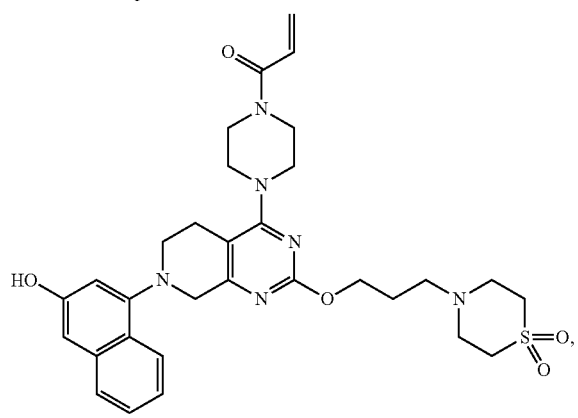
26
-continued
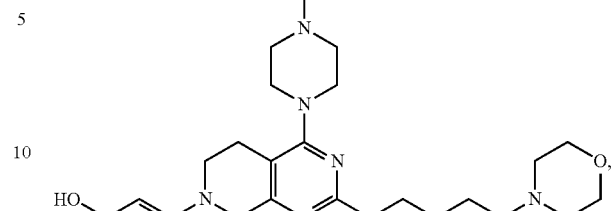
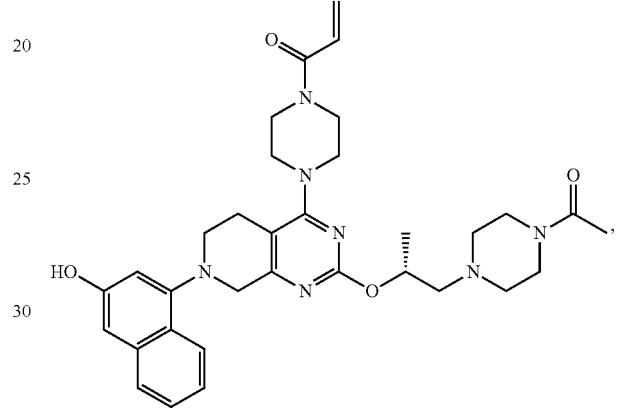
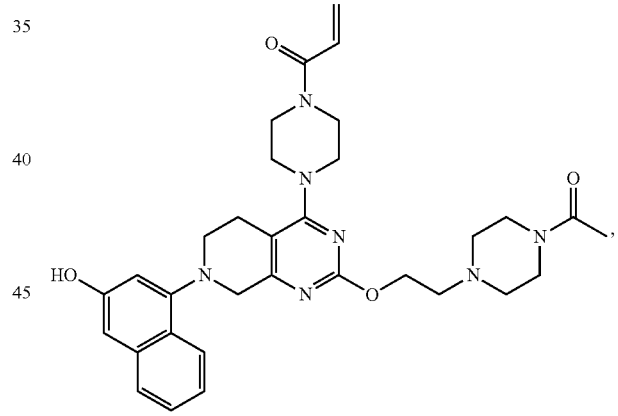
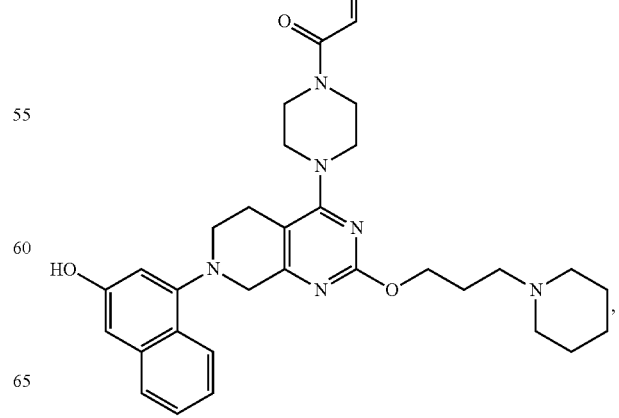

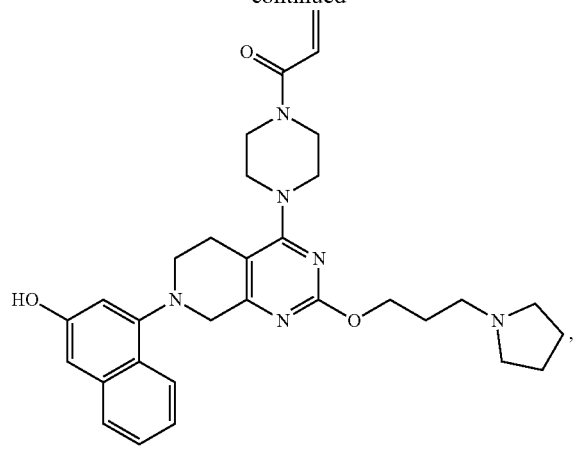
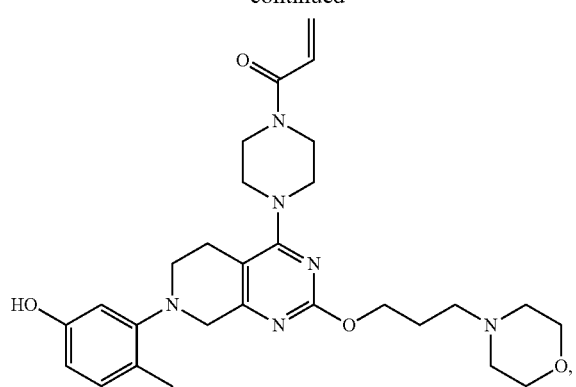
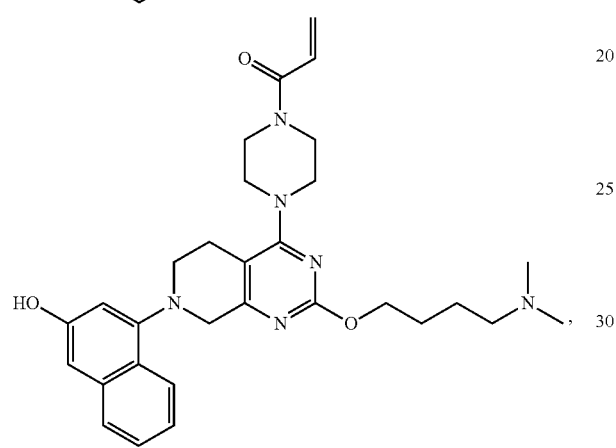
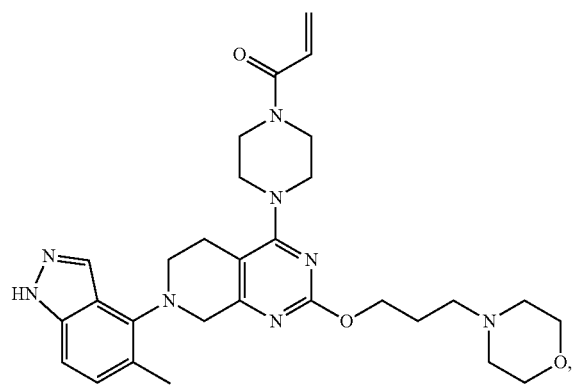
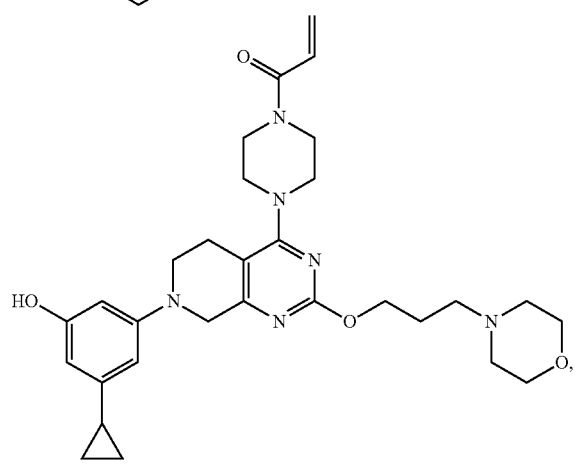
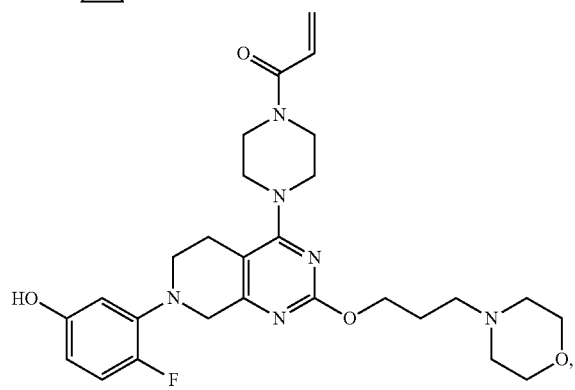
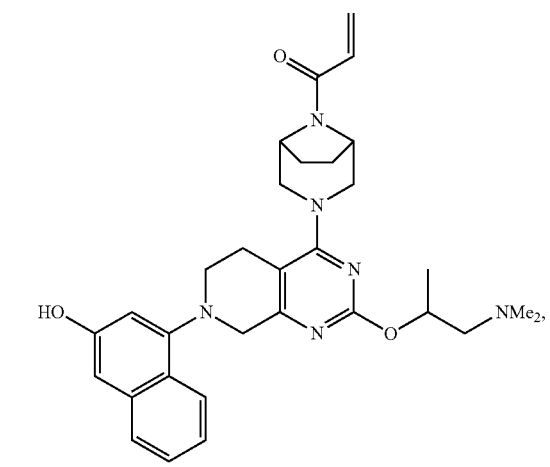

29
-continued
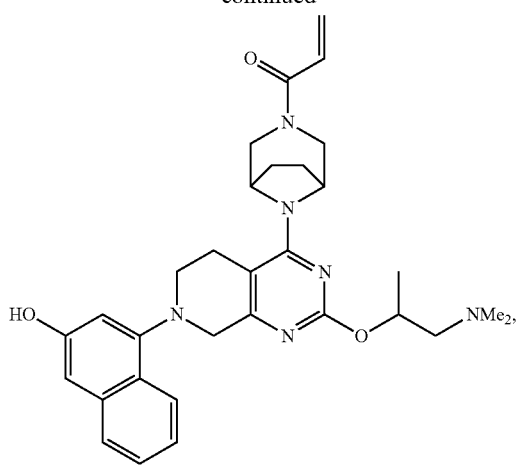
30
-continued
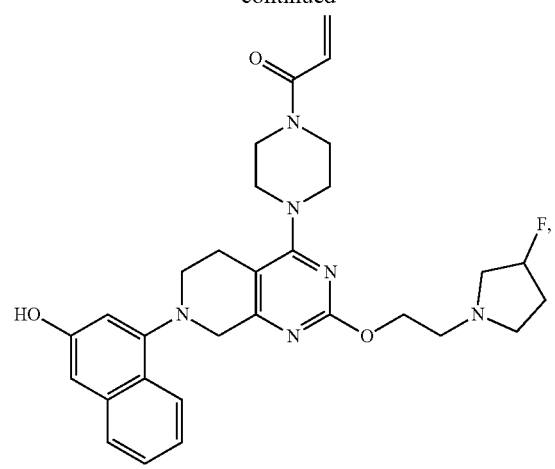
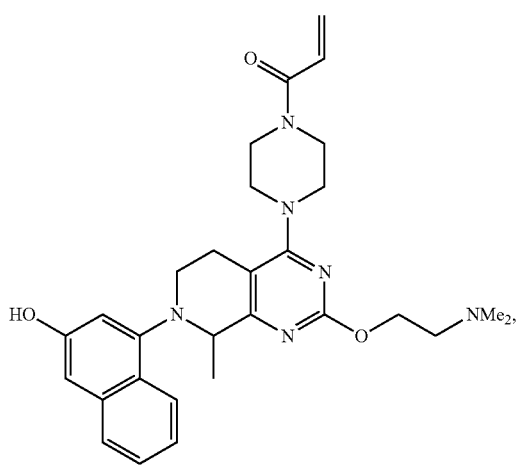
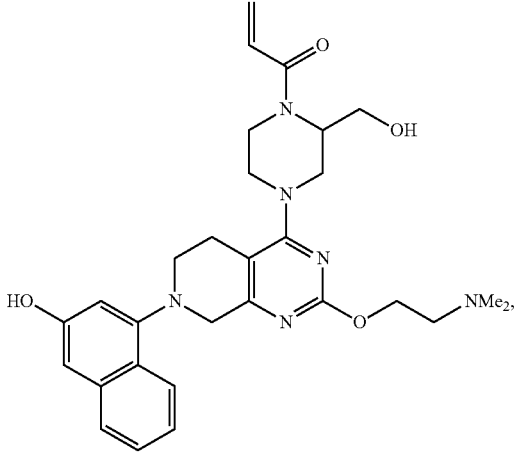
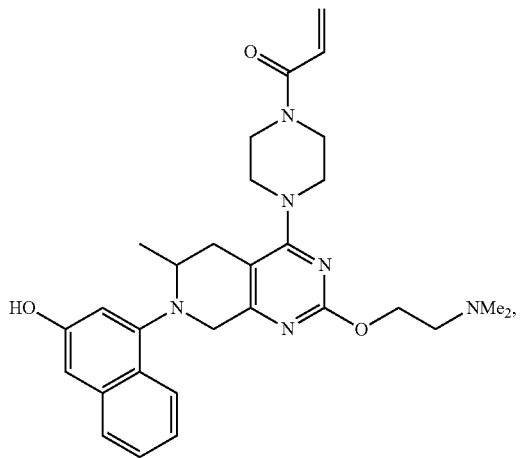
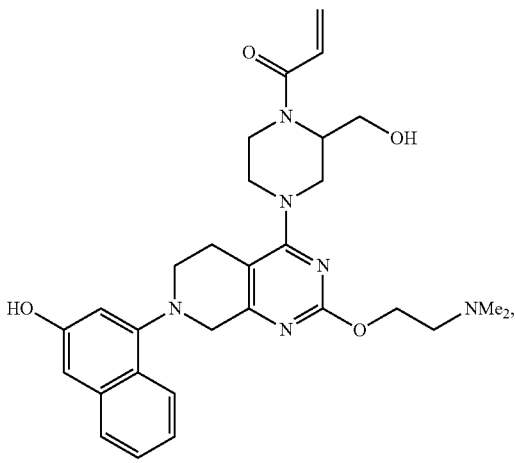

31
-continued
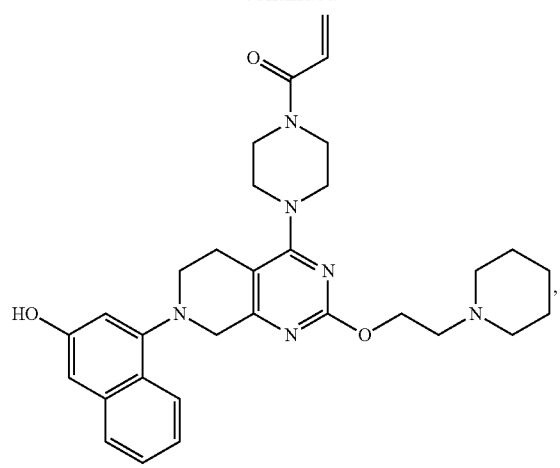
32
-continued
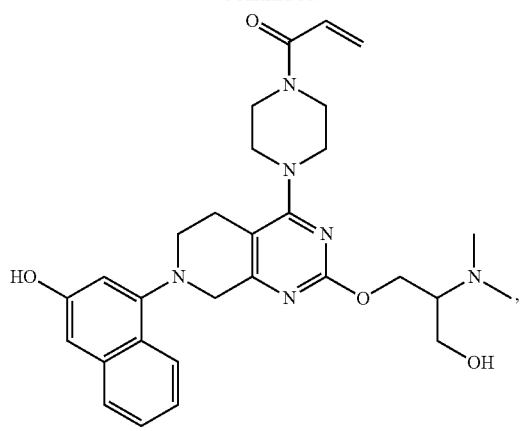
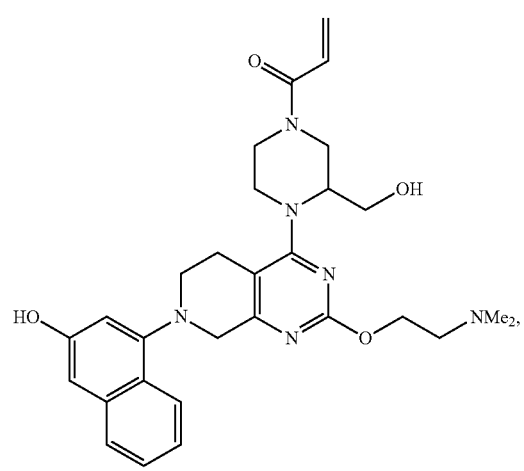
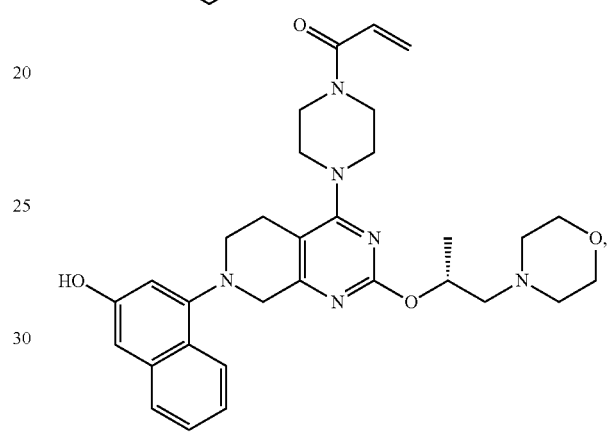
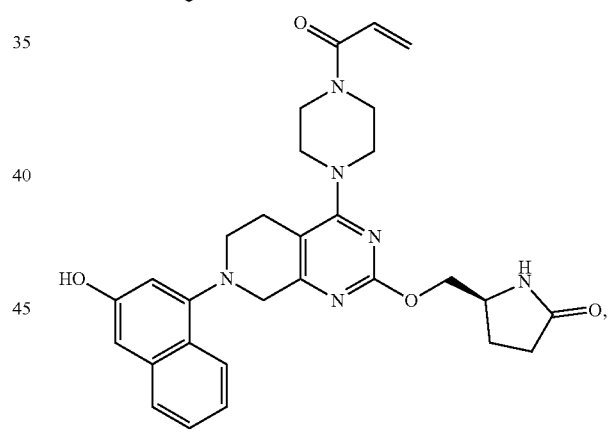
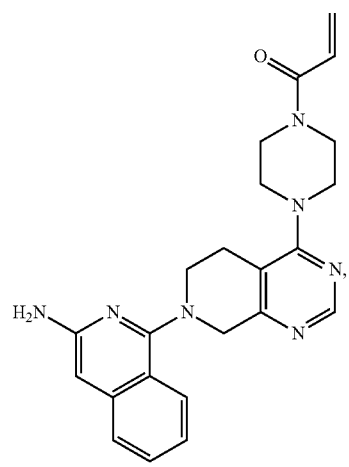

33
-continued
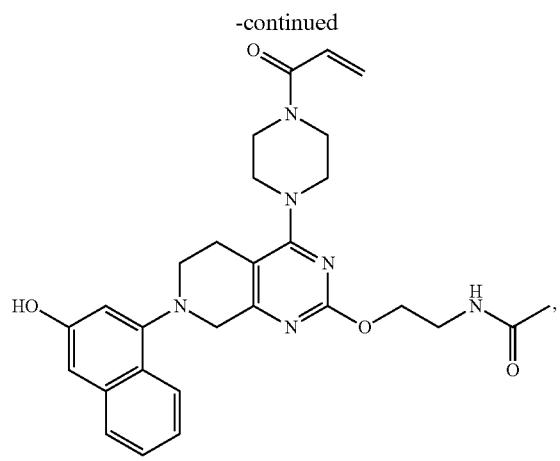
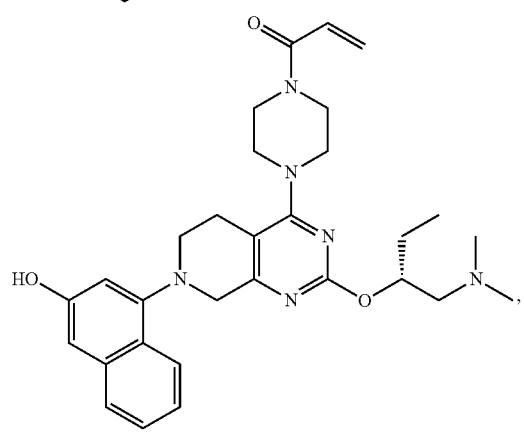
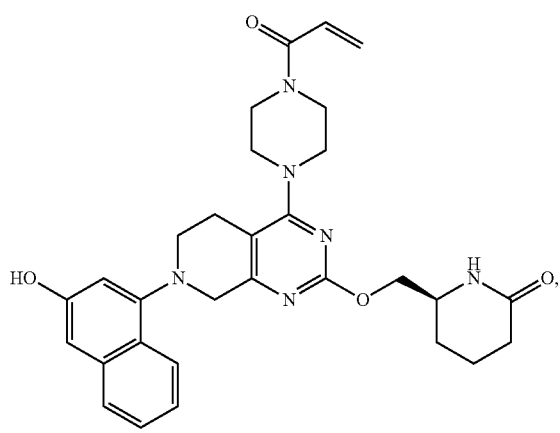
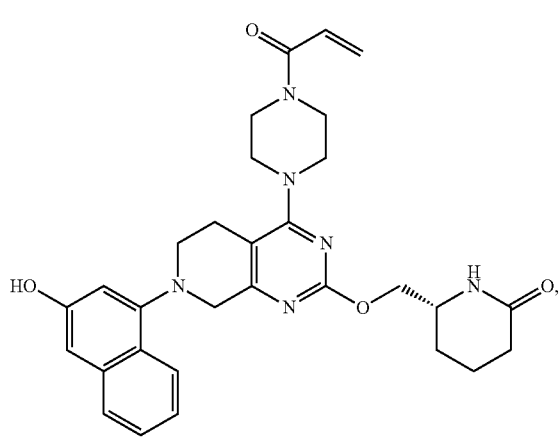
34
-continued
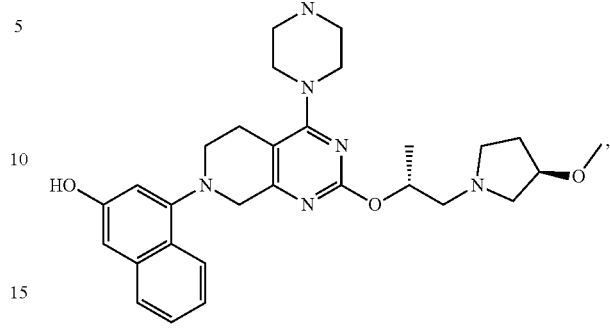
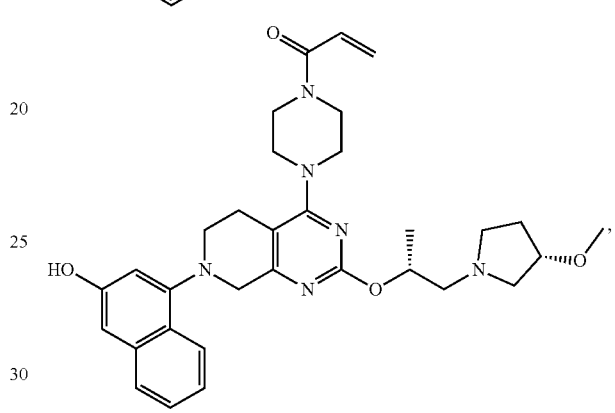
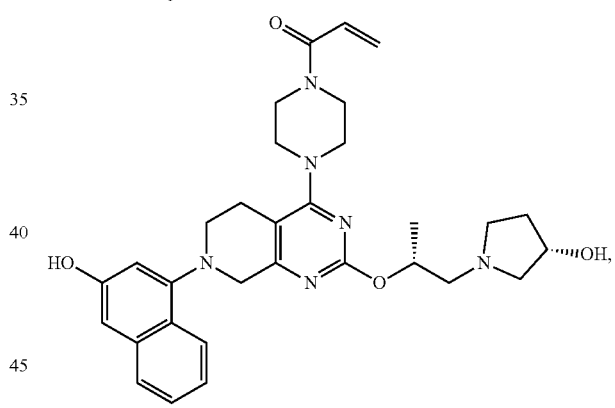
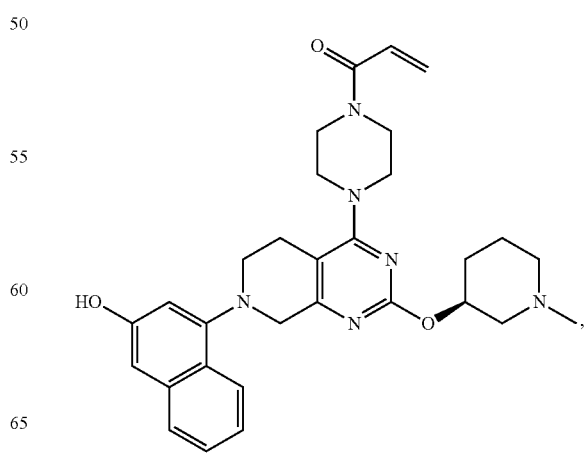

35
-continued
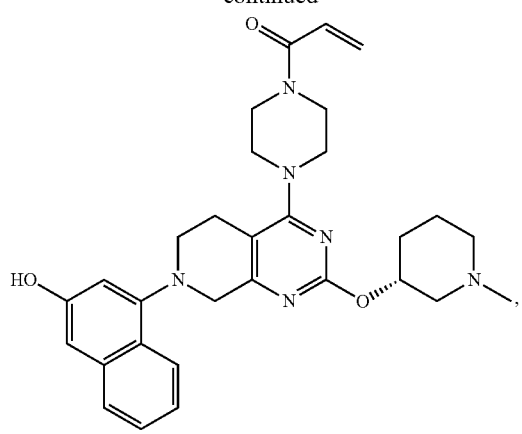
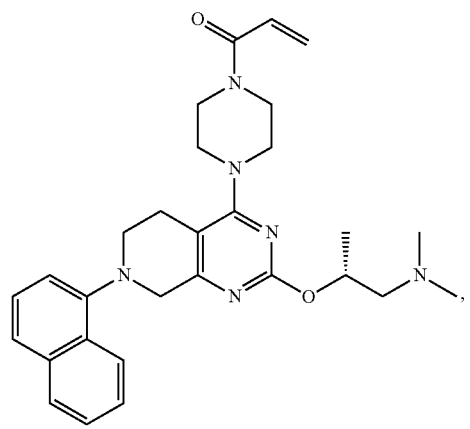
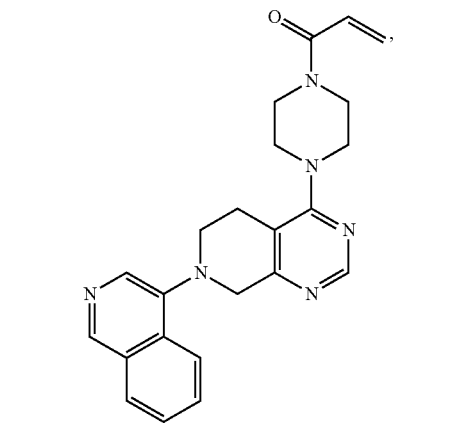
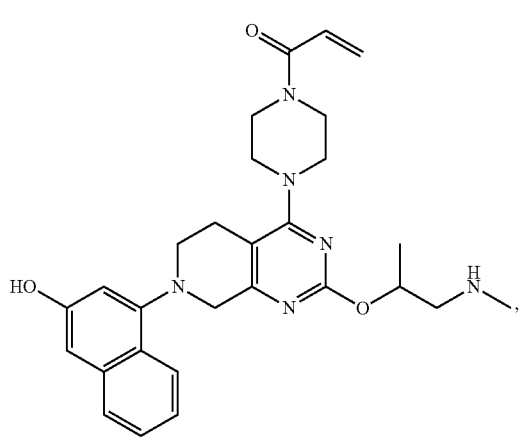
36
-continued
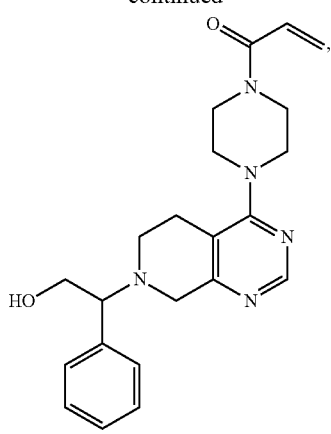
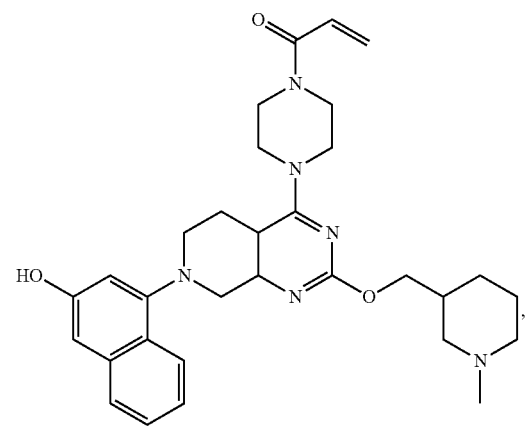
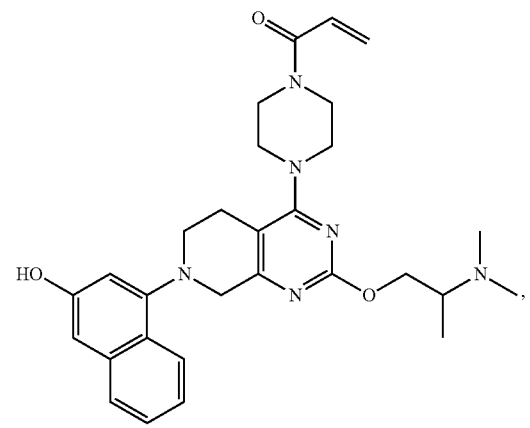
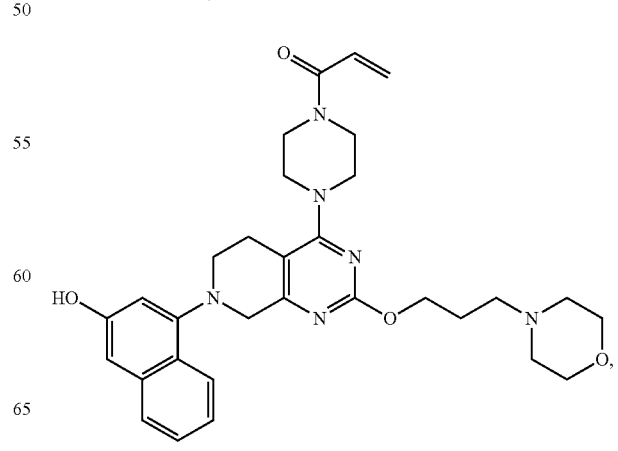

37
-continued
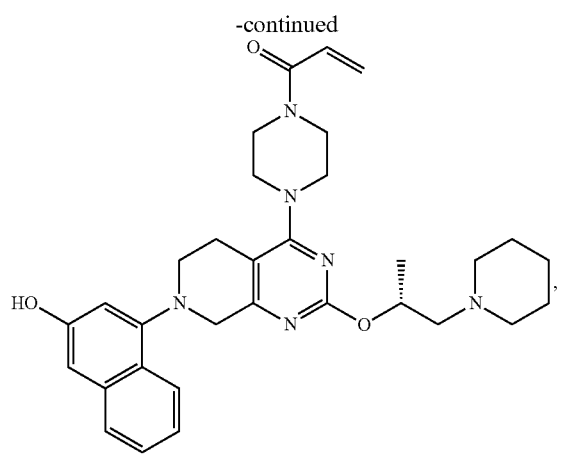
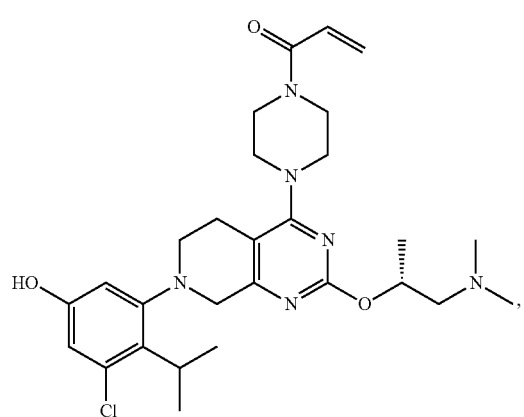
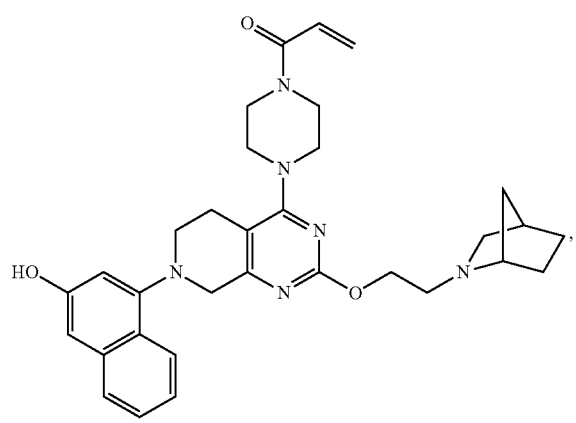
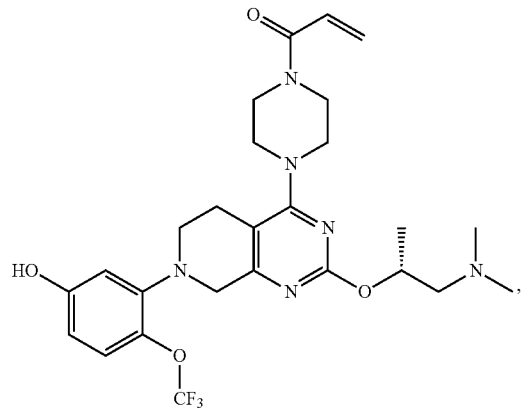
38
-continued
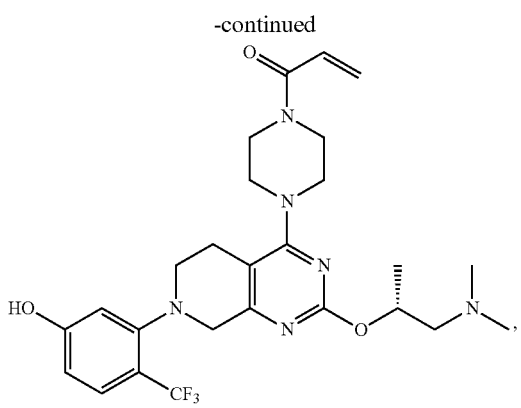
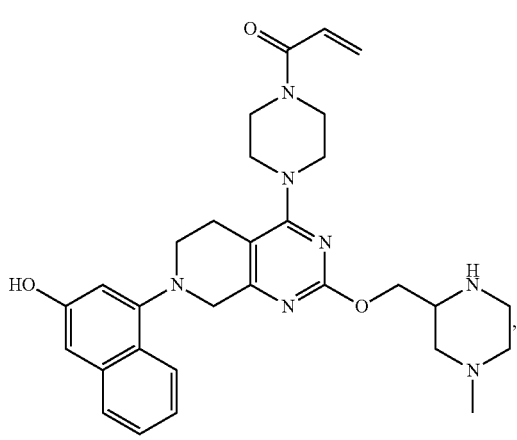
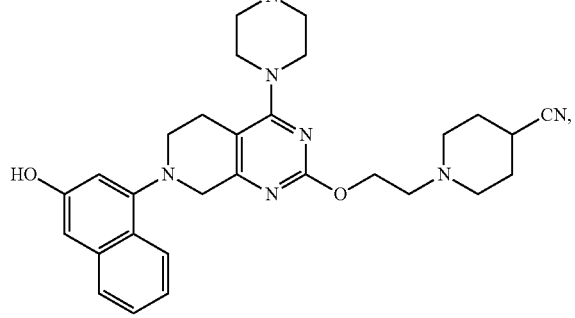
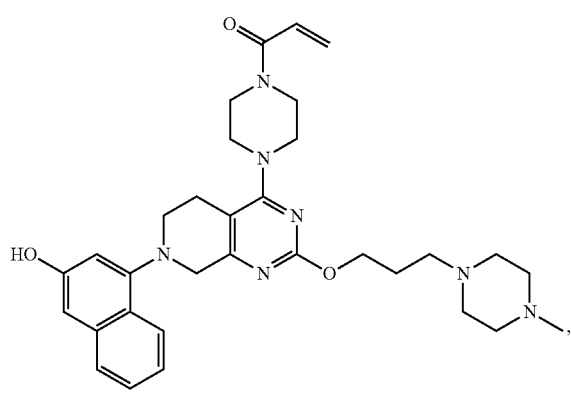

39
-continued
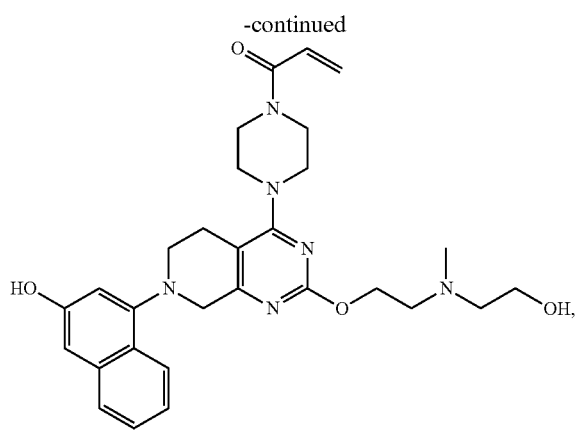
40
-continued
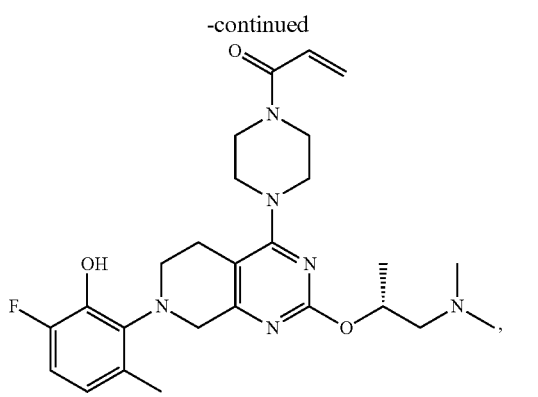
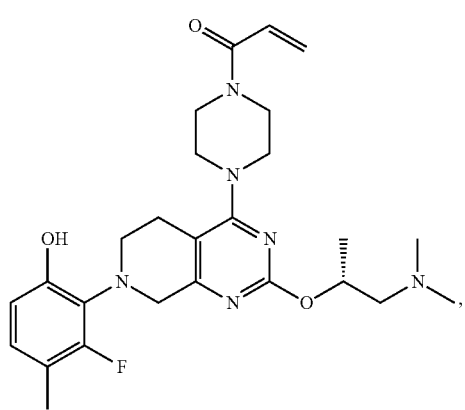
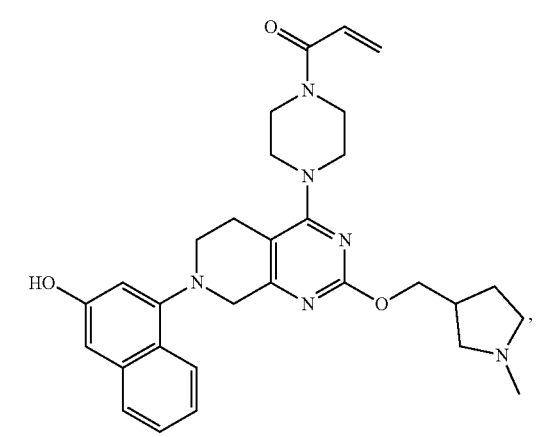
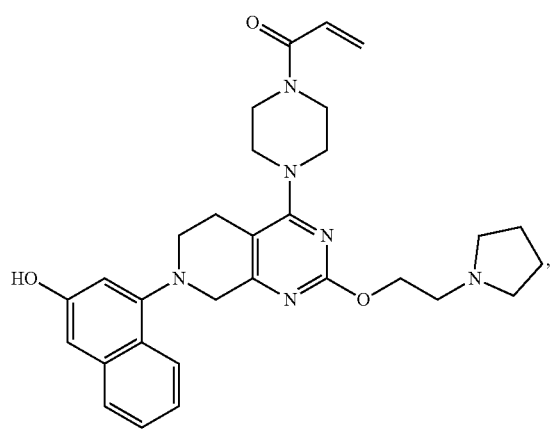
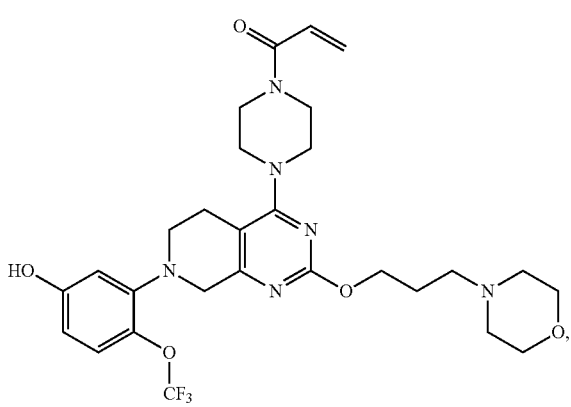
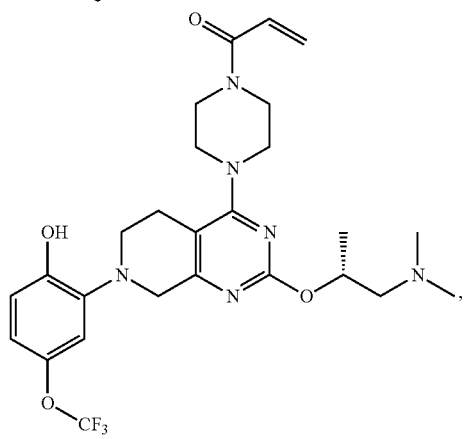

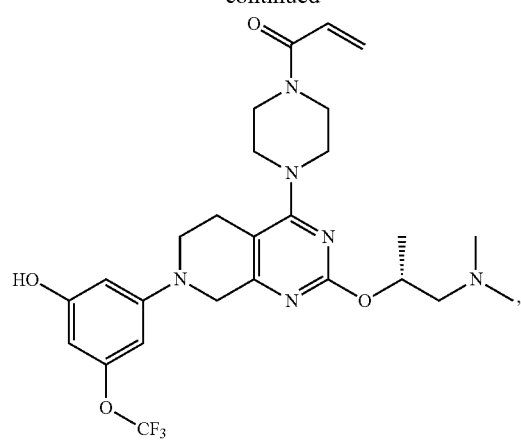
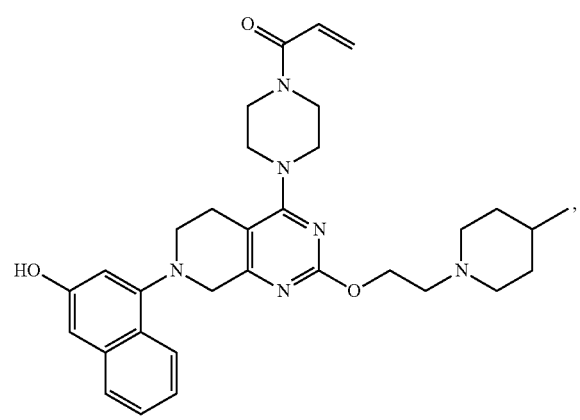
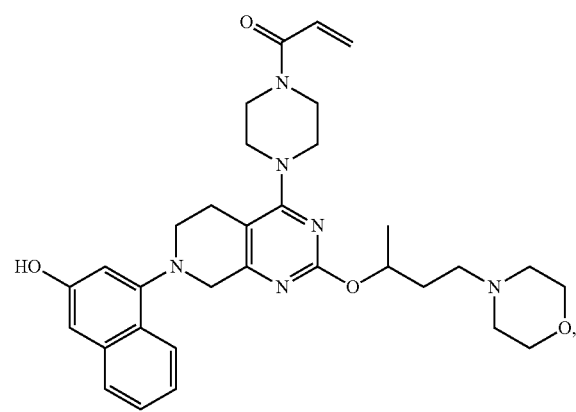
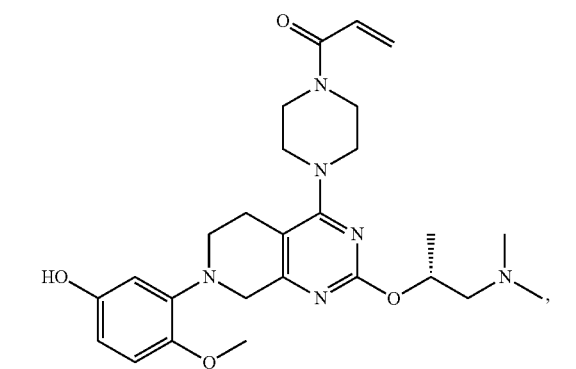
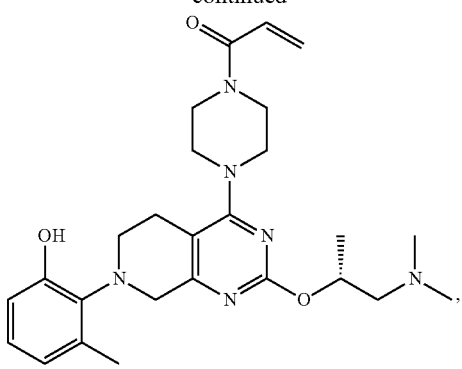
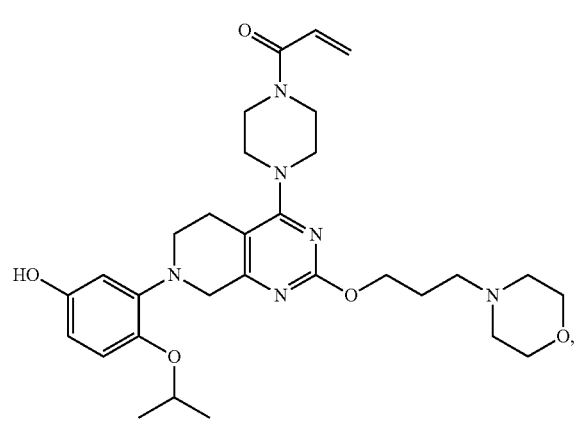
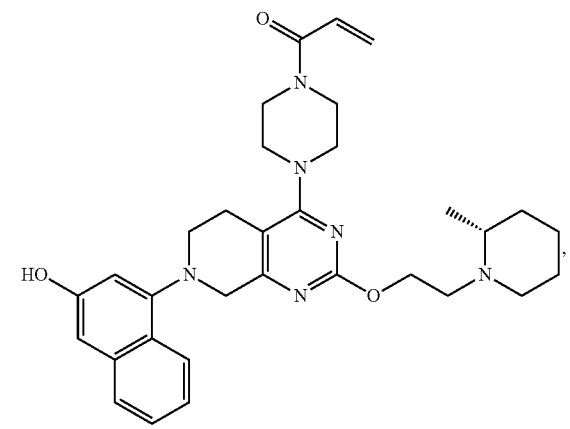
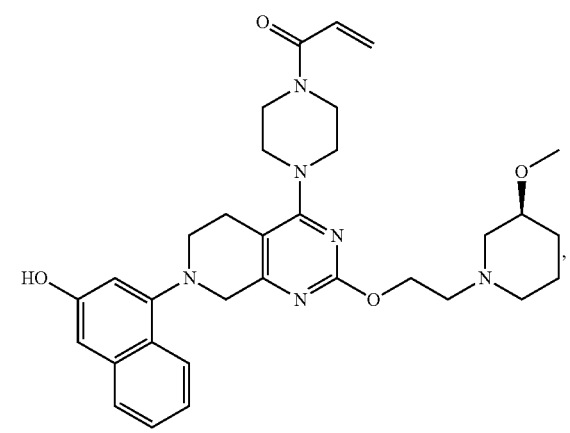

43
-continued
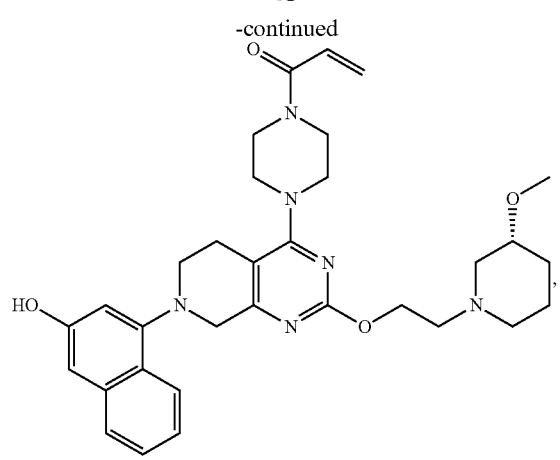
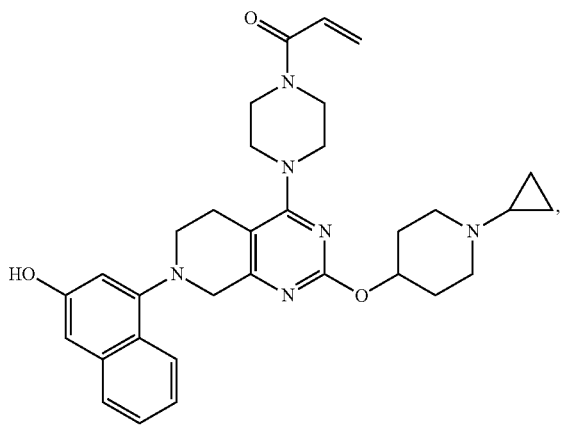
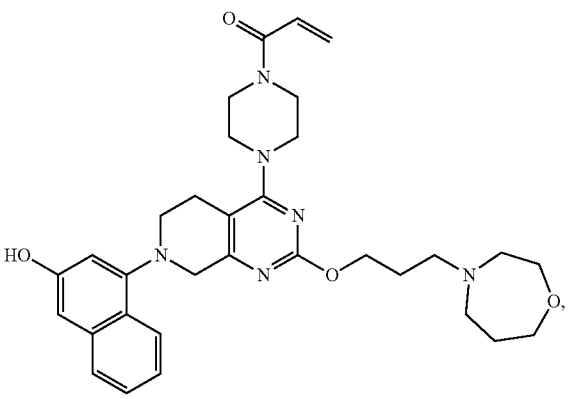
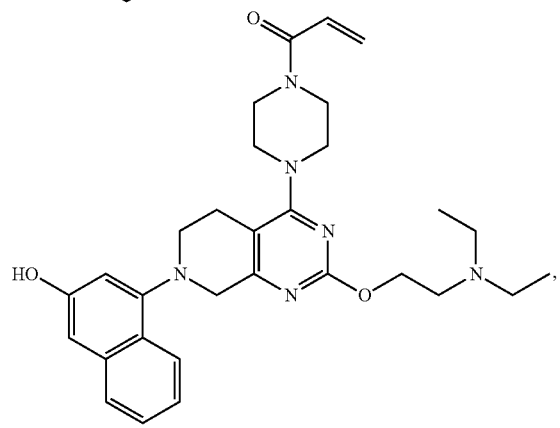
44
-continued
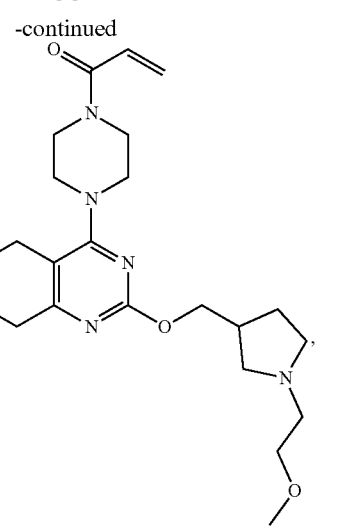
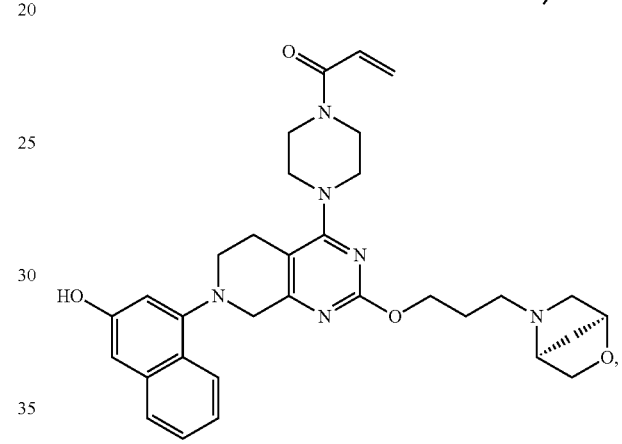
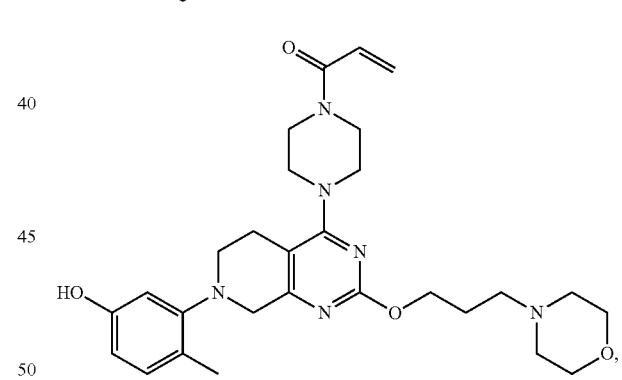
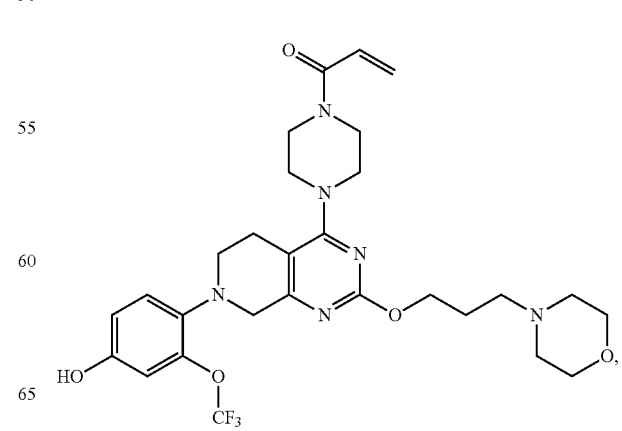

-continued
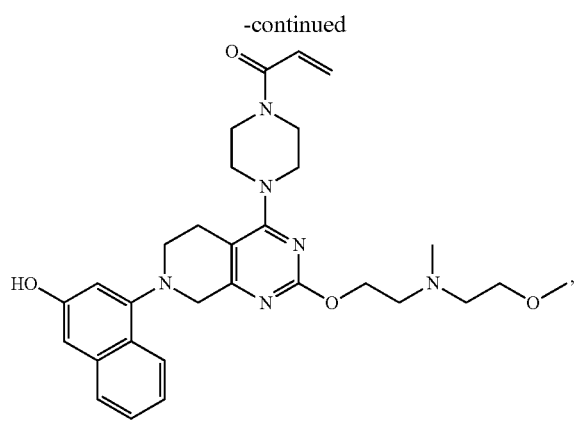
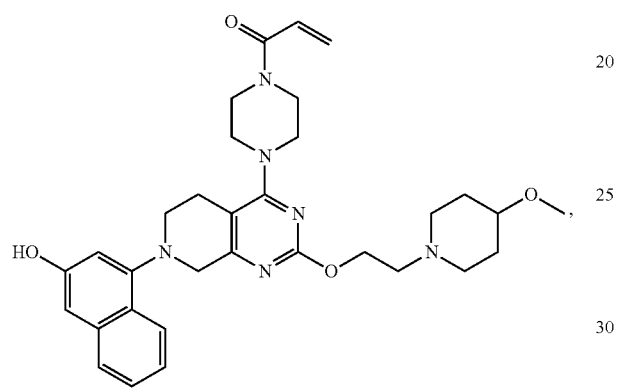
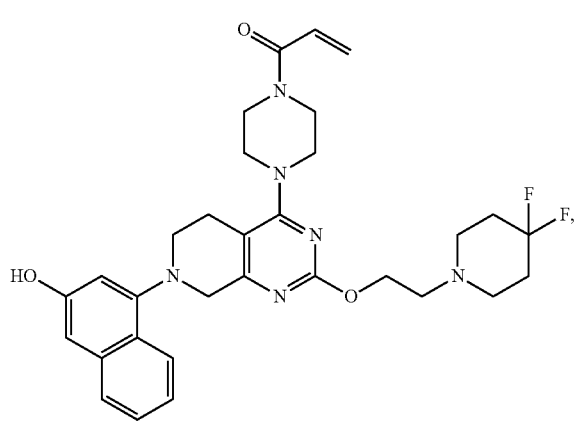
-continued
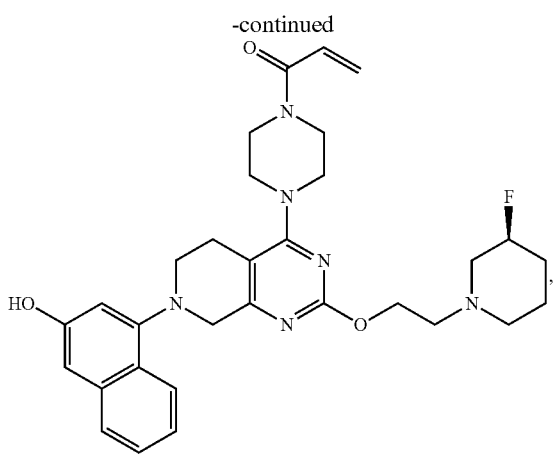
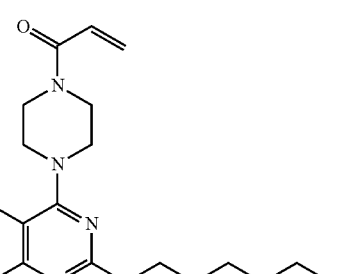
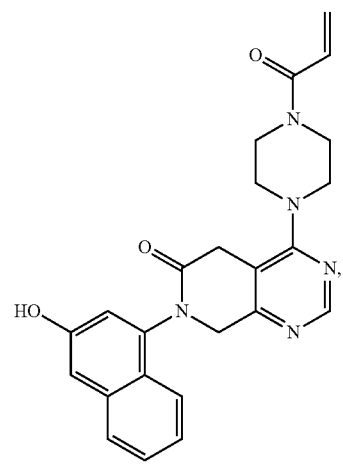

47
-continued
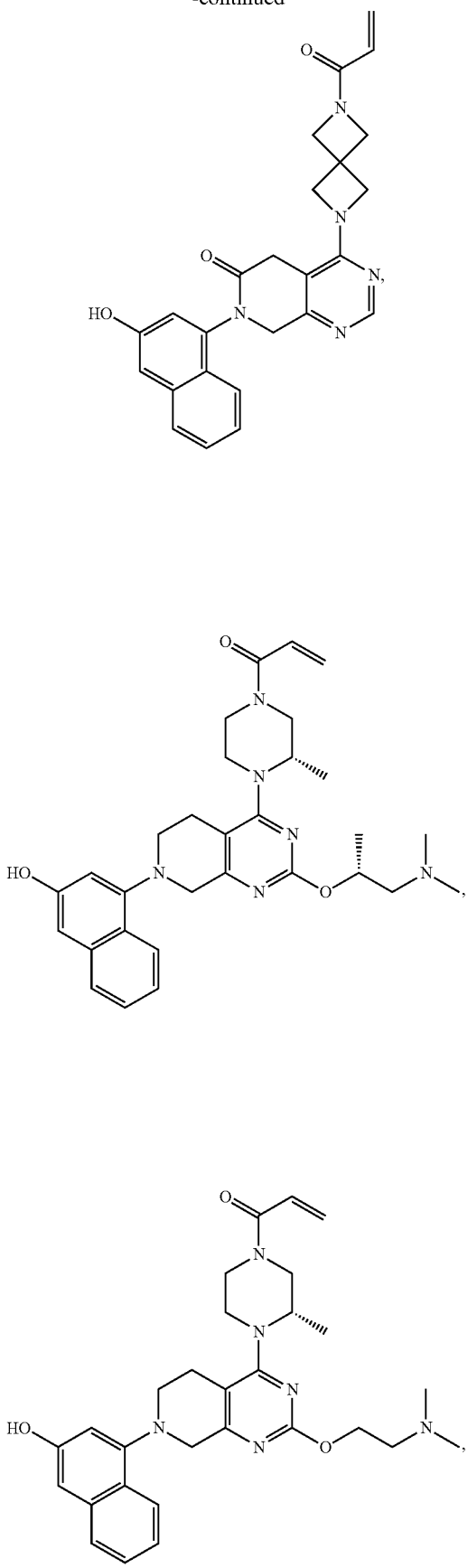
48
-continued
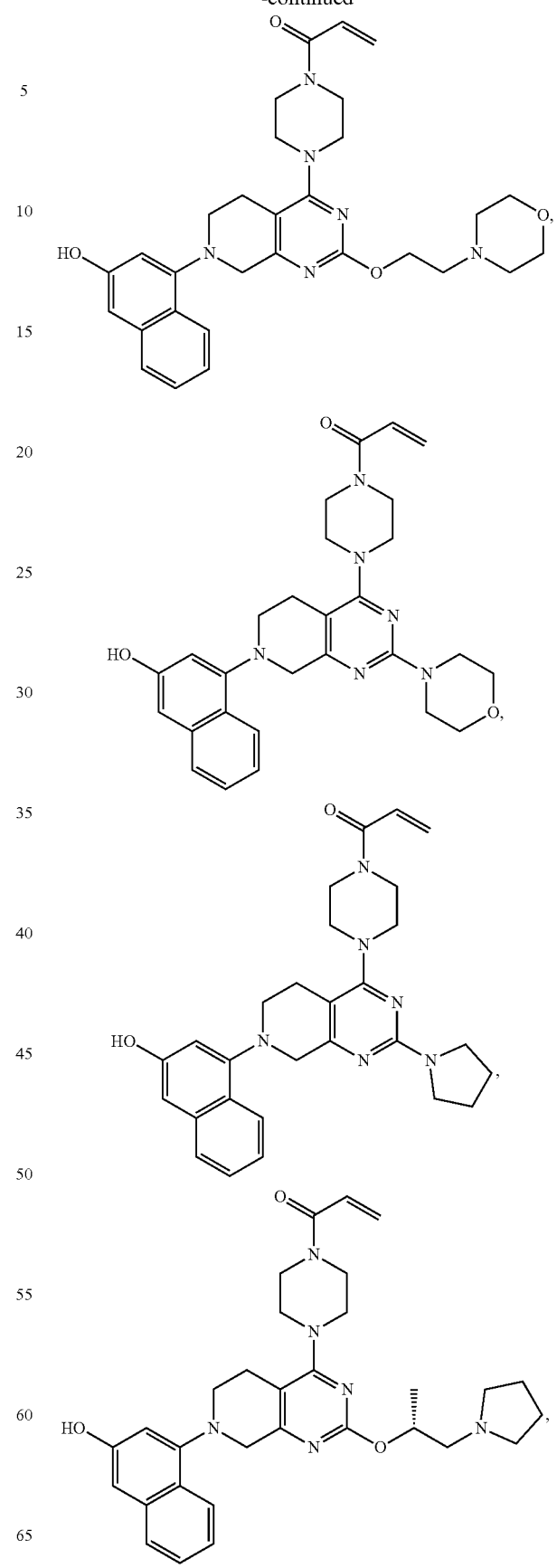

49
-continued
50
-continued
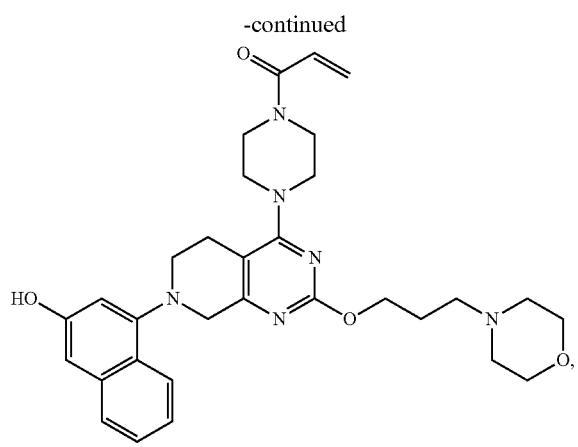
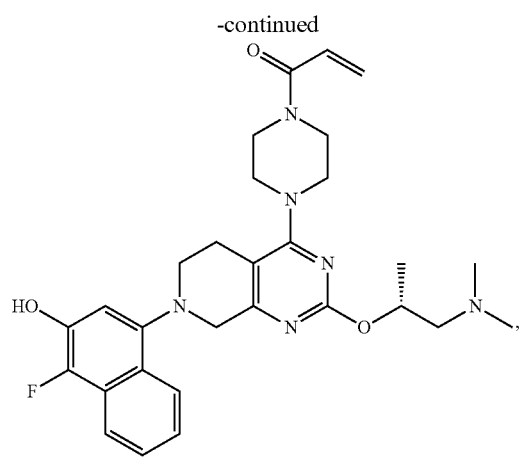
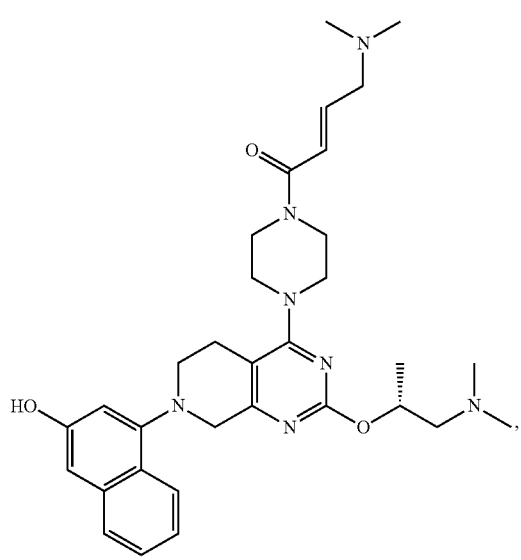
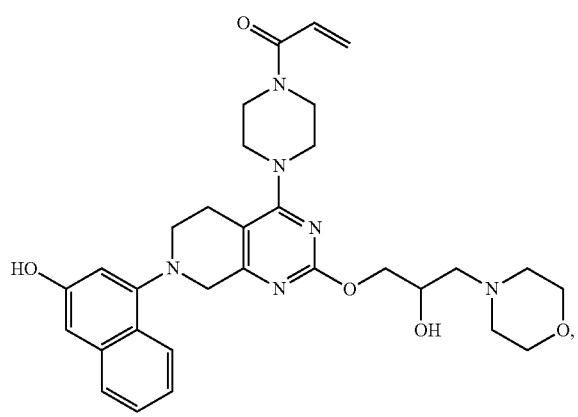
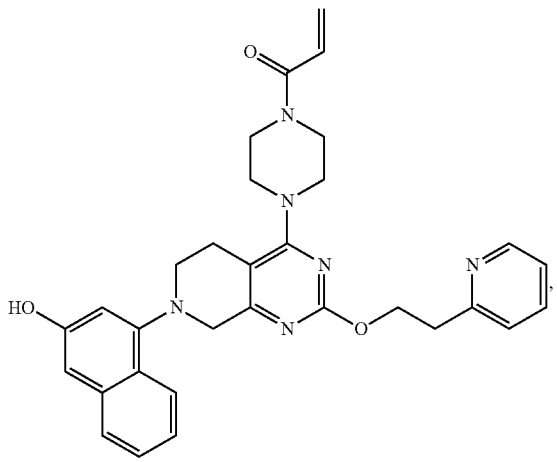

51
-continued
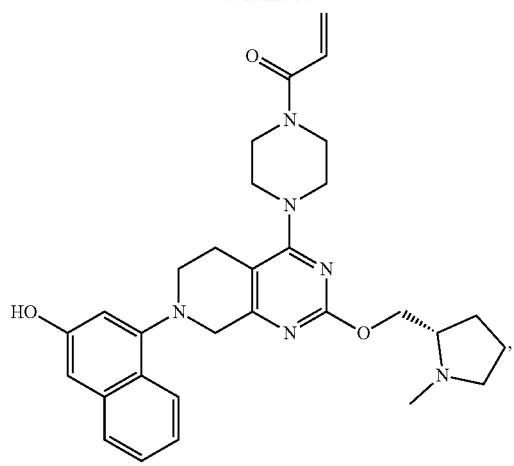
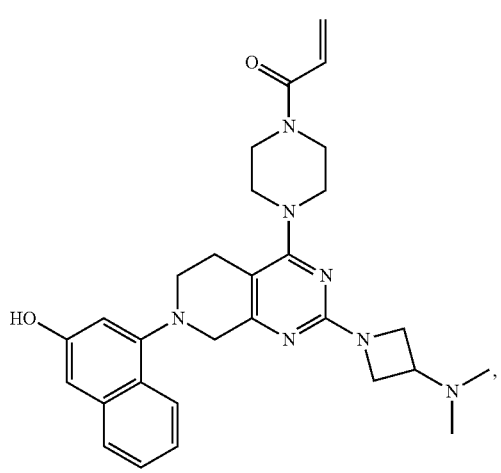
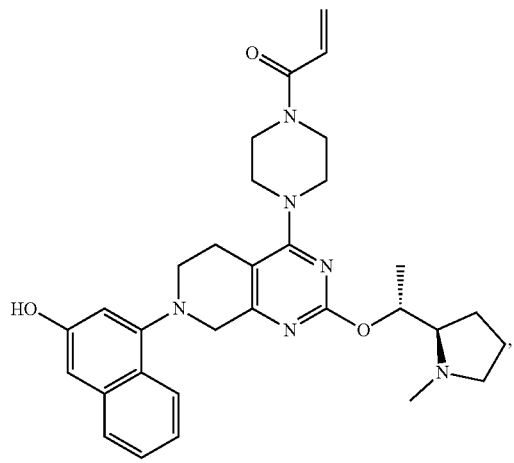
52
-continued
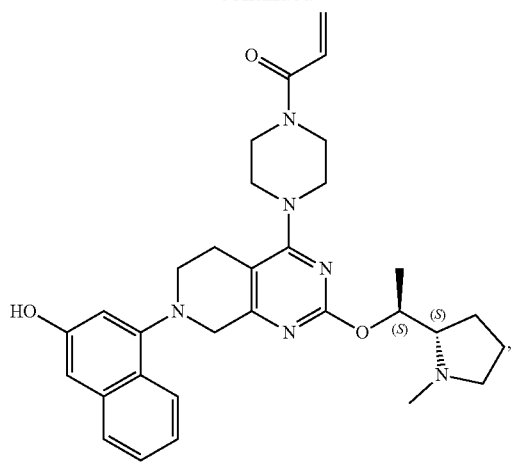
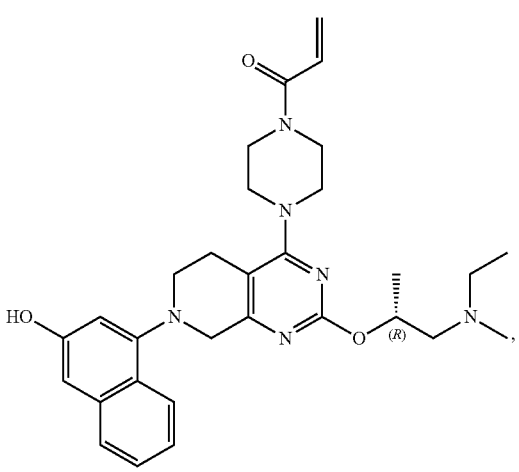
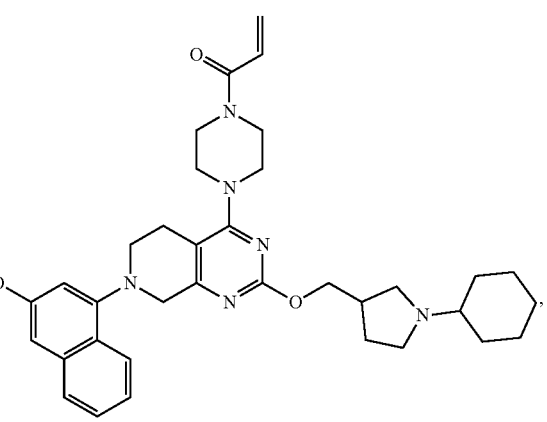

53
-continued
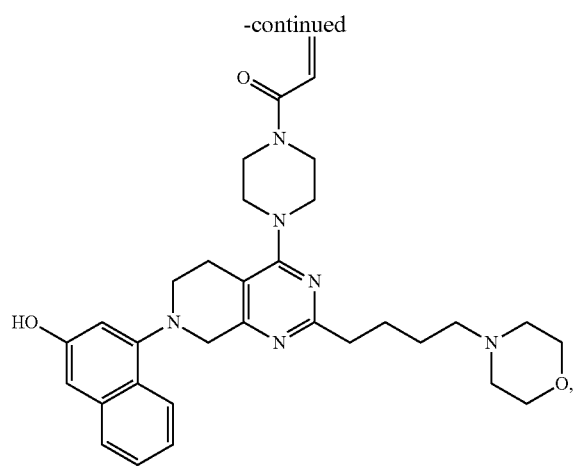
54
-continued
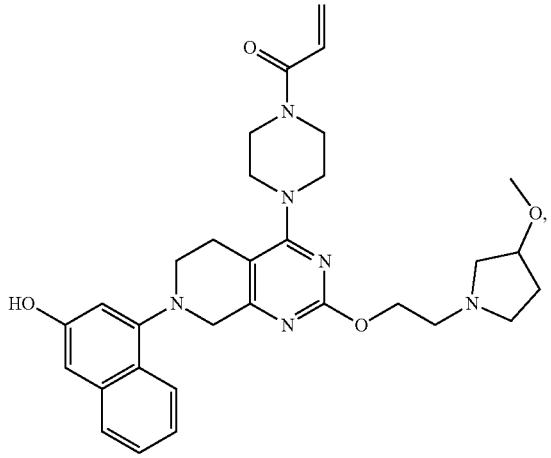
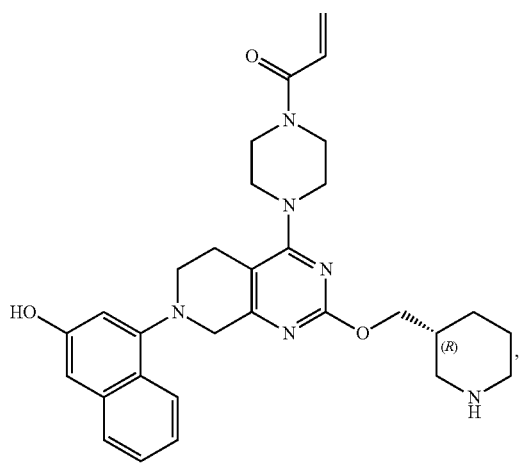
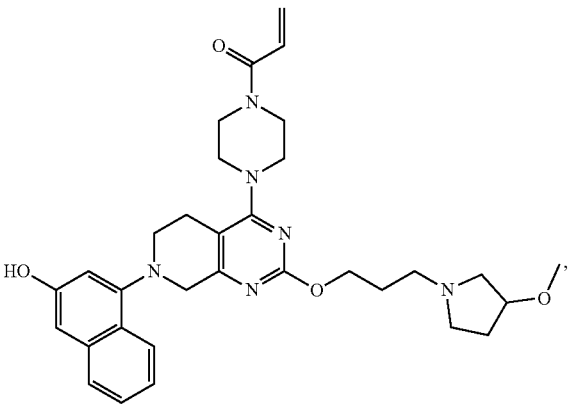
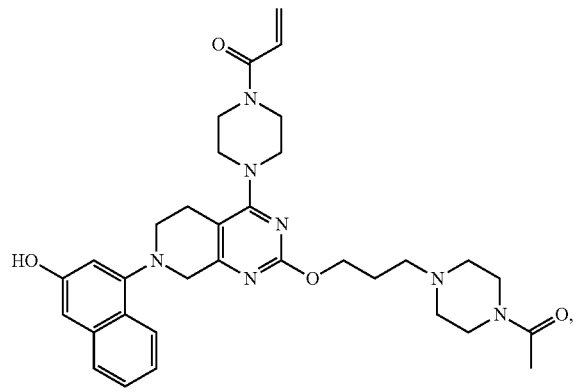
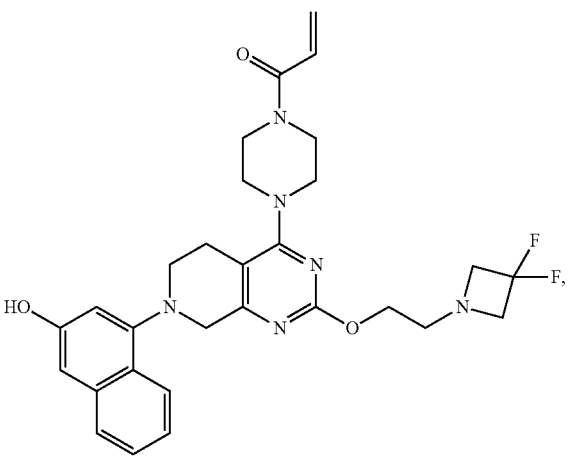

55
-continued
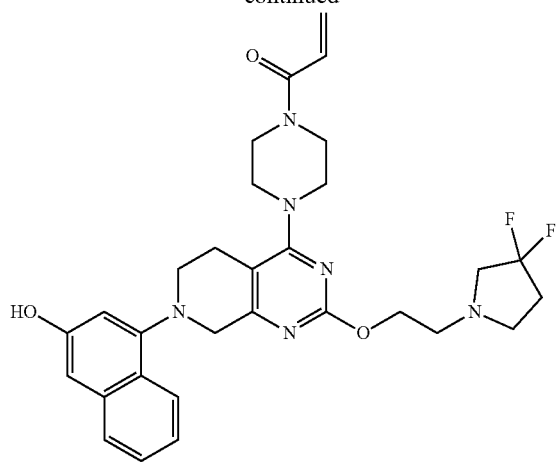
56
-continued
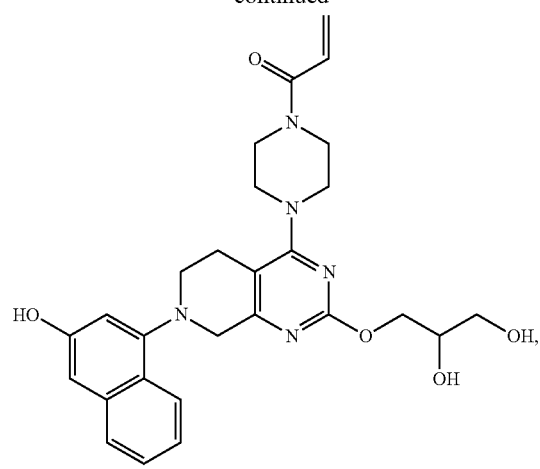
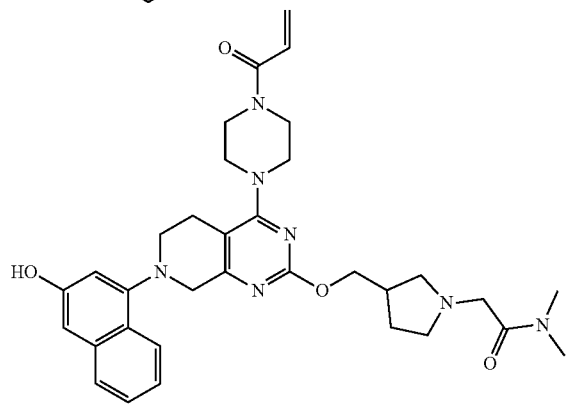
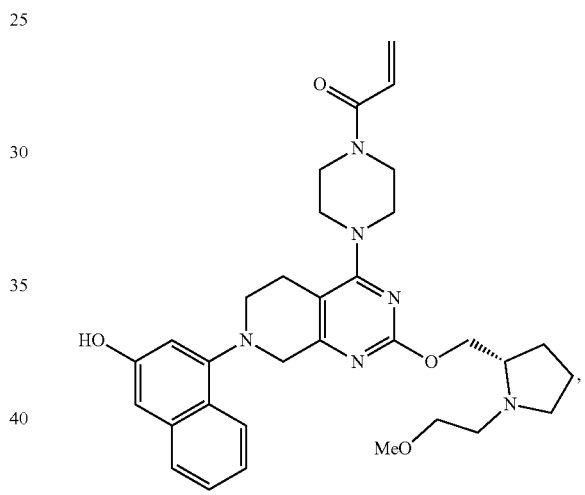
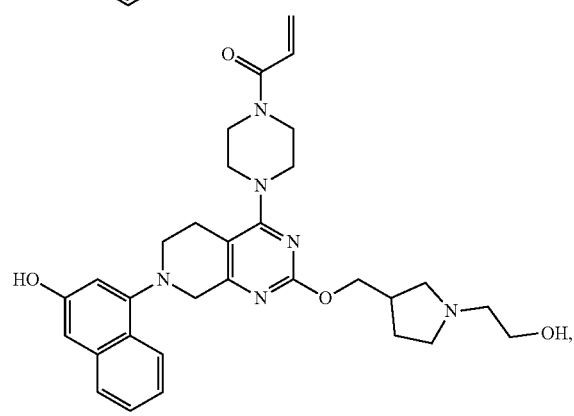
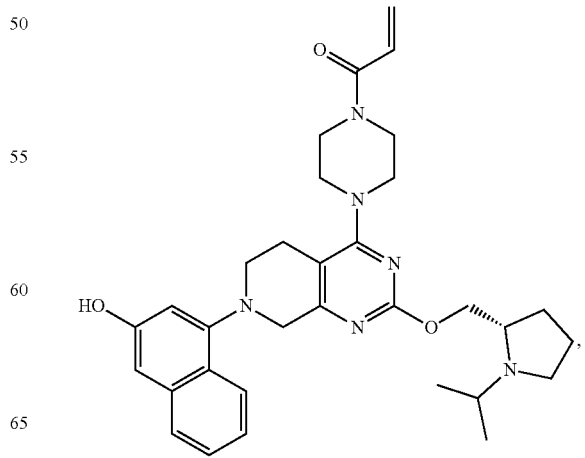

57
-continued
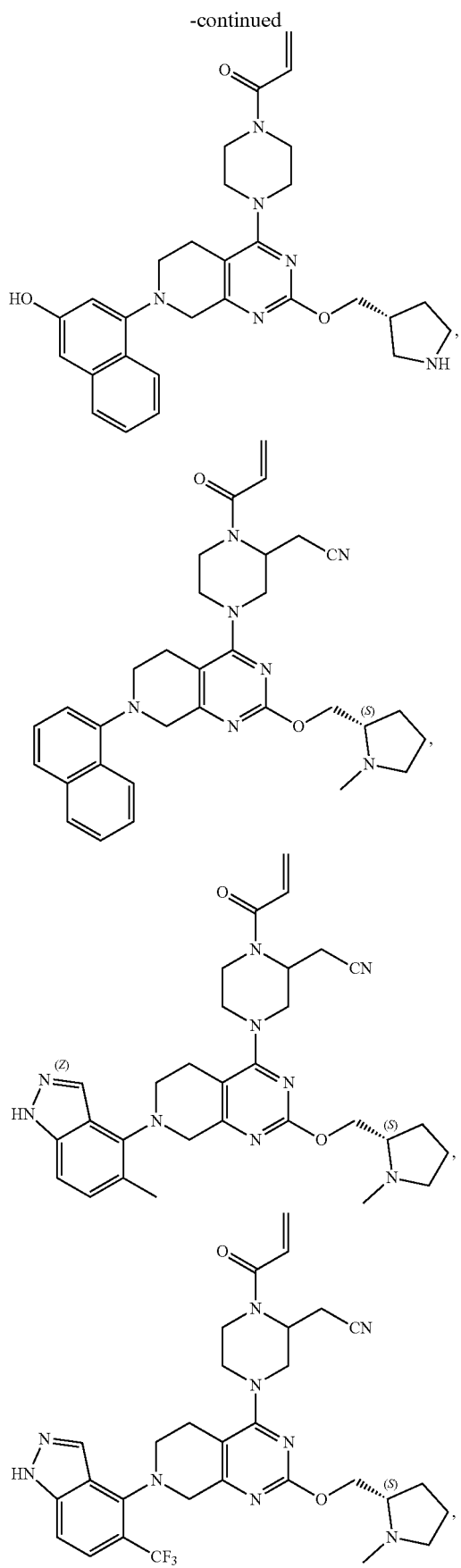
58
-continued
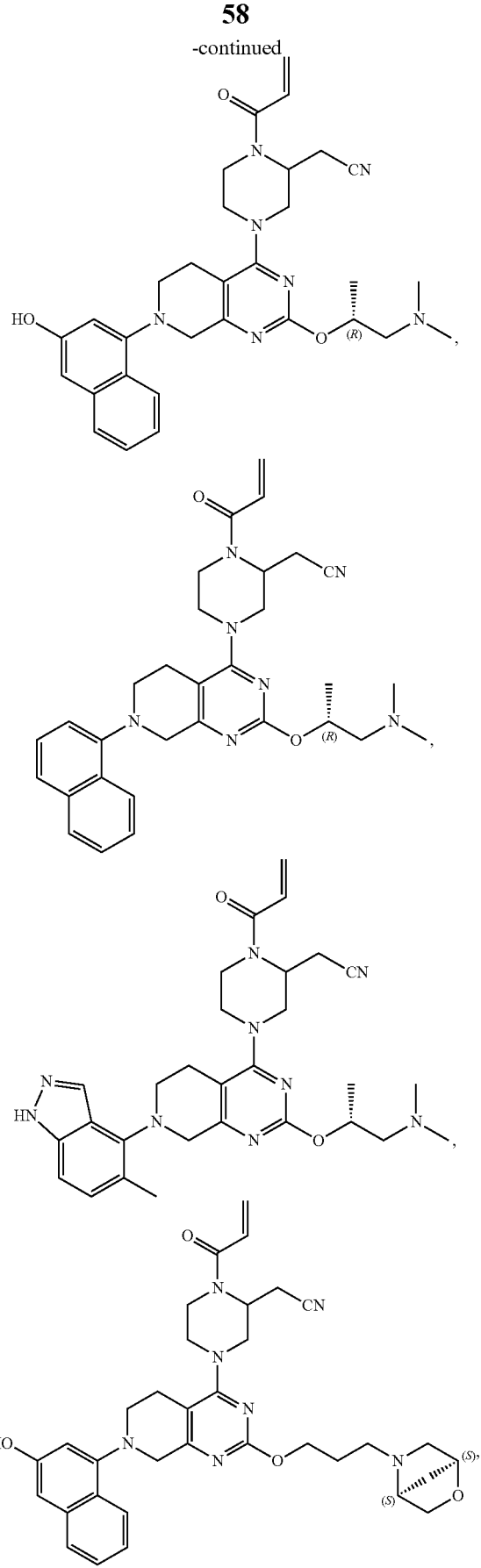

-continued
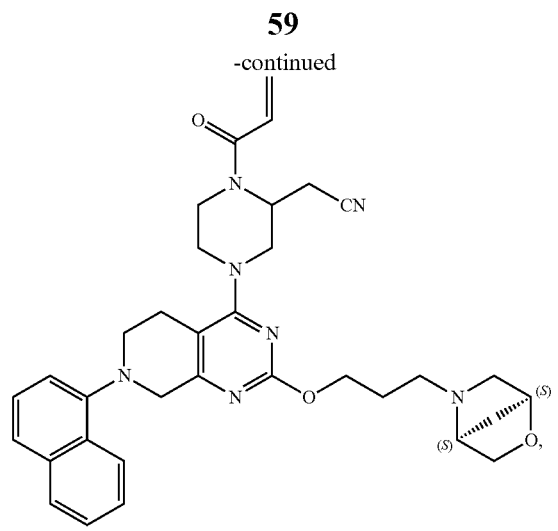
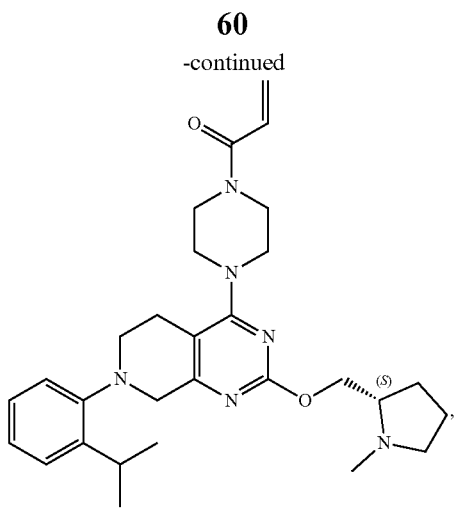
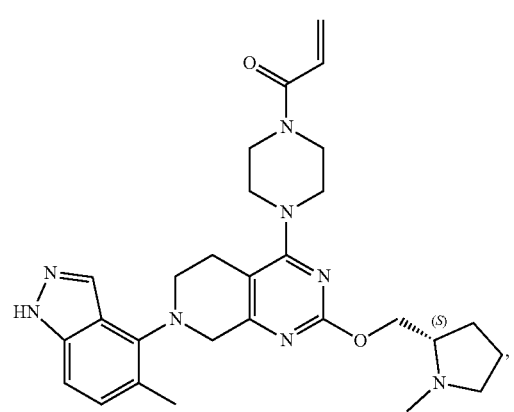
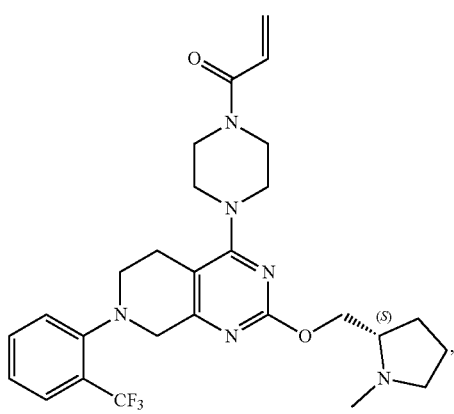
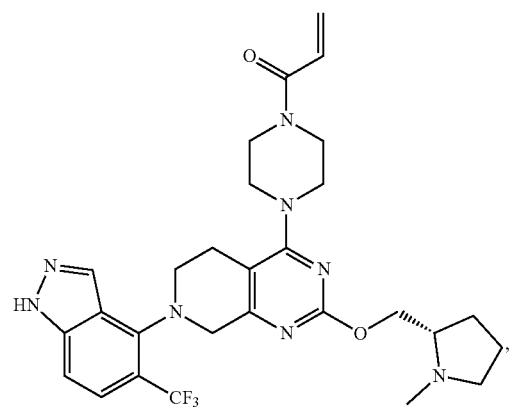
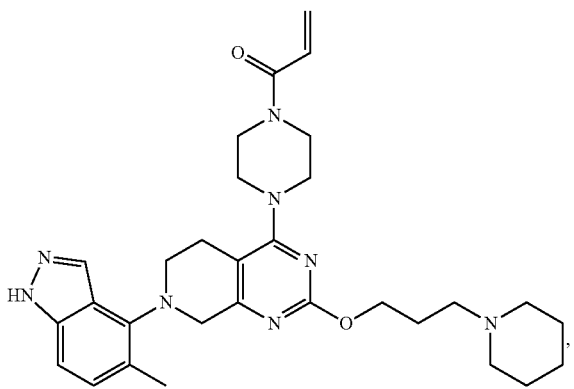
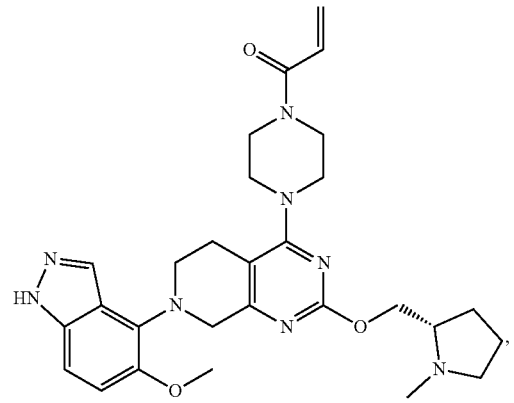
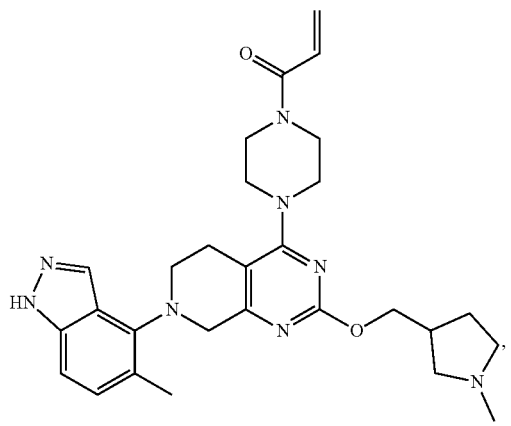

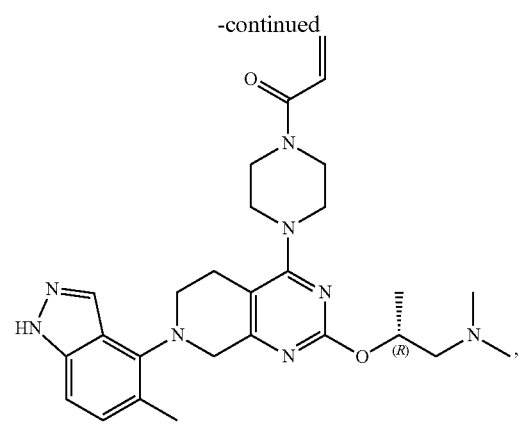
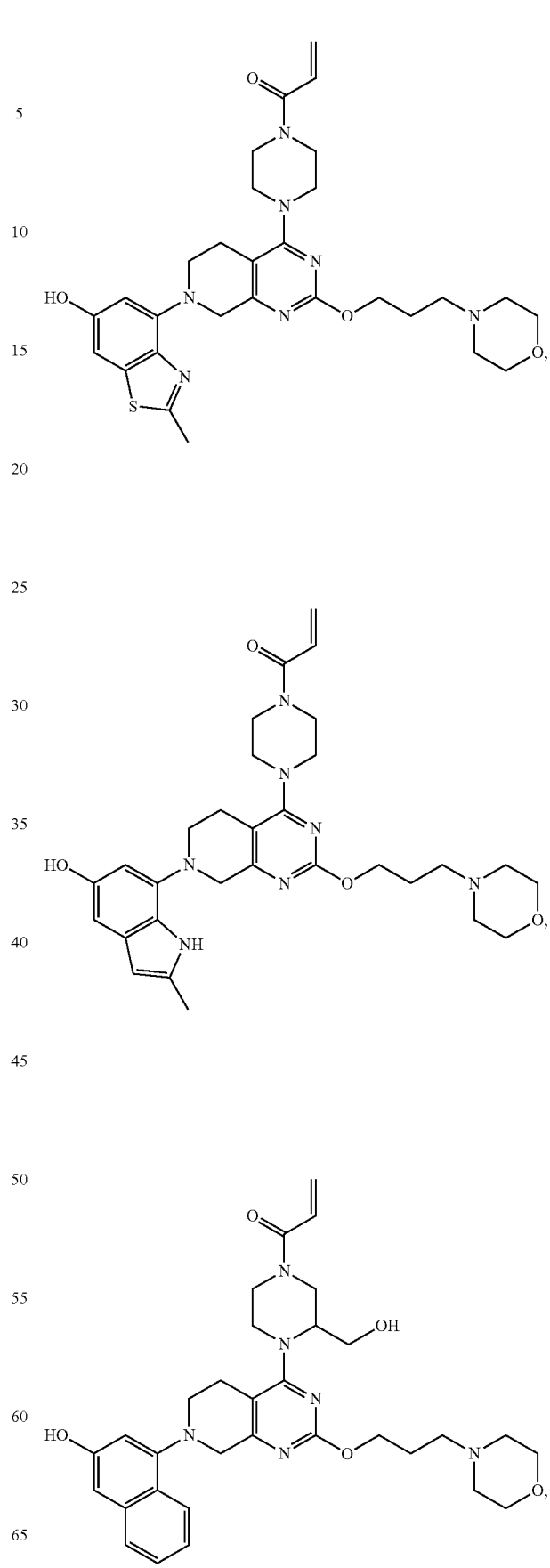

-continued
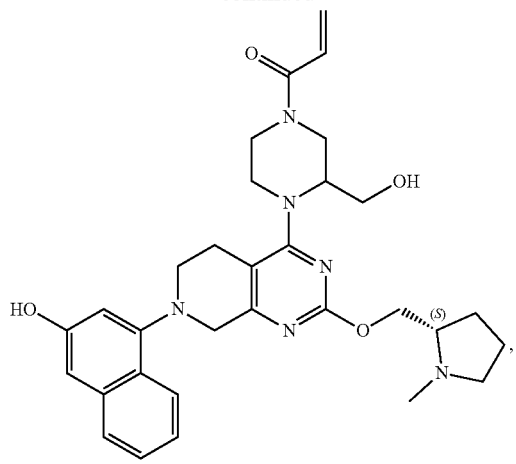
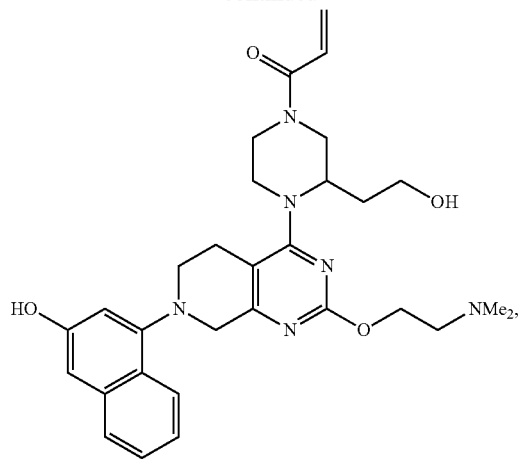
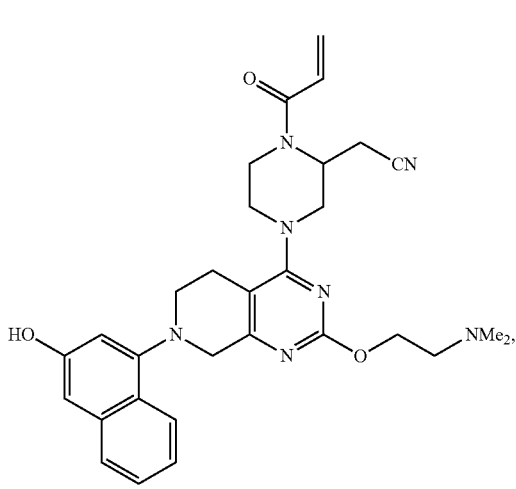
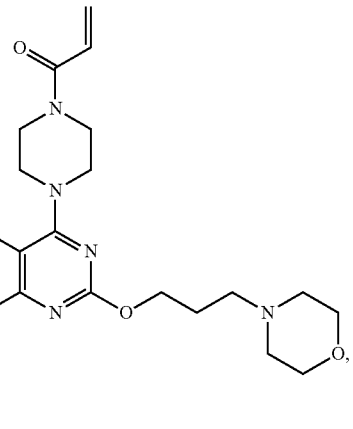
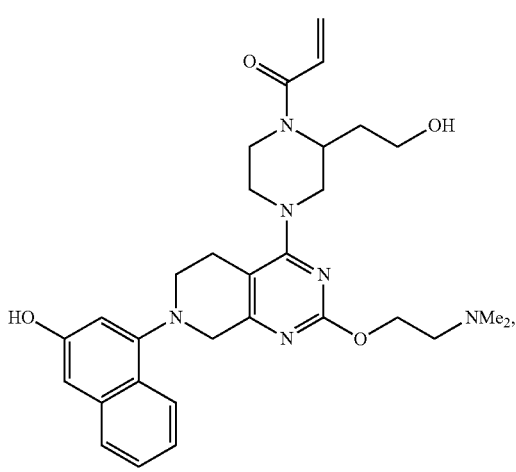
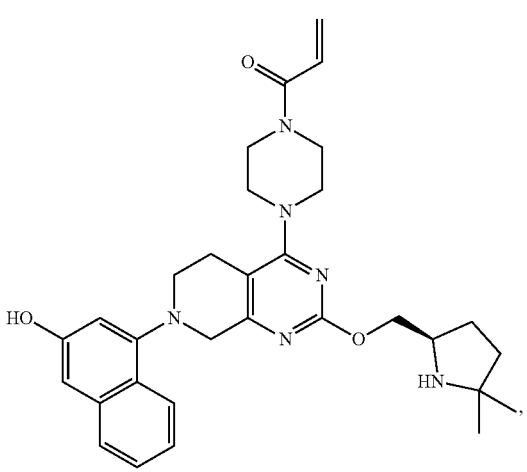

-continued
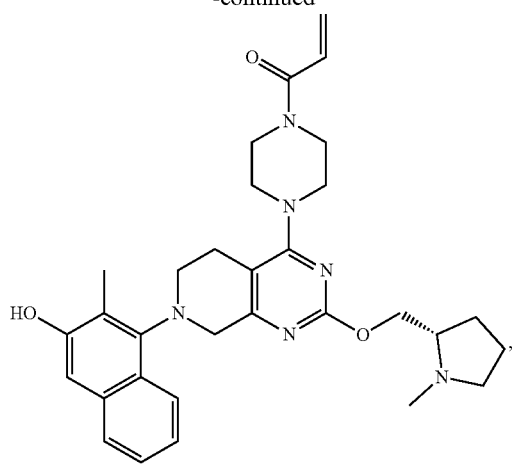
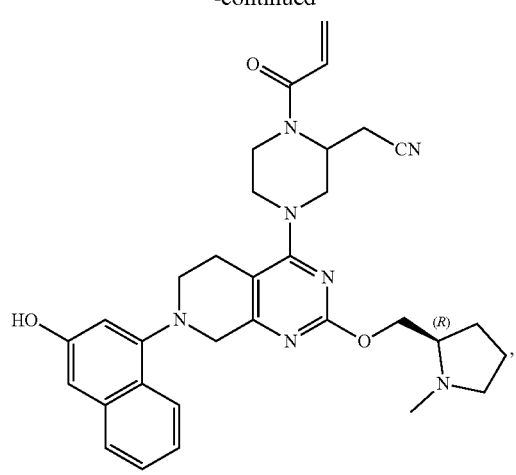
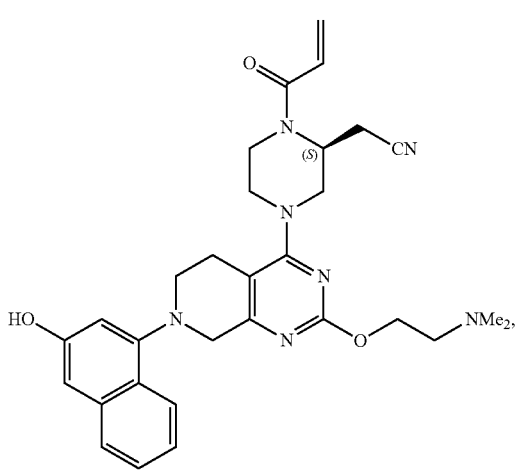
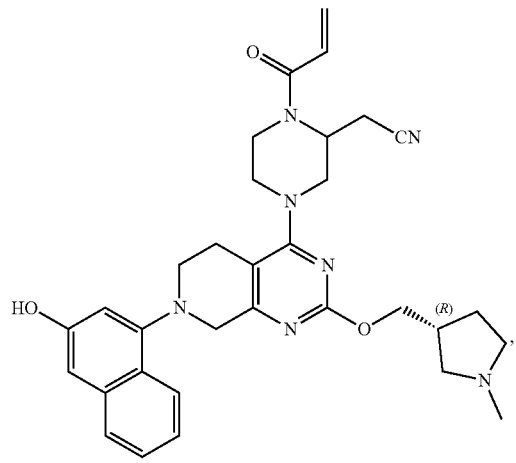
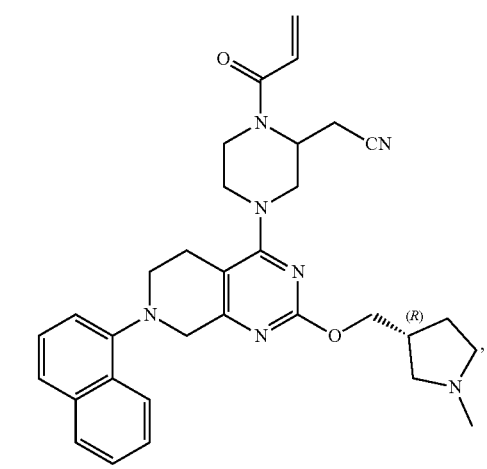
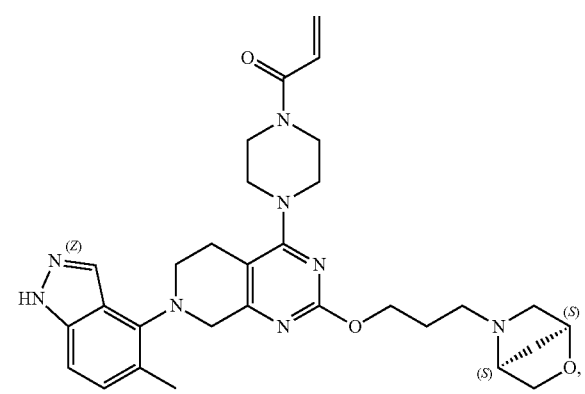

67
-continued
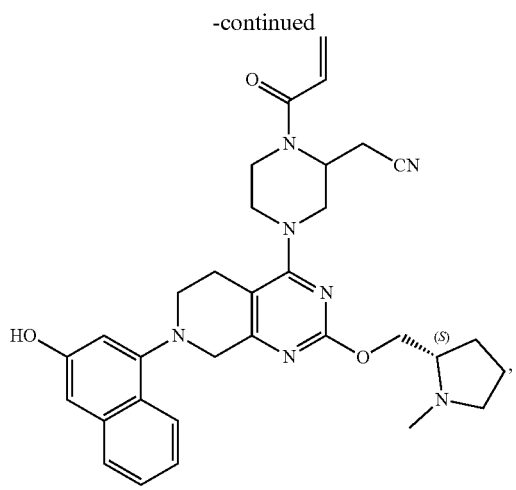
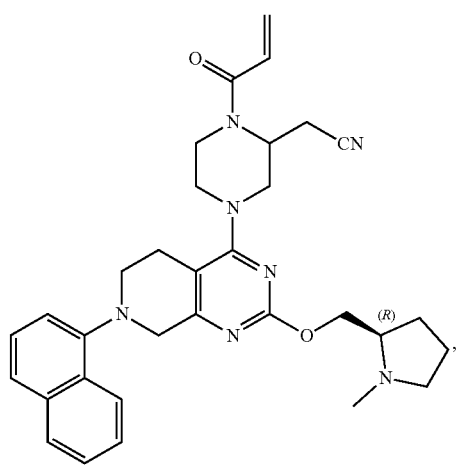
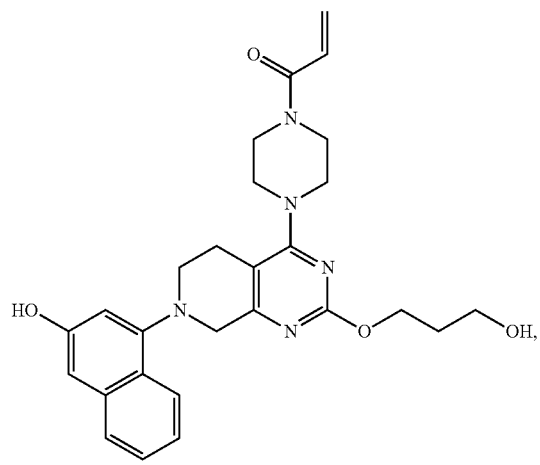
68
-continued
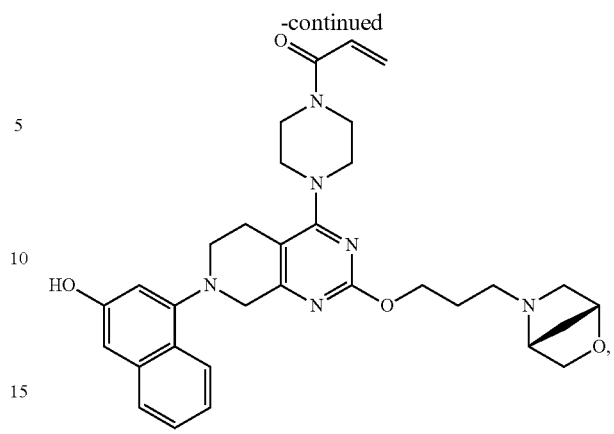
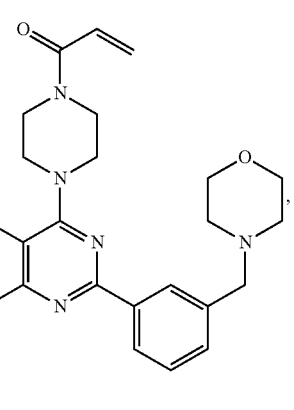
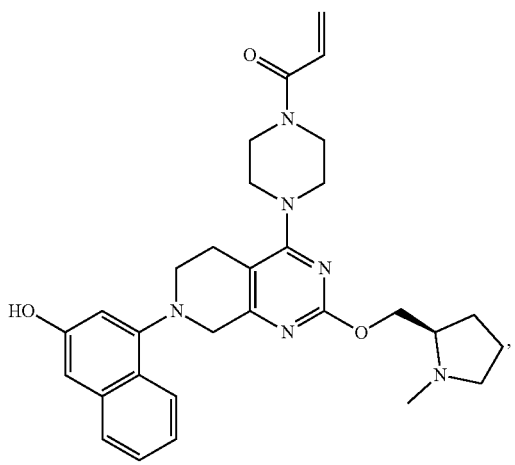

69
-continued
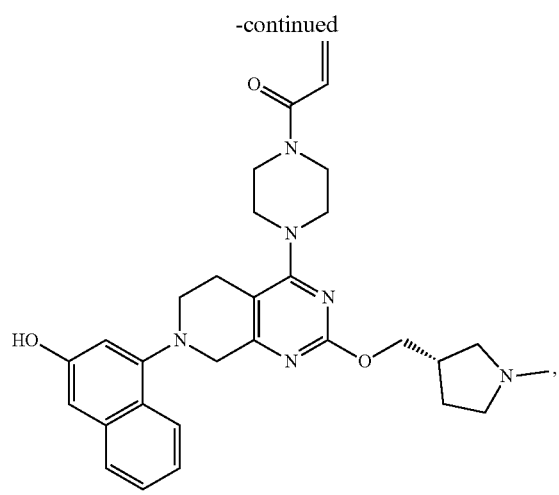
70
-continued
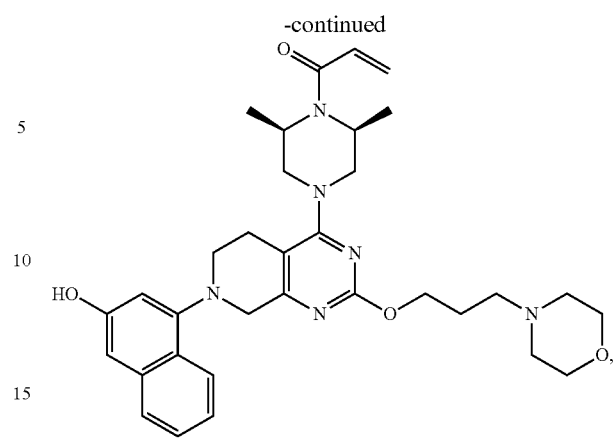
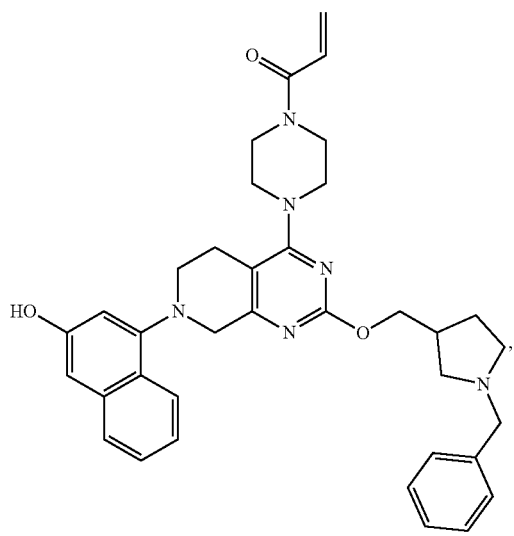
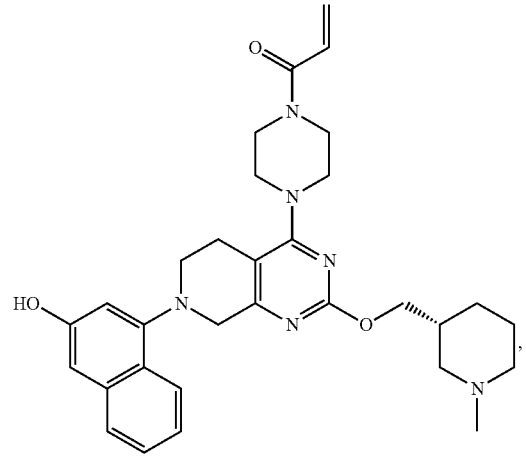
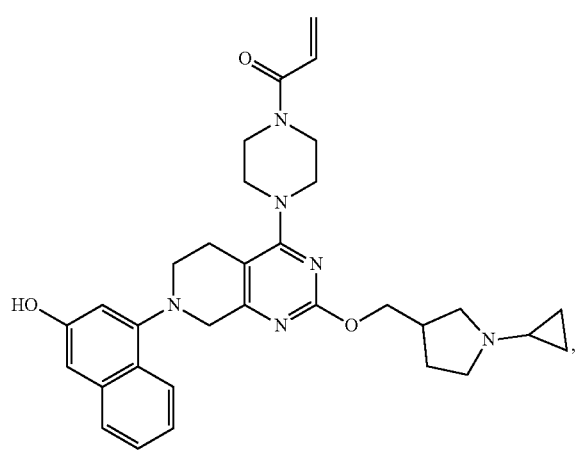
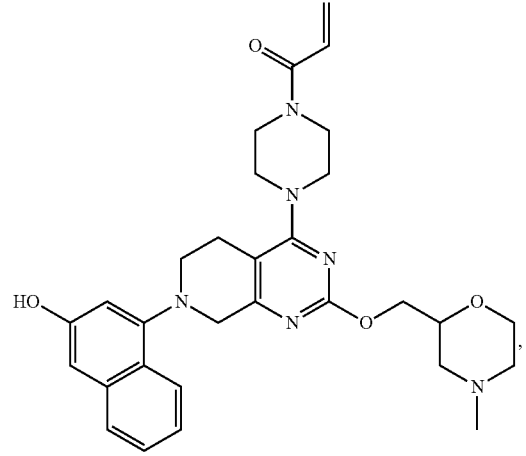

71
-continued
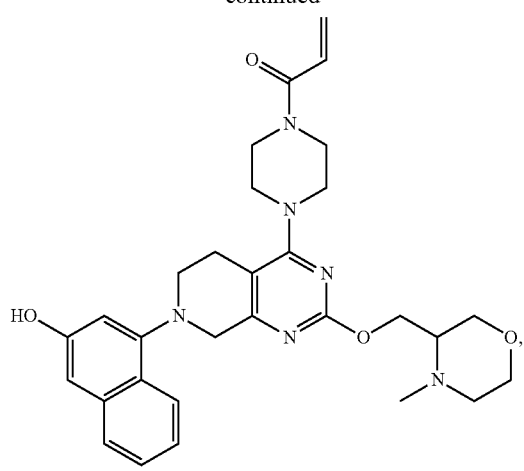
72
-continued
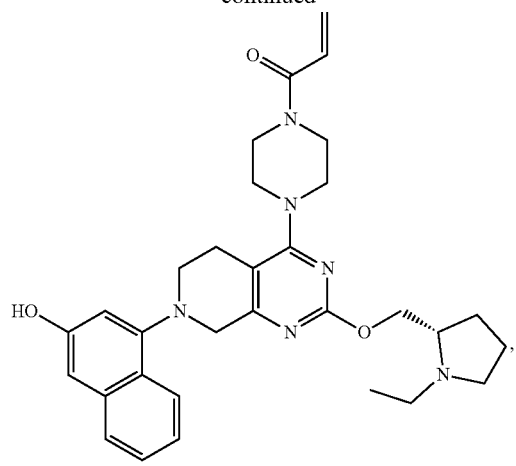

73
-continued
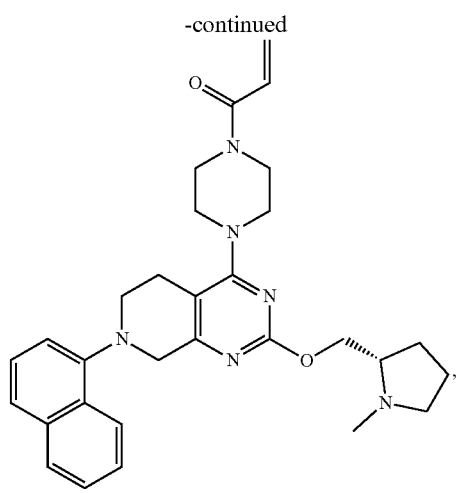
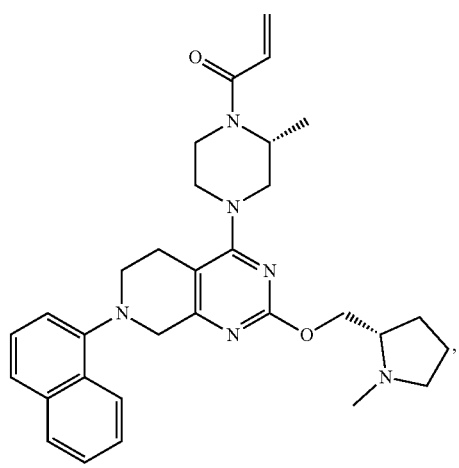
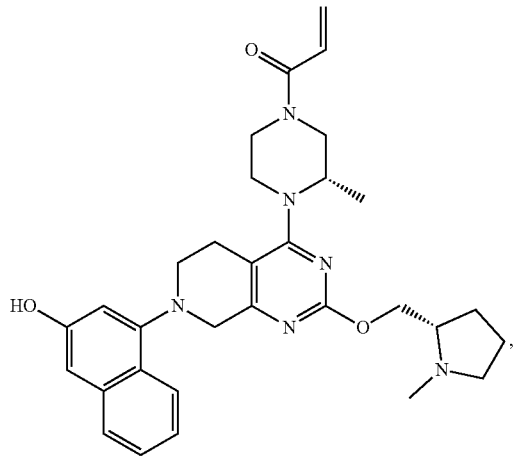
74
-continued
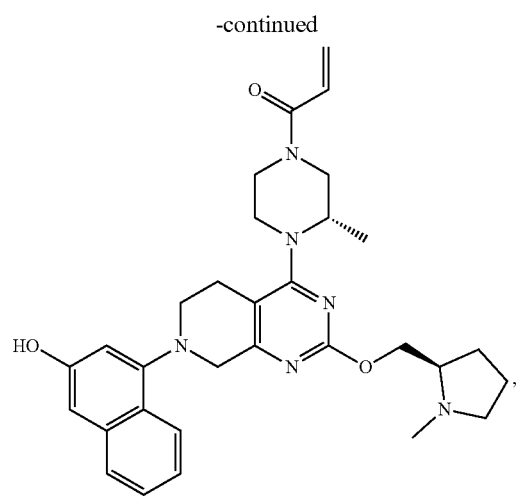
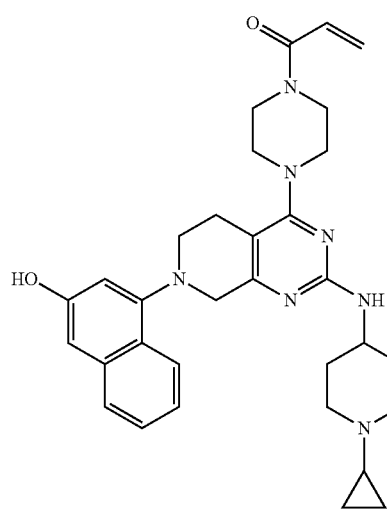
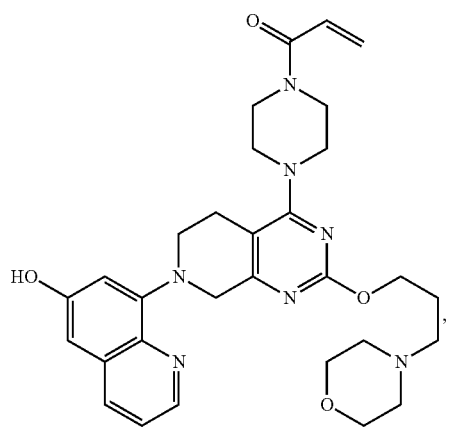

75
-continued
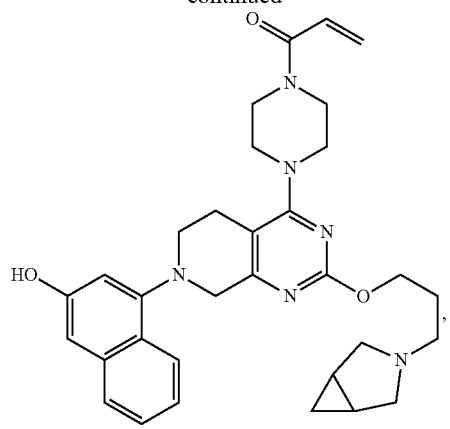
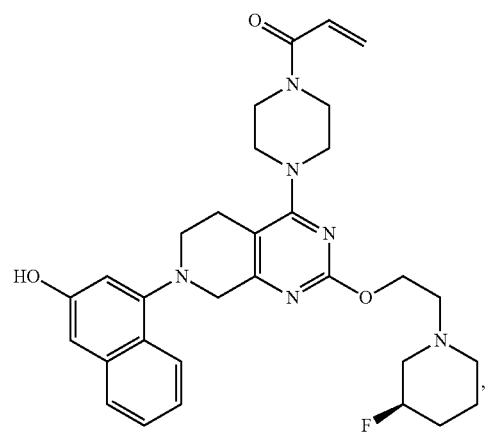
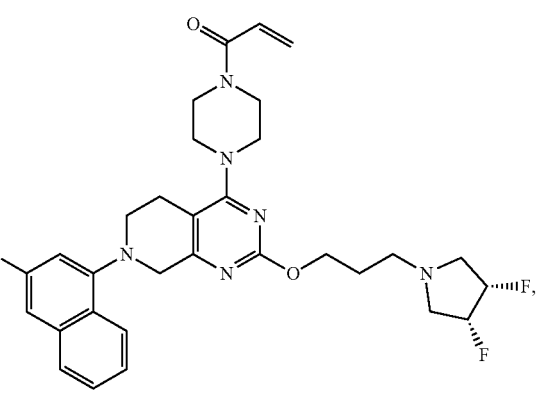
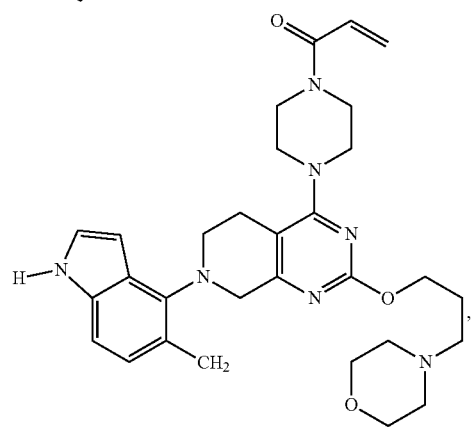
76
-continued
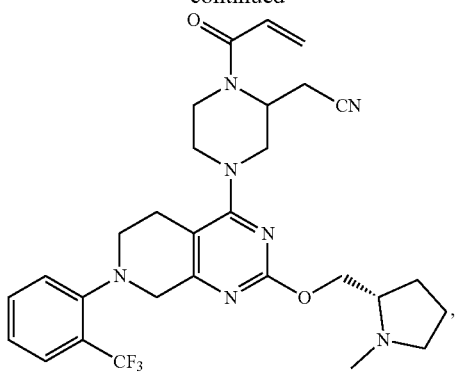
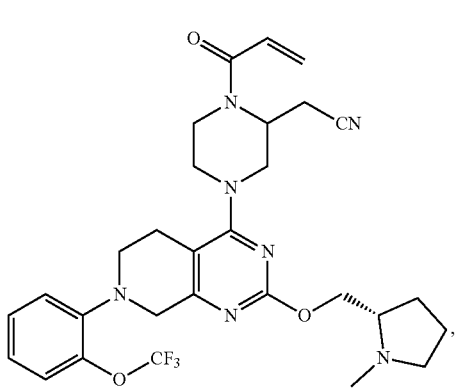
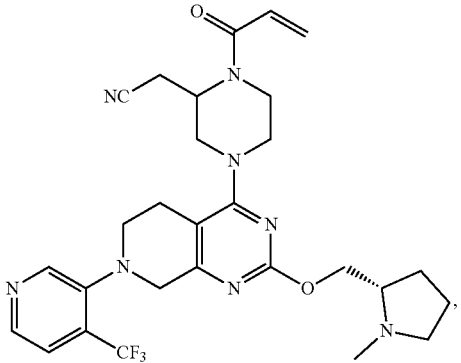
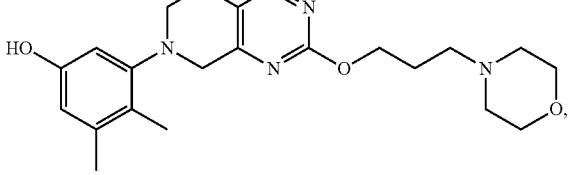

77
-continued
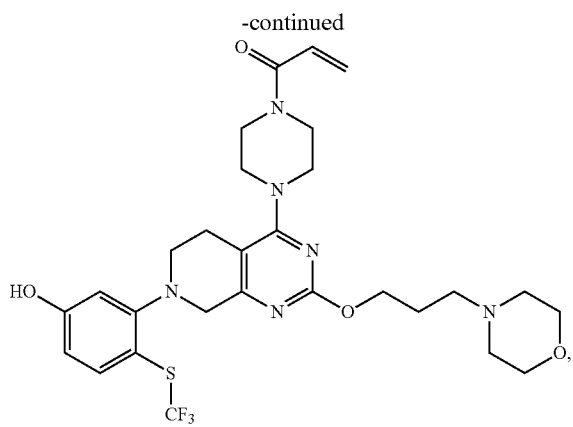
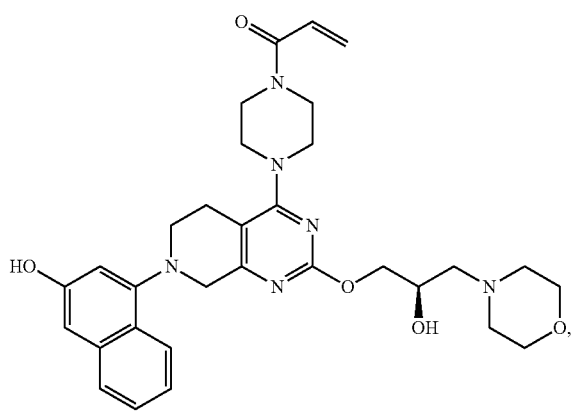
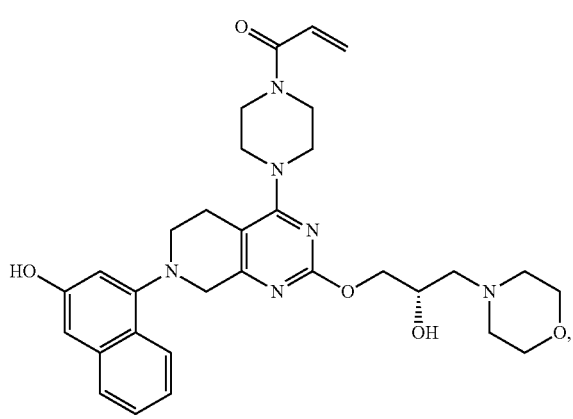
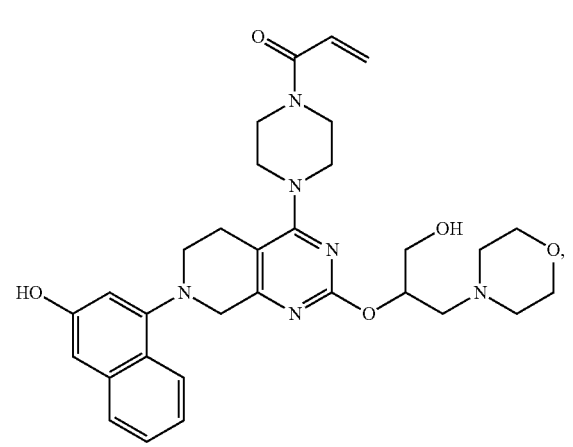
78
-continued
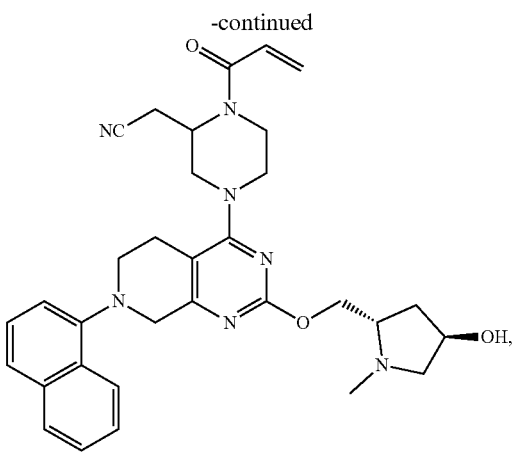
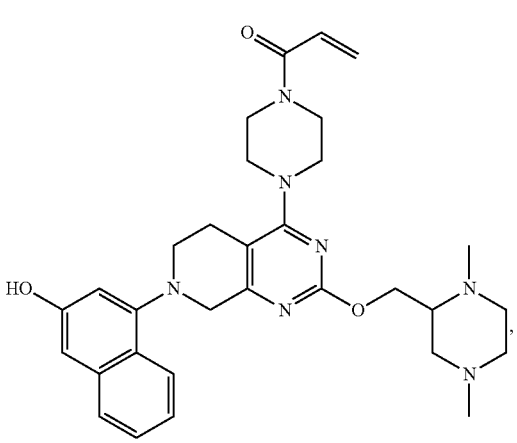
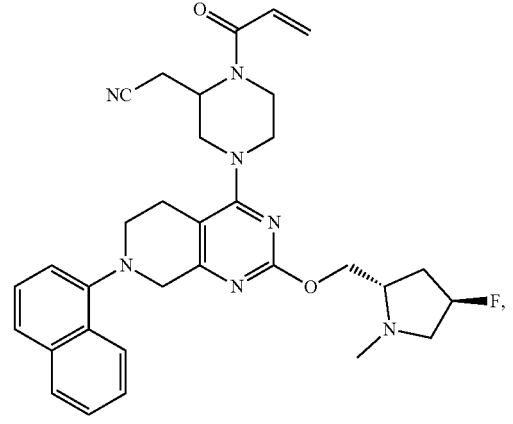
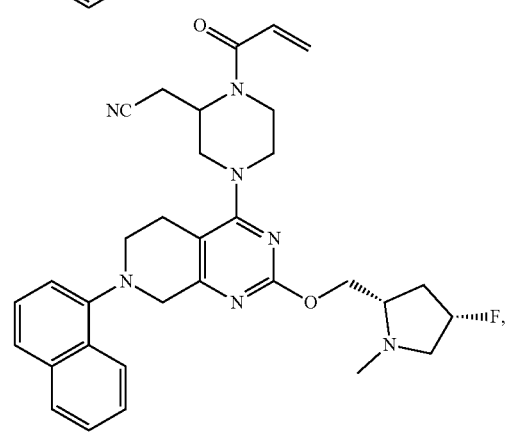

-continued
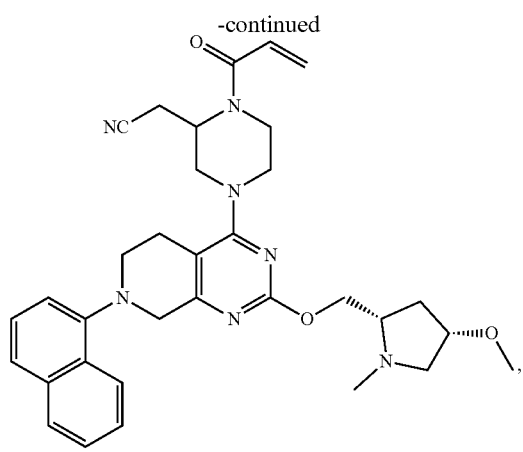
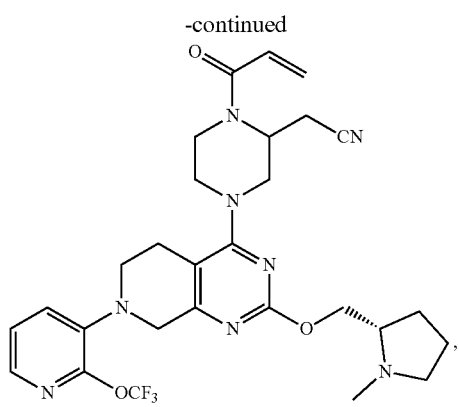

81
-continued
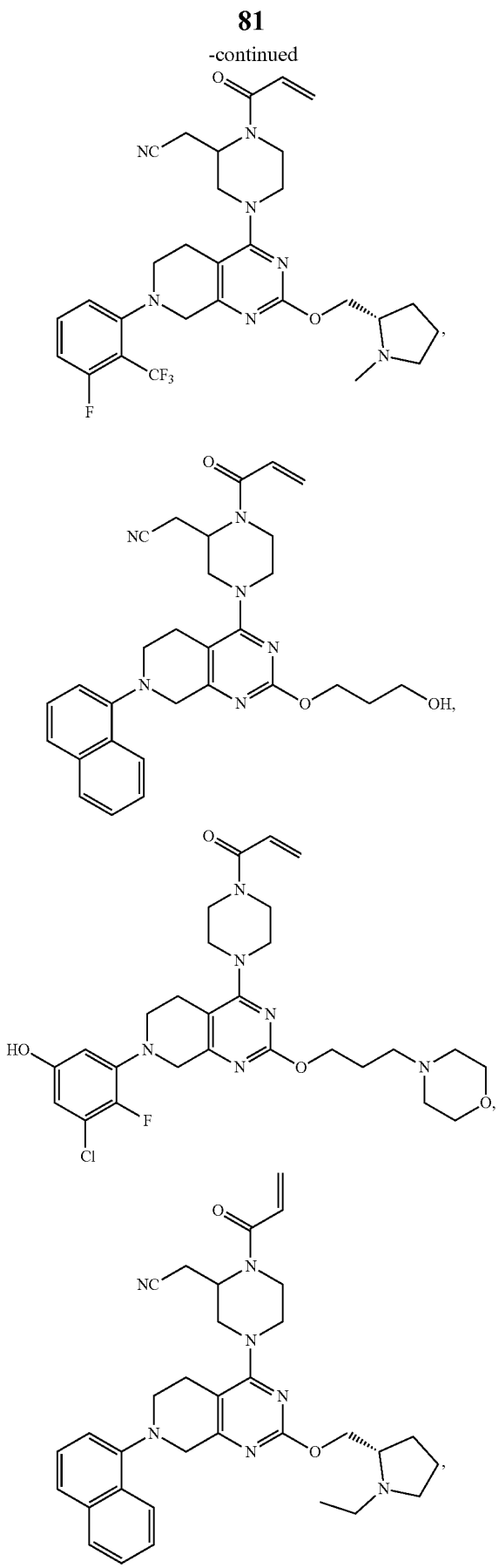
82
-continued
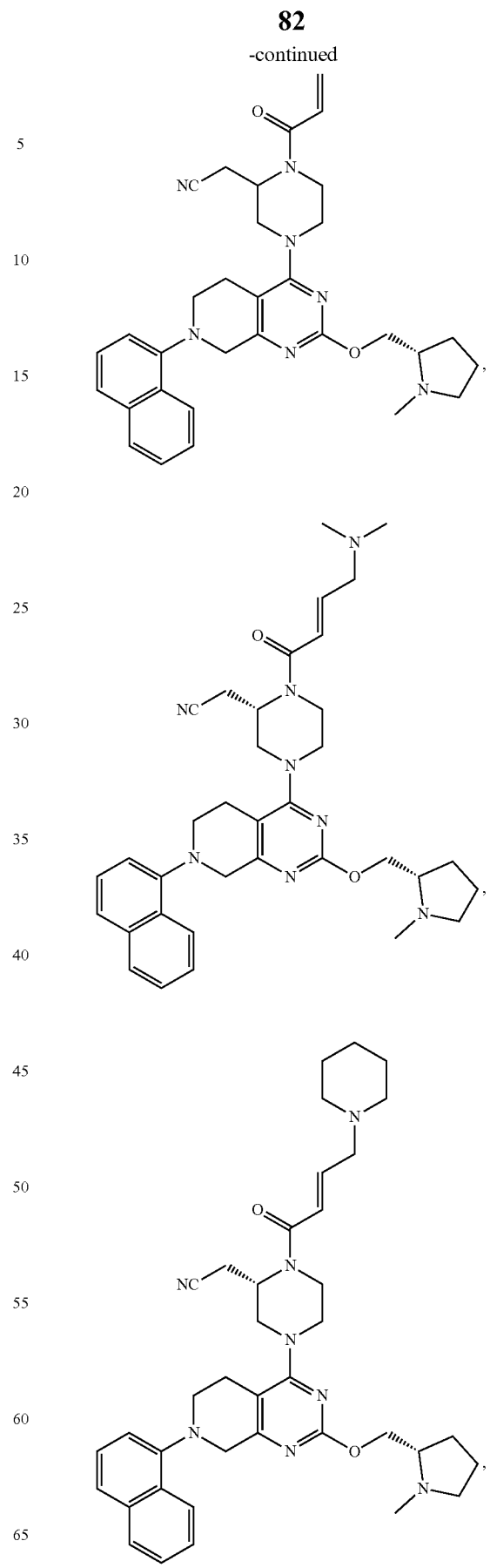

83
-continued
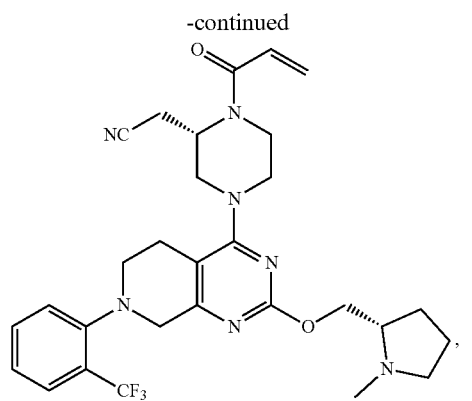
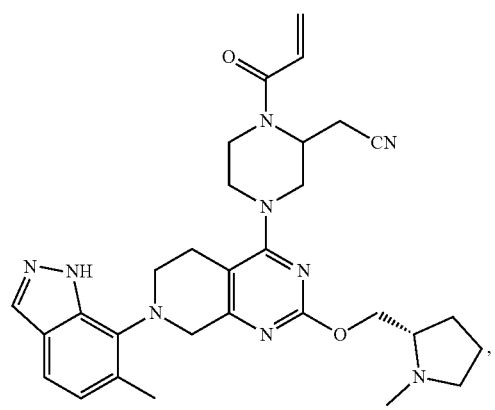
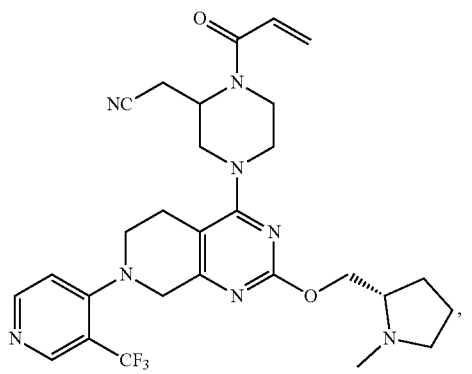
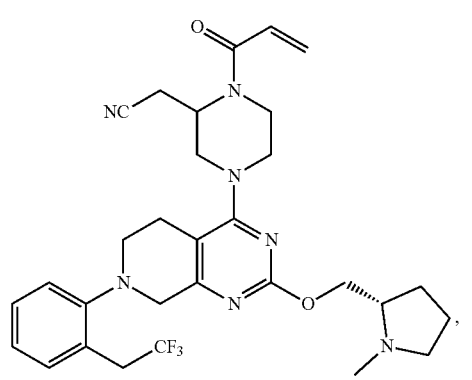
84
-continued
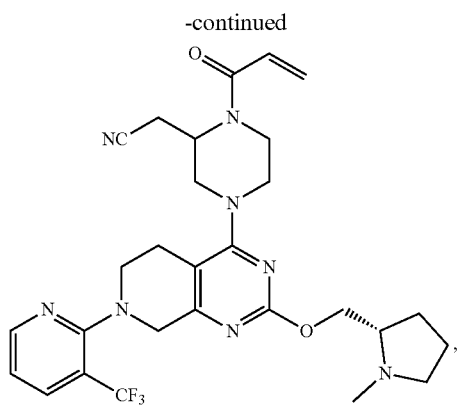
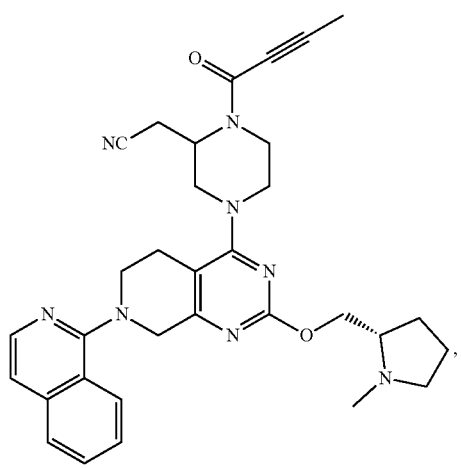
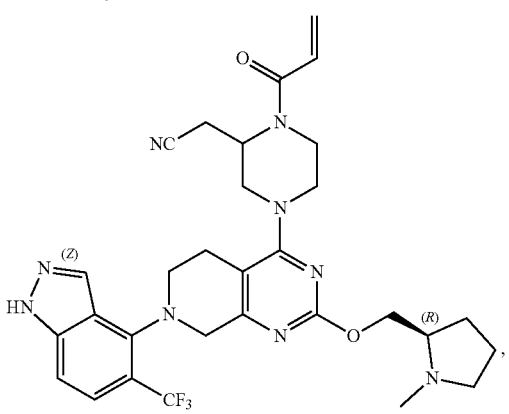
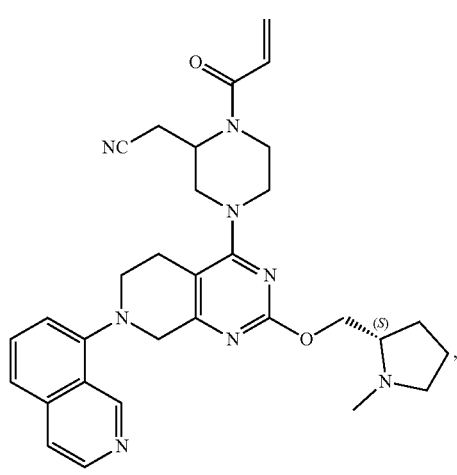

-continued
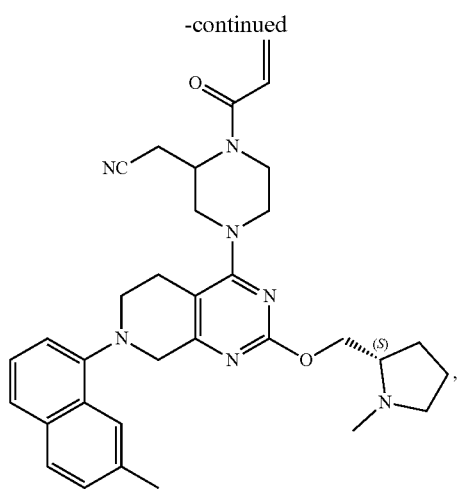
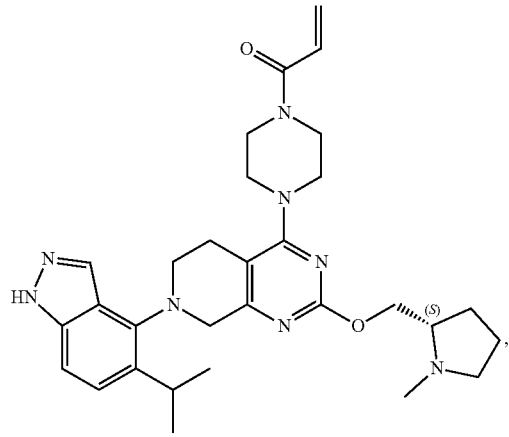
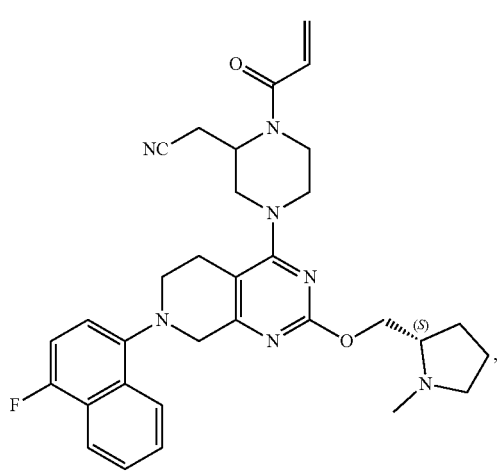
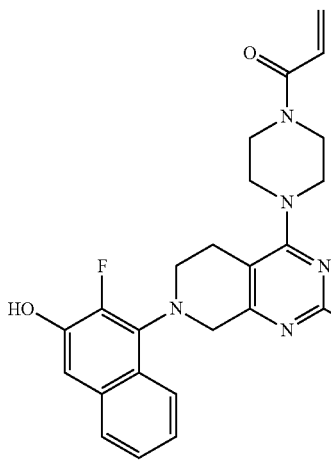
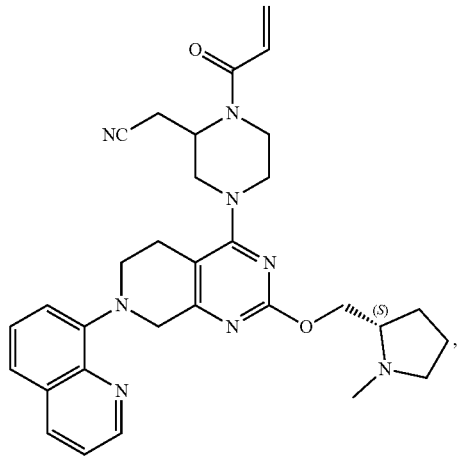
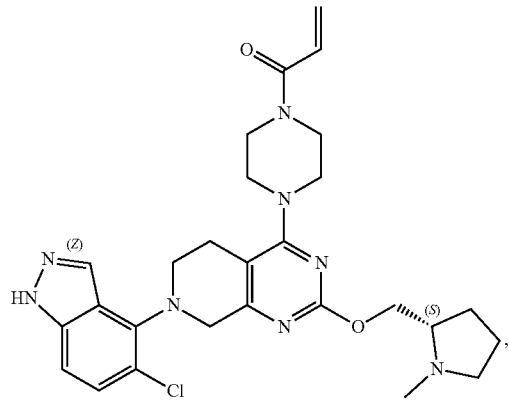

87
-continued
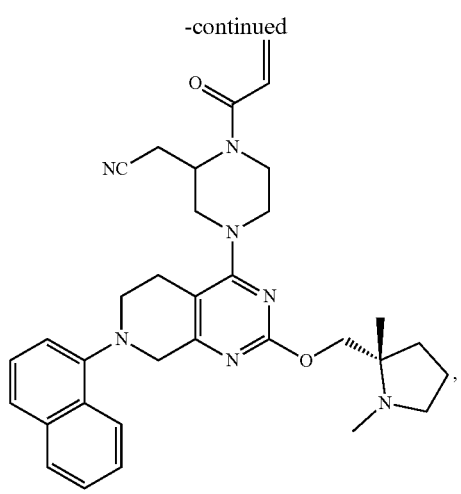
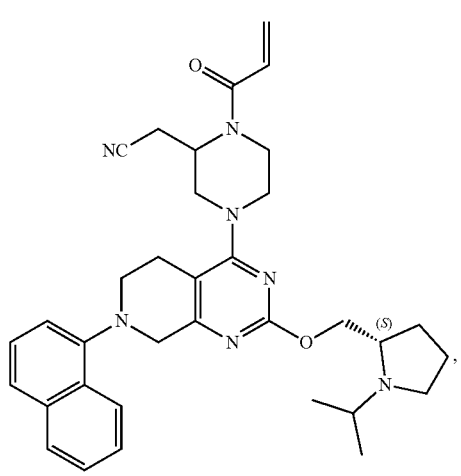
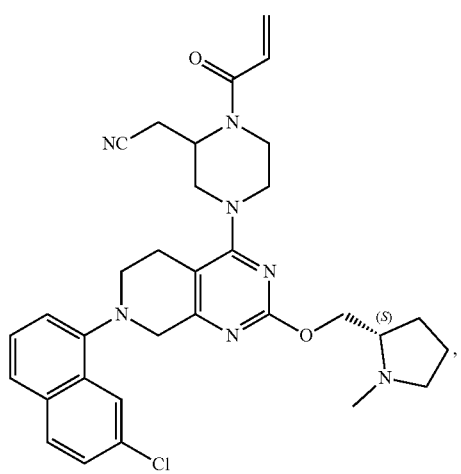
88
-continued
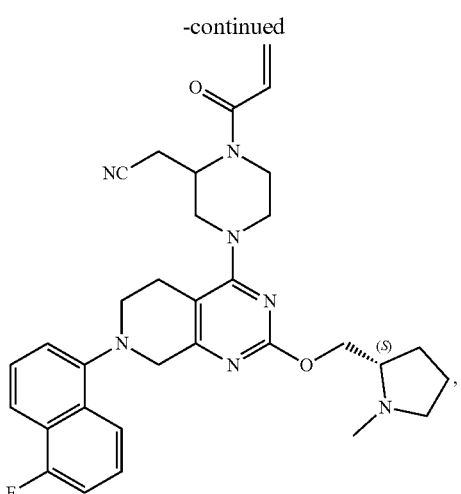
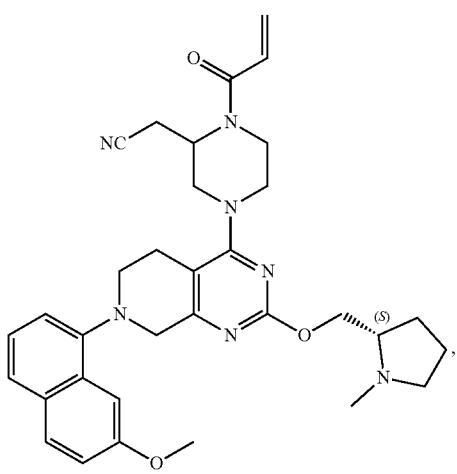
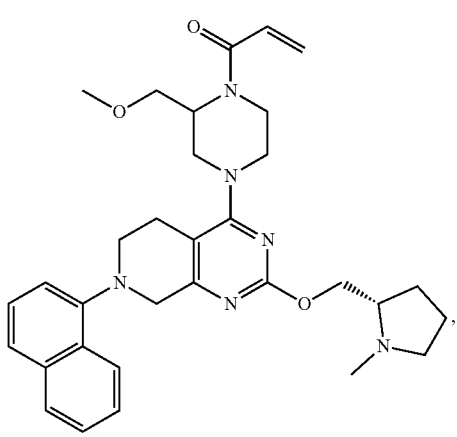

89
-continued
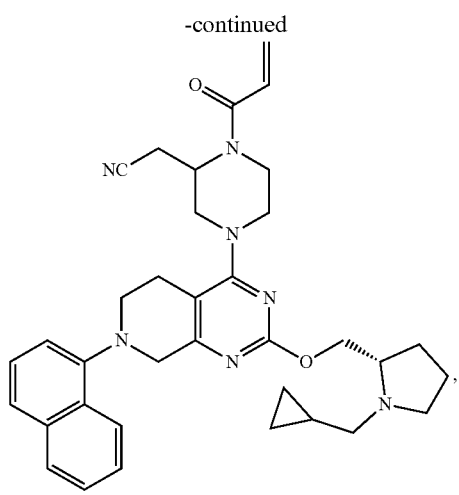
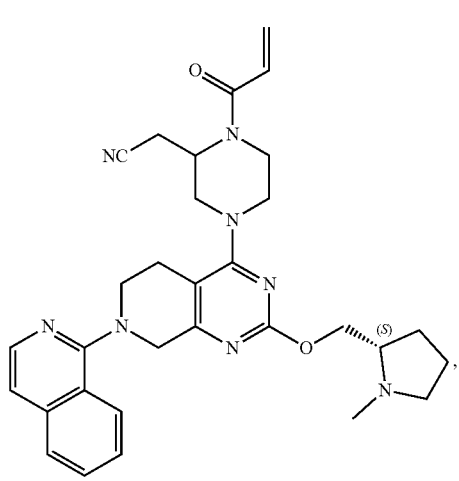
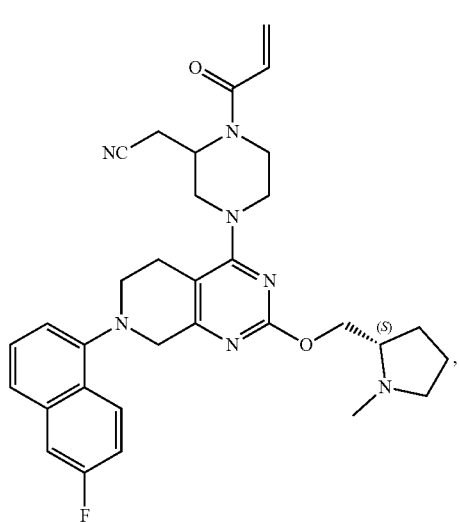
90
-continued
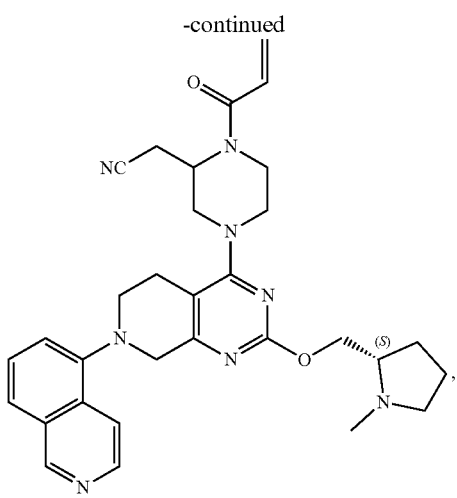
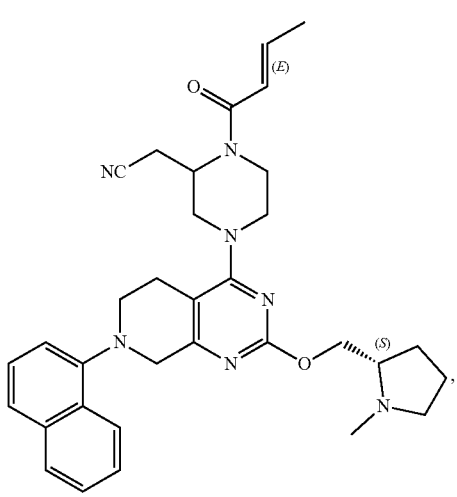
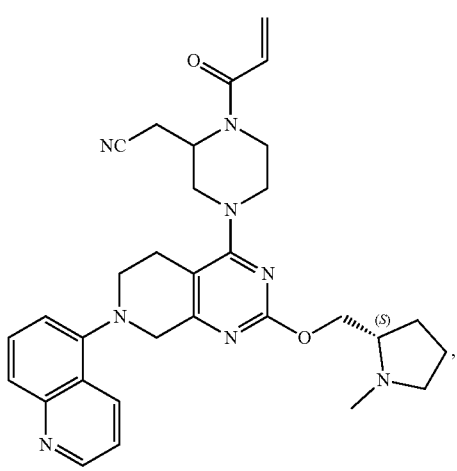

91
-continued
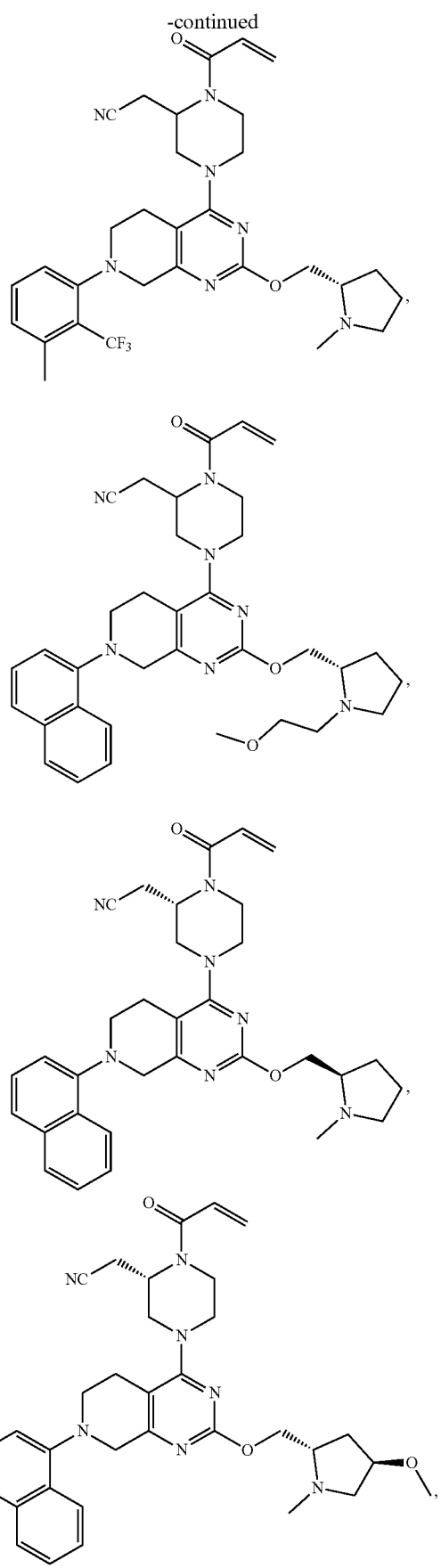
92
-continued
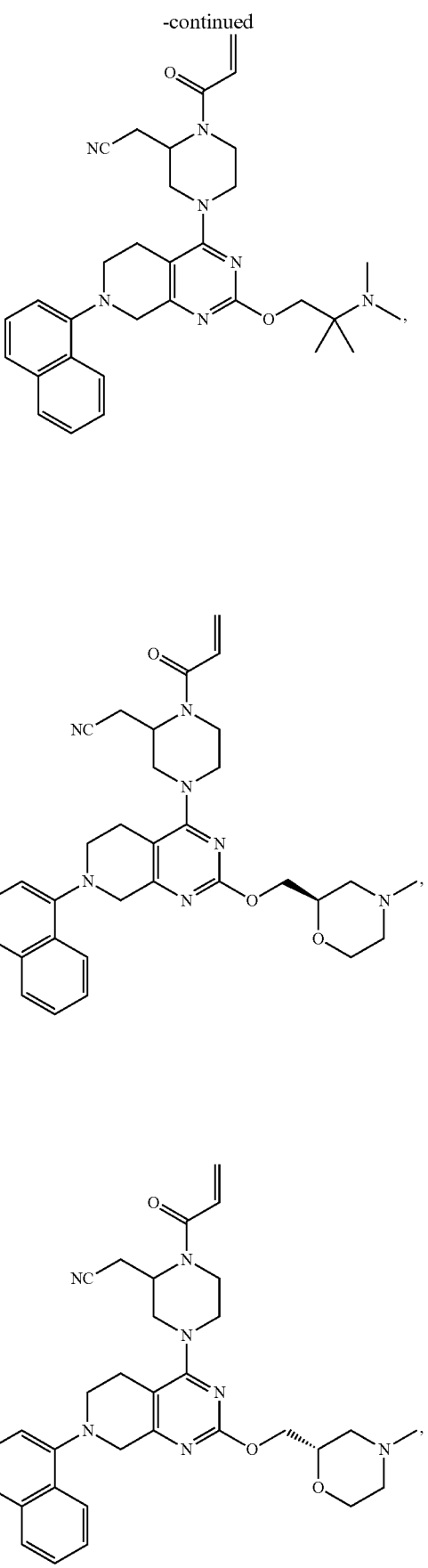

93
-continued
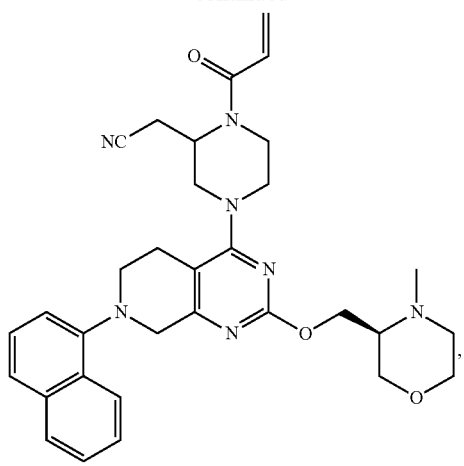
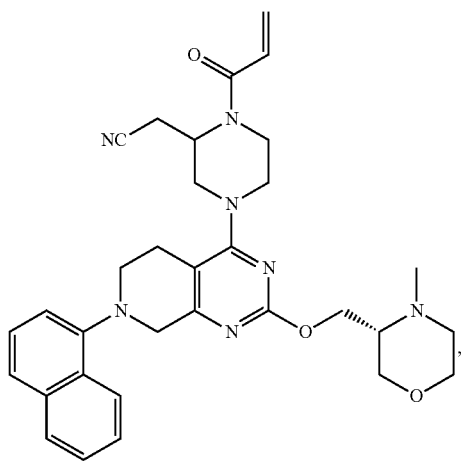
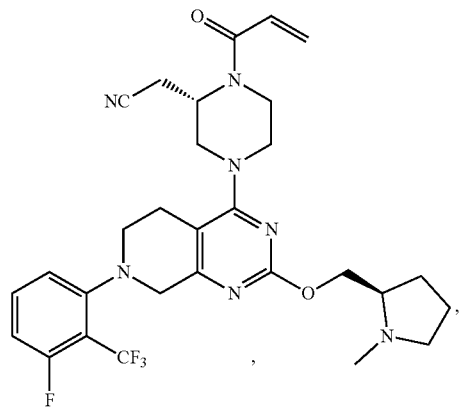
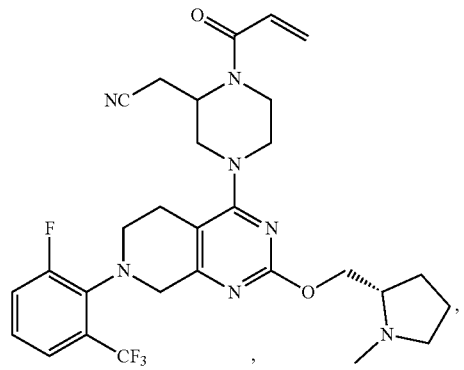
94
-continued
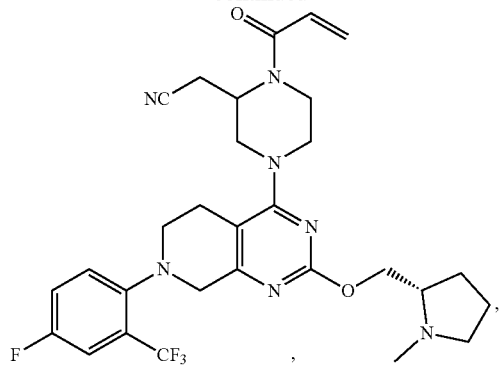
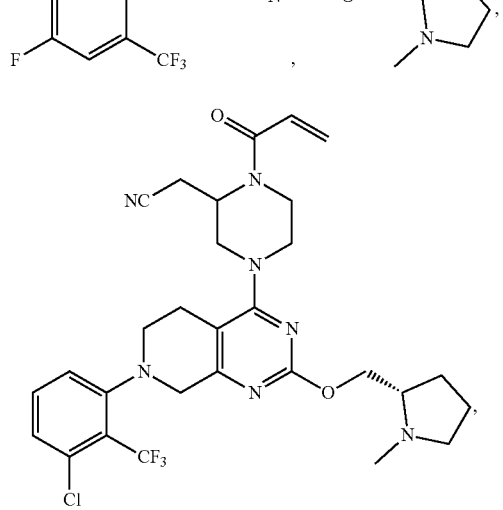
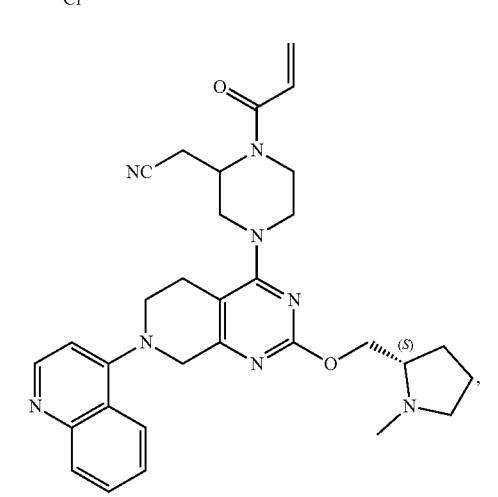
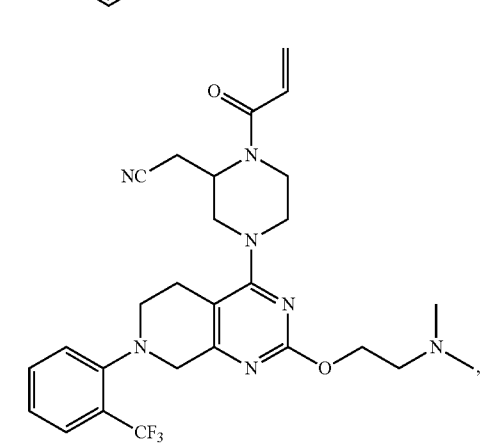

95
-continued

96
-continued

97
-continued
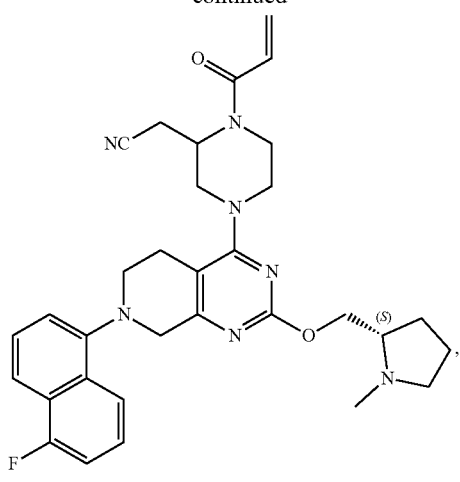
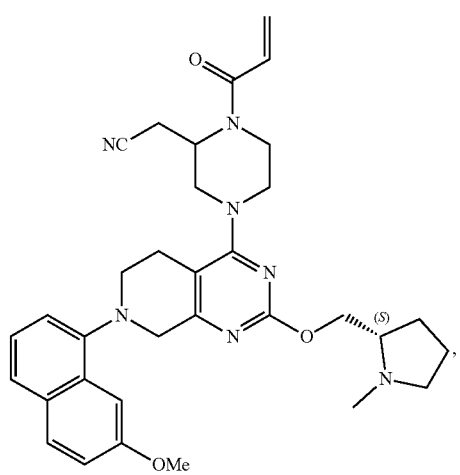
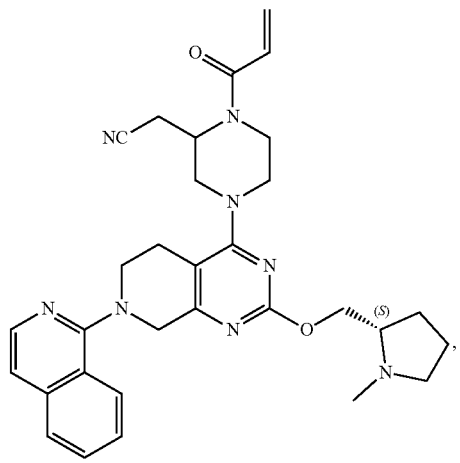
98
-continued
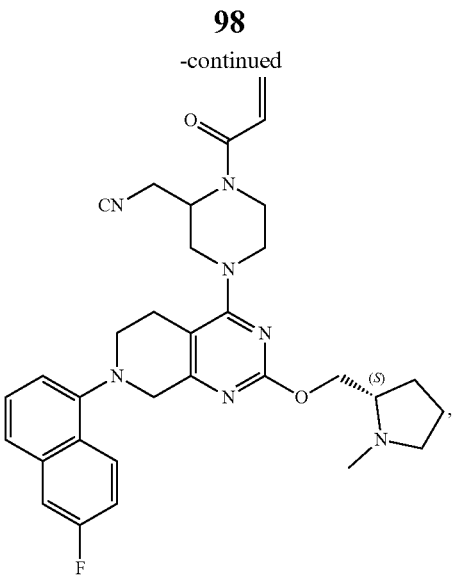
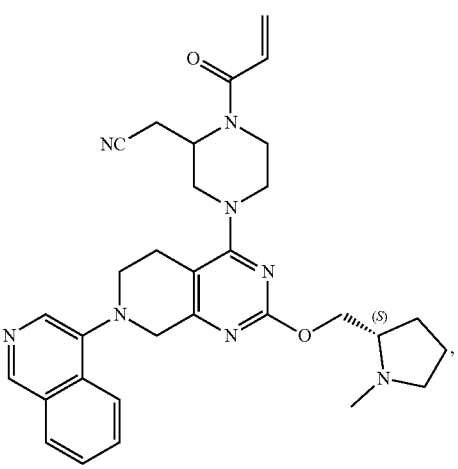
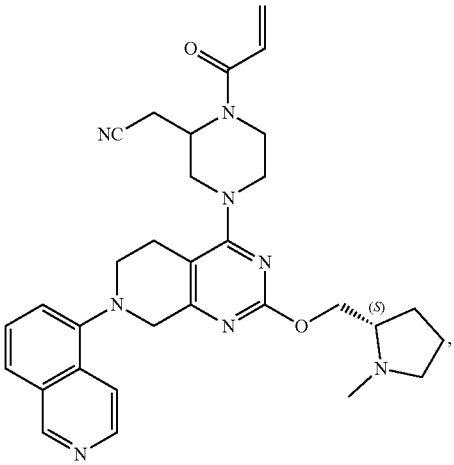

99
-continued
100
-continued
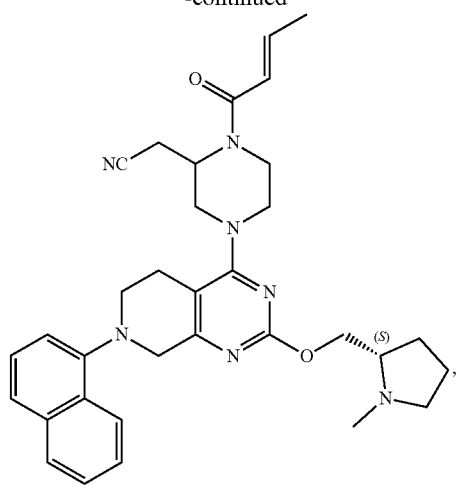
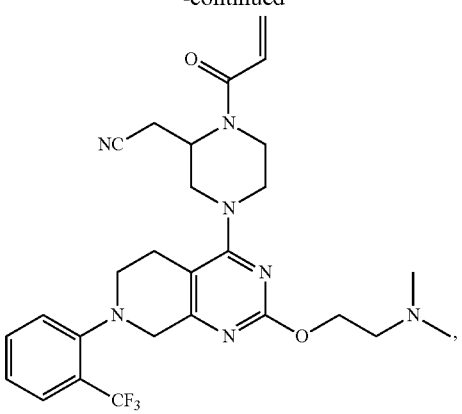
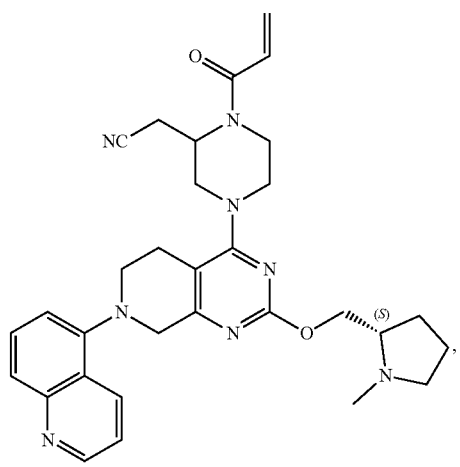
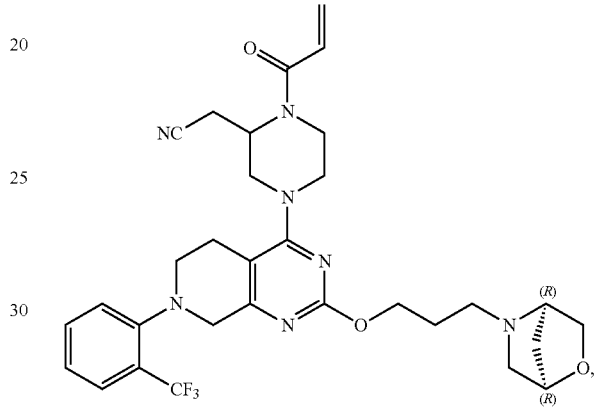
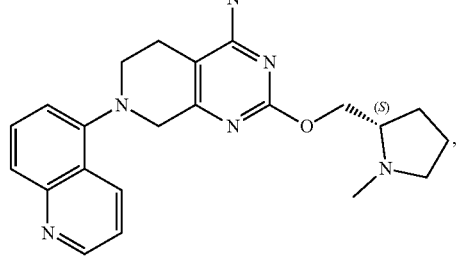
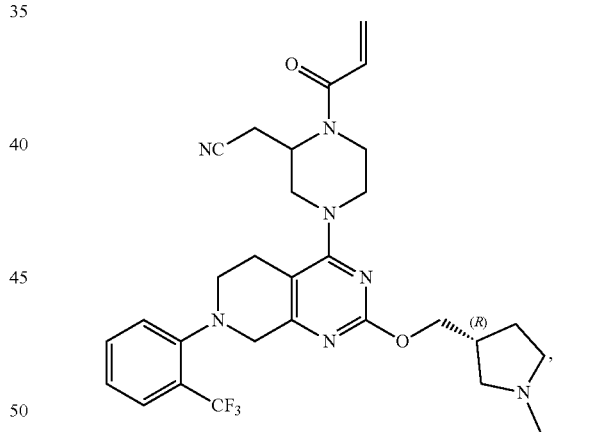
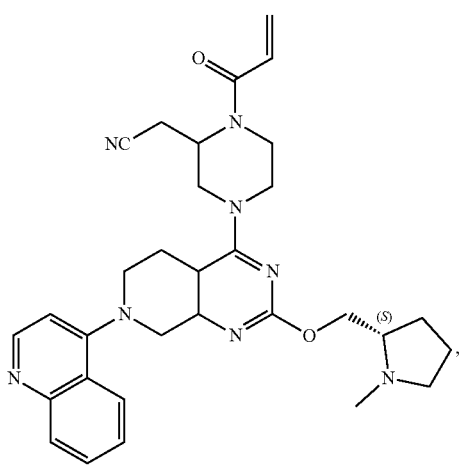
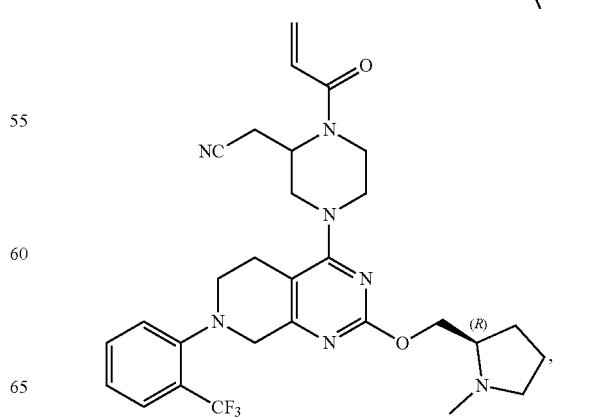
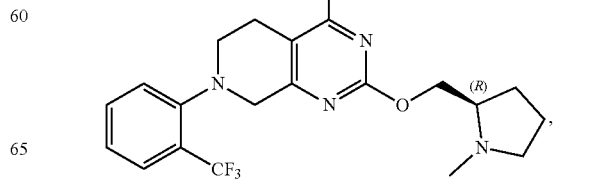

101
-continued
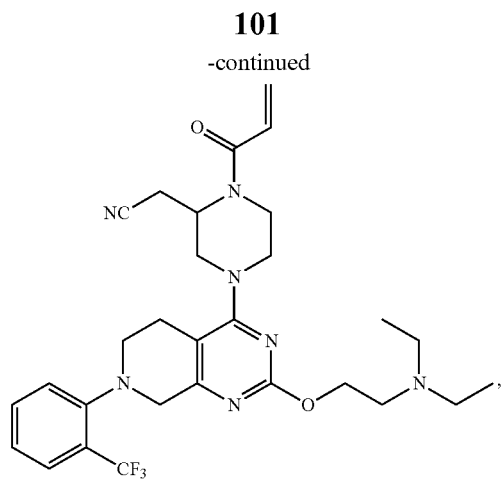
102
-continued
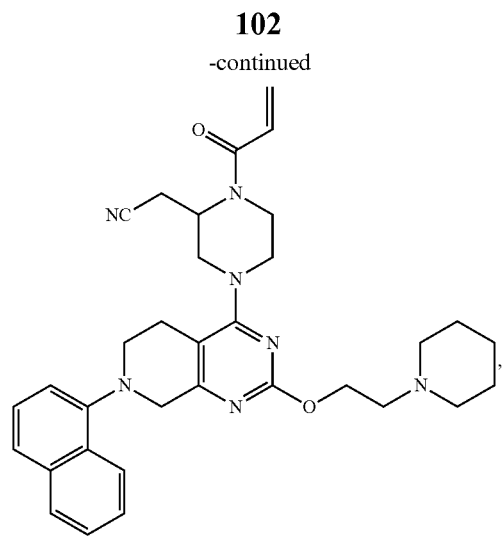
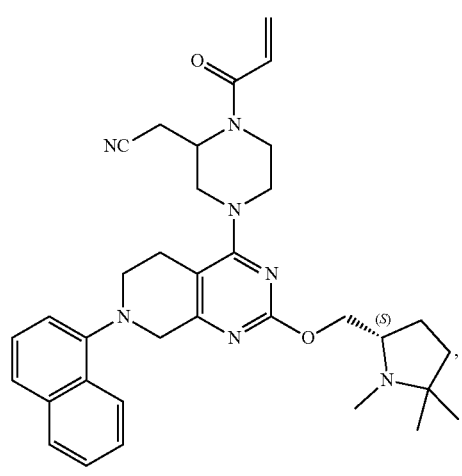
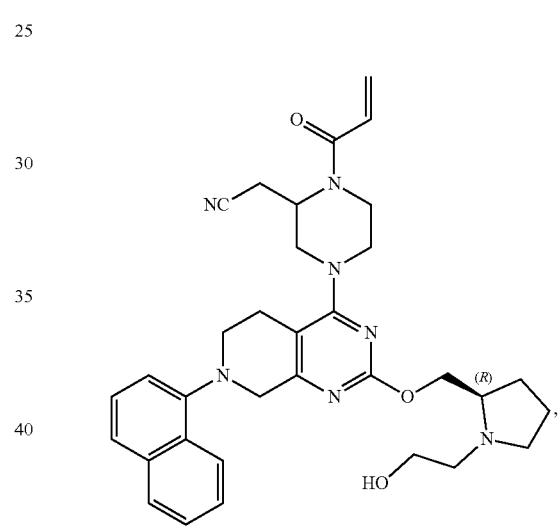
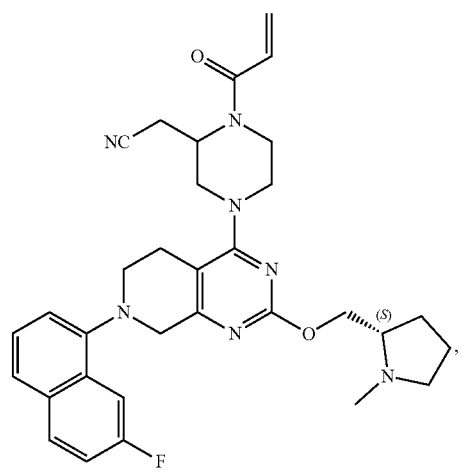
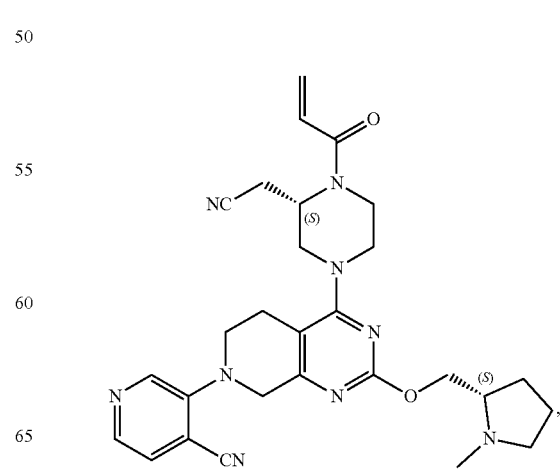

103
-continued
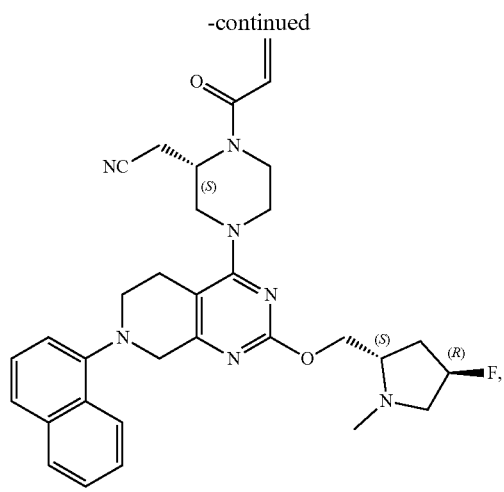
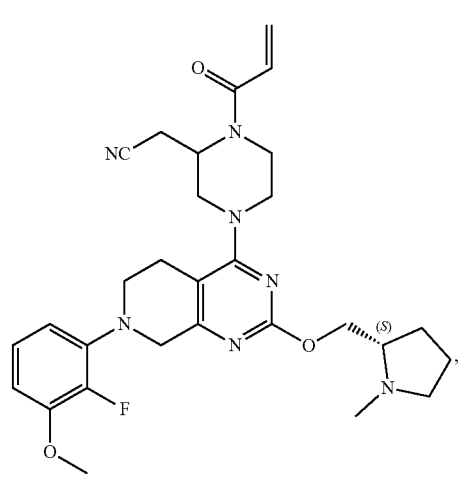
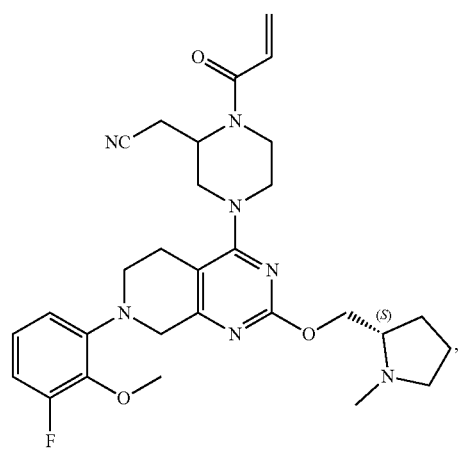
104
-continued
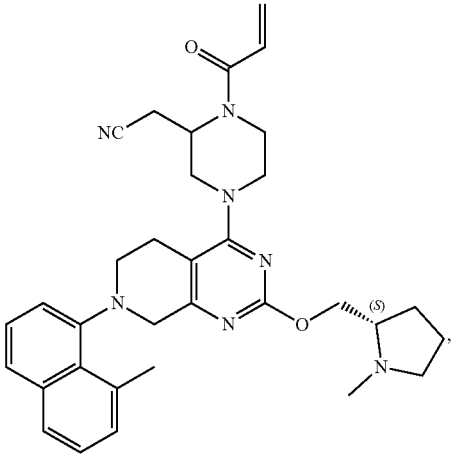
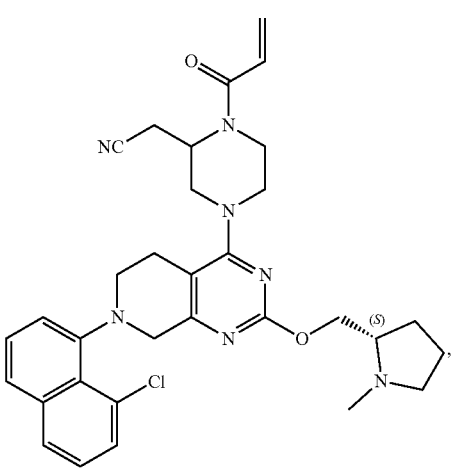
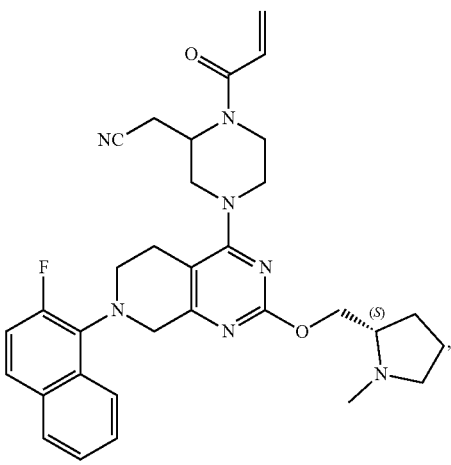

105
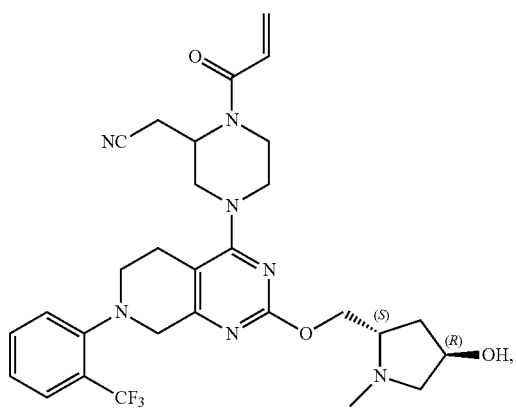
106
-continued
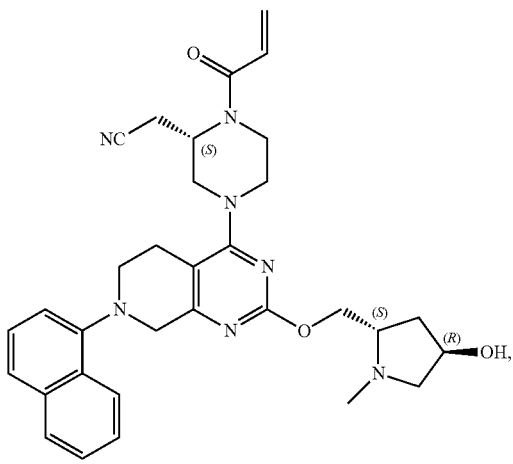
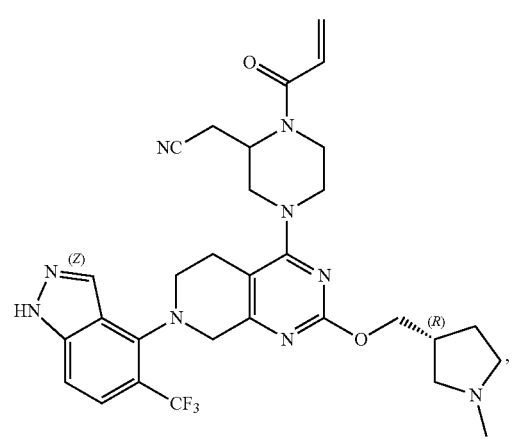
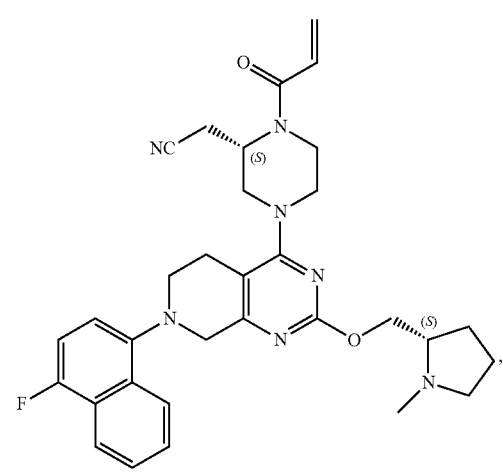
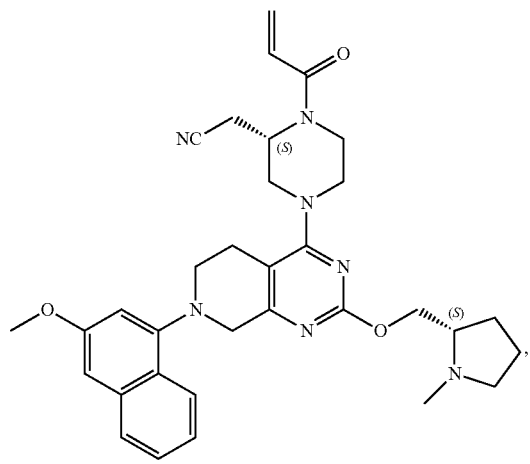
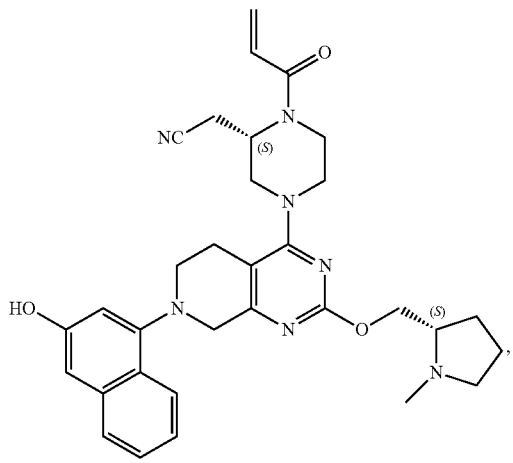

107
-continued
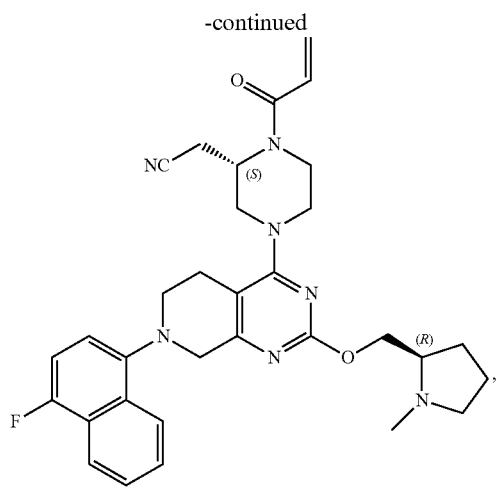
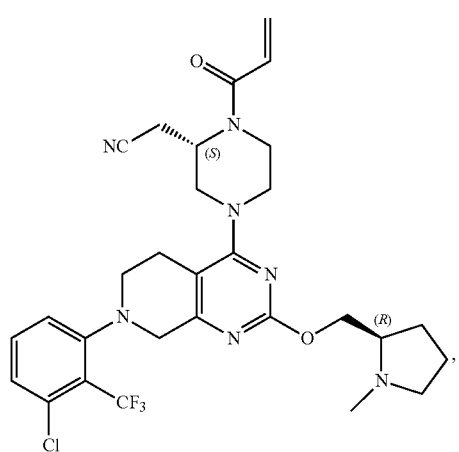
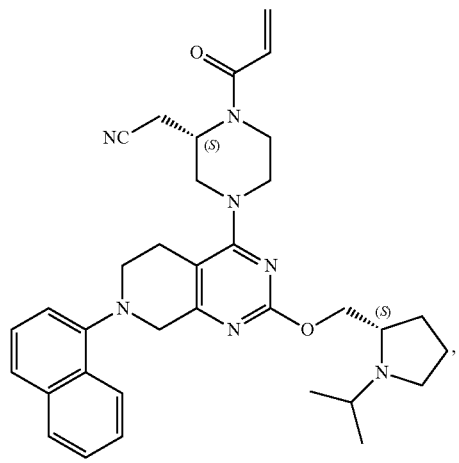
108
-continued
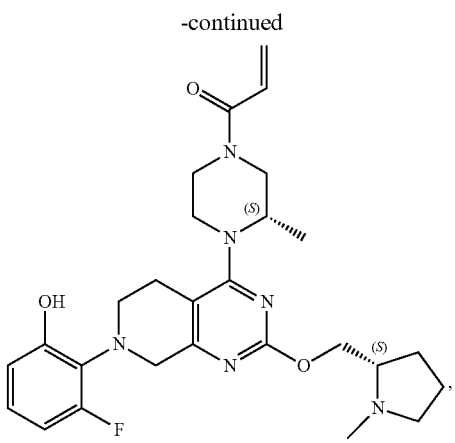
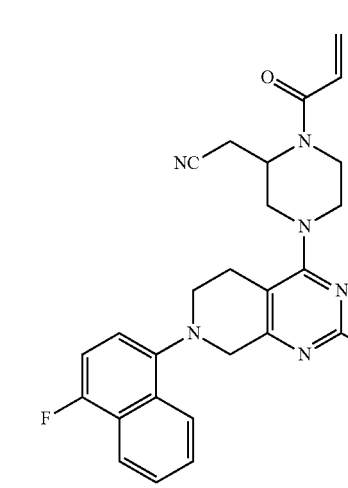
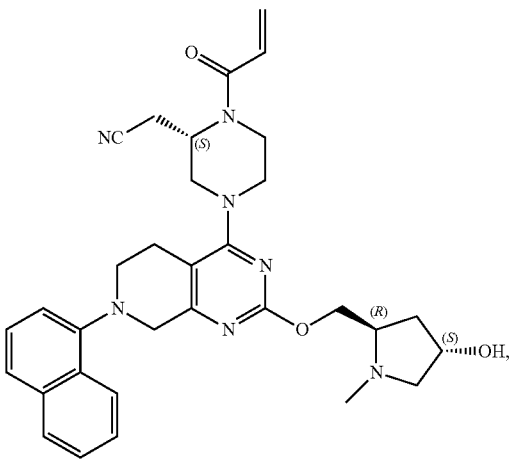

109
-continued
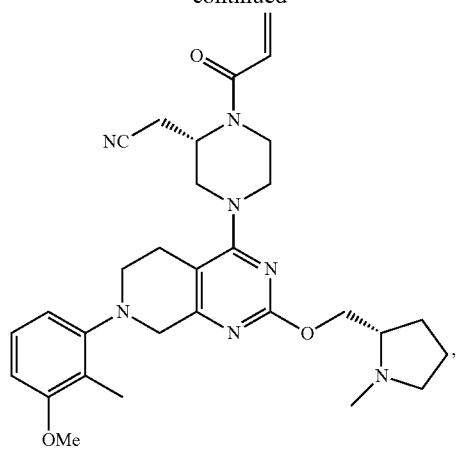
110
-continued
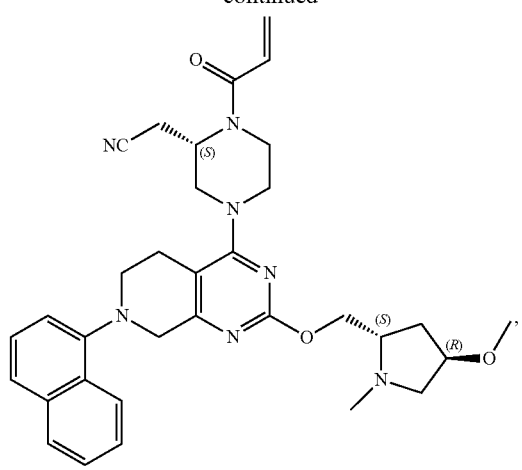
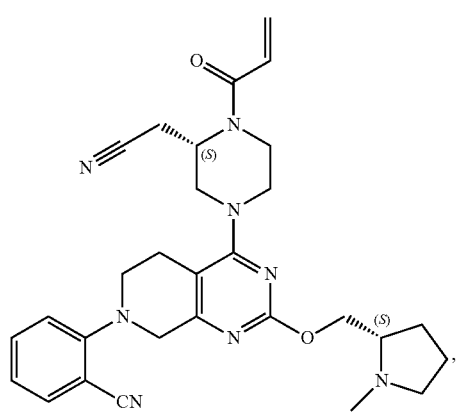
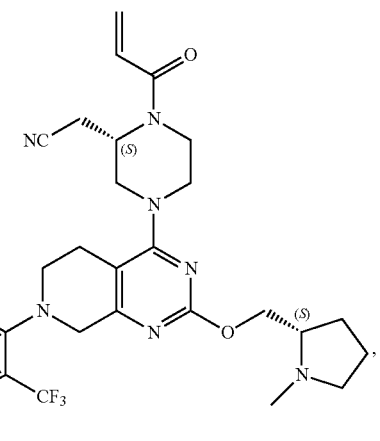
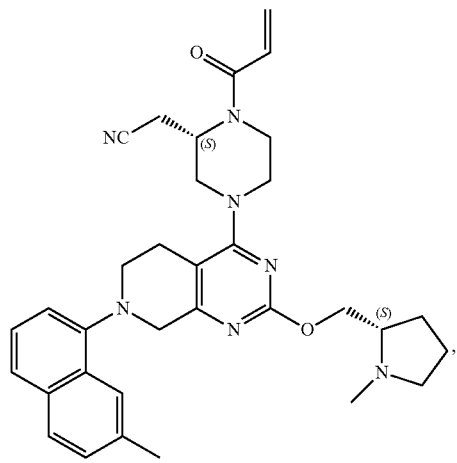
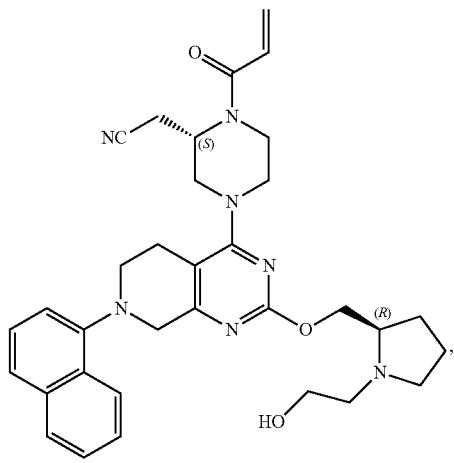

111
-continued
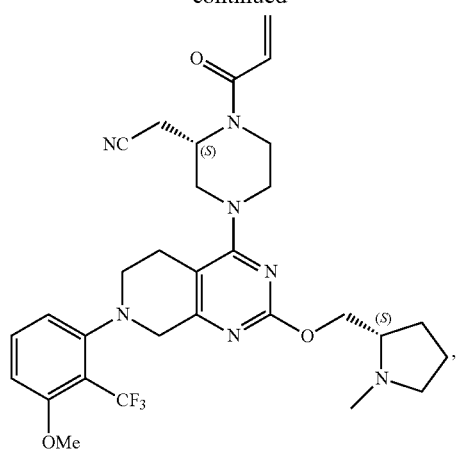
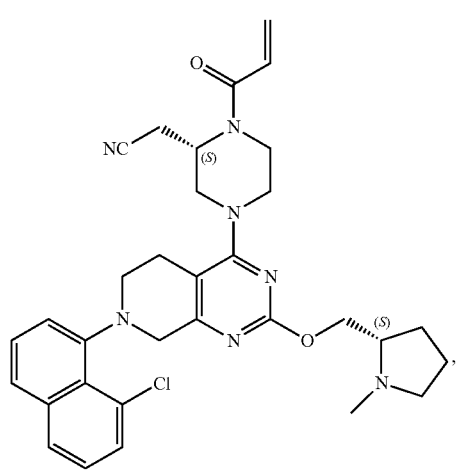
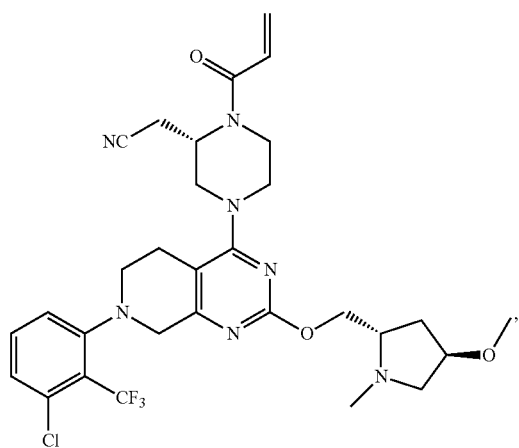
112
-continued
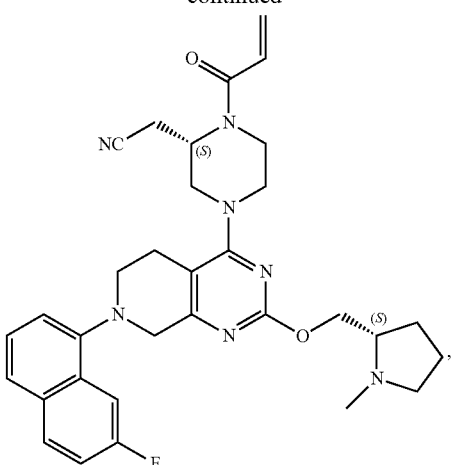
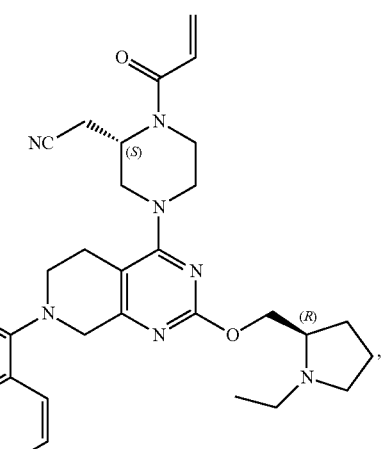
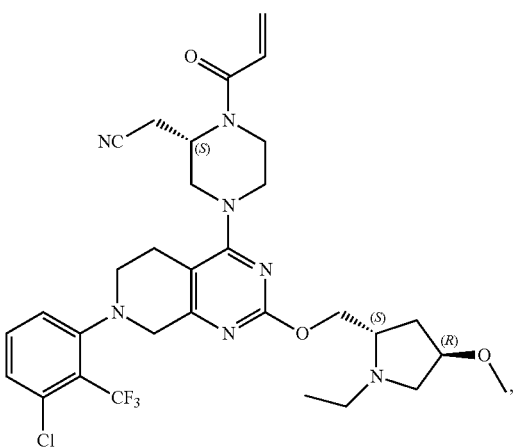

113
-continued

114
-continued

115
-continued
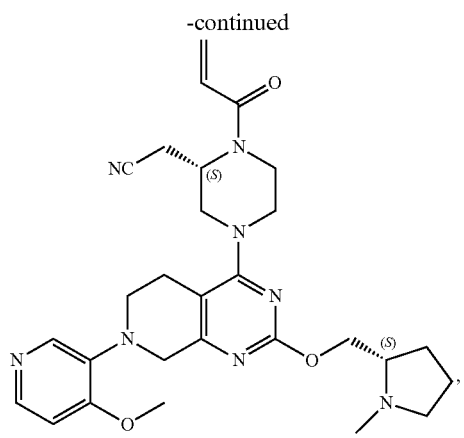
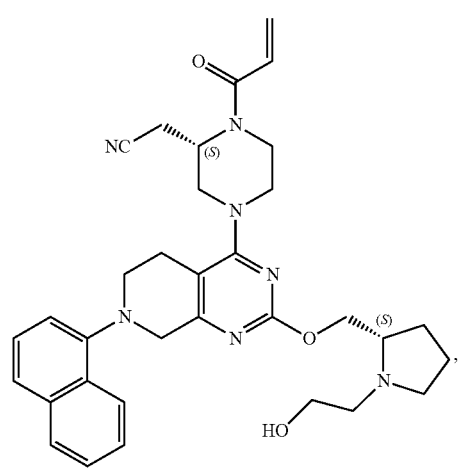
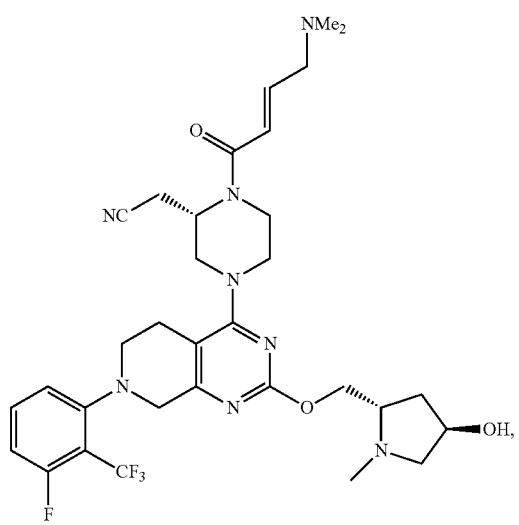
116
-continued
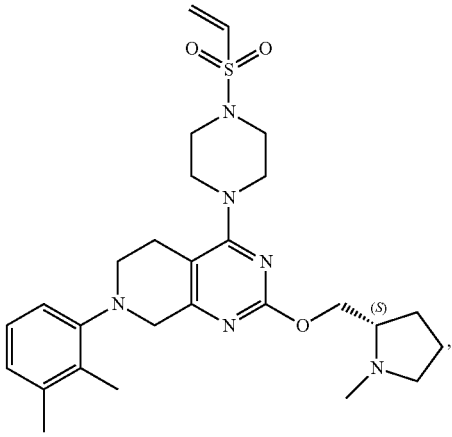
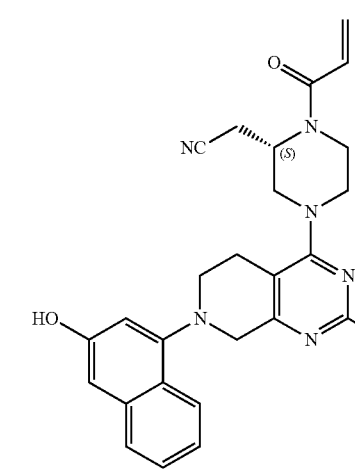
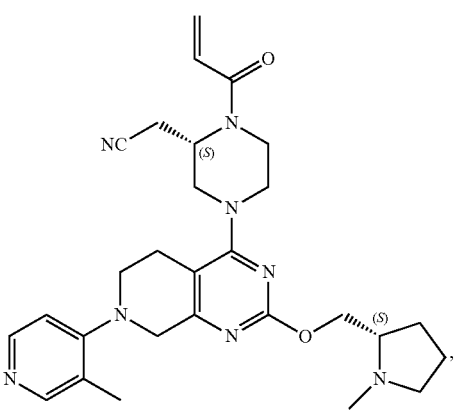

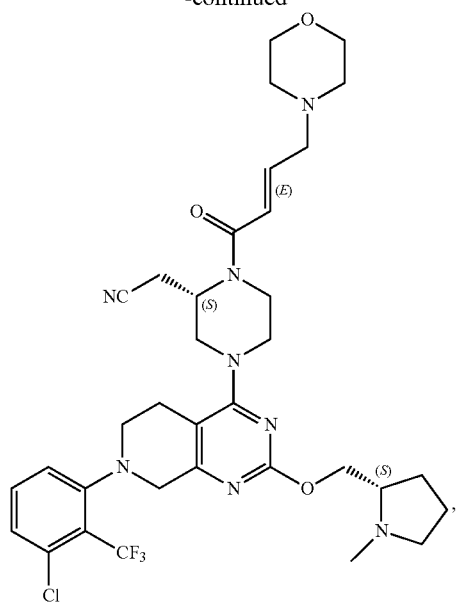
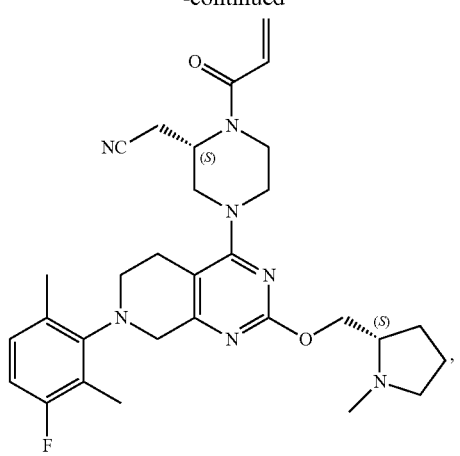
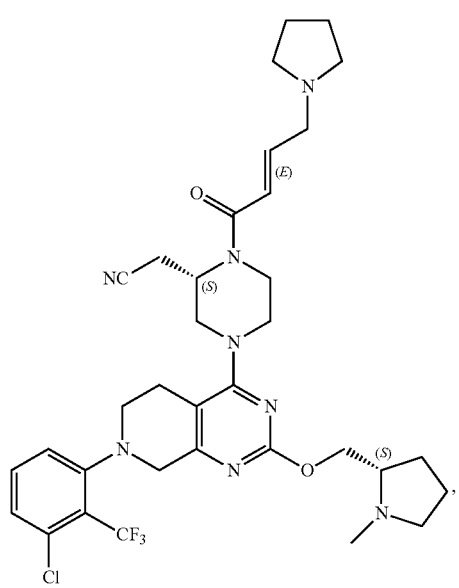
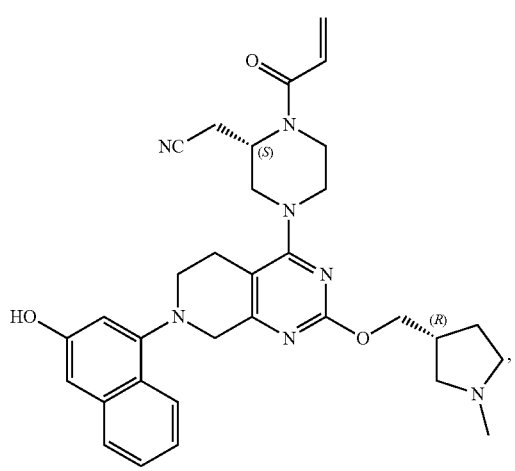
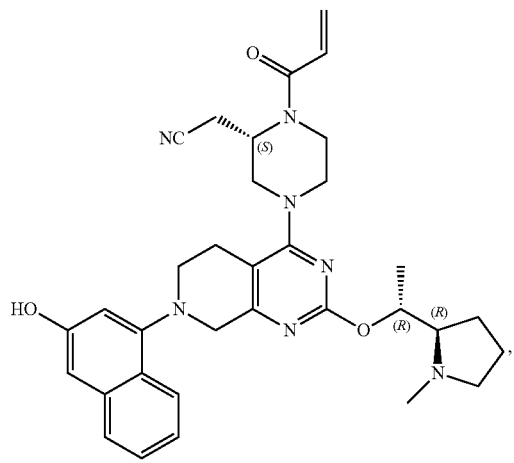
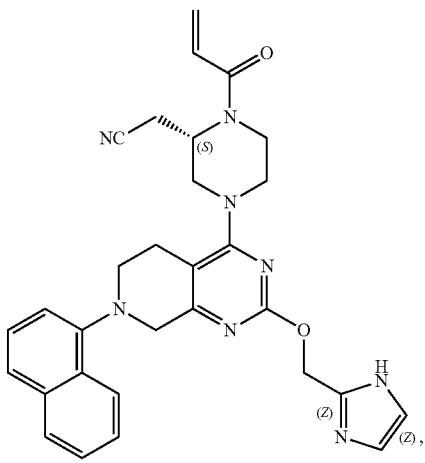

119 -continued

120 -continued

121
-continued
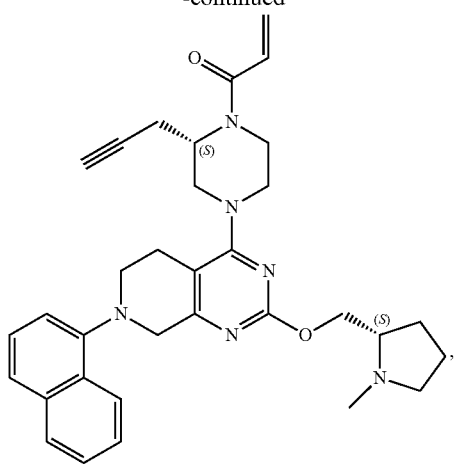
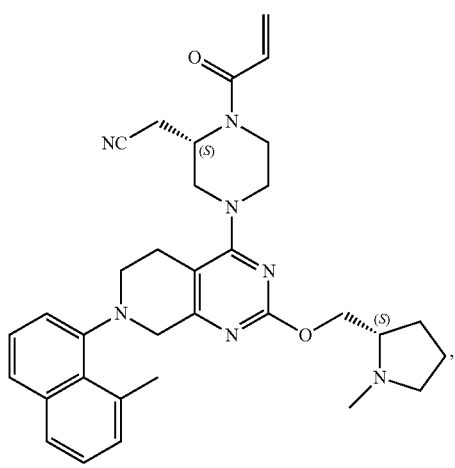
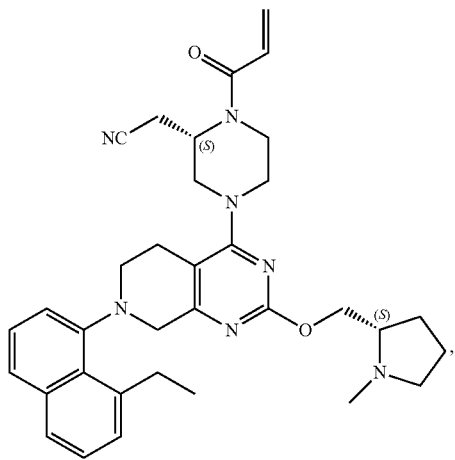
122
-continued
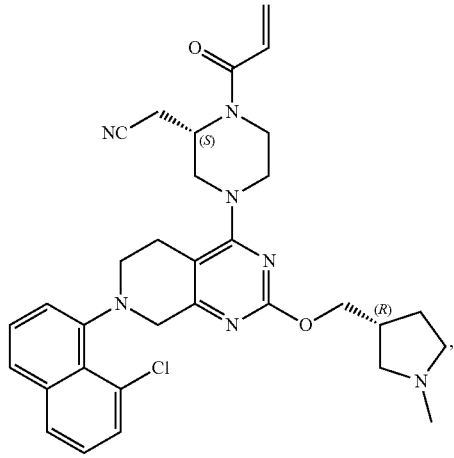
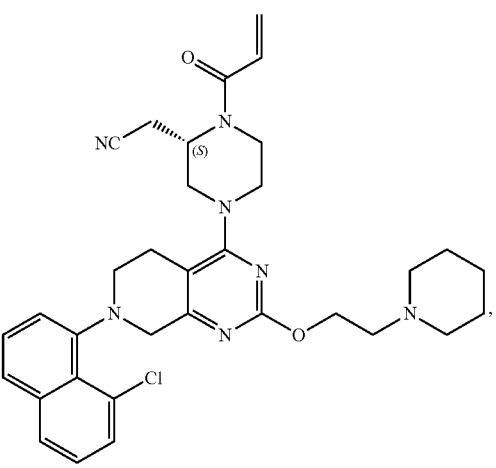
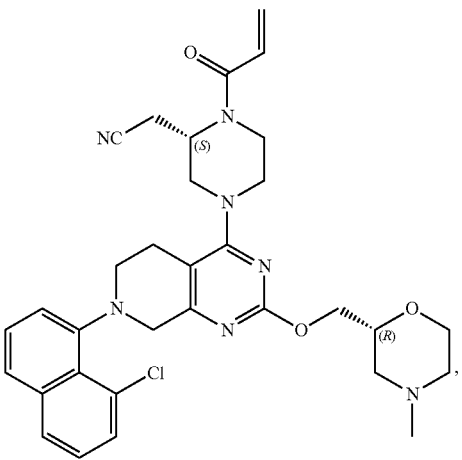

123
-continued
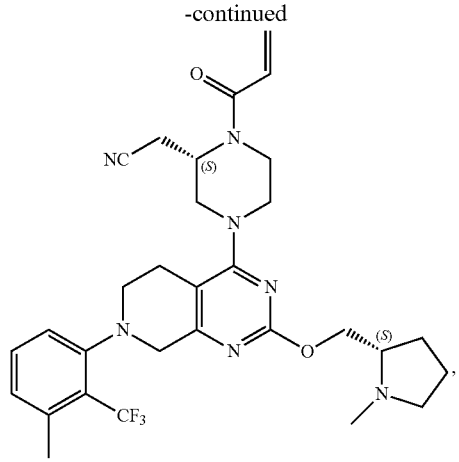
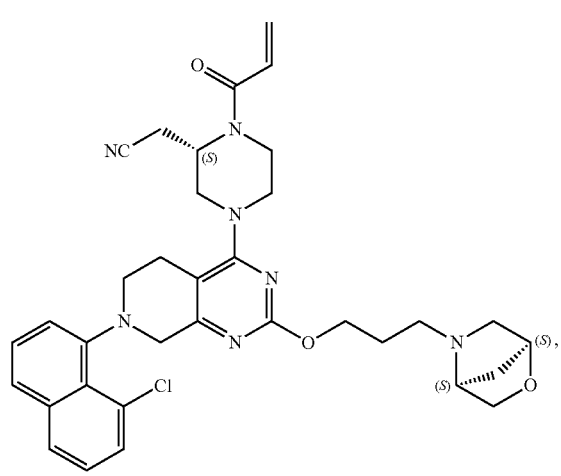
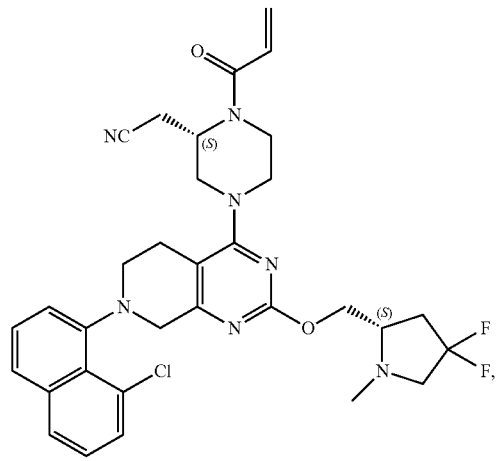
124
-continued
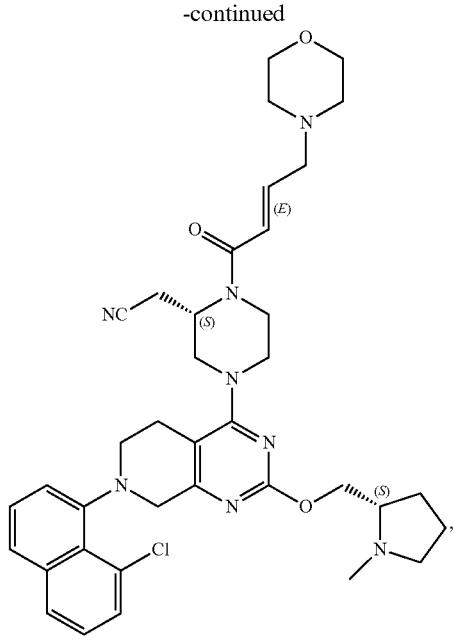
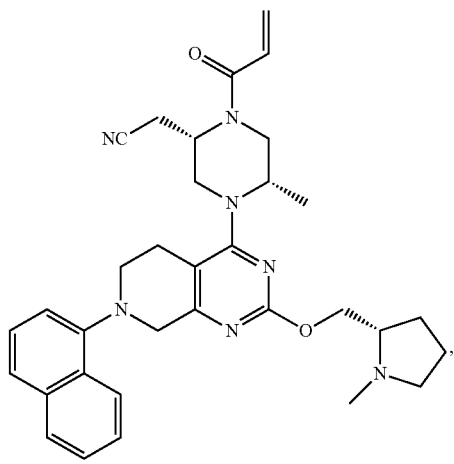
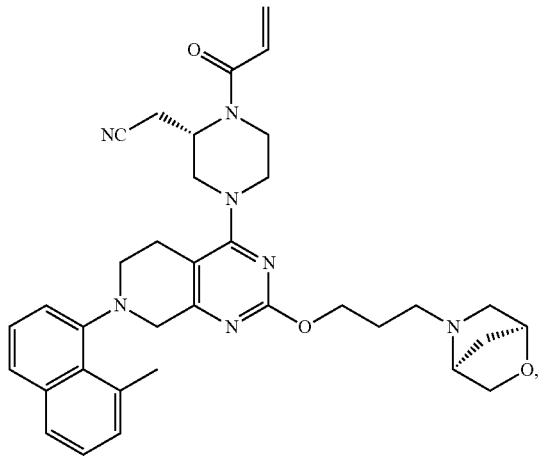

125
-continued
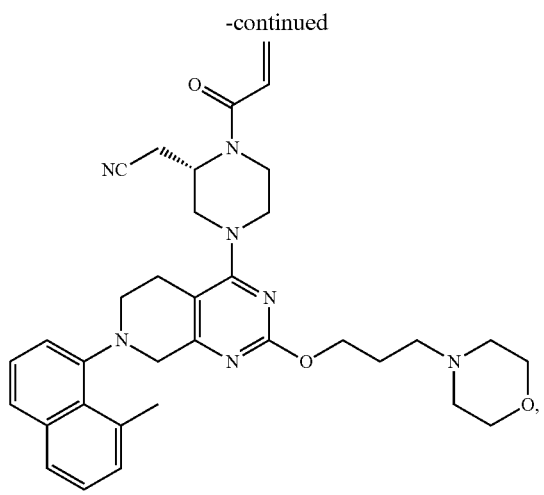
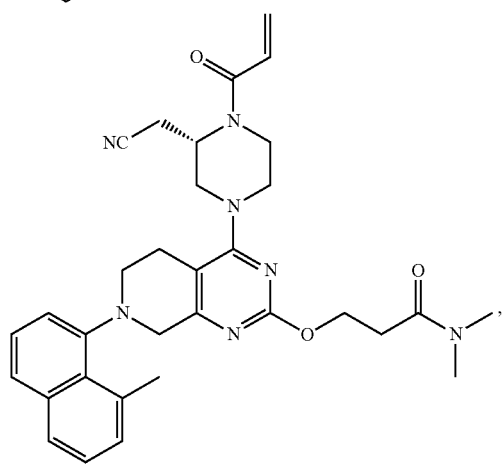
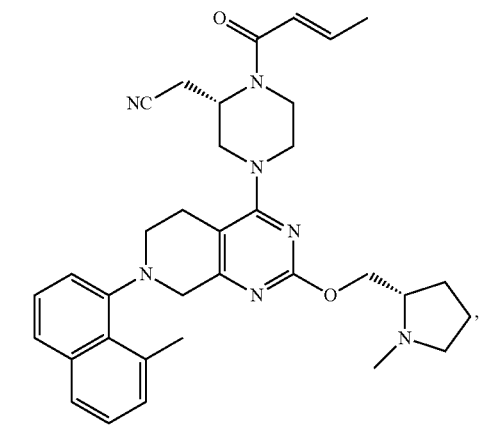
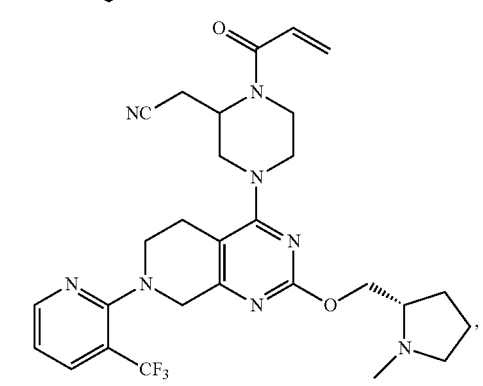
126
-continued
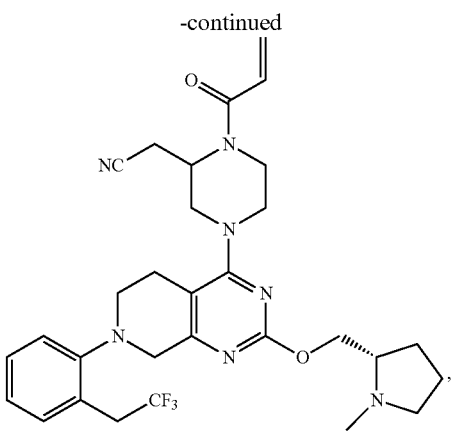
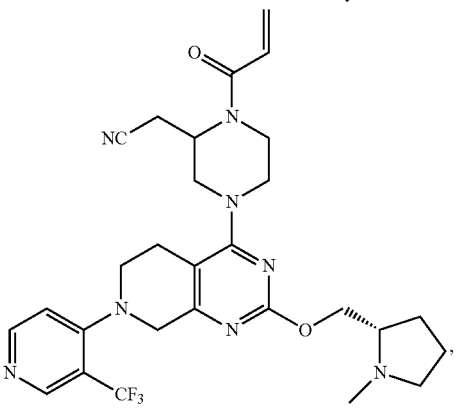
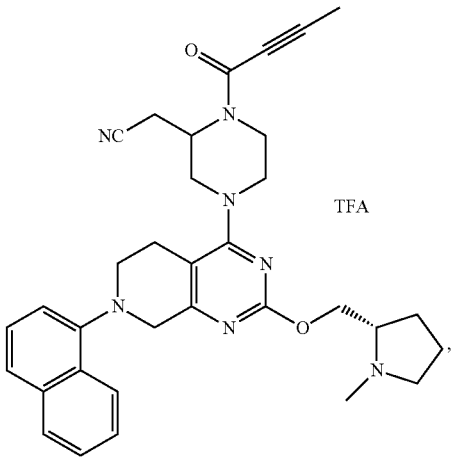

127
-continued
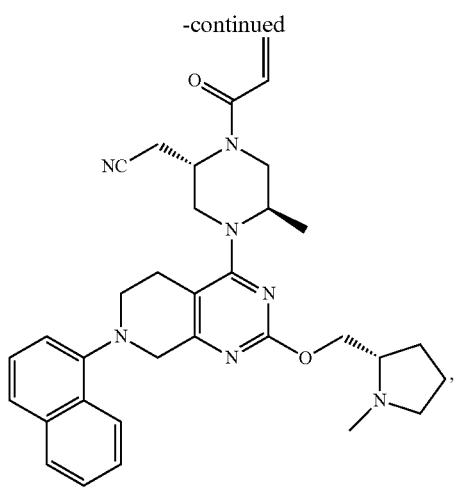
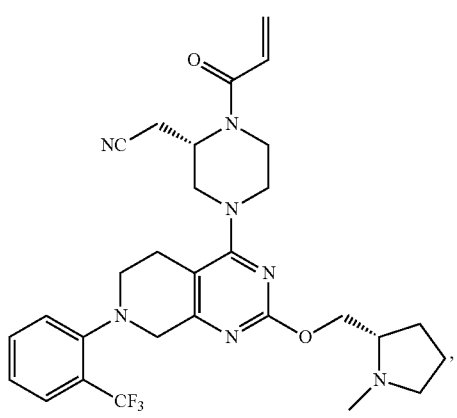
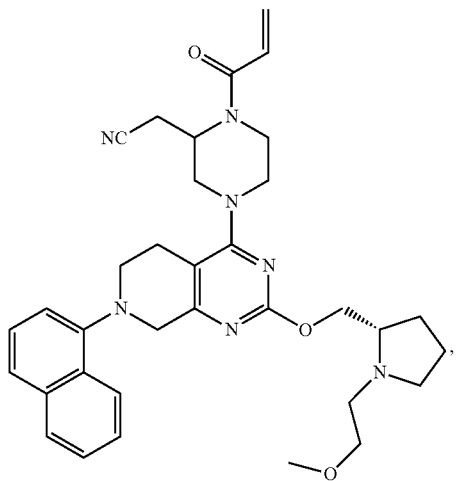
128
-continued
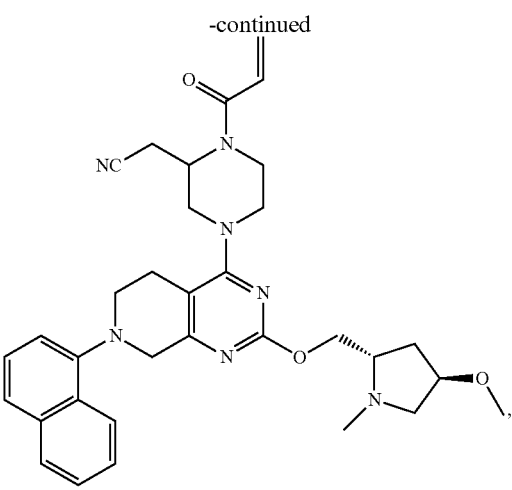
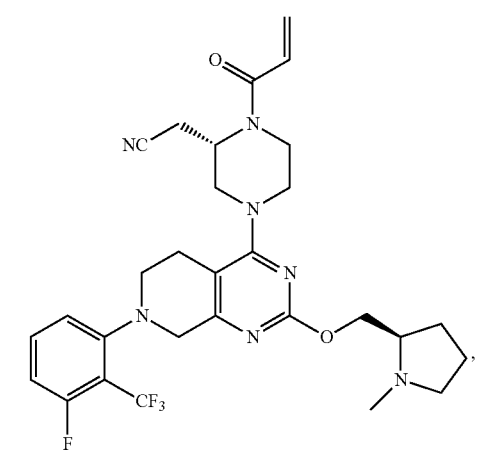
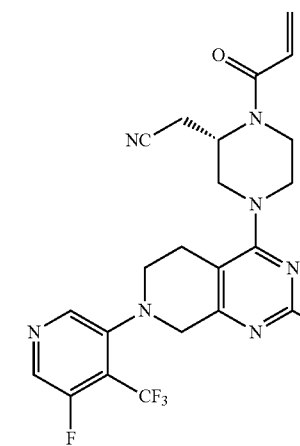

129
-continued
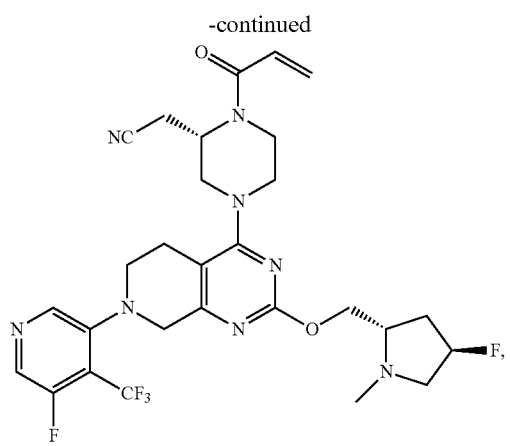
130
-continued
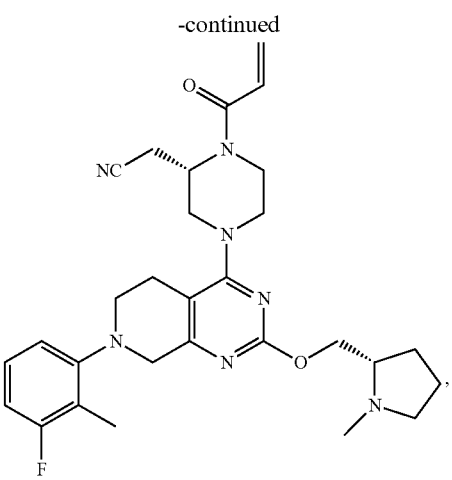
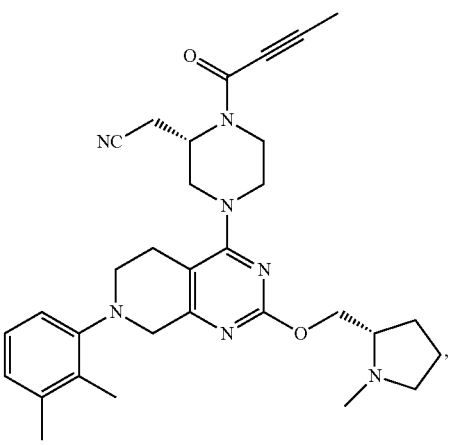
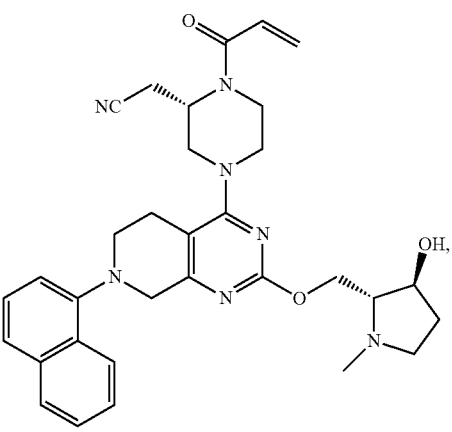

131
-continued
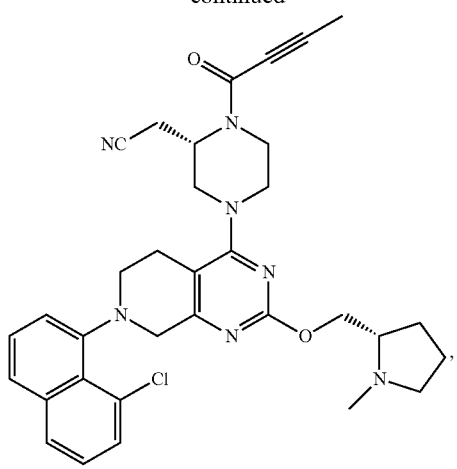
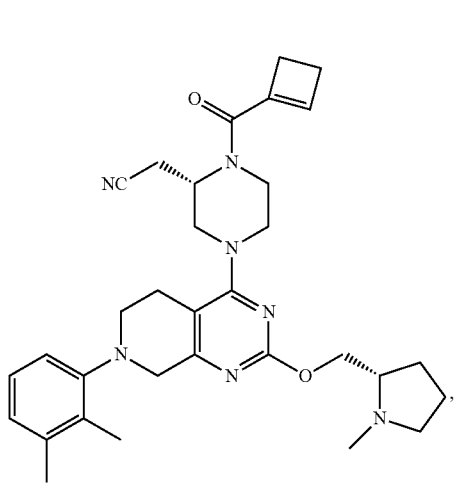
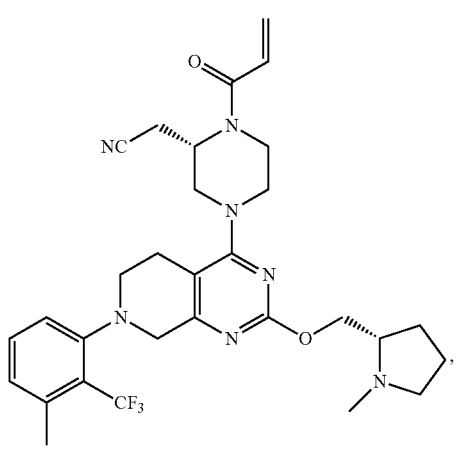
132
-continued
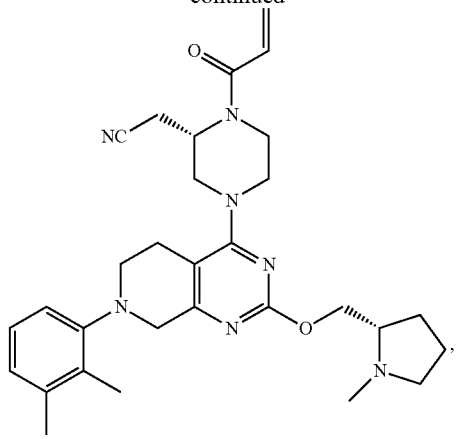
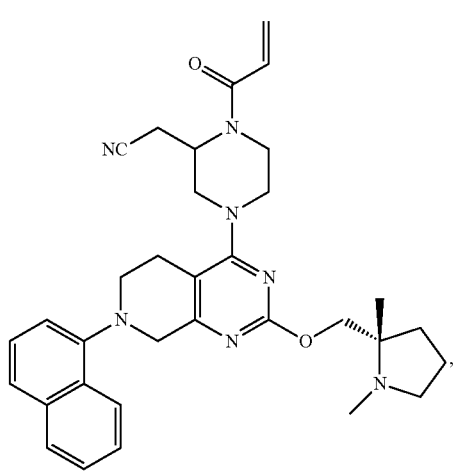
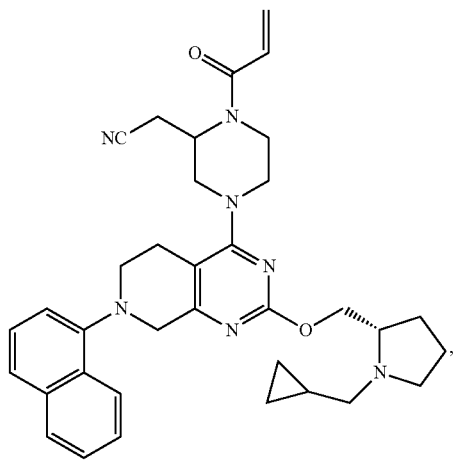

-continued
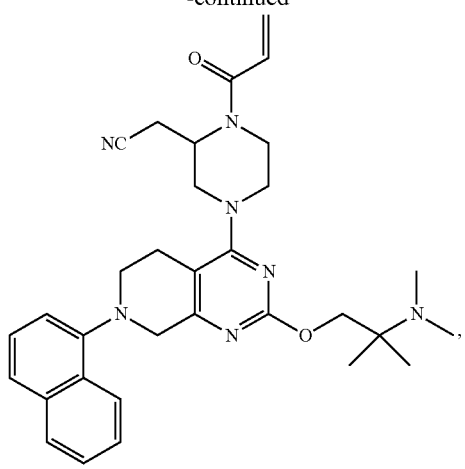
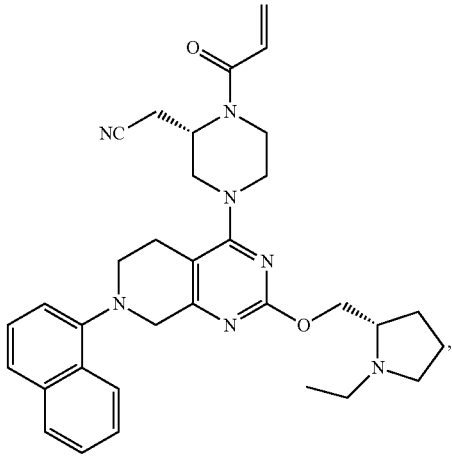
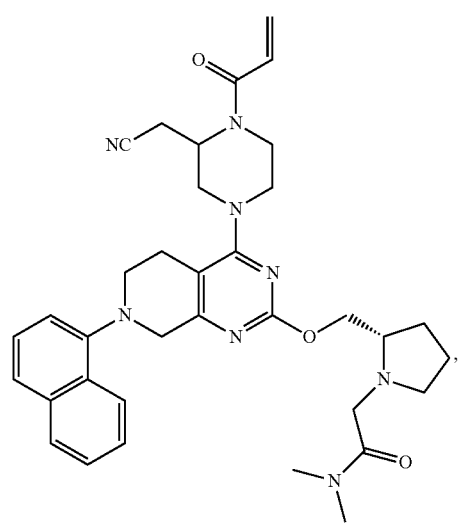
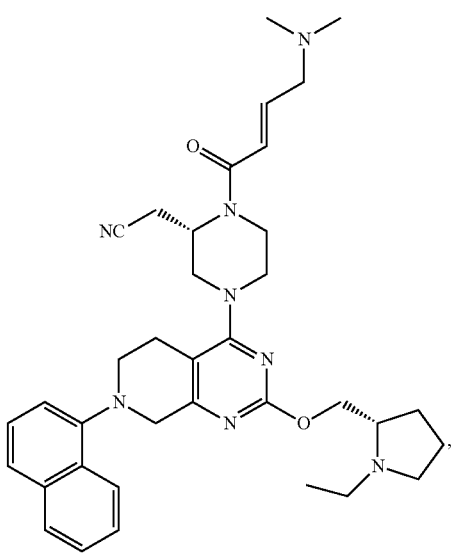
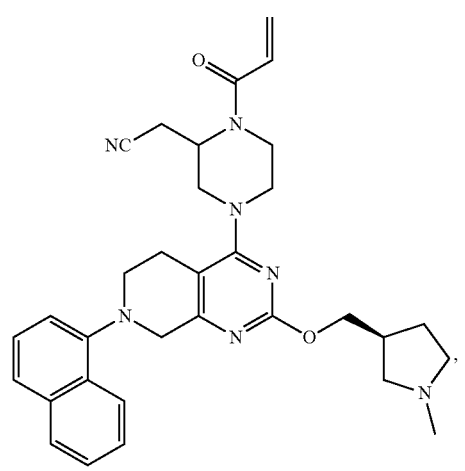
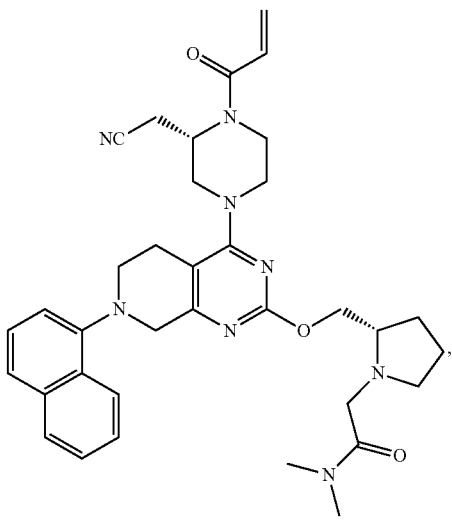

135
-continued
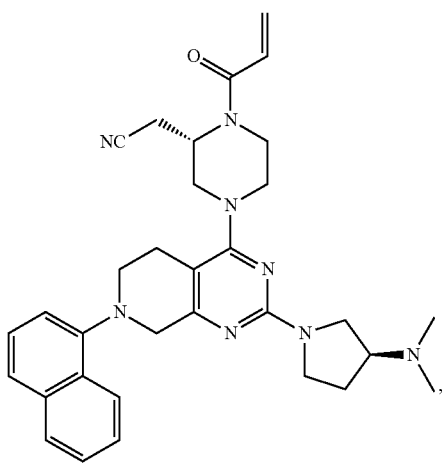
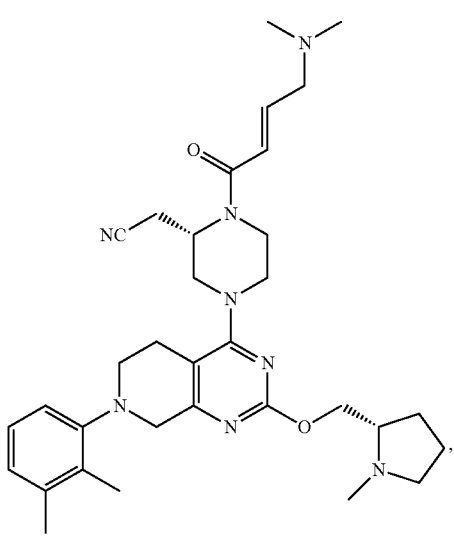
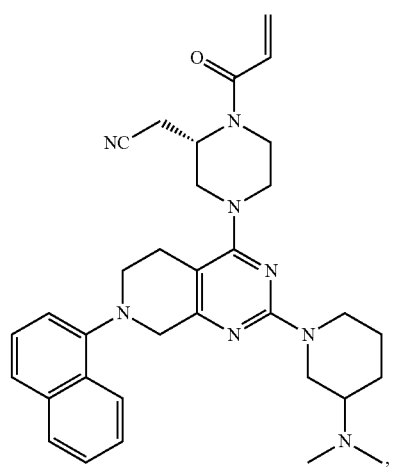
136
-continued
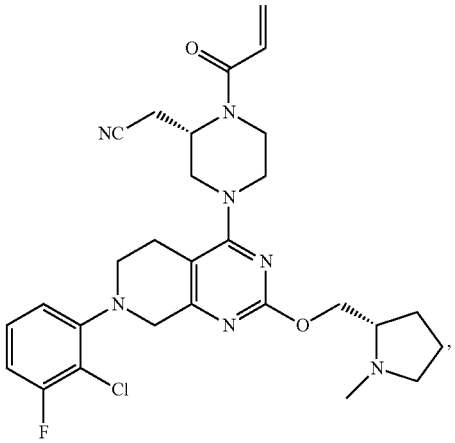
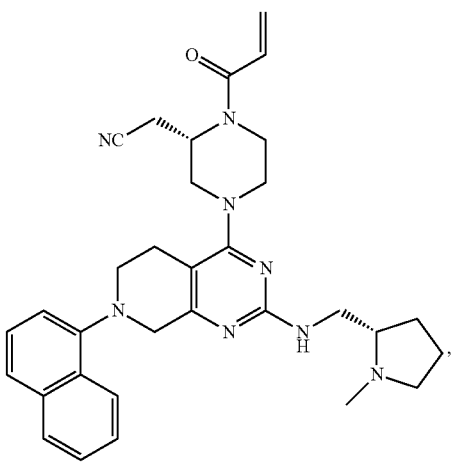

137
-continued
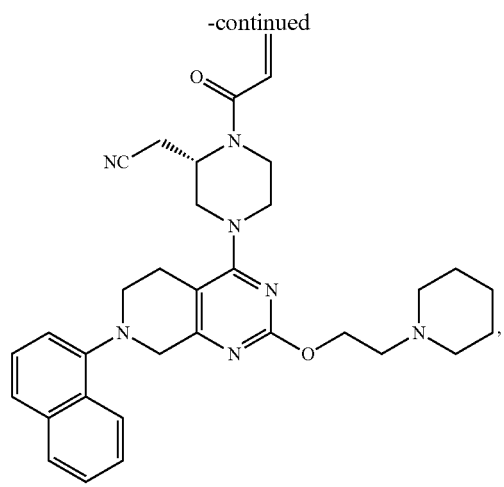
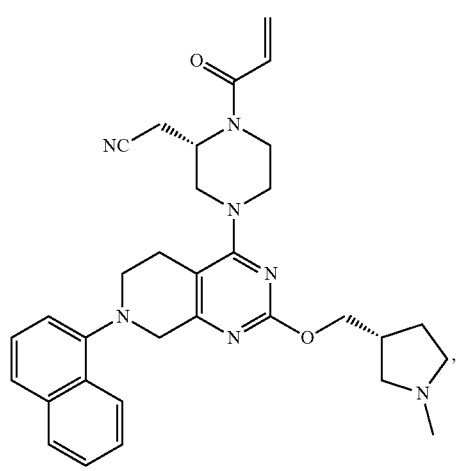
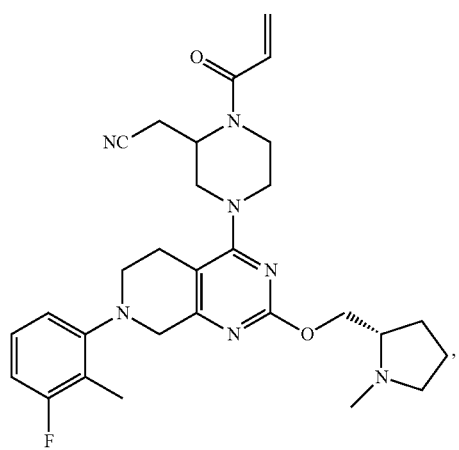
138
-continued
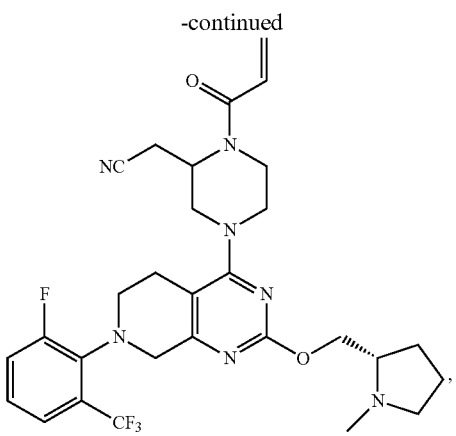
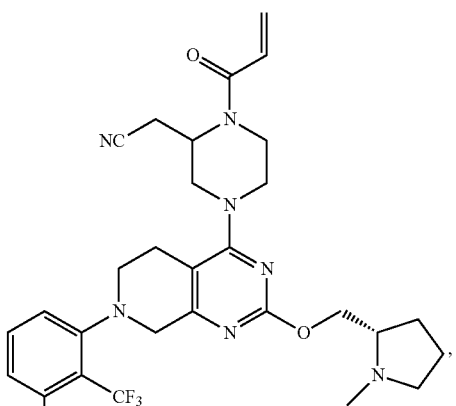
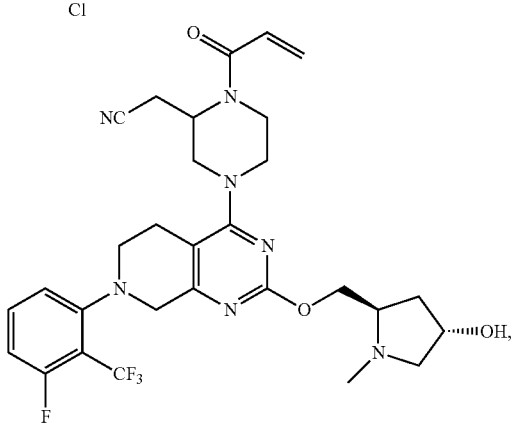

-continued
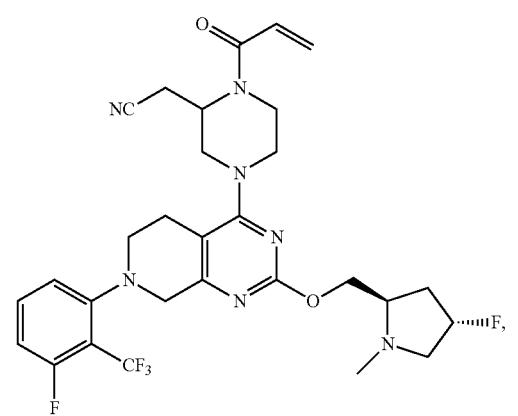
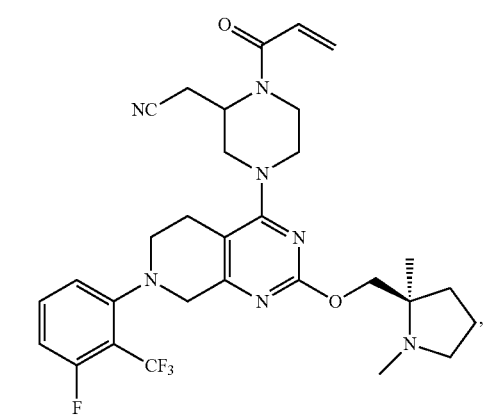
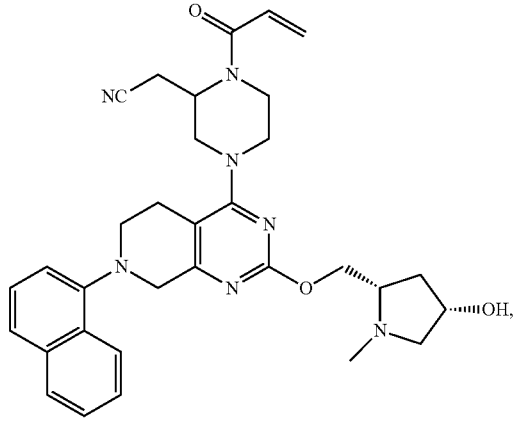
-continued
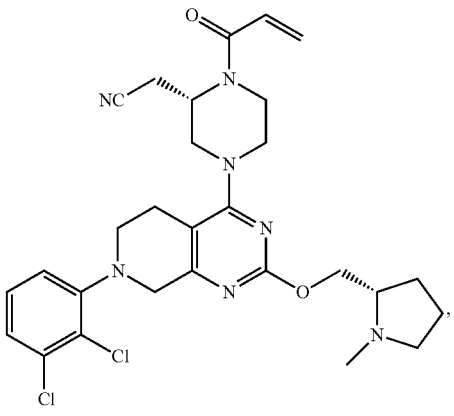
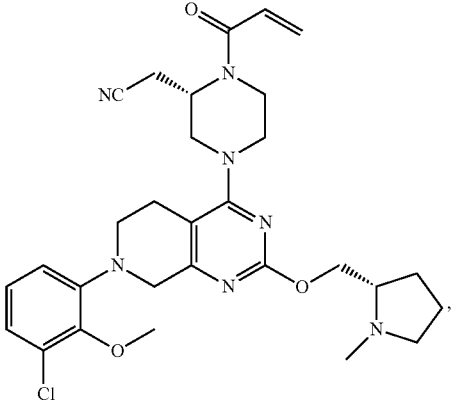
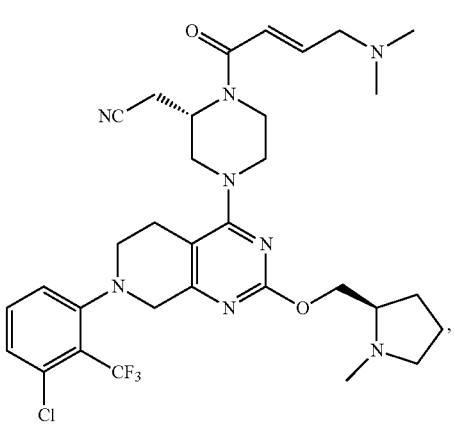

141
-continued
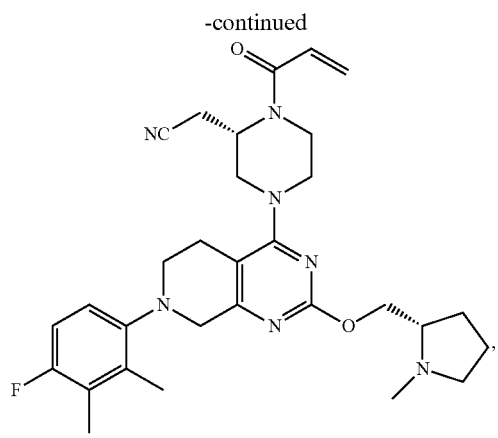
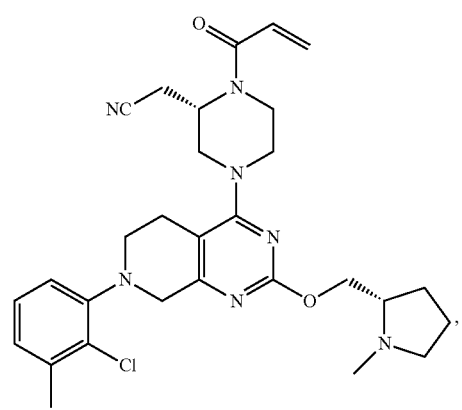
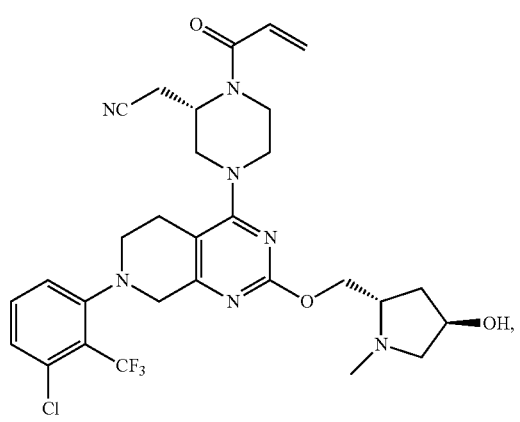
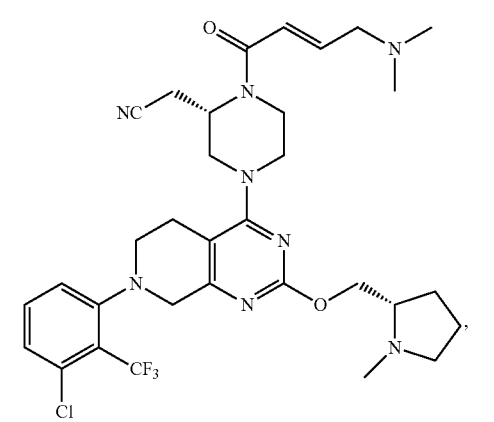
142
-continued
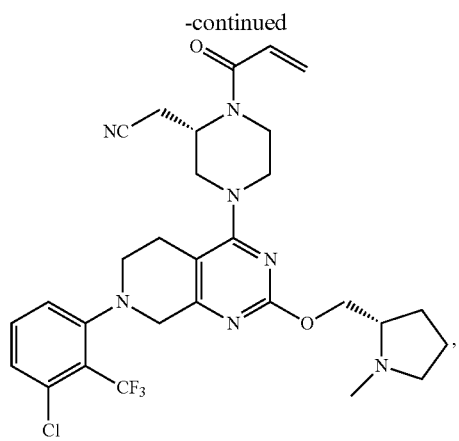
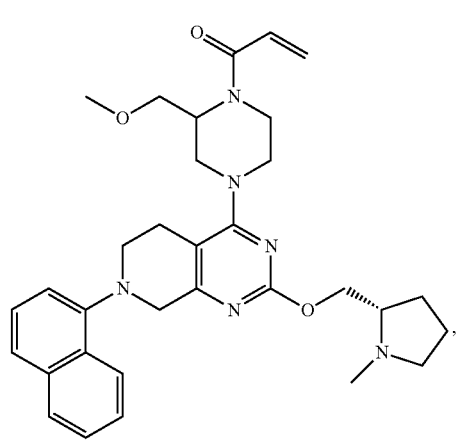
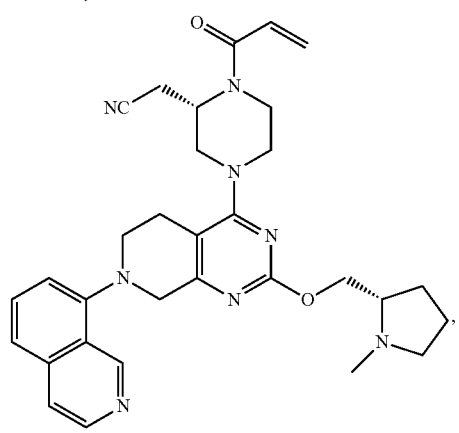
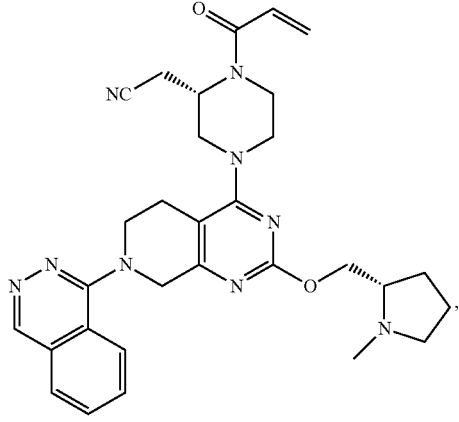

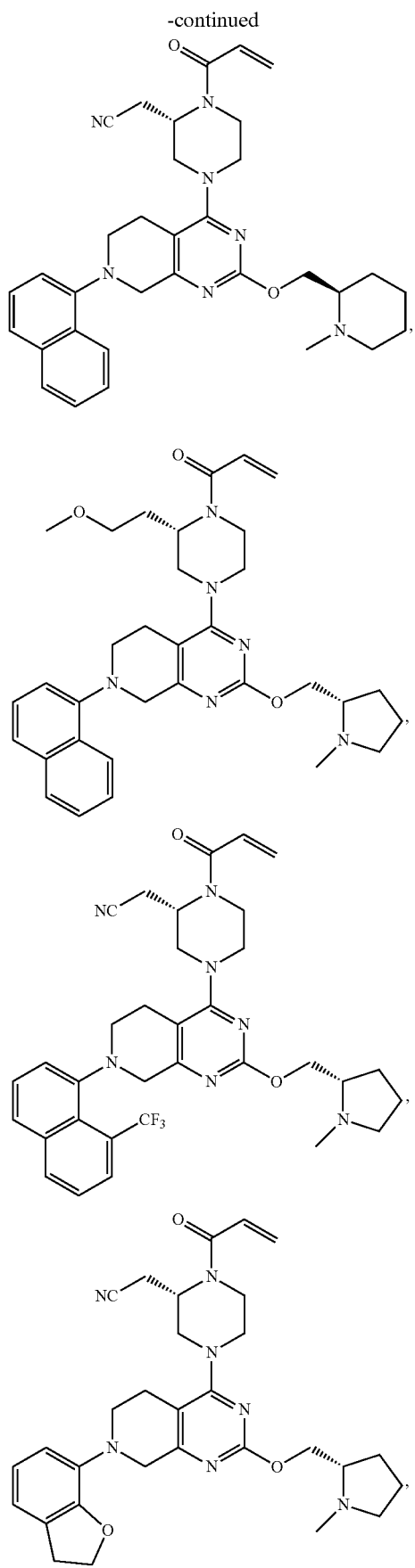

145
-continued
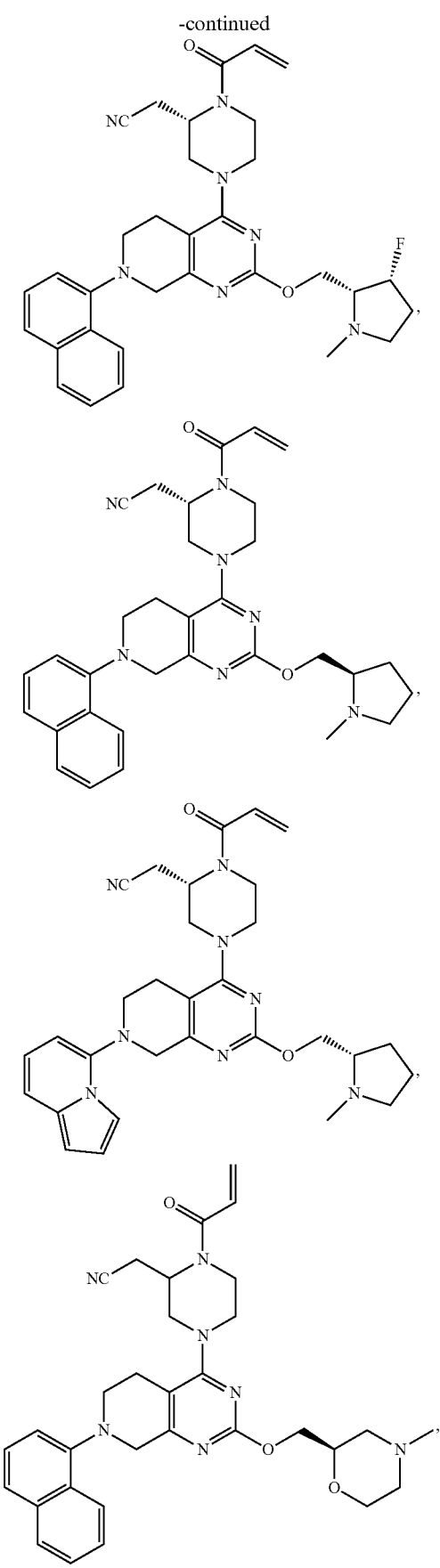
146
-continued
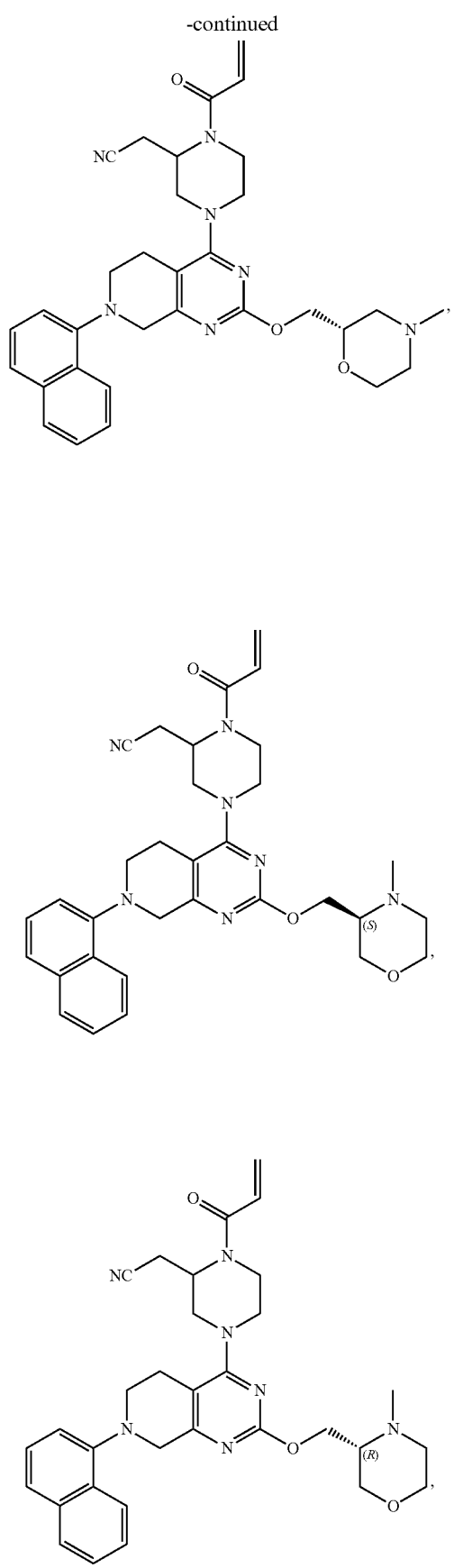

147
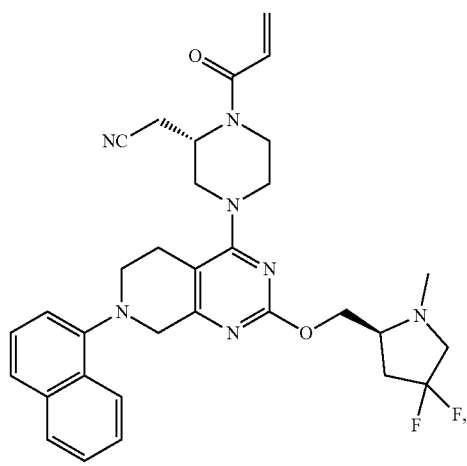
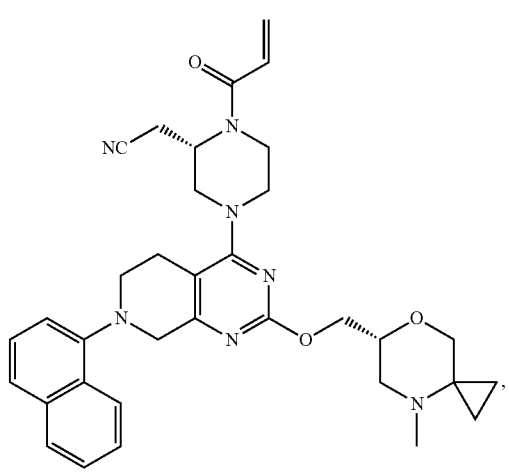
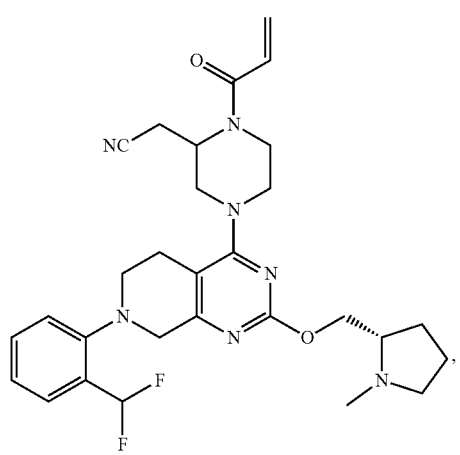
148
-continued
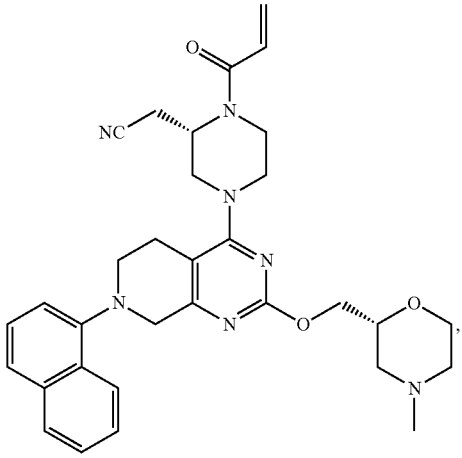
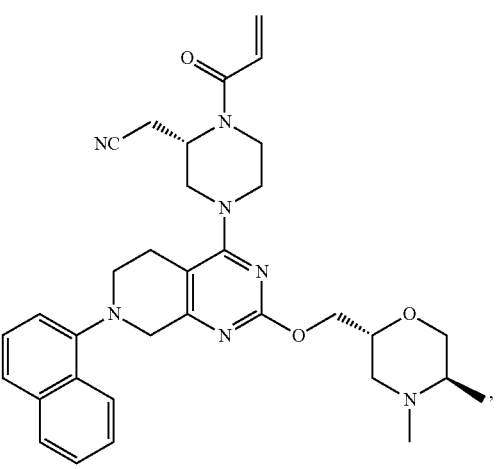
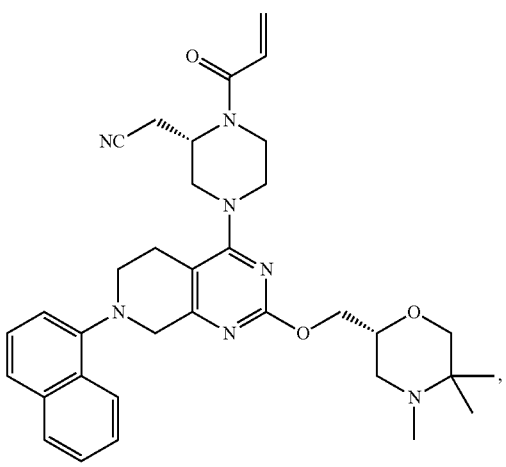

149
-continued
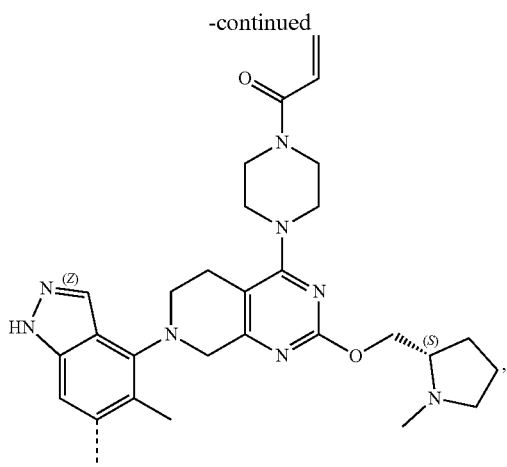
150
-continued
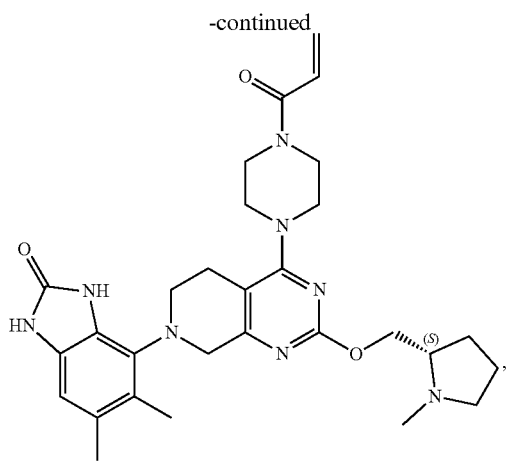
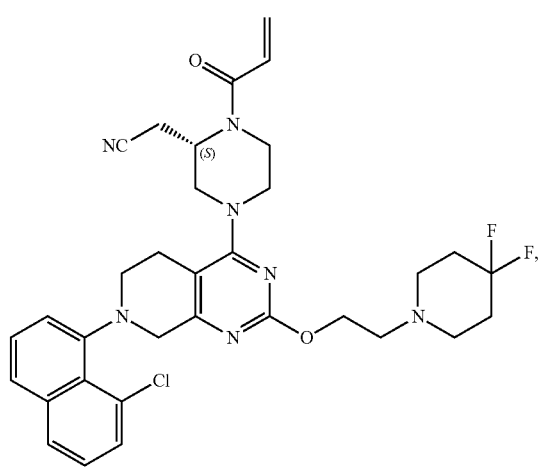
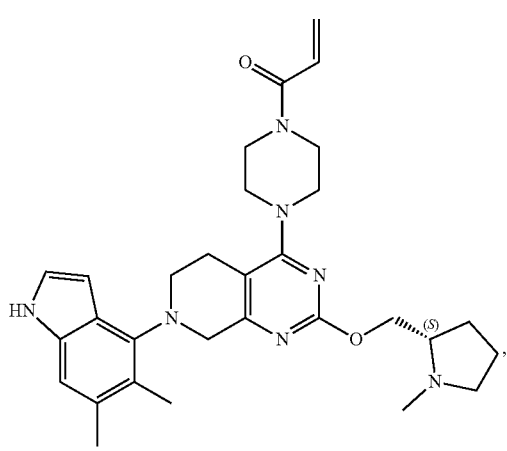
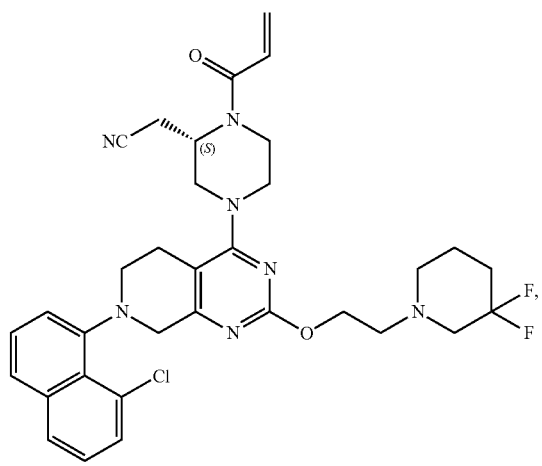
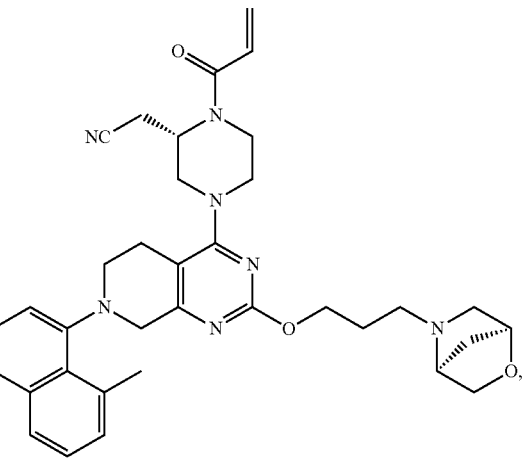

151
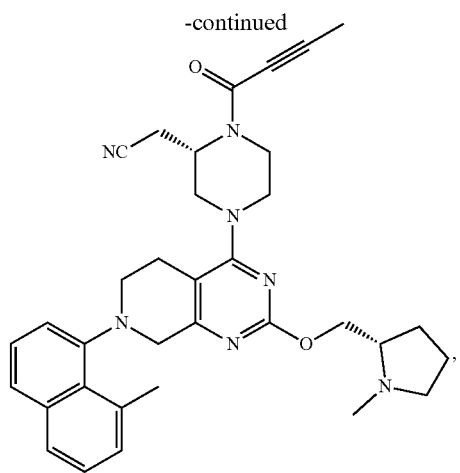
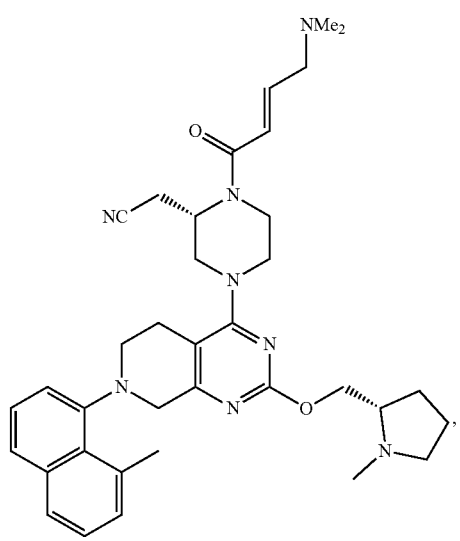
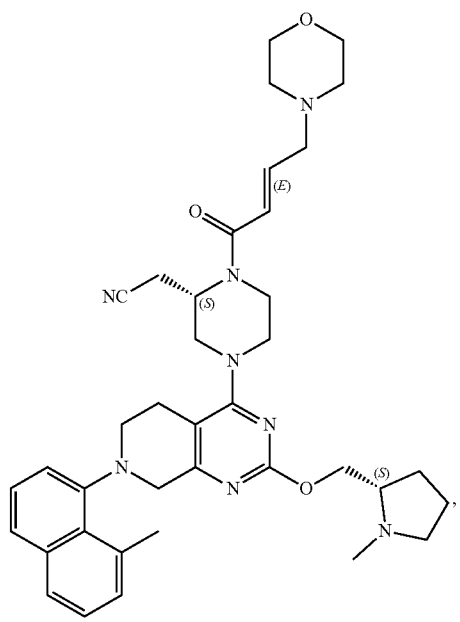
152
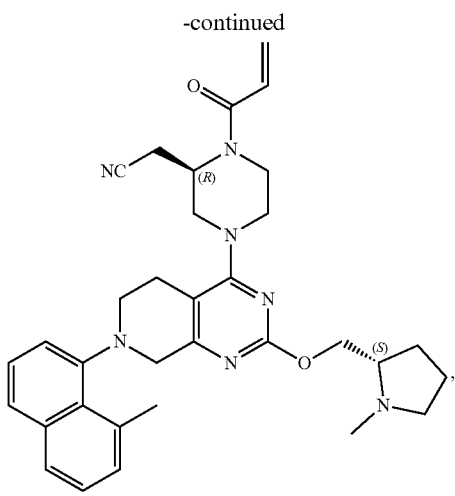
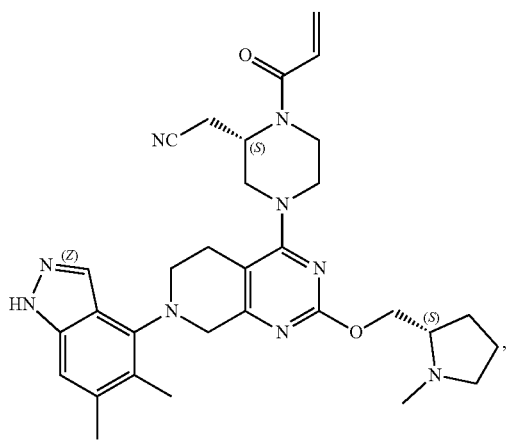
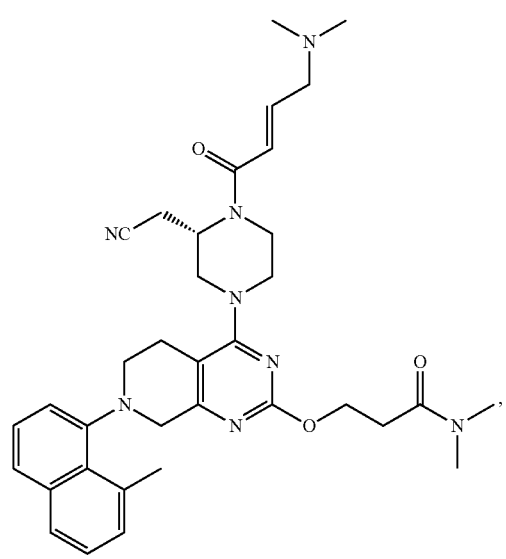

153 -continued
154 -continued
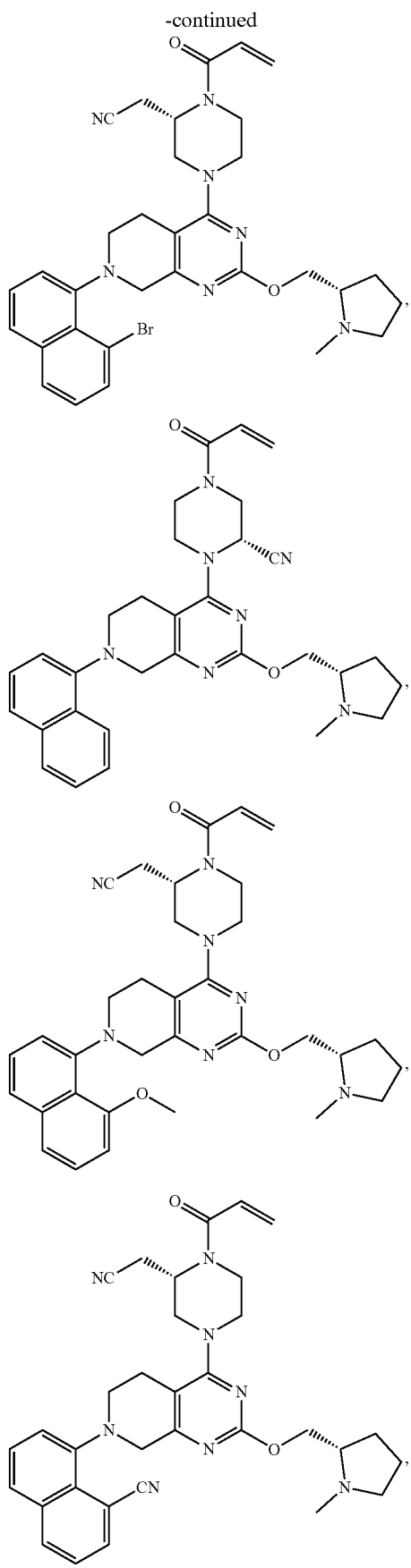

-continued
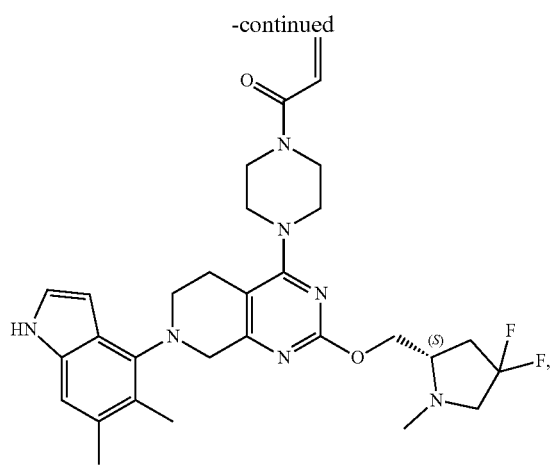
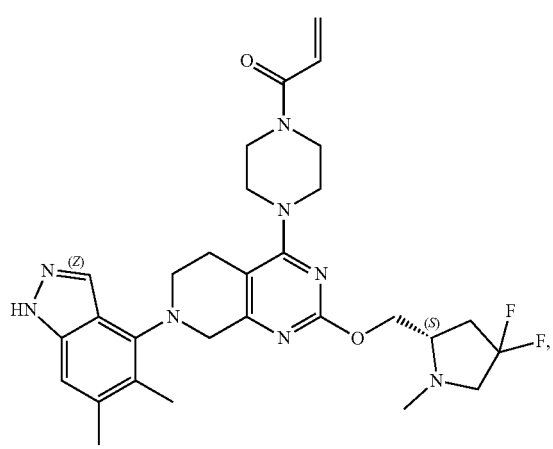
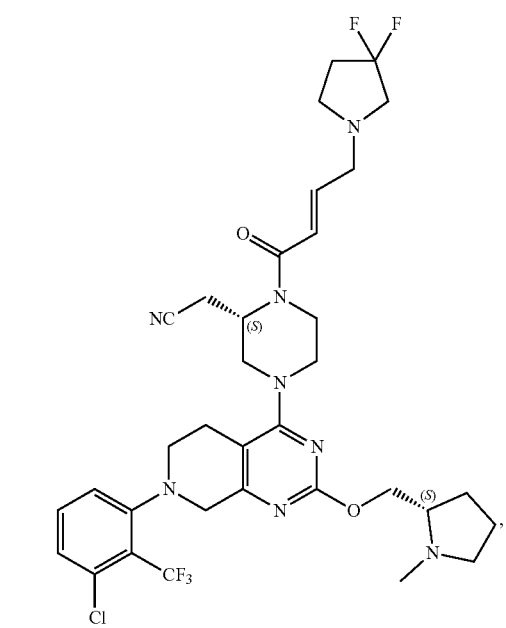
-continued
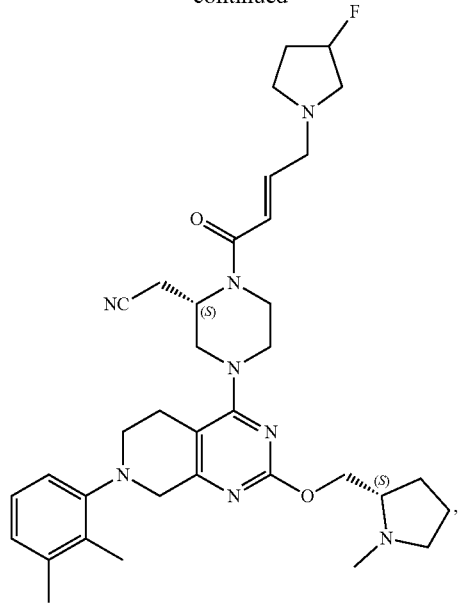
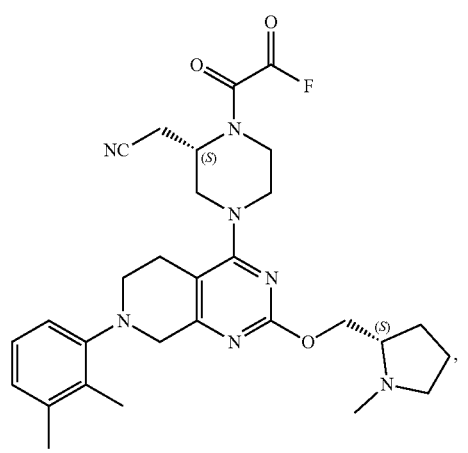
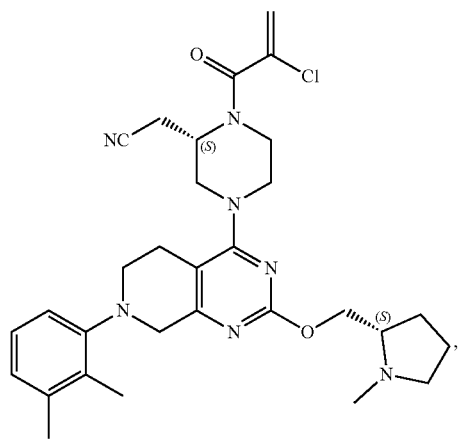

157
-continued
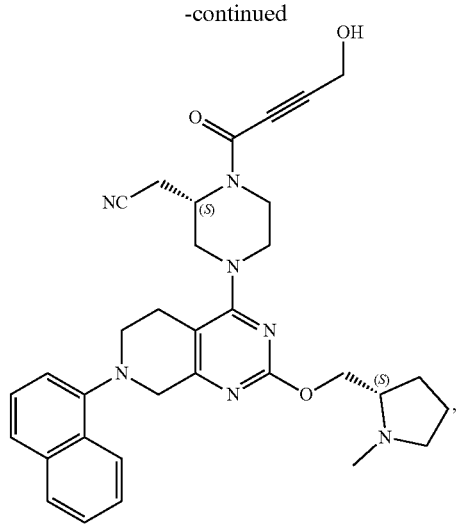
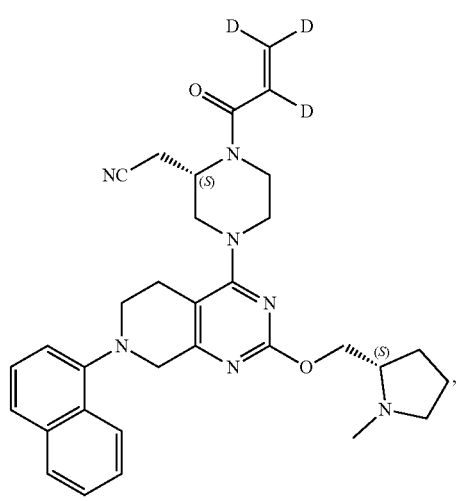
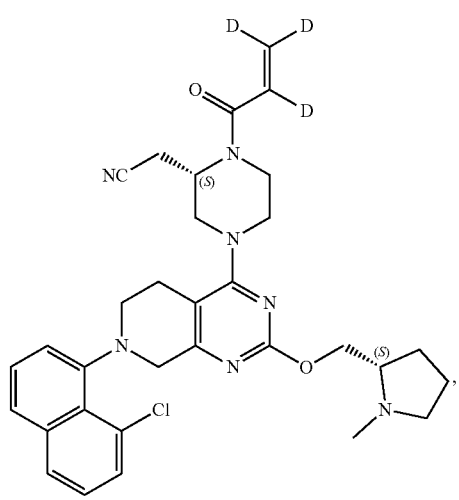
158
-continued
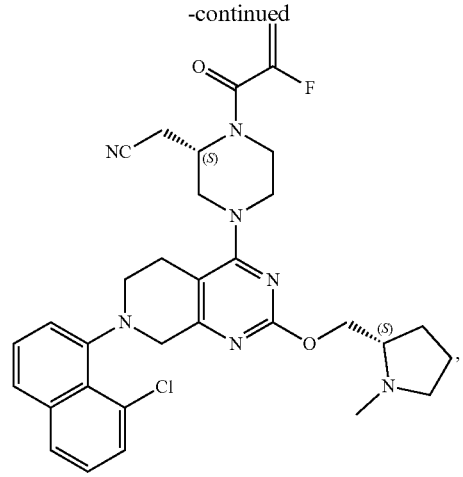
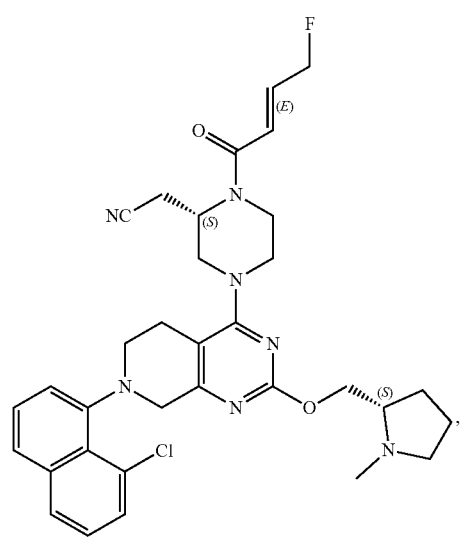
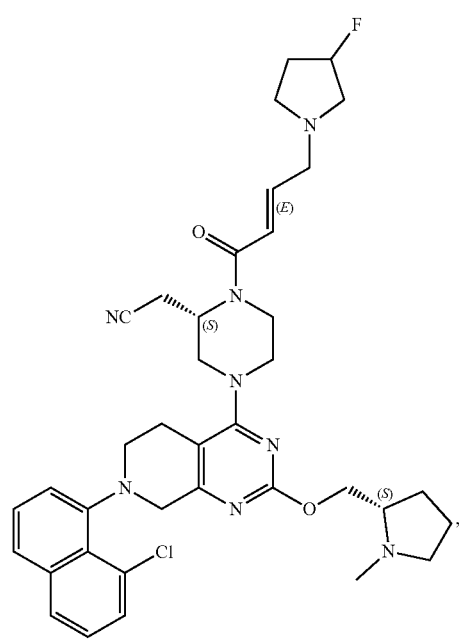

159
-continued
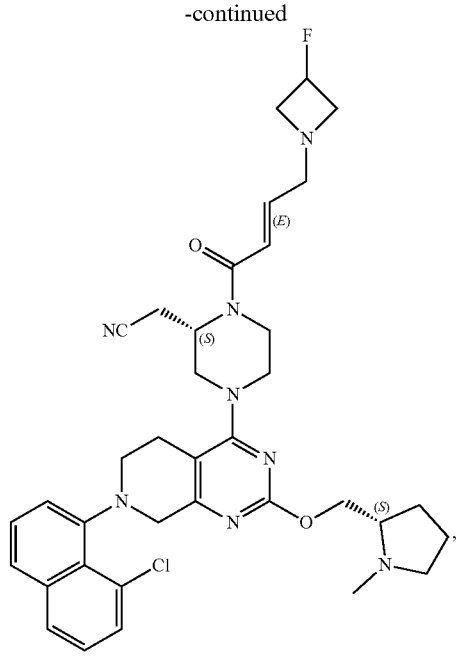
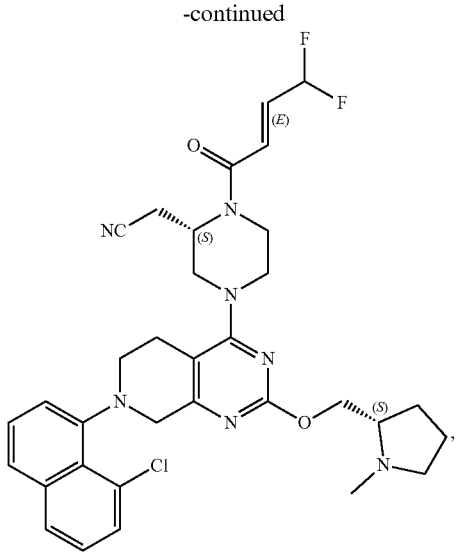
160
-continued
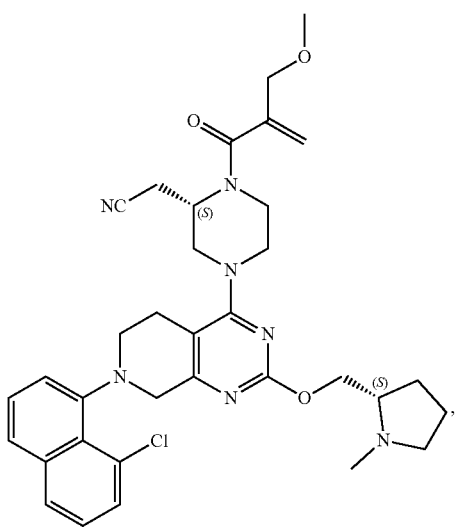
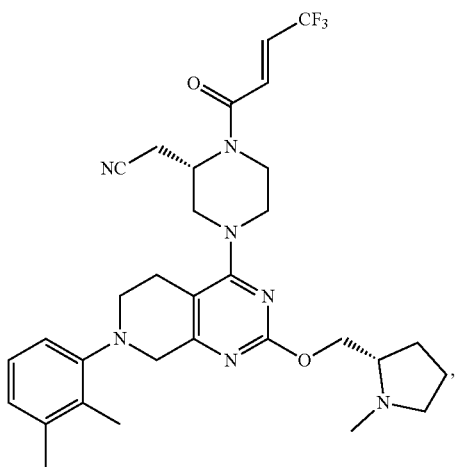

161
-continued
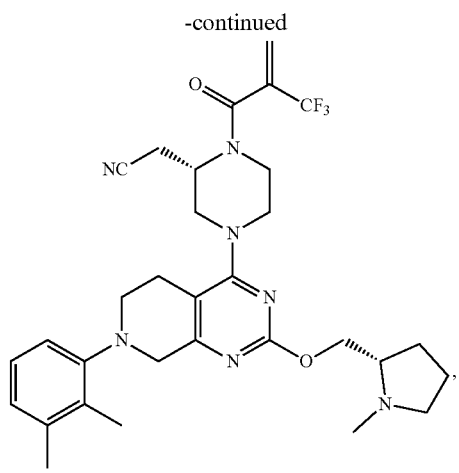
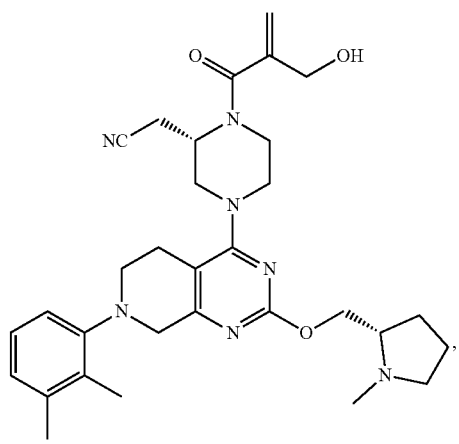
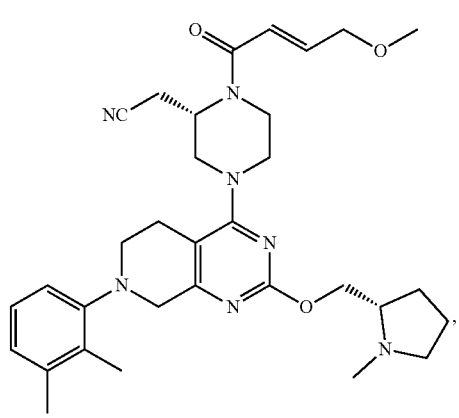
162
-continued
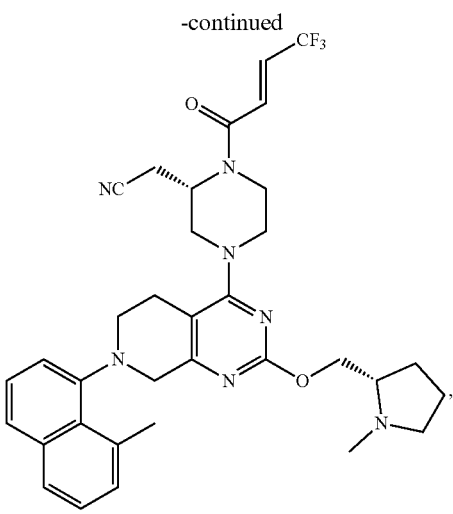
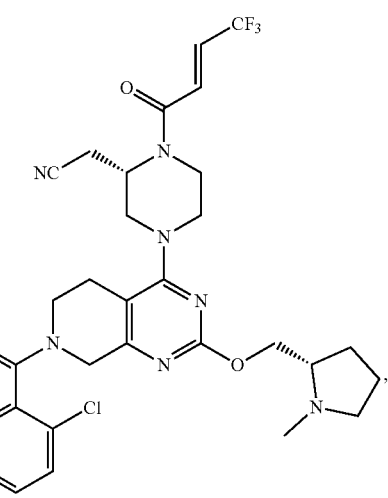
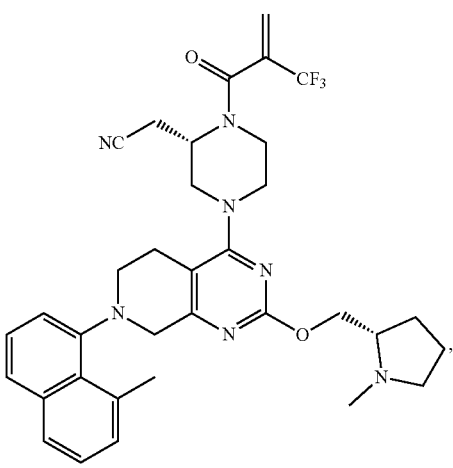

163
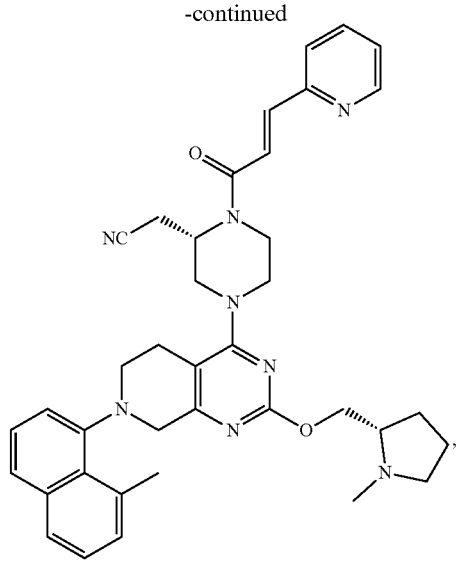
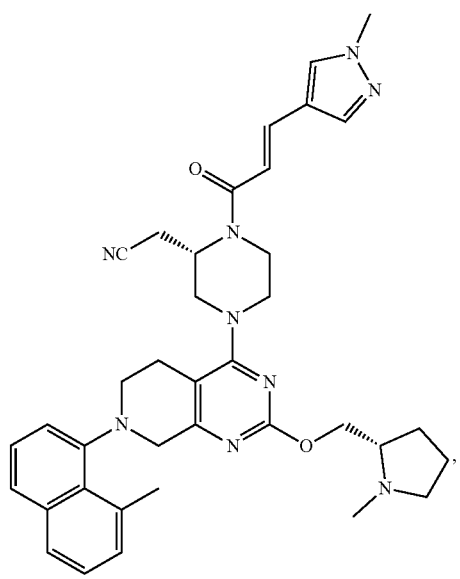
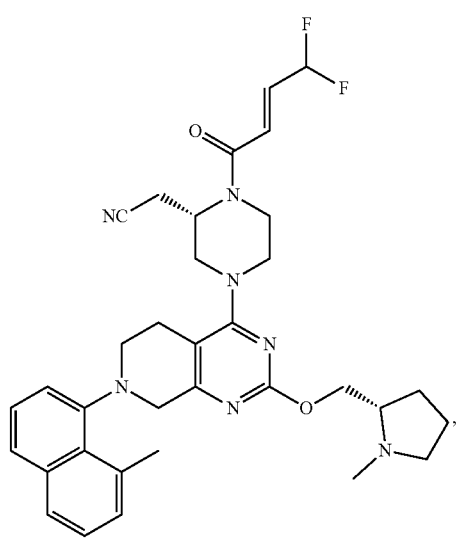
164
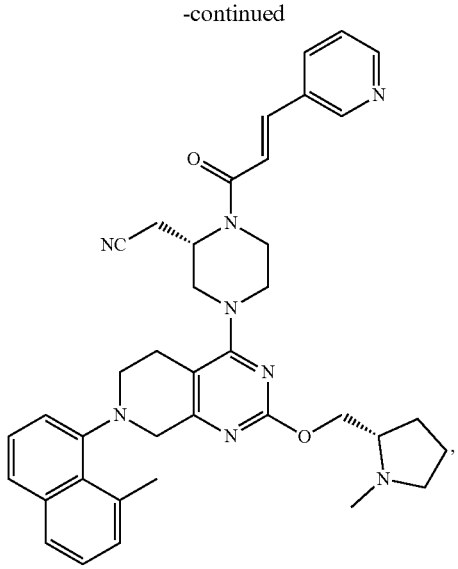
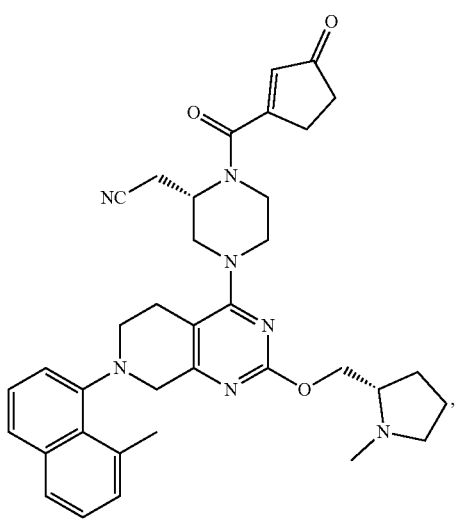
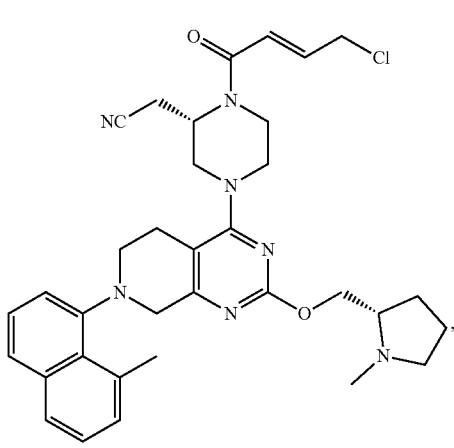

165
-continued
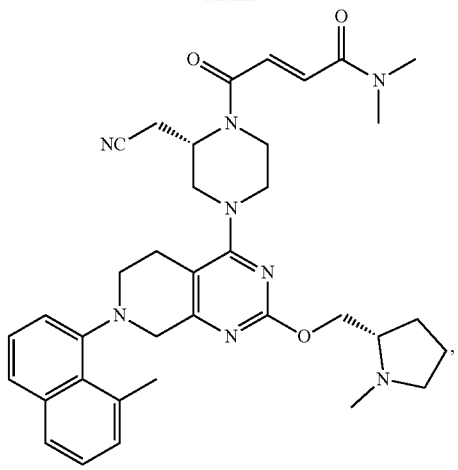
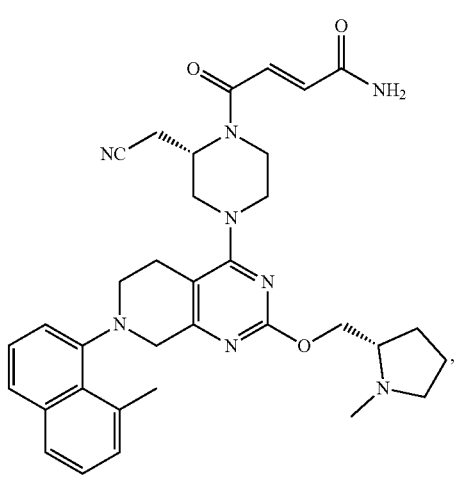
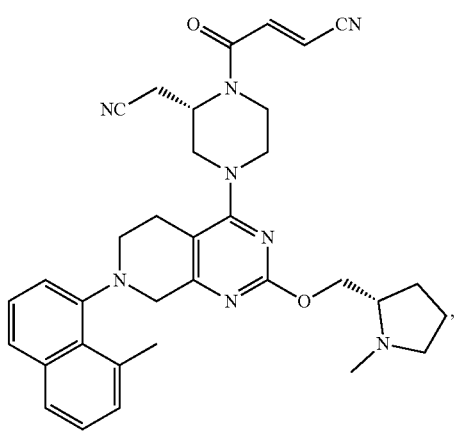
166
-continued
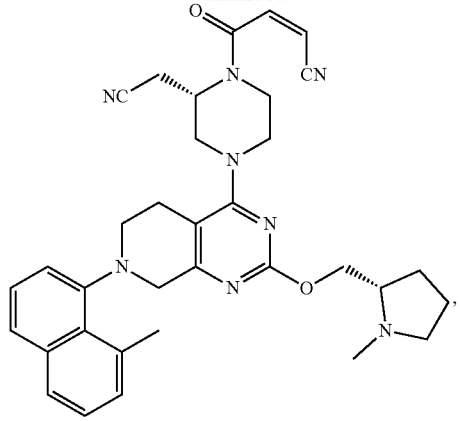
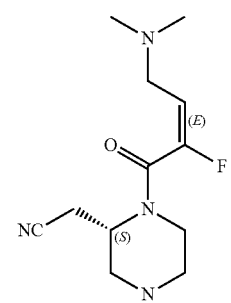
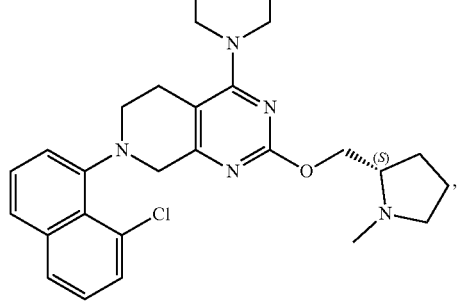

167
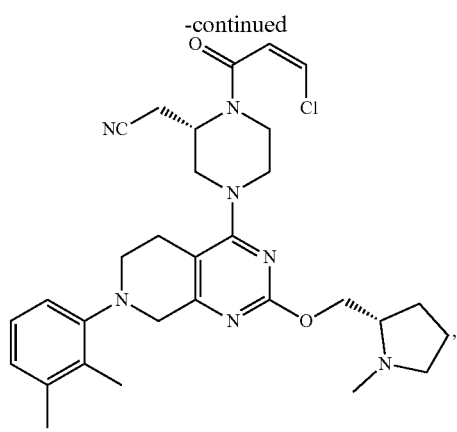
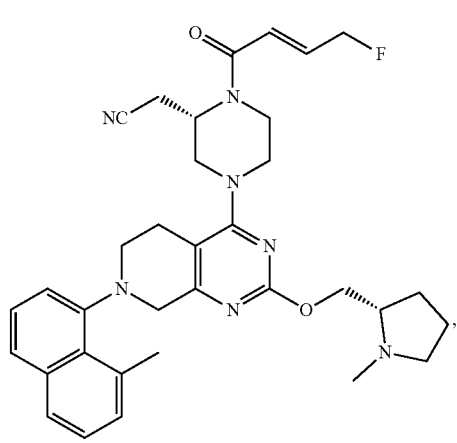
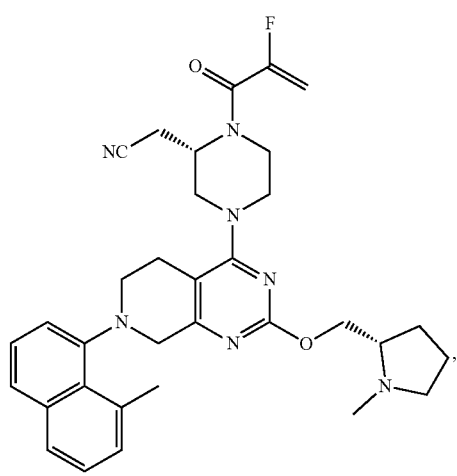
168
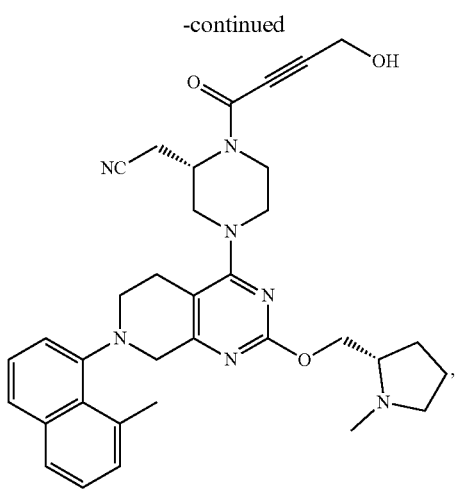
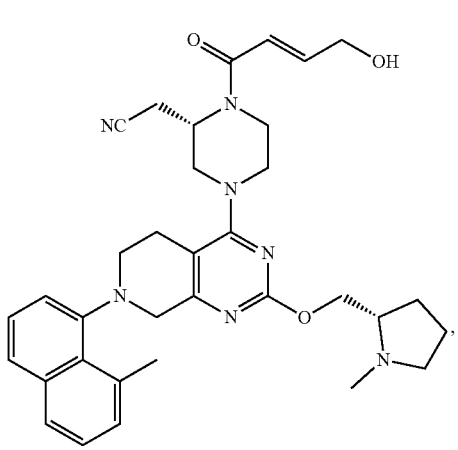

169
-continued
170
-continued
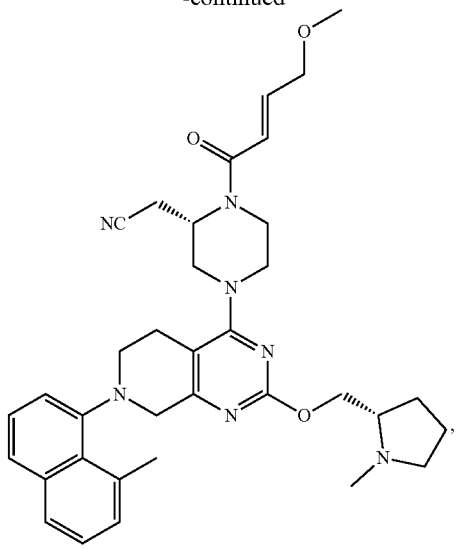
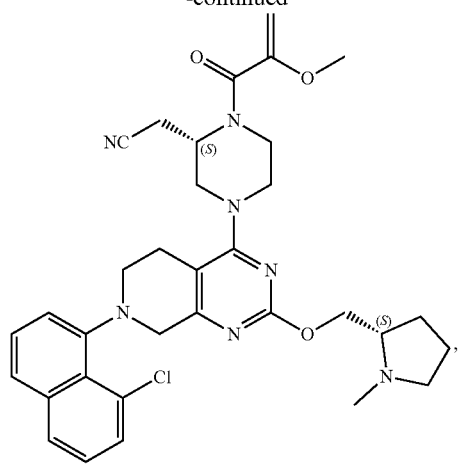
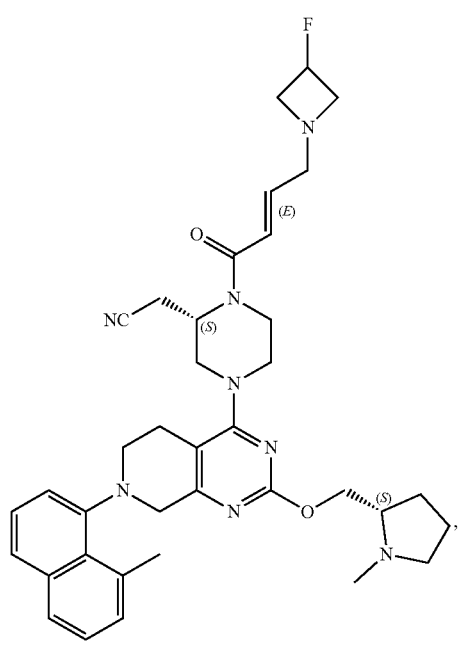

171
-continued
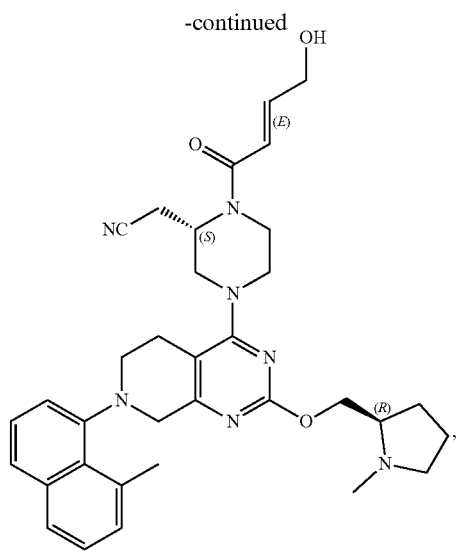
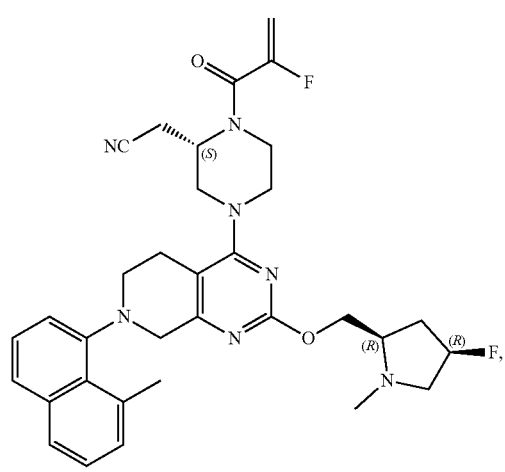
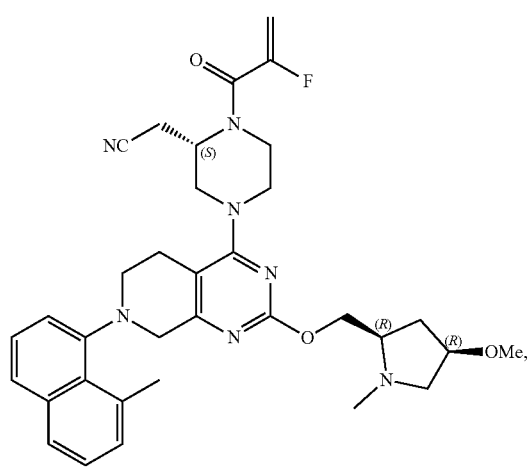
172
-continued
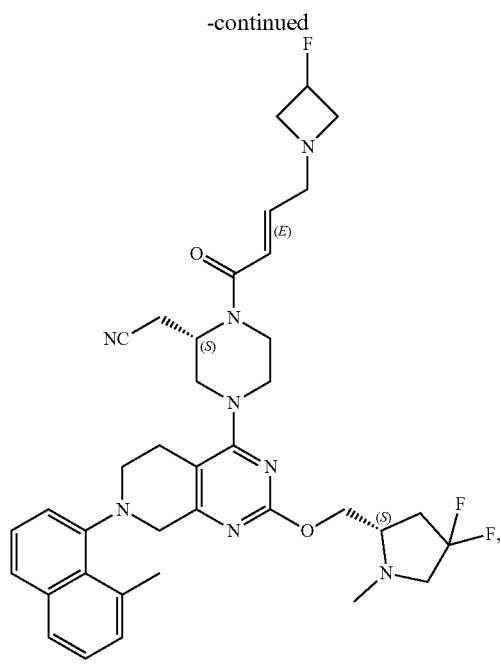
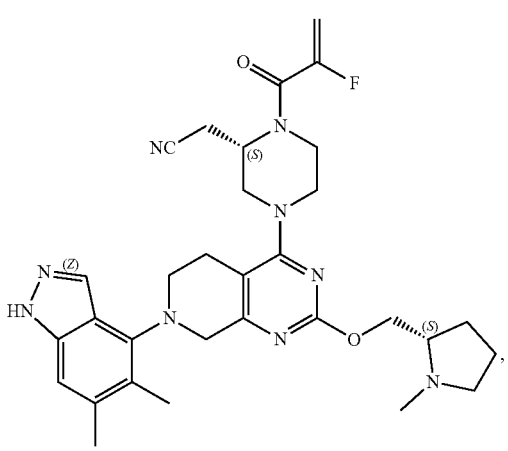
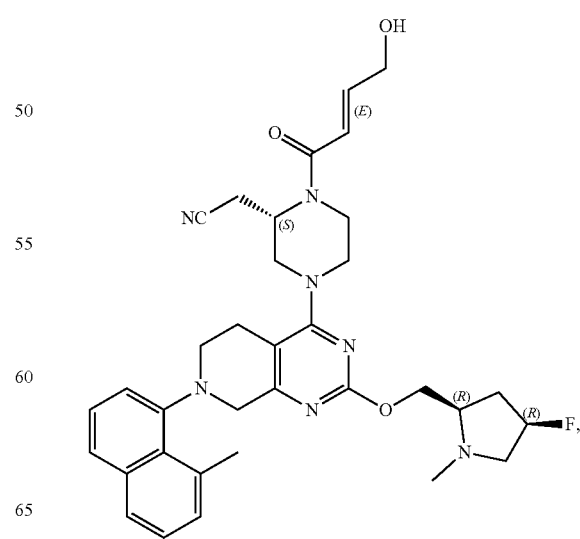

173
-continued
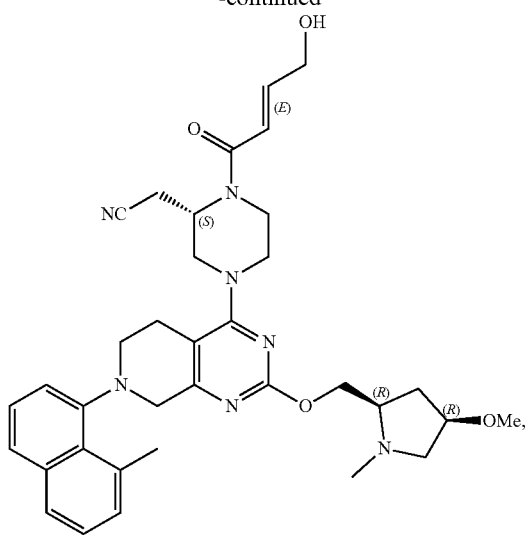
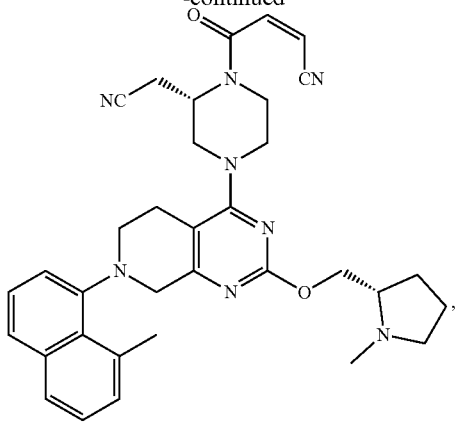
174
-continued
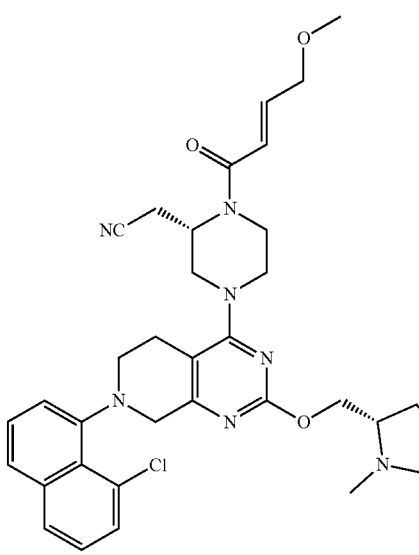
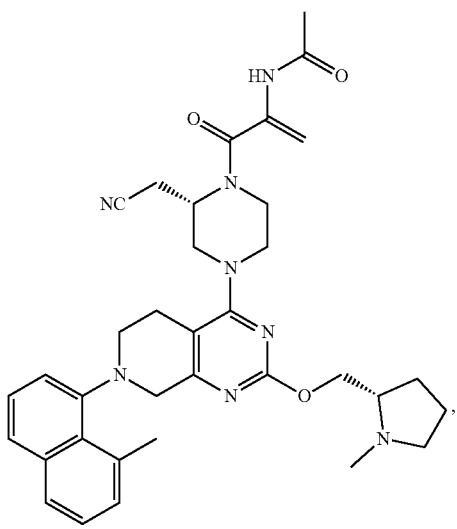

175
-continued
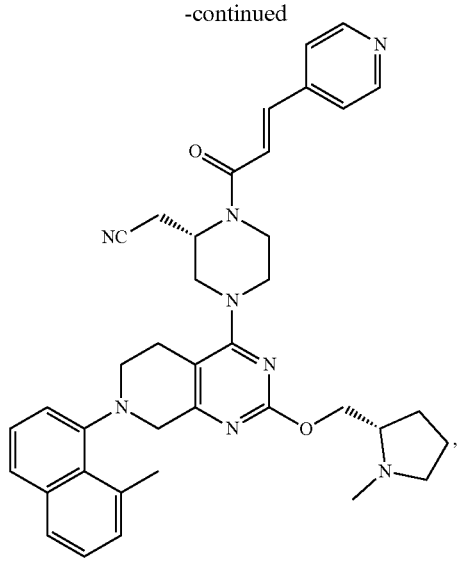
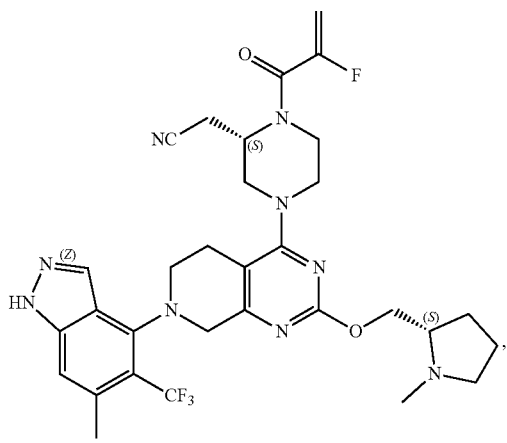
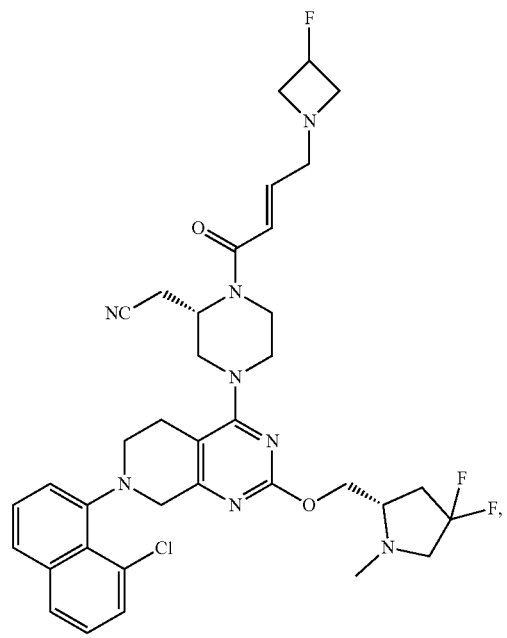
176
-continued
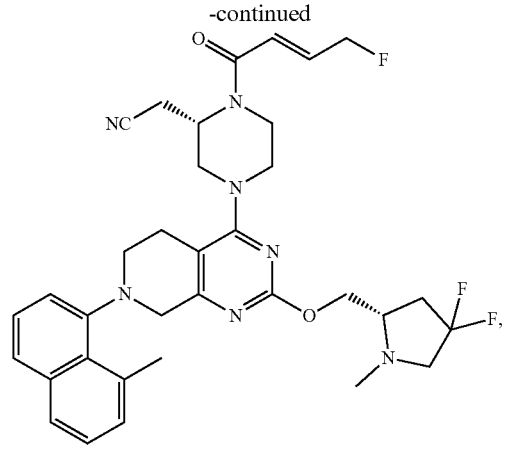
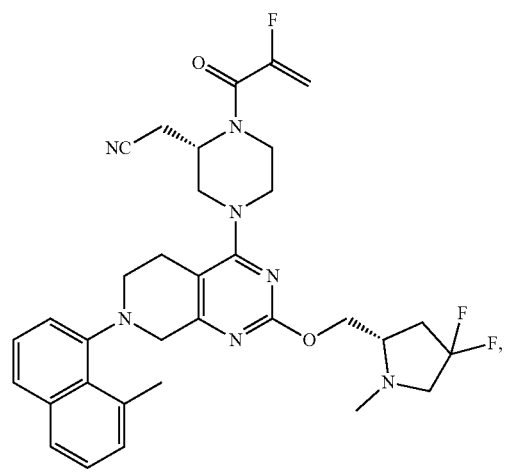
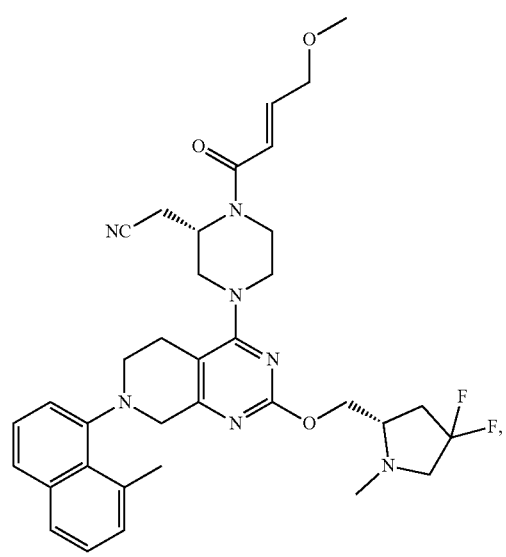

177
-continued
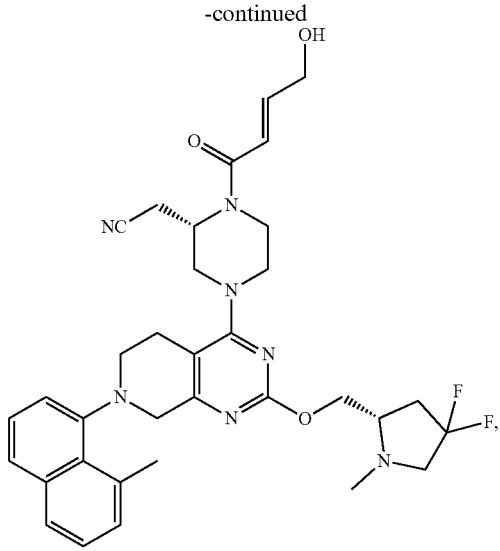
178
-continued
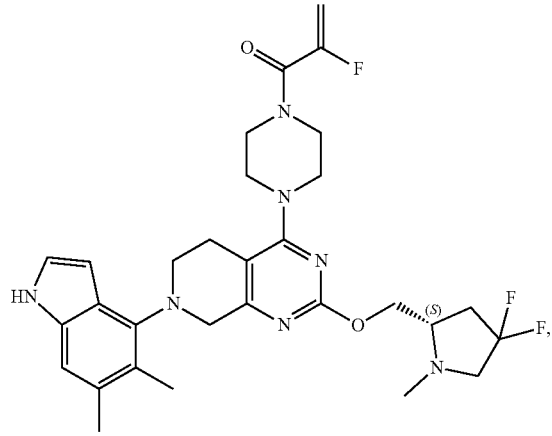
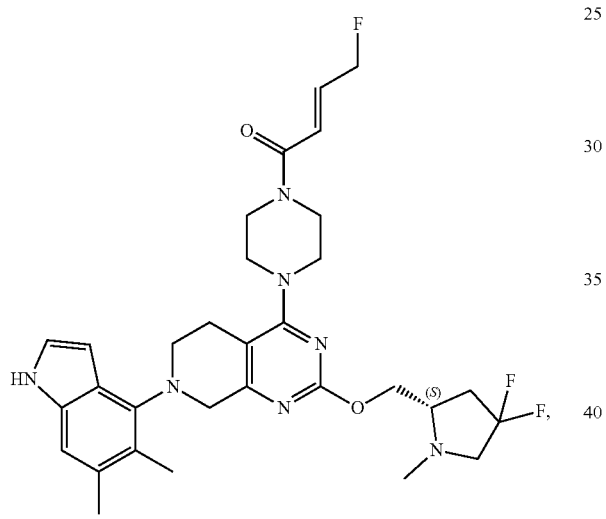
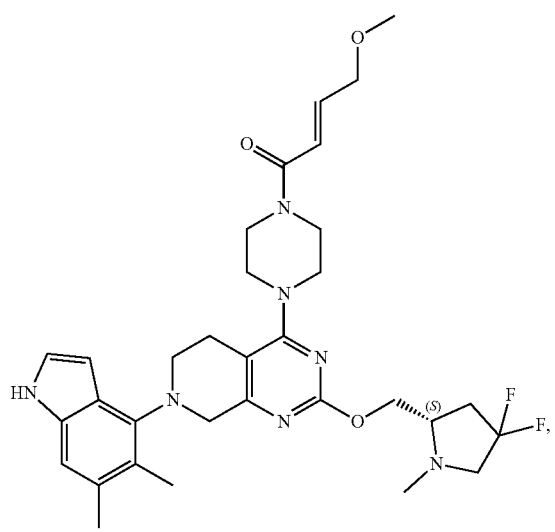

179
-continued
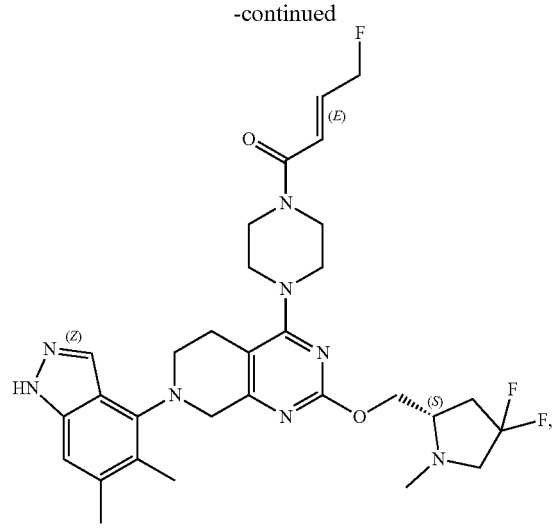
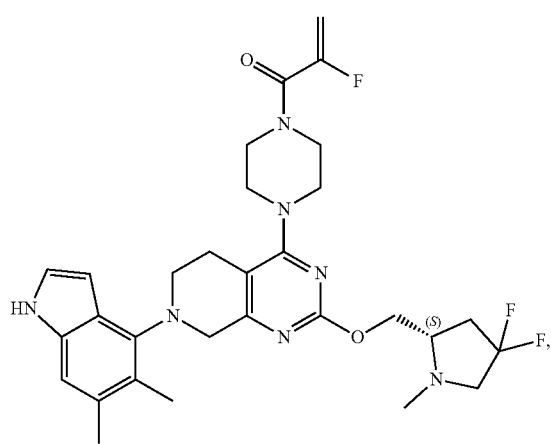
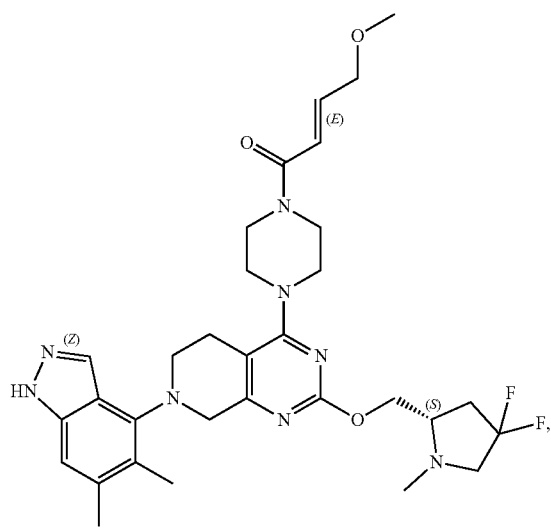
180
-continued
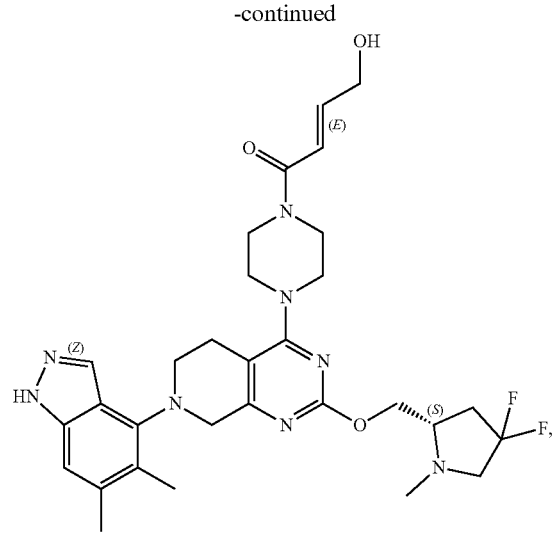
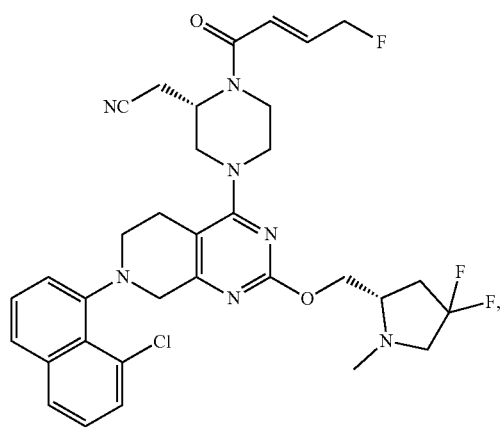
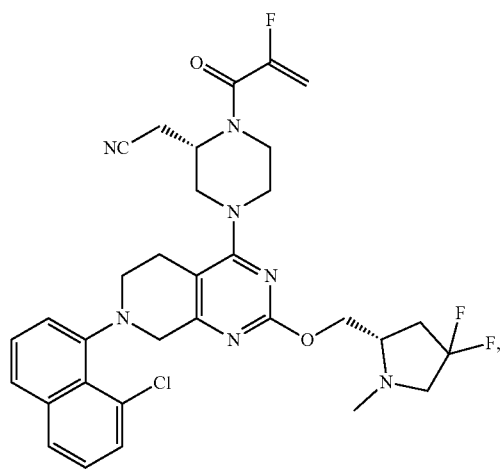

181
-continued
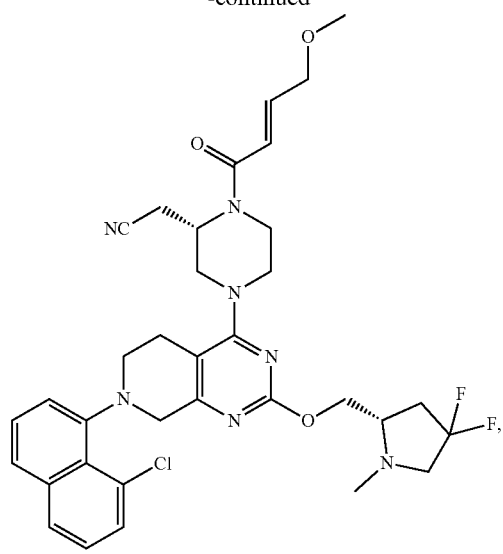
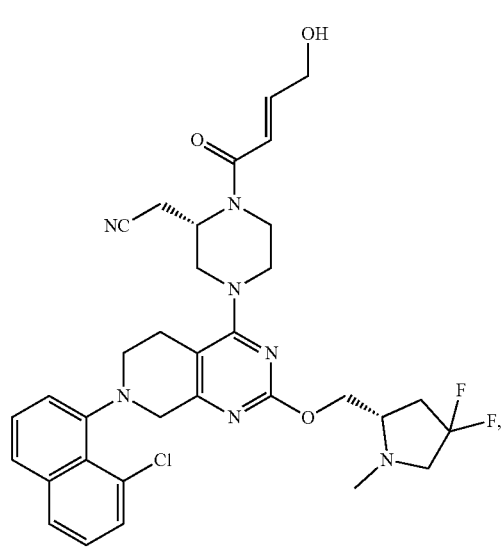
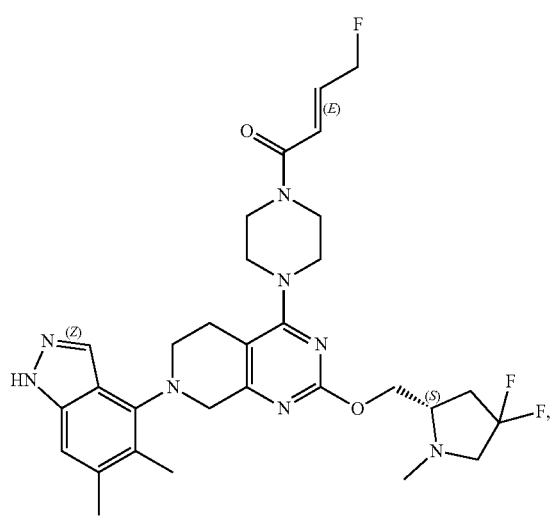
182
-continued
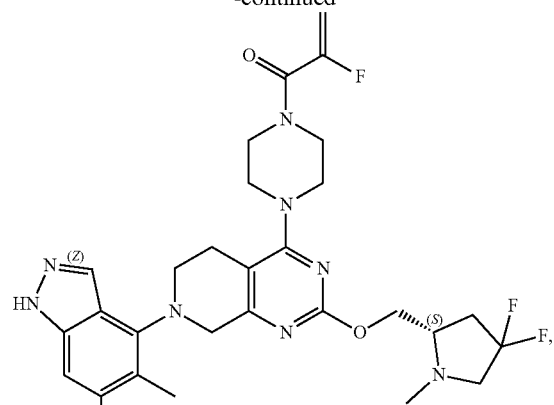
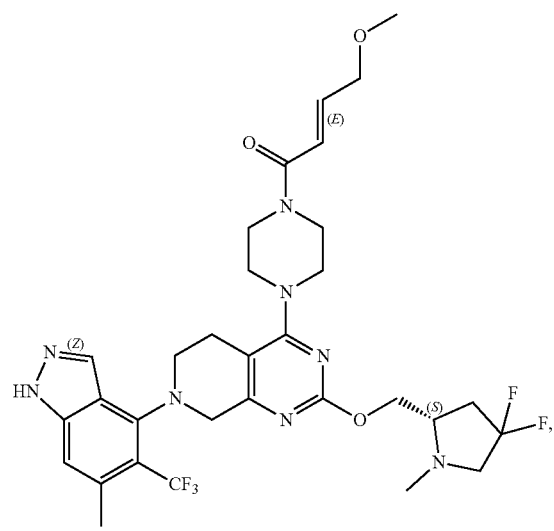
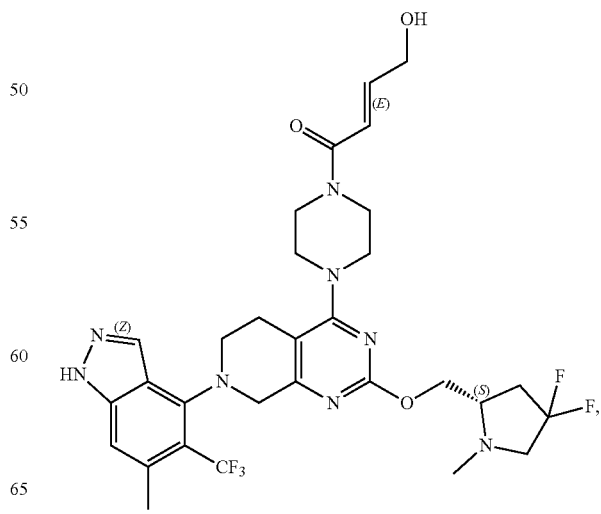

183
-continued
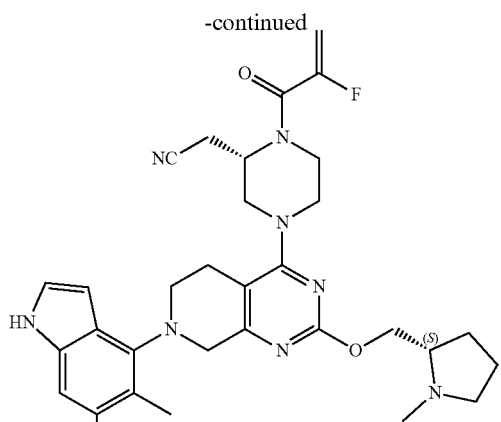
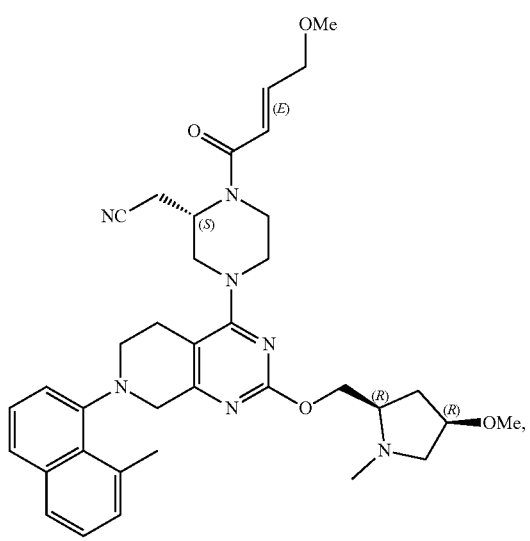
184
-continued
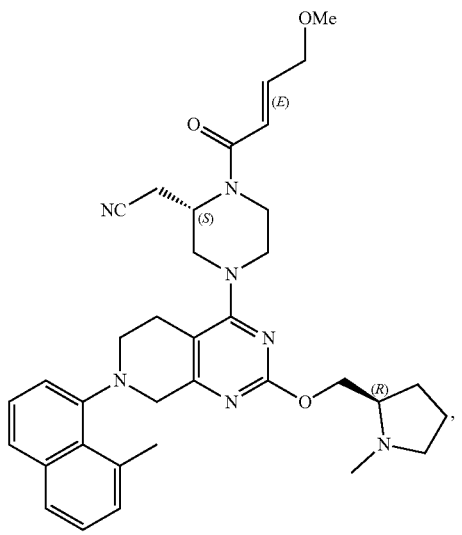
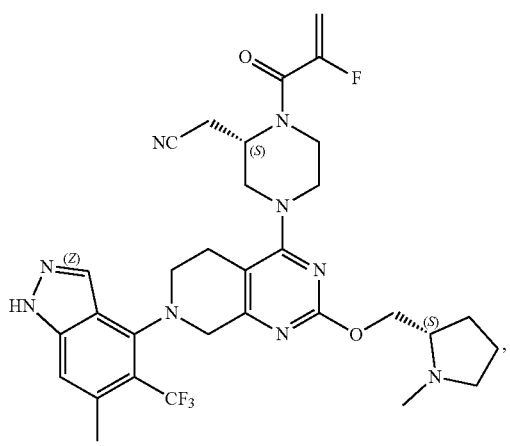
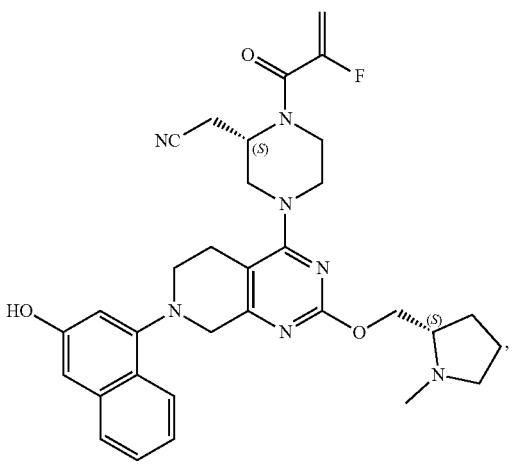

185
-continued
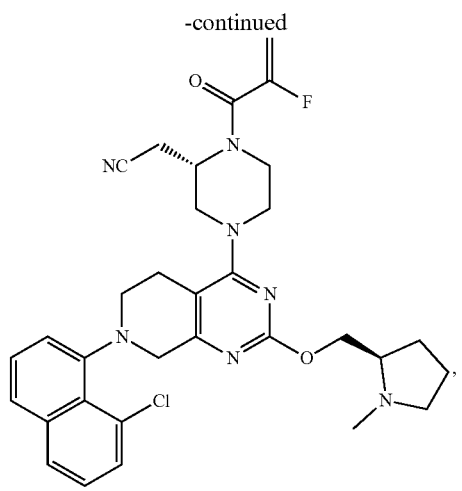
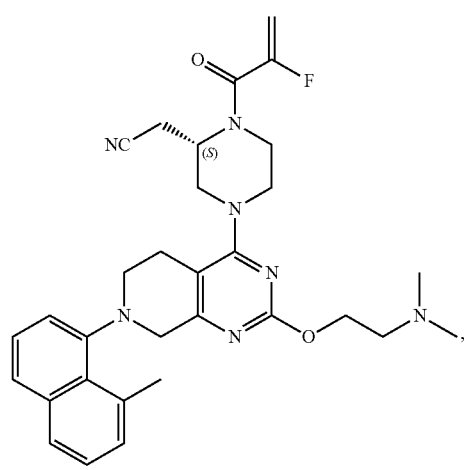
186
-continued
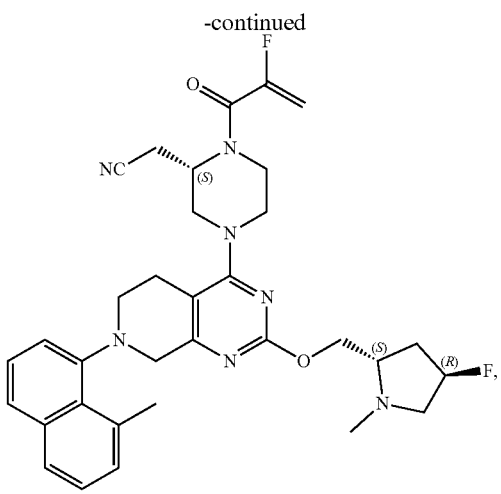
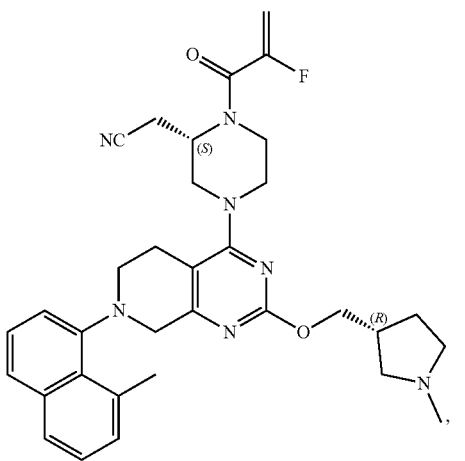

187
-continued
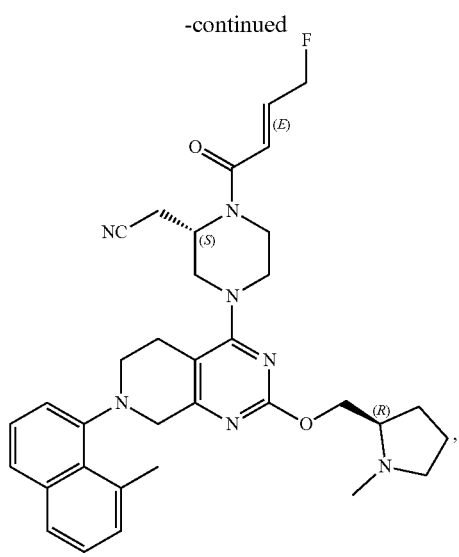
188
-continued
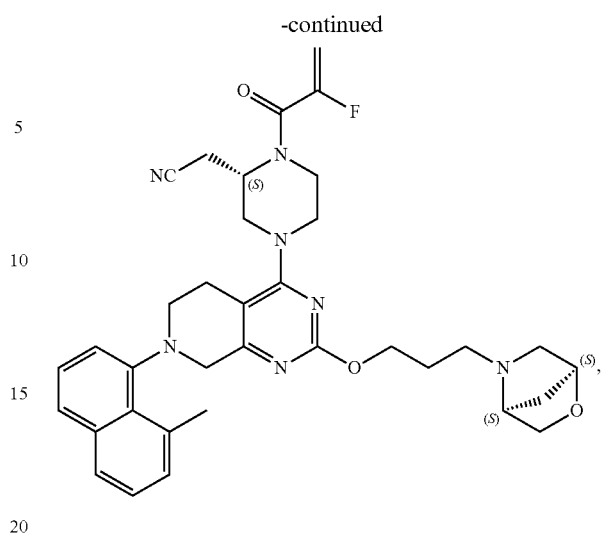
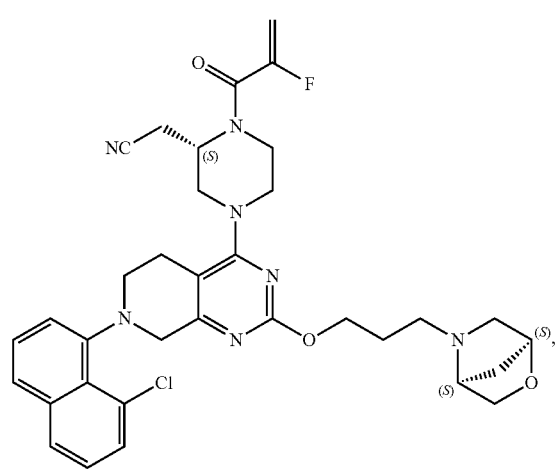
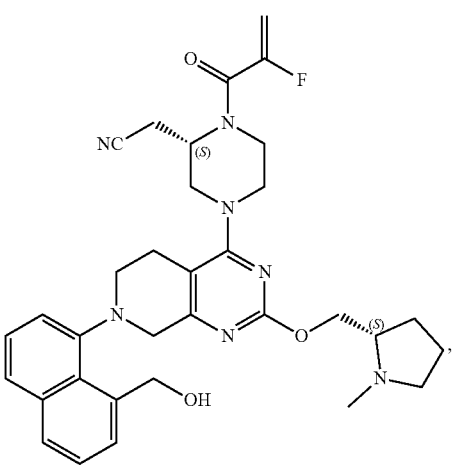
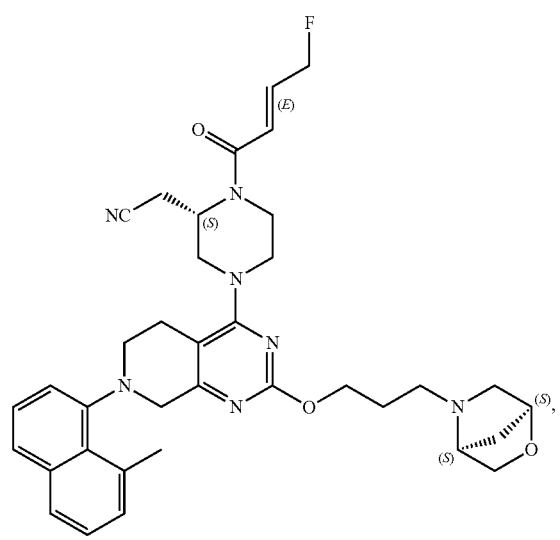
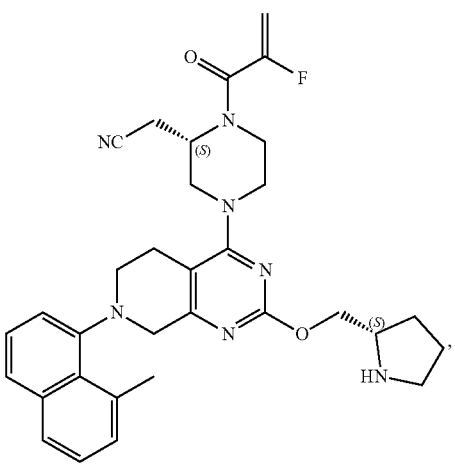

189
-continued
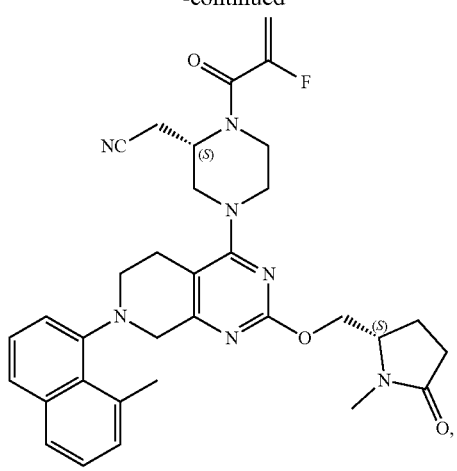
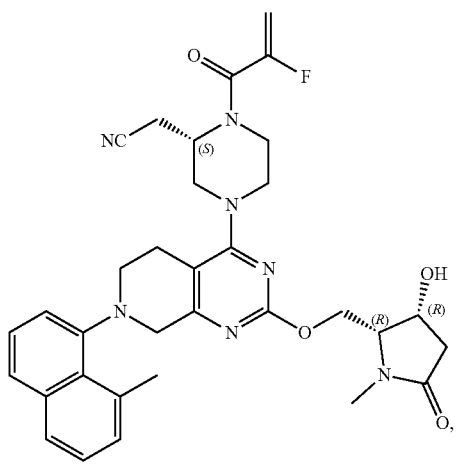
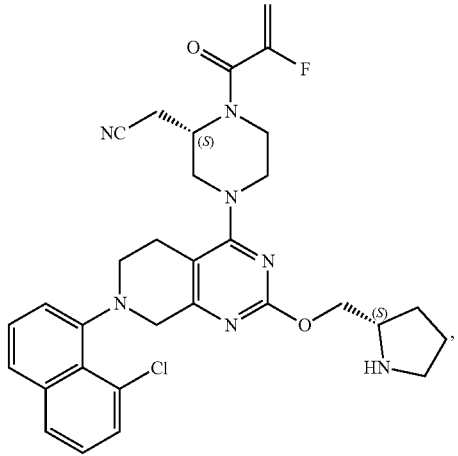
190
-continued
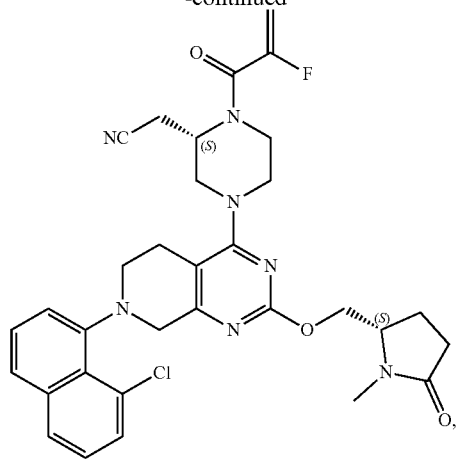
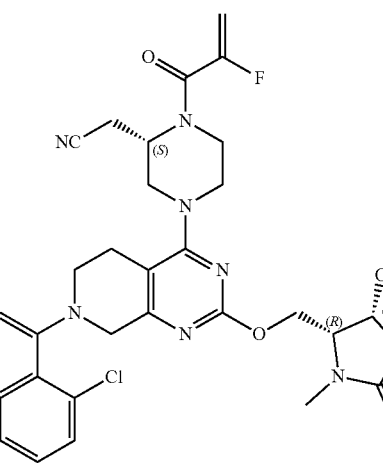
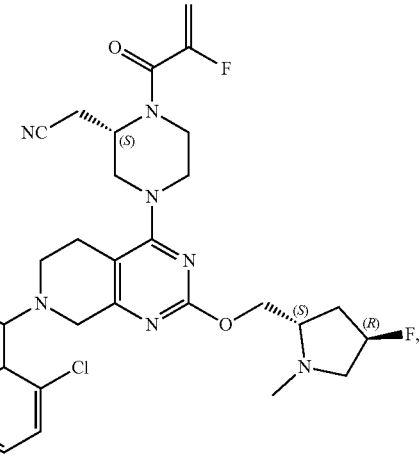

191
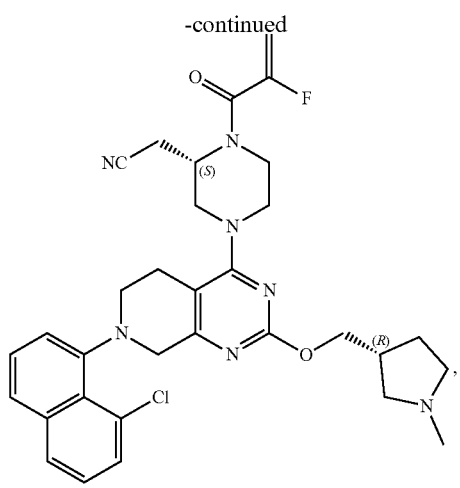
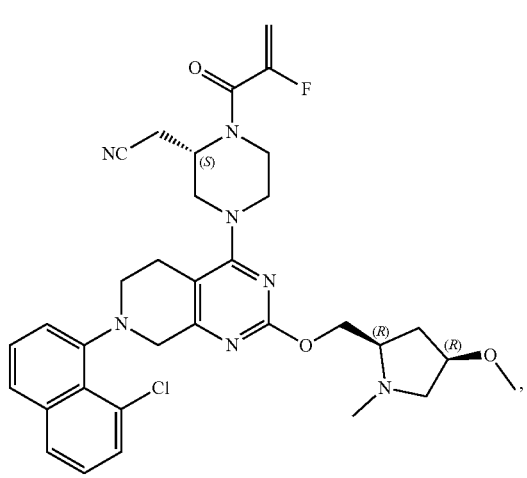
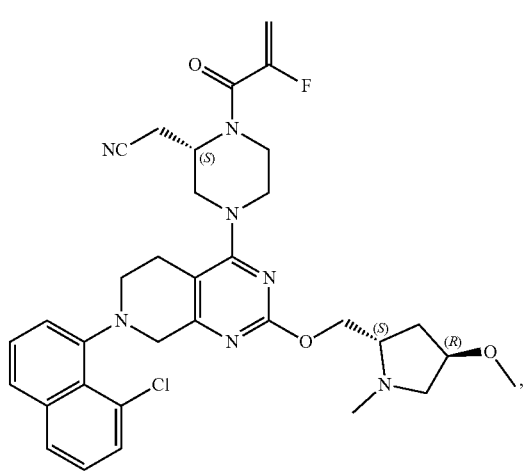
192
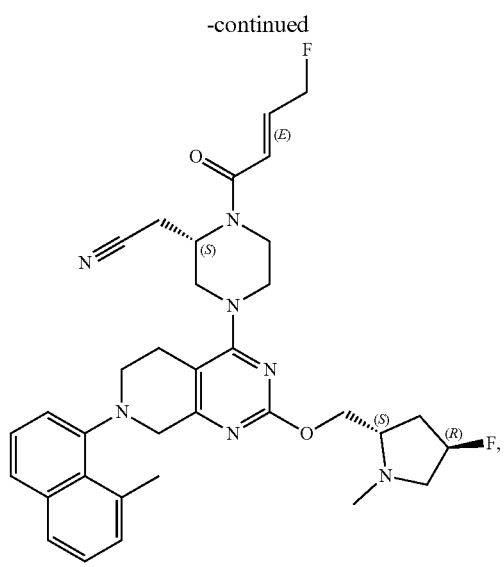
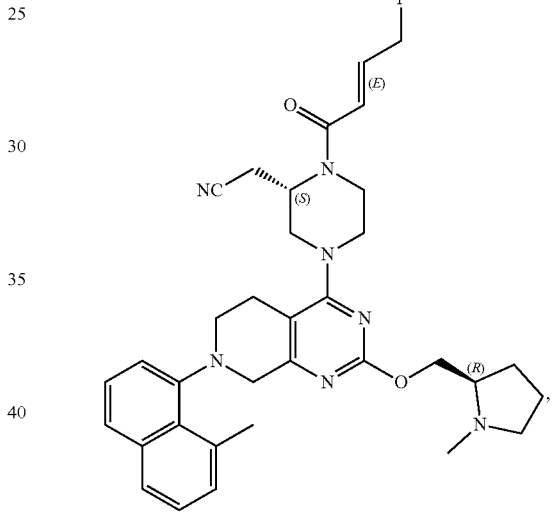
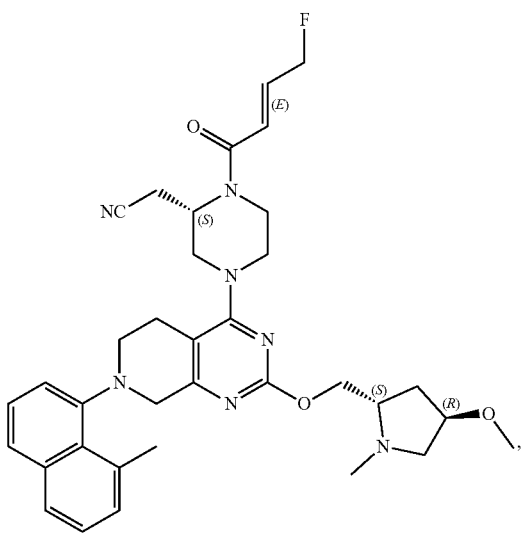

193
-continued
194
-continued
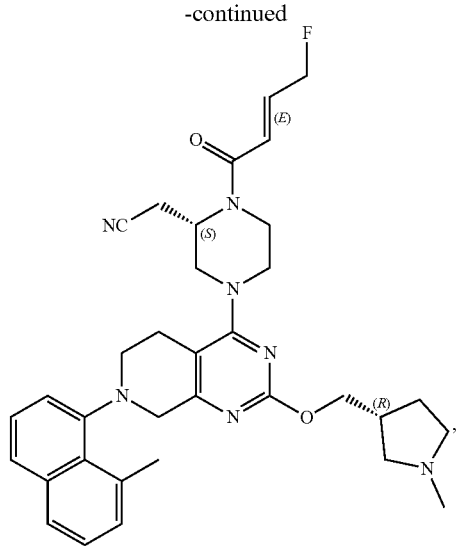
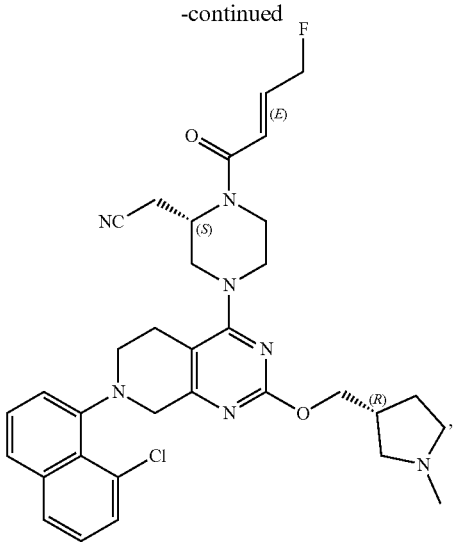

195
-continued
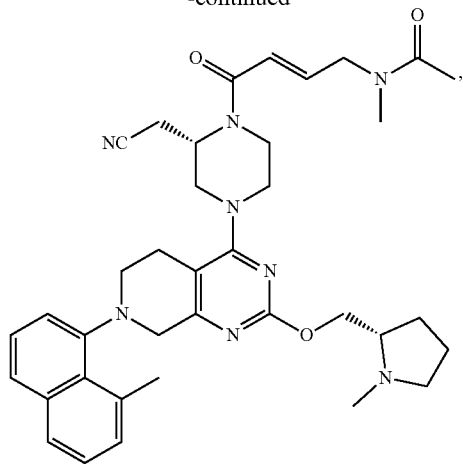
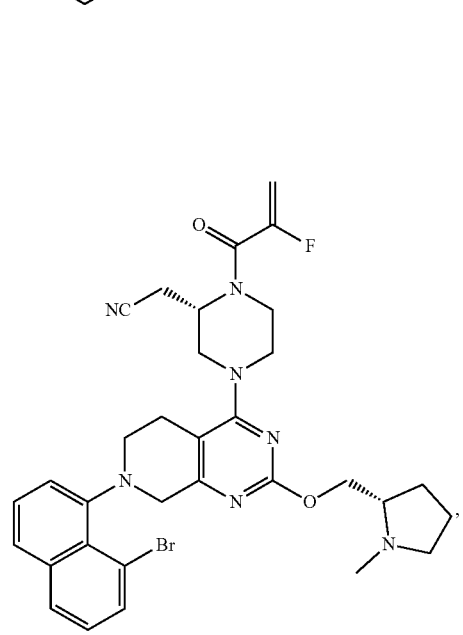
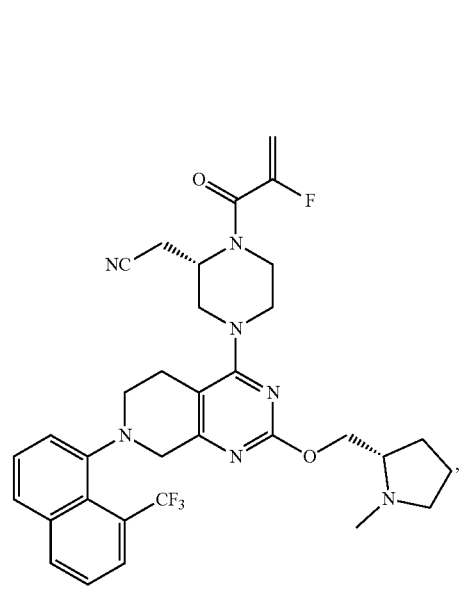
196
-continued
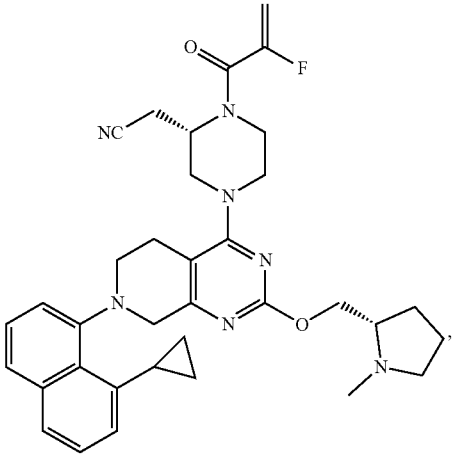
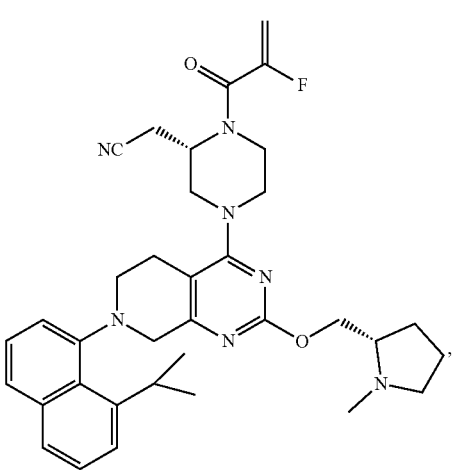
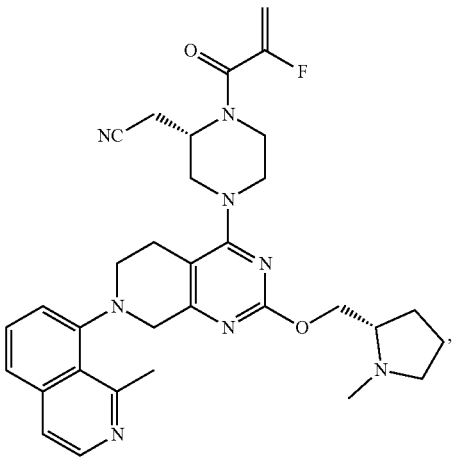

197
-continued
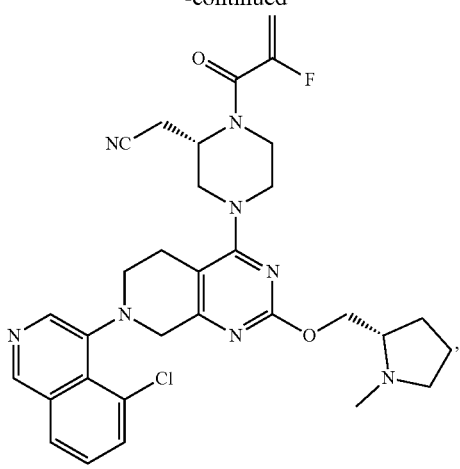
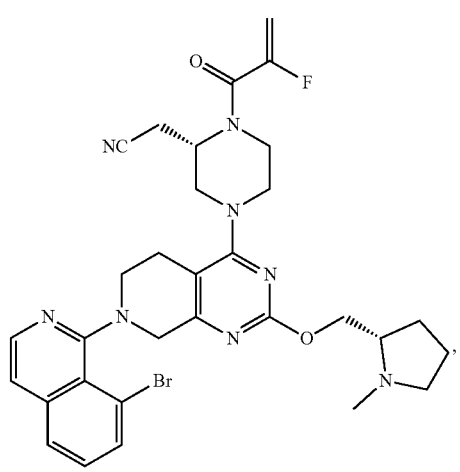
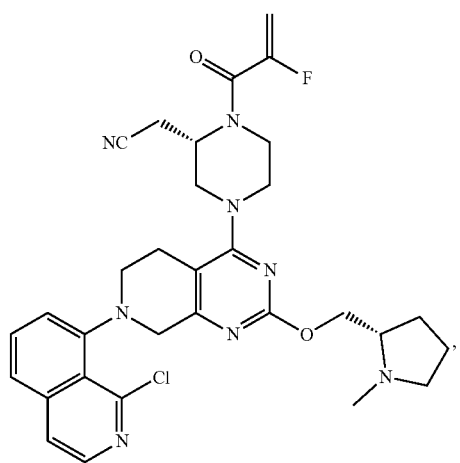
198
-continued
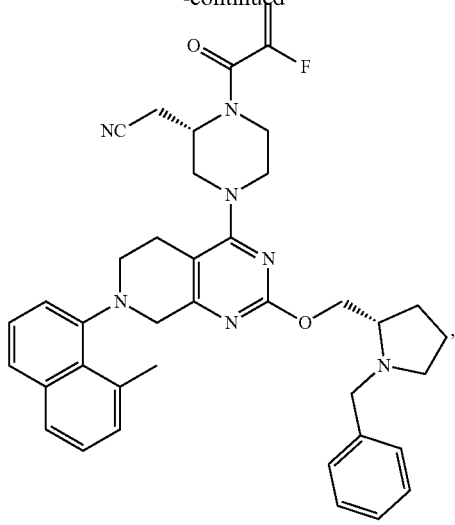
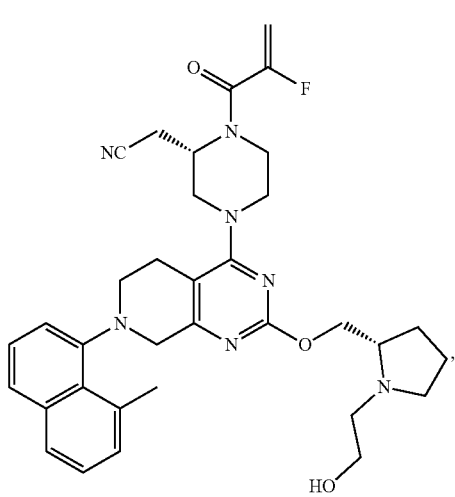
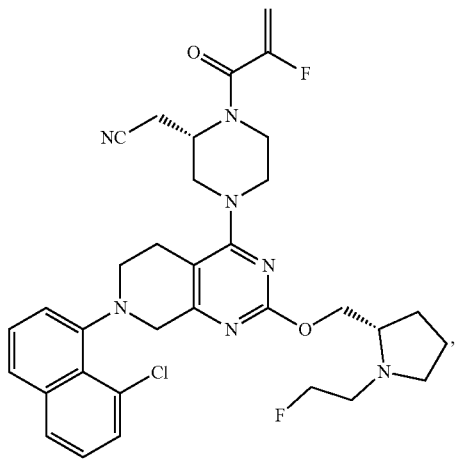

199
-continued
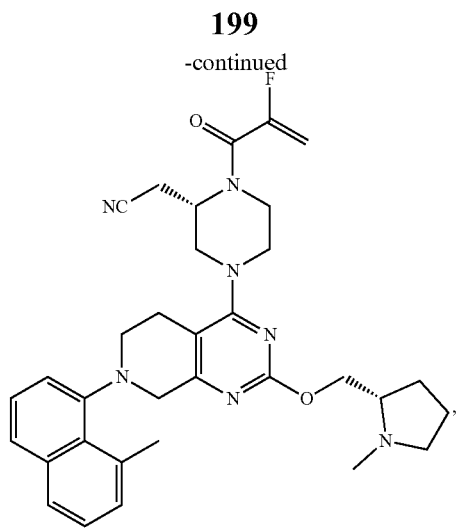
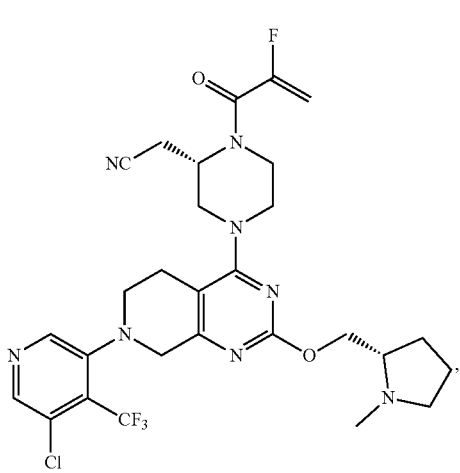
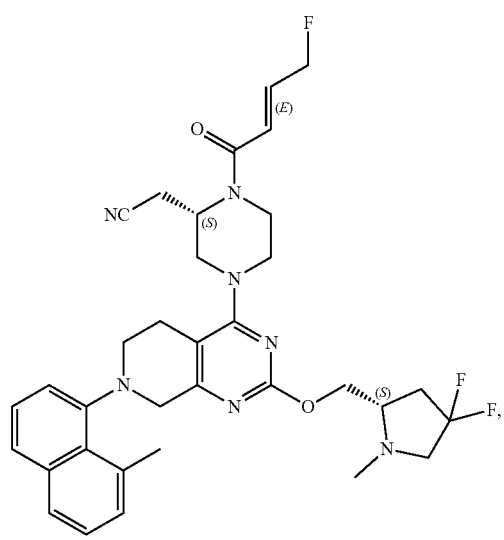
200
-continued
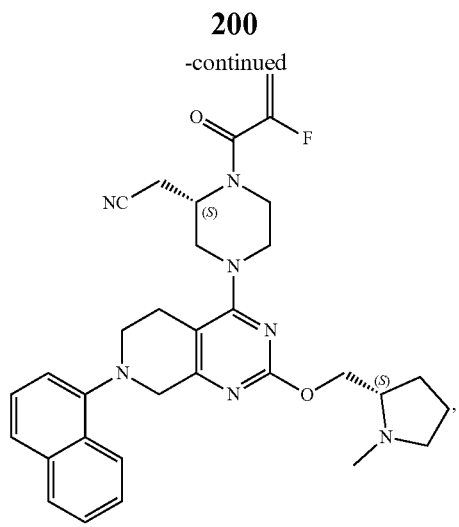
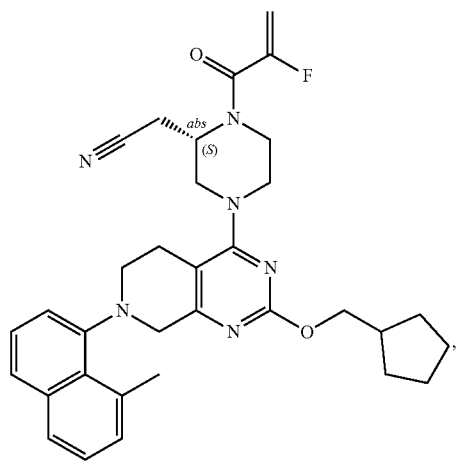
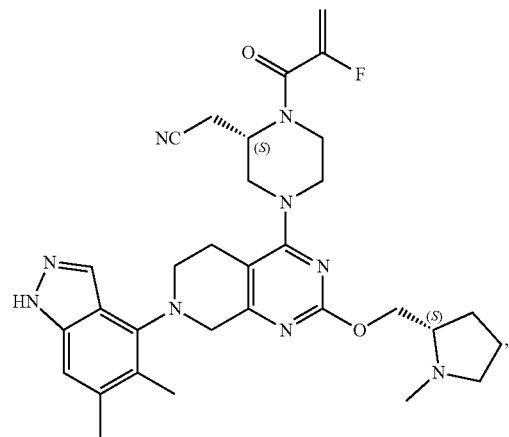

201
-continued
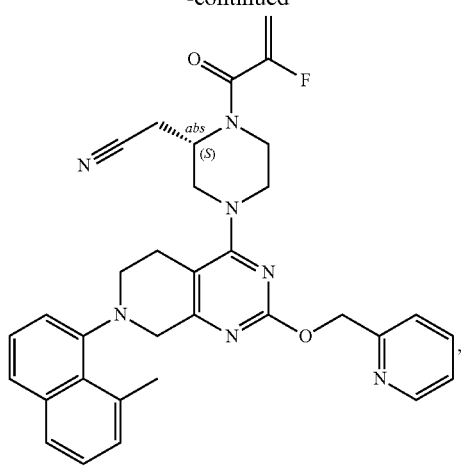
202
-continued
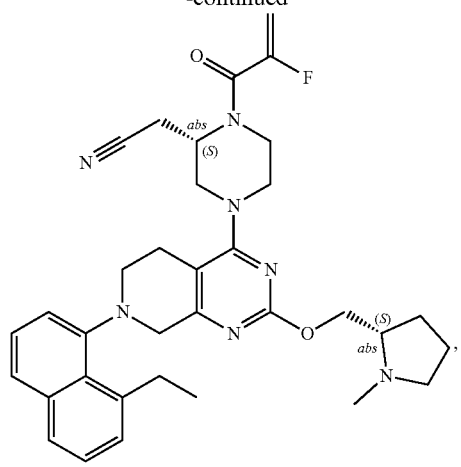
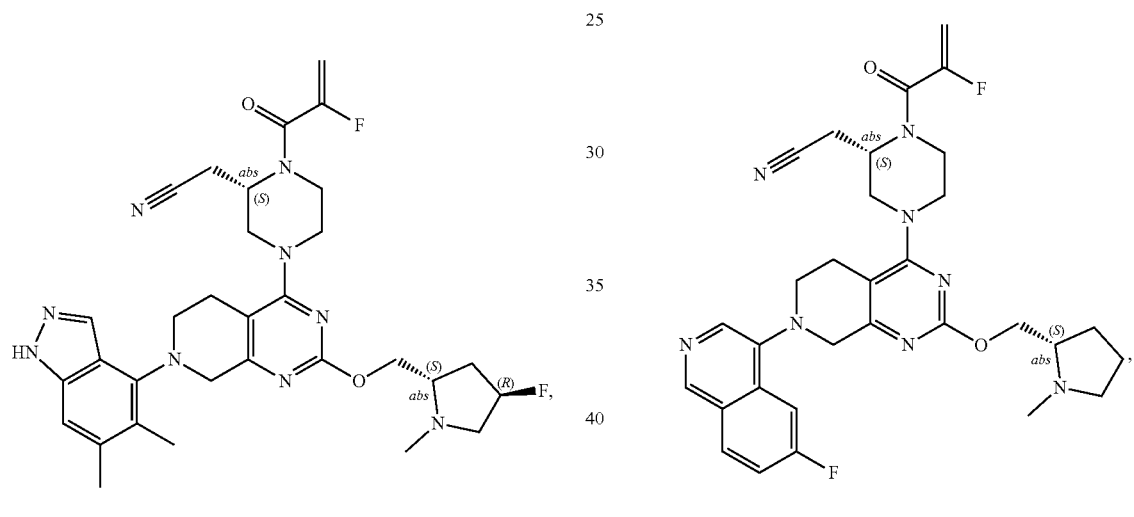
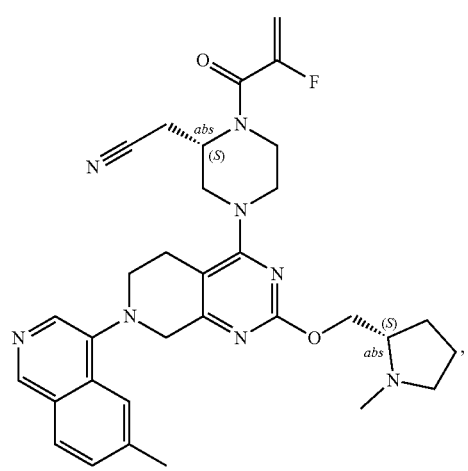
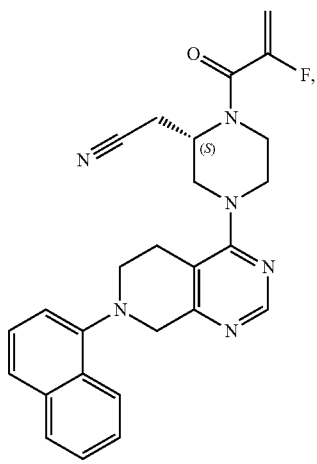

203
-continued
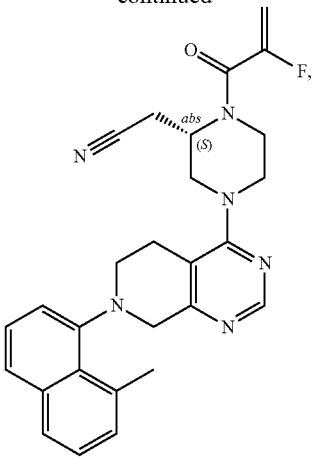
204
-continued
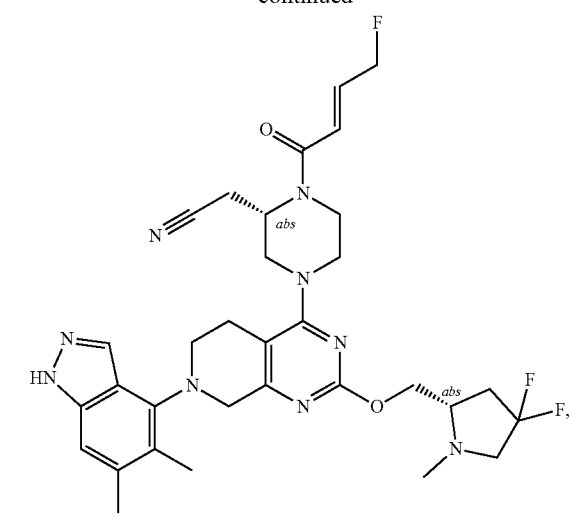
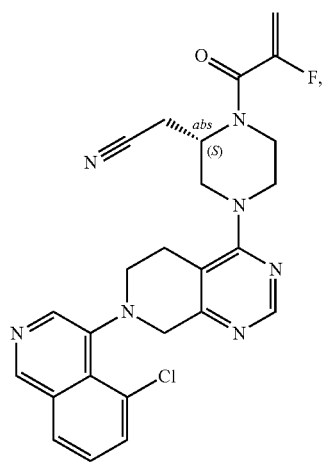
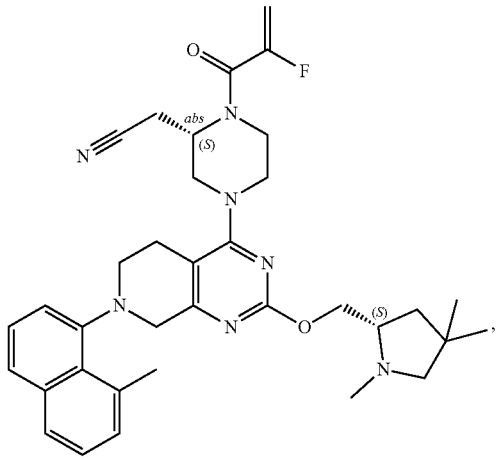
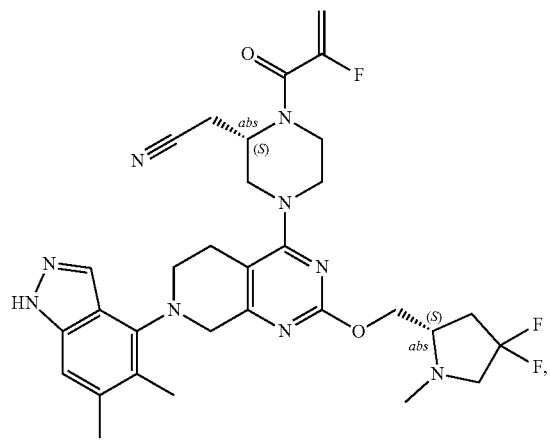
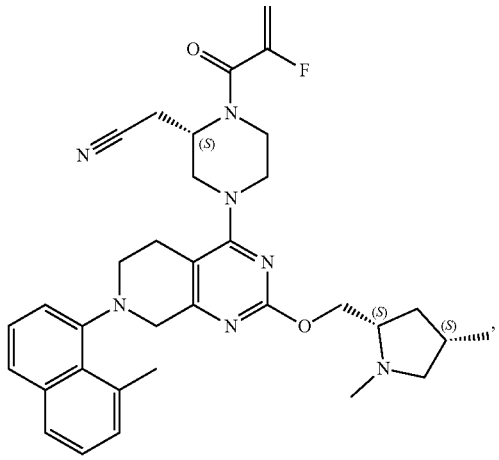

-continued

207
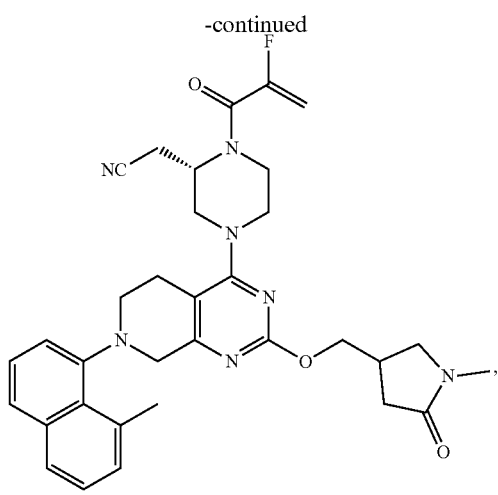
208
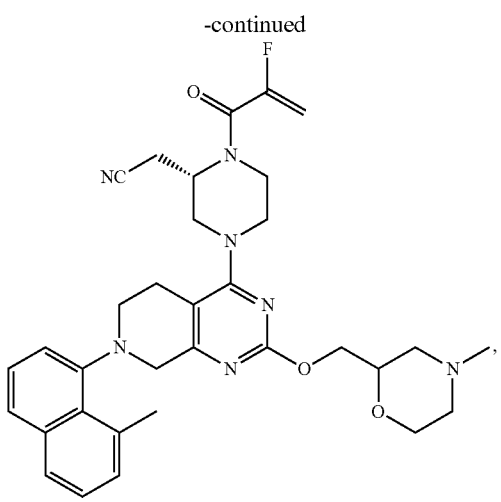
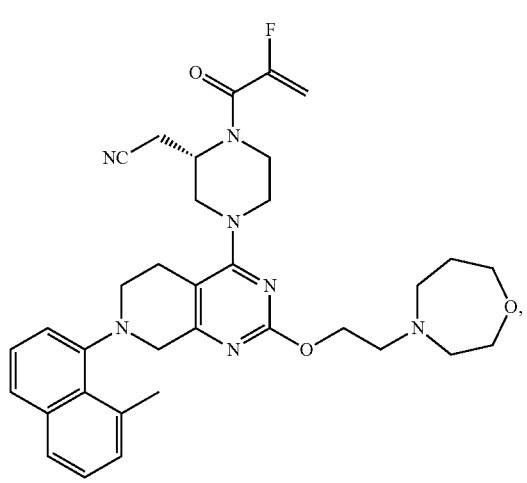
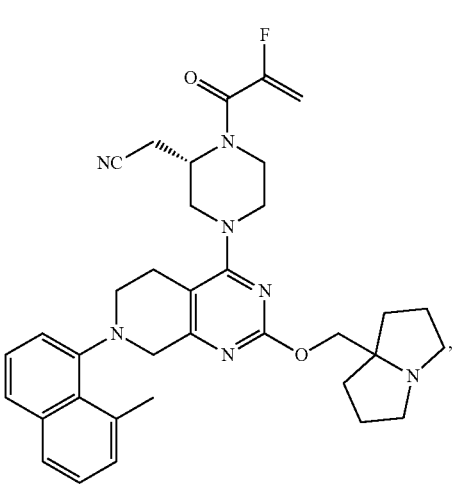
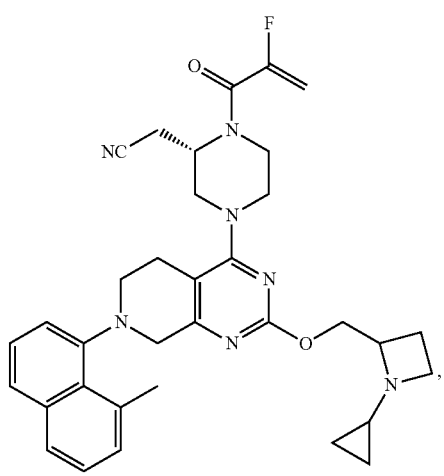
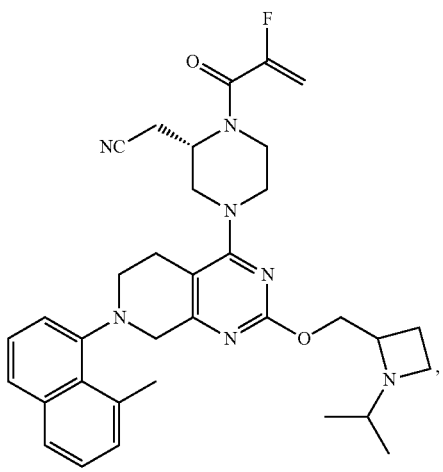

209
-continued
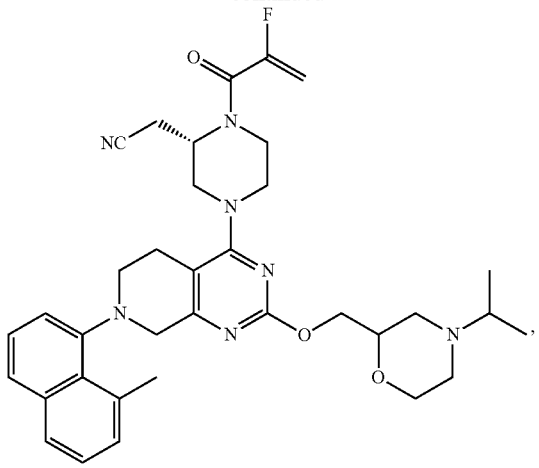
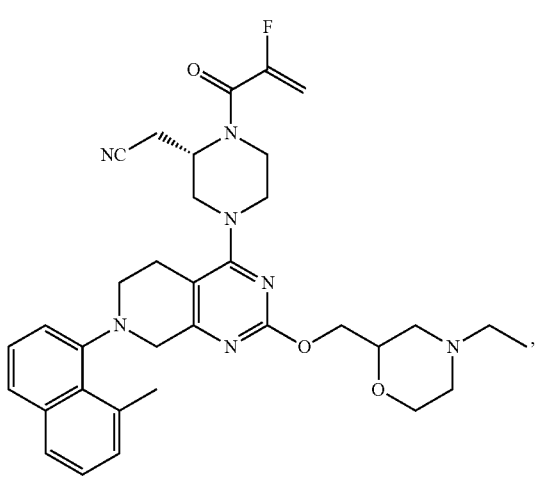
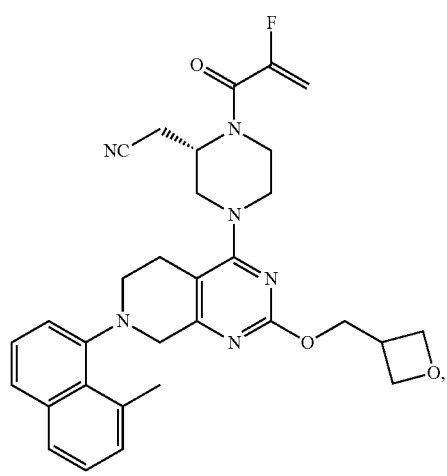
210
-continued
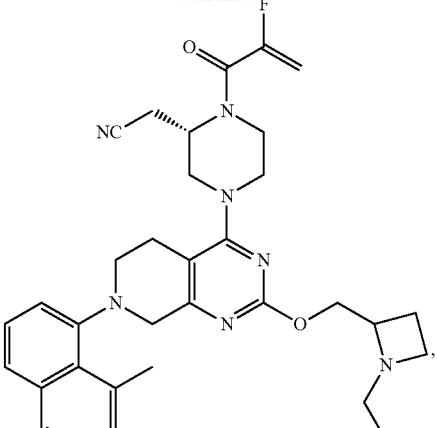
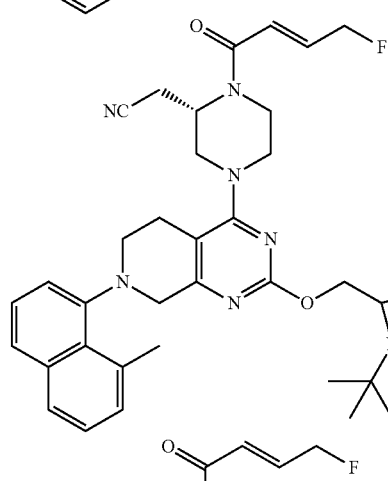
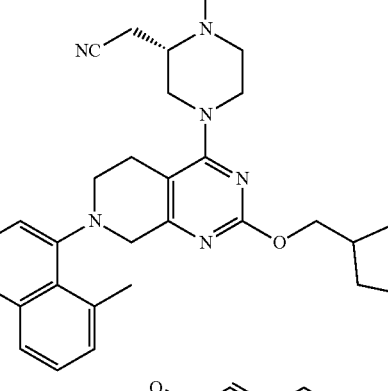
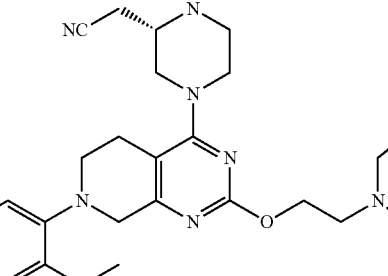

-continued
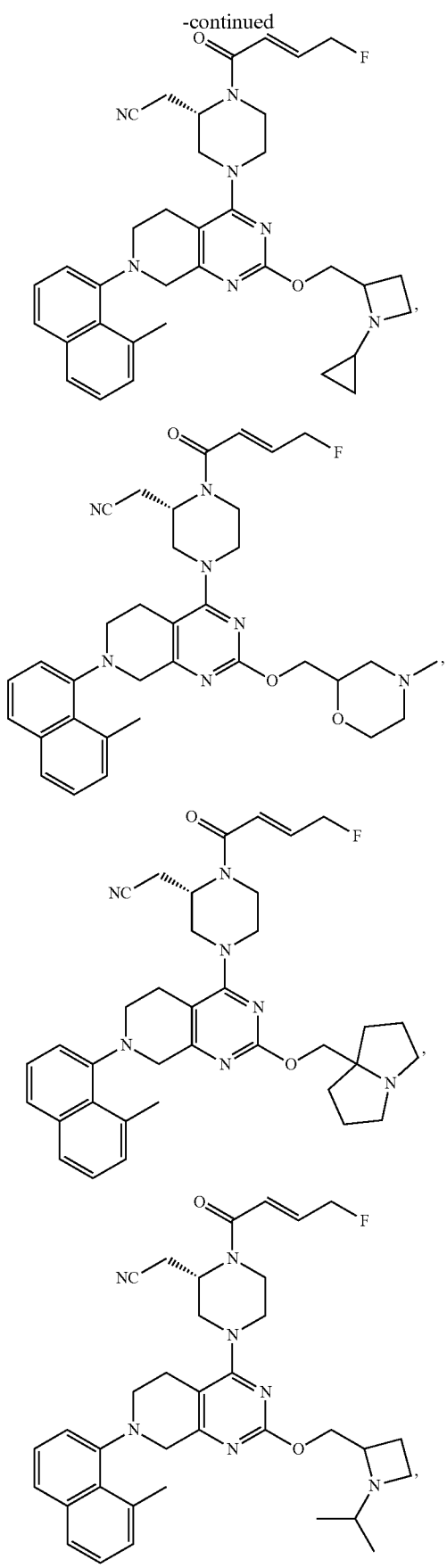
-continued
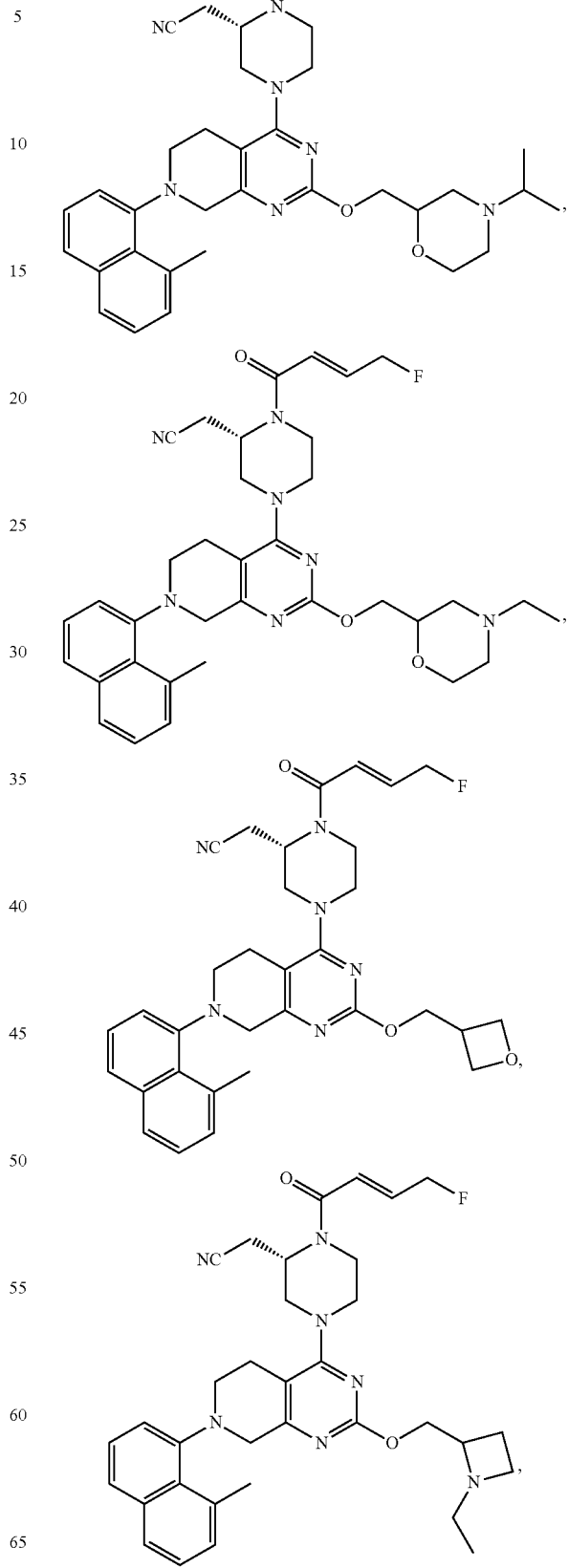

213
-continued
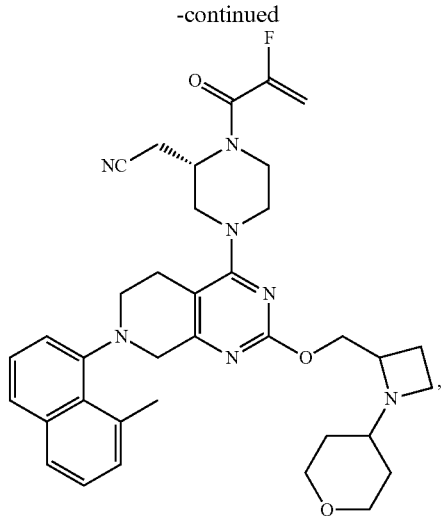
214
-continued
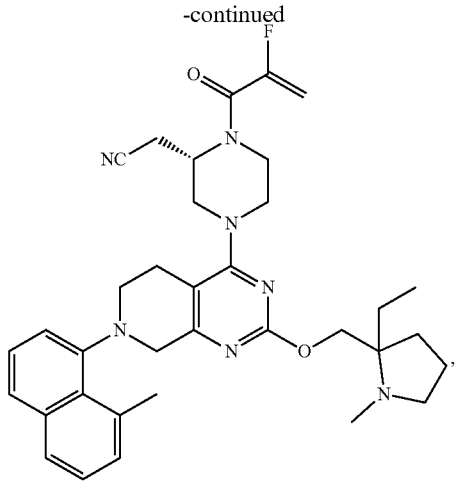
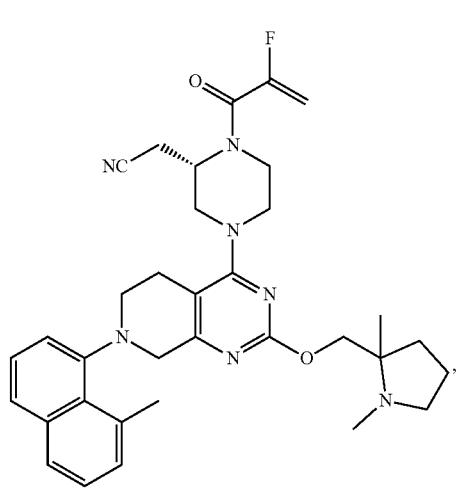
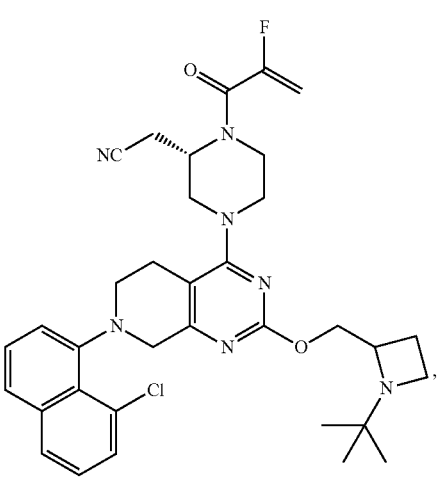
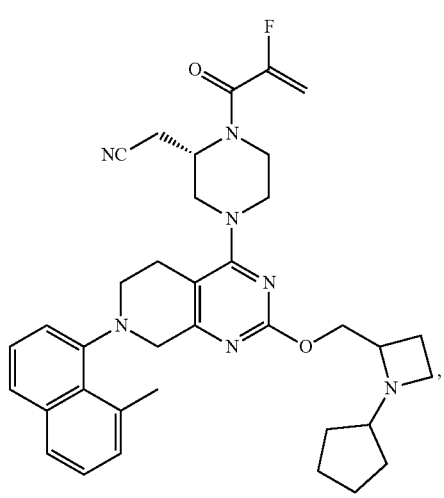
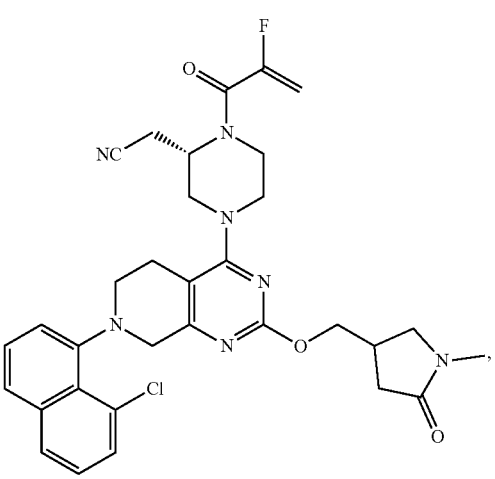

215
-continued

216
-continued

217
-continued
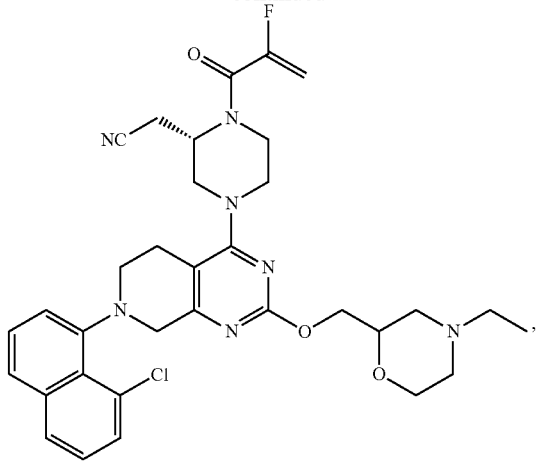
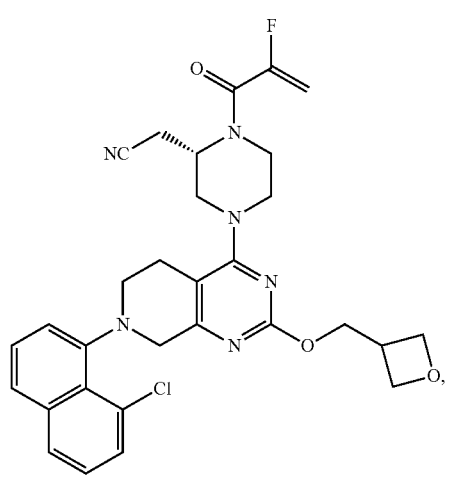
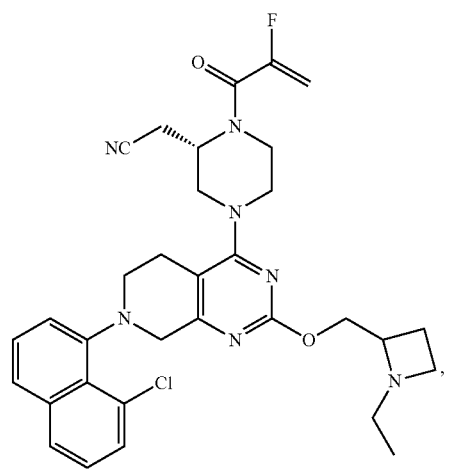
218
-continued
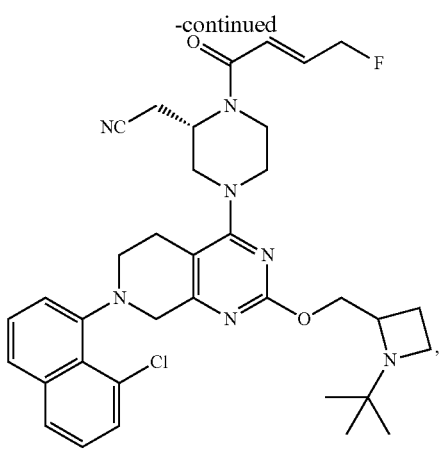
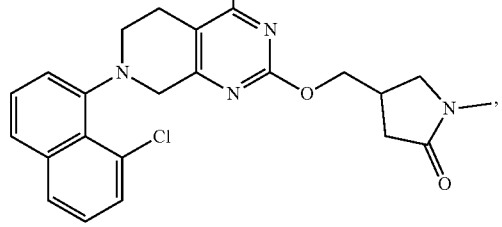
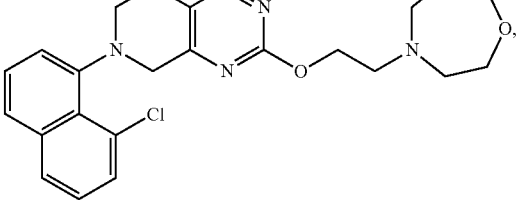
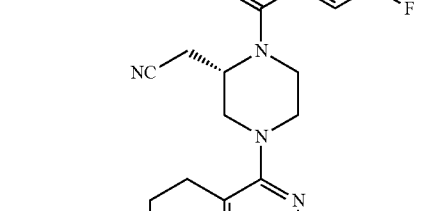

219
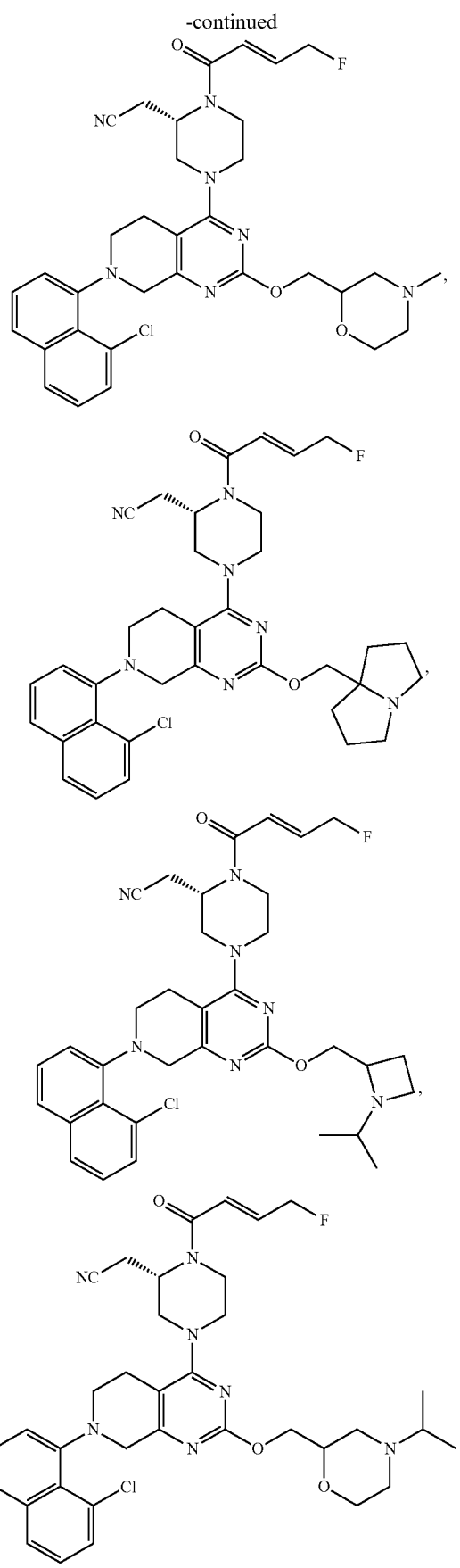
220
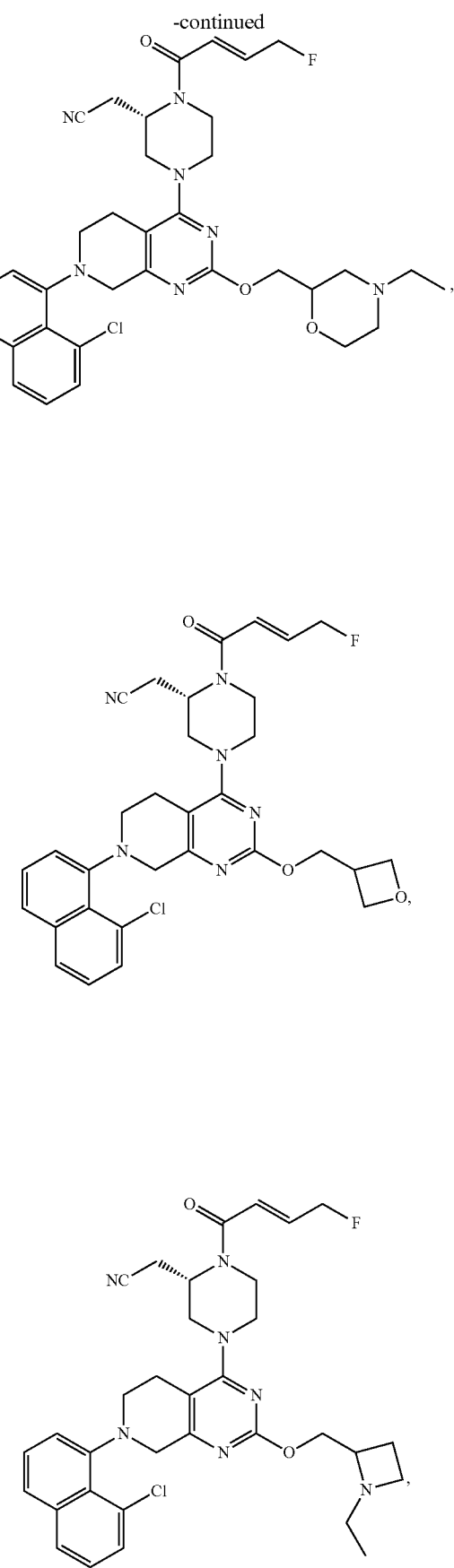

-continued
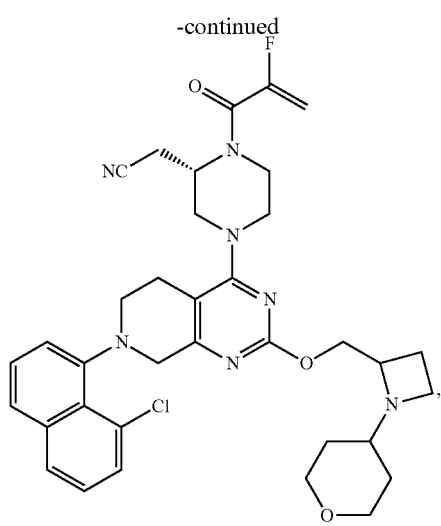
-continued
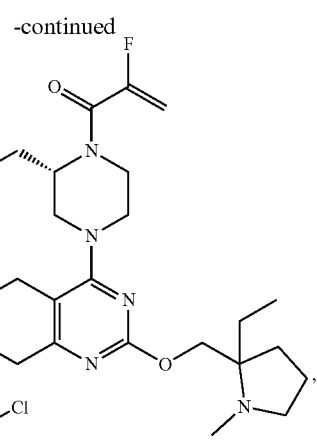
and
and pharmaceutically acceptable salts thereof.
In one embodiment, the KRas G12C inhibitor is selected from:
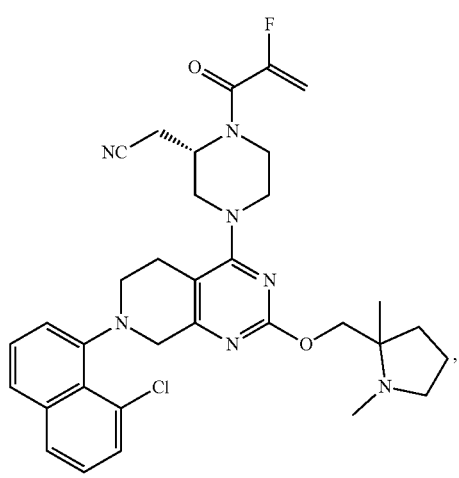
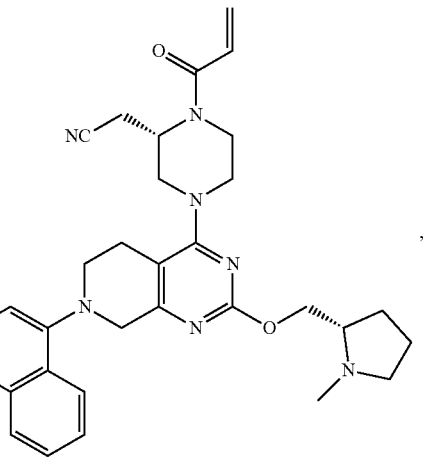
,
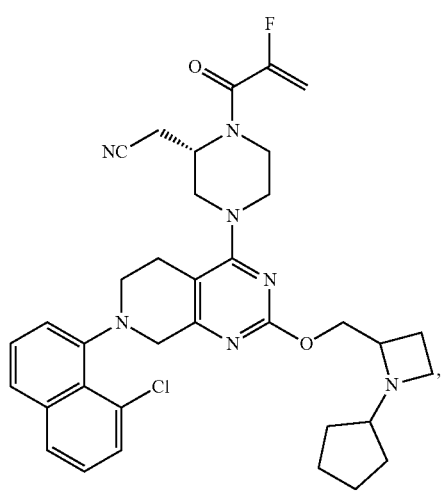
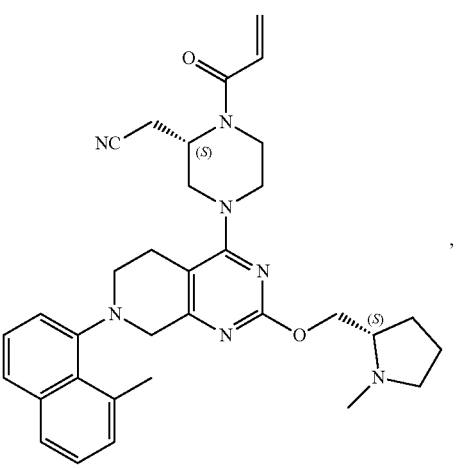
, -continued

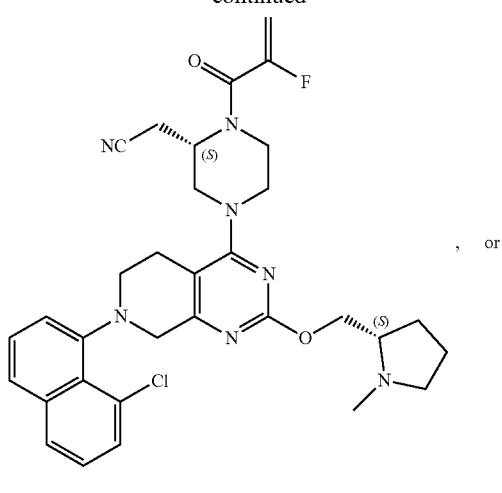

, or

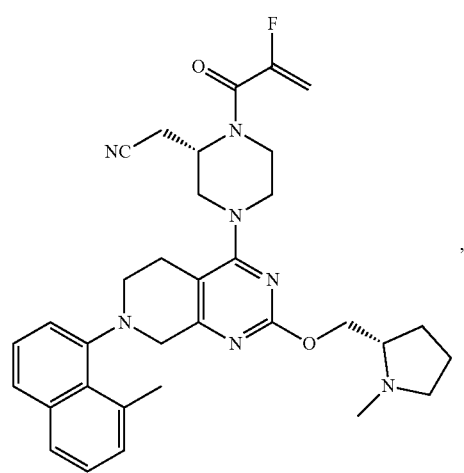 [SMILES: C=C(F)C(=O)N1CCN(c2nc(OC[C@@H]3CCCN3C)nc3c2CCN(c2cccc4cccc(C)c24)C3)C[C@@H]1CC#N]

and pharmaceutically acceptable salts thereof.

In one embodiment, the KRas G12C inhibitor is:

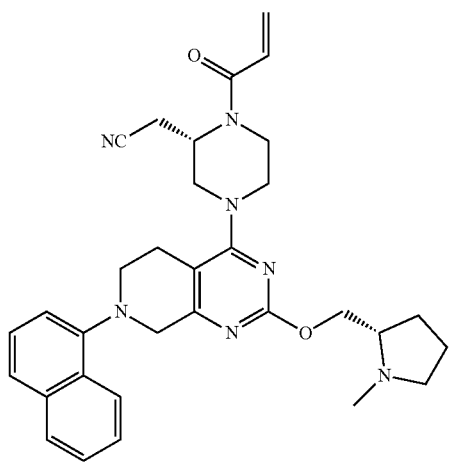 [SMILES: C=CC(=O)N1CCN(c2nc(OC[C@@H]3CCCN3C)nc3c2CCN(c2cccc4ccccc24)C3)C[C@@H]1CC#N]

(also referred to as Example 234) or a pharmaceutically acceptable salt thereof.

In one embodiment, the KRas G12C inhibitor is:

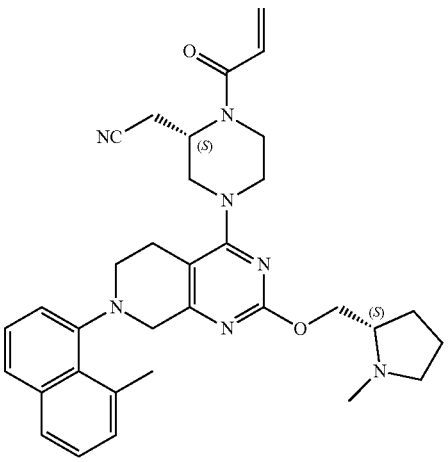

(also referred to as Example 359) or a pharmaceutically acceptable salt thereof.

In one embodiment, the KRas G12C inhibitor is:

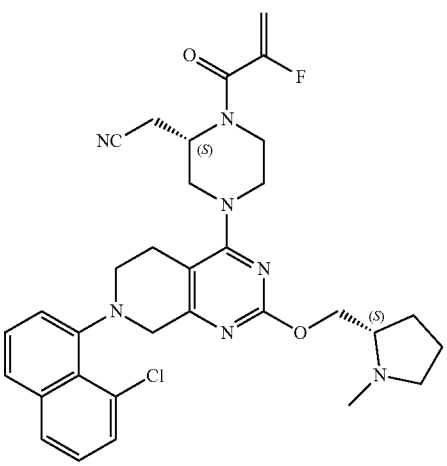

(also referred to as Example 478) or a pharmaceutically acceptable salt thereof.

In one embodiment, the KRas G12C inhibitor is:

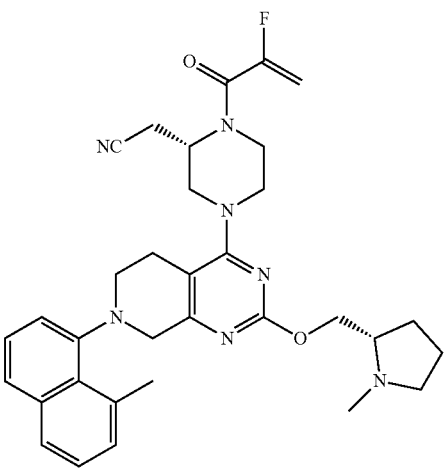 [SMILES: C=C(F)C(=O)N1CCN(c2nc(OC[C@@H]3CCCN3C)nc3c2CCN(c2cccc4cccc(C)c24)C3)C[C@@H]1CC#N]

(also referred to as Example 507) or a pharmaceutically acceptable salt thereof.

The KRas G12C inhibitors used in the methods of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

In one embodiment, the KRas G12C inhibitor compounds of Formula I, Formula I-A, or Formula I-B used in the methods include trifluoroacetic acid salts of the above compounds.

Methods for manufacturing the KRas G12C inhibitors disclosed herein are known. For example, commonly owned published international PCT application numbers WO2017201161 and WO2019099524 describe general reaction schemes for preparing compounds of Formula I, Formula I-A, or Formula I-B and also provide detailed synthetic routes for the preparation of each KRas G12C inhibitor disclosed herein.

The PD-1/PD-L1 inhibitors and the KRas G12C compounds of Formula (I), Formula I-A, or Formula I-B or pharmaceutically acceptable salts thereof may be separately formulated into pharmaceutical compositions.

Pharmaceutical Compositions

In another aspect, the invention provides pharmaceutical compositions comprising a PD-1/PD-L1 inhibitor and pharmaceutical compositions comprising a KRas G12C inhibitor or a pharmaceutically acceptable salt thereof according to the invention, wherein said compositions further comprise a pharmaceutically acceptable carrier, excipient, or diluent, that may be used in the methods disclosed herein. The KRas G12C inhibitor may be independently formulated by any method well known in the art and may be prepared for administration by any route, including, without limitation, parenteral, oral, sublingual, transdermal, topical, intranasal, intratracheal, intravenously or intrarectal. In certain embodiments, the pharmaceutical composition comprising a KRas G12C inhibitor, or a pharmaceutically acceptable salt or a pharmaceutical composition thereof, is administered intravenously. In one embodiment, the pharmaceutical composition comprising a KRas G12C inhibitor is administered orally. In one embodiment, the pharmaceutical composition comprising a PD-1/PD-L1 inhibitor is administered parenterally, including via subcutaneous, intracutaneous, intravenous, intramuscular, intraarticular, intraarterial, intrasynovial, intrasternal, intrathecal, intralesional and intracranial injection or infusion techniques. In one embodiment, the pharmaceutical composition comprising a PD-1/PD-L1 inhibitor is administered intravenously.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound or agent is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned compositions of the KRas G12C inhibitor is in the range from about 0.01 to 300 mg/kg, for example 0.1 to 100 mg/kg per day, and as a further example 0.5 to about 25 mg per kilogram body weight of the recipient per day. The effective dosage range of the pharmaceutically acceptable carrier or diluent can be calculated based on the weight of the parent compound to be delivered. If the derivative exhibits activity in itself, the effective dosage can be estimated as above using the weight of the derivative, or by other means known to those skilled in the art.

The pharmaceutical compositions comprising a PD-1/PD-L1 inhibitor and the pharmaceutical compositions comprising a KRas G12C inhibitor may be used in any of the methods of use described herein.

Co-Administration

The components of the pharmaceutical combinations described herein comprising a PD-1/PD-L1 inhibitor and/or a KRas G12C inhibitor or a pharmaceutically acceptable salt thereof, for use in any of the methods herein may be for simultaneous, separate or sequential use. In one embodiment, the PD-1/PD-L1 inhibitor is administered prior to administration of the KRas G12C inhibitor compound of Formula (I), Formula I-A or Formula I-B, or a pharmaceutically acceptable salt or a pharmaceutical composition thereof. In another embodiment, the PD-1/PD-L1 inhibitor or a pharmaceutical composition thereof is administered after administration of the KRas G12C inhibitor compound of Formula (I), Formula I-A or Formula I-B, or a pharmaceutically acceptable salt or a pharmaceutical composition thereof. In another embodiment, the PD-1/PD-L1 inhibitor, or a pharmaceutical composition thereof, is administered at about the same time as administration of the KRas G12C inhibitor compound of Formula (I), Formula I-A or Formula I-B, or a pharmaceutically acceptable salt or a pharmaceutical composition thereof. In one embodiment, the PD-1/PD-L1 inhibitor or a pharmaceutical composition thereof and the KRas G12C inhibitor, or a pharmaceutically acceptable salt or a pharmaceutical composition thereof, can be formulated into separate or individual dosage forms which can be co-administered simultaneously or one after the other.

Separate administration of each inhibitor, at different times and by different routes, in some cases would be advantageous. Thus, the components of the combination, i.e. the KRas G12C inhibitor compound of Formula (I), Formula I-A or Formula I-B, or a pharmaceutically acceptable salt or a pharmaceutical composition thereof and the PD-1/PD-L1 inhibitor or a pharmaceutical composition thereof, need not be necessarily administered at essentially the same time or in any order.

Oncology drugs are typically administered at the maximum tolerated dose ("MTD"), which is the highest dose of drug that does not cause unacceptable side effects. In one embodiment, the KRas G12C inhibitor, or a pharmaceutically acceptable salt or a pharmaceutical composition thereof, and the PD-1/PD-L1 inhibitor or a pharmaceutical composition thereof are each dosed at their respective MTDs. In one embodiment, the KRas G12C inhibitor, or a pharmaceutically acceptable salt or a pharmaceutical composition thereof, is dosed at its MTD and the PD-1/PD-L1 inhibitor or a pharmaceutical composition thereof is dosed in an amount less than its MTD. In one embodiment, the KRas G12C inhibitor, or a pharmaceutically acceptable salt or a pharmaceutical composition thereof, is dosed at an amount less than its MTD and the PD-1/PD-L1 inhibitor or a pharmaceutical composition thereof is dosed at its MTD. In one embodiment, the KRas G12C inhibitor, or a pharmaceutically acceptable salt or a pharmaceutical composition thereof, and the PD-1/PD-L1 inhibitor or a pharmaceutical composition thereof are each dosed at less than their respective MTDs. The administration can be so timed that the peak pharmacokinetic effect of one inhibitor coincides with the peak pharmacokinetic effect of the other.

In one embodiment, a single dose of KRas G12C inhibitor compound of Formula (I), Formula I-A or Formula I-B, or a pharmaceutically acceptable salt or a pharmaceutical composition thereof, is administered per day (i.e., in about 24 hour intervals) (i.e., QD). In another embodiment, two doses of the KRas G12C inhibitor compound of Formula (I), Formula I-A or Formula I-B, or a pharmaceutically acceptable salt or a pharmaceutical composition thereof, are administered per day (i.e., BID). In another embodiment, three doses of the KRas G12C inhibitor compound of Formula (I), Formula I-A or Formula I-B, or a pharmaceutically acceptable salt or a pharmaceutical composition thereof, are administered per day (i.e., TID). In one of any of said embodiments, the KRAS inhibitor is administered orally.

Examples of PD-1/PD-L1 inhibitors suitable for the provided compositions and methods include, but are not limited to, PD-1 antibodies, including but not limited to nivolumab (Opdivo®), pembrolizumab (Keytruda®), cemiplimab (Libtayo®) and tislelizumab, and biosimilars thereof, and anti-PD-L1 antibodies including, but not limited to, atezolizumab (Tecentriq®), avelumab (Bavencio®), and durvalumab (Imfinzi®), and biosimilars thereof.

In one embodiment, a single dose of the PD-1/PD-L1 inhibitor is administered. In one embodiment, the PD-1/PD-L1 inhibitor is administered once every two weeks. In one embodiment, the PD-1/PD-L1 inhibitor is administered once every three weeks. In one embodiment, the PD-1/PD-L1 inhibitor is administered once every four weeks. In one embodiment, the PD-1/PD-L1 inhibitor is nivolumab and is administered once every two weeks. In one embodiment, the PD-1/PD-L1 inhibitor is nivolumab and is administered once every four weeks. In one embodiment, the PD-1/PD-L1 inhibitor is pembrolizumab and is administered once every three weeks. In one embodiment, the PD-1/PD-L1 inhibitor is atezolizumab and is administered once every three weeks. In one embodiment, the PD-1/PD-L1 inhibitor is cemiplimab and is administered once every three weeks. In one embodiment, the PD-1/PD-L1 inhibitor is tislelizumab and is administered once every three weeks. In one embodiment, the PD-1/PD-L1 inhibitor is avelumab and is administered once every two weeks. In one embodiment, the PD-1/PD-L1 inhibitor is durvalumab and is administered once every two weeks. In one of any of said embodiments, the PD-1/PD-L1 inhibitor is administered intravenously.

Combination Therapies

In one aspect of the invention, provided herein are methods of treating cancer in a subject in need thereof, comprising administering to the subject a therapeutically effective amount of a combination of a PD-1/PD-L1 inhibitor or a pharmaceutical composition thereof and a KRAS G12C inhibitor of Formula (I), Formula I-A or Formula I-B, or a pharmaceutically acceptable salt or a pharmaceutical composition thereof. In one embodiment, the cancer is a KRas G12C-associated cancer. In one embodiment, the KRas G12C-associated cancer is lung cancer. In one embodiment, the KRas G12C-associated cancer is colorectal cancer.

In one embodiment, the invention provides for methods for inducing a durable complete response in a subject having cancer, comprising administering to the subject a therapeutically effective amount of a combination of a KRas G12C inhibitor compound of Formula (I), Formula I-A, or Formula I-B, or a pharmaceutically acceptable salt or a pharmaceutical composition thereof and a PD-1/PD-L1 inhibitor or a pharmaceutical composition thereof, wherein the subject exhibits a durable complete response.

In one embodiment, the combination therapy comprises a combination of a compound having the formula:

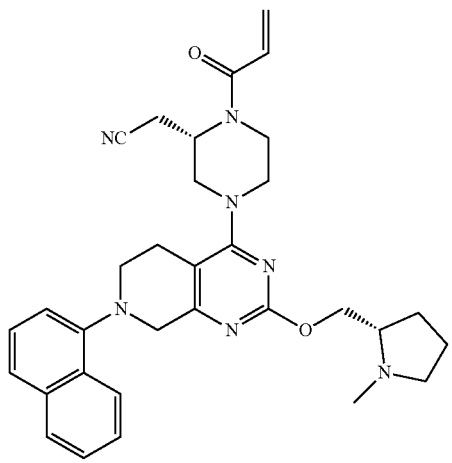

(also referred to herein as Example No. 234) or a pharmaceutically acceptable salt thereof, and a PD-1/PD-L1 inhibitor. In one embodiment, the PD-1/PD-L1 inhibitor is nivolumab. In one embodiment, the PD-1/PD-L1 inhibitor is pembrolizumab. In one embodiment, the PD-1/PD-L1 inhibitor is cemiplimab. In one embodiment, the PD-1/PD-L1 inhibitor is tislelizumab. In one embodiment, the PD-1/PD-L1 inhibitor is atezolizumab. In one embodiment, the PD-1/PD-L1 inhibitor is avelumab. In one embodiment, the PD-1/PD-L1 inhibitor is durvalumab.

In one embodiment, the combination therapy comprises a combination of a compound having the formula:

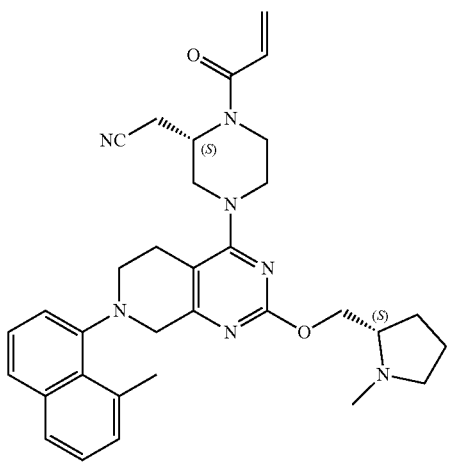

(also referred to herein as Example No. 359) or a pharmaceutically acceptable salt thereof, and a PD-1/PD-L1 inhibitor. In one embodiment, the PD-1/PD-L1 inhibitor is nivolumab. In one embodiment, the PD-1/PD-L1 inhibitor is pembrolizumab. In one embodiment, the PD-1/PD-L1 inhibitor is cemiplimab. In one embodiment, the PD-1/PD-L1 inhibitor is tislelizumab. In one embodiment, the PD-1/PD-L1 inhibitor is atezolizumab. In one embodiment, the PD-1/PD-L1 inhibitor is avelumab. In one embodiment, the PD-1/PD-L1 inhibitor is durvalumab.

In one embodiment, the combination therapy comprises a combination of a compound having the formula:

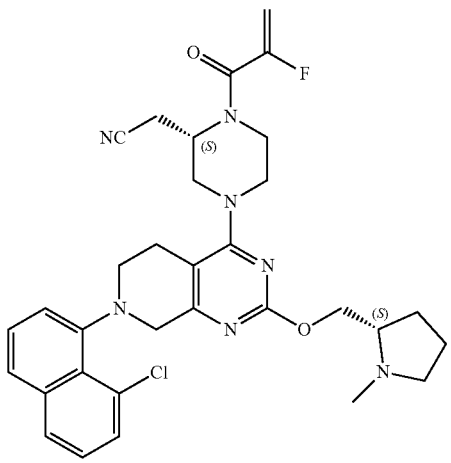

(also referred to herein as Example No. 478) or a pharmaceutically acceptable salt thereof, and a PD-1/PD-L1 inhibitor. In one embodiment, the PD-1/PD-L1 inhibitor is nivolumab. In one embodiment, the PD-1/PD-L1 inhibitor is pembrolizumab. In one embodiment, the PD-1/PD-L1 inhibitor is cemiplimab. In one embodiment, the PD-1/PD-L1 inhibitor is tislelizumab. In one embodiment, the PD-1/PD-L1 inhibitor is atezolizumab. In one embodiment, the PD-1/PD-L1 inhibitor is avelumab. In one embodiment, the PD-1/PD-L1 inhibitor is durvalumab.

In one embodiment, the combination therapy comprises a combination of a compound having the formula:

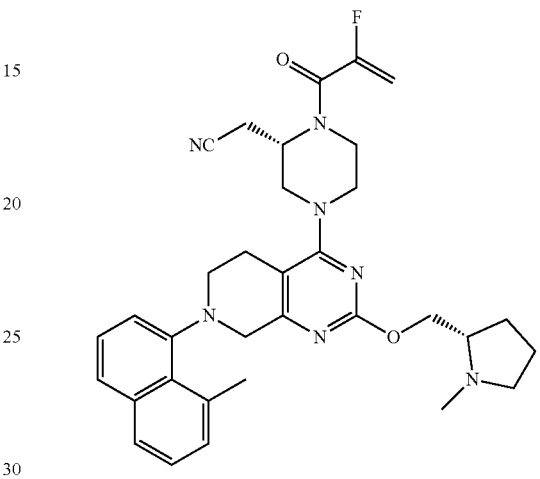

(also referred to herein as Example No. 507) or a pharmaceutically acceptable salt thereof, and a PD-1/PD-L1 inhibitor. In one embodiment, the PD-1/PD-L1 inhibitor is nivolumab. In one embodiment, the PD-1/PD-L1 inhibitor is pembrolizumab. In one embodiment, the PD-1/PD-L1 inhibitor is cemiplimab. In one embodiment, the PD-1/PD-L1 inhibitor is tislelizumab. In one embodiment, the PD-1/PD-L1 inhibitor is atezolizumab. In one embodiment, the PD-1/PD-L1 inhibitor is avelumab. In one embodiment, the PD-1/PD-L1 inhibitor is durvalumab.

By negatively modulating the activity of KRas G12C, the methods described herein are designed to inhibit undesired cellular proliferation resulting from enhanced KRas G12C activity that can lead to immune suppression and resistance to PD-1/PD-L1 inhibitors. The degree of covalent modification of KRas G12C may be monitored in vitro using well known methods, including those described in published international PCT application numbers WO2017201161 and WO2019099524. In addition, the inhibitory activity of combination in cells may be monitored, for example, by measuring the inhibition of KRas G12C activity of the amount of phosphorylated ERK to assess the effectiveness of treatment and dosages may be adjusted accordingly by the attending medical practitioner. Methods for determining the expression of PD-1 and PD-L1 are well known and may be used to monitor PD-1 status during treatment.

The combinations and methods provided herein may be used for the treatment of a KRas G12C-associated cancer in a subject in need thereof, comprising administering to said subject a therapeutically effective amount of a combination of a PD-1/PD-L1 inhibitor, or a pharmaceutical composition thereof and a KRas G12C inhibitor compound of Formula (I), Formula I-A, or Formula I-B, or pharmaceutically acceptable salts or pharmaceutical compositions thereof, wherein the PD-1/PD-L1 inhibitor synergistically increases the sensitivity of the KRas G12C-associated cancer to the KRas G12C inhibitor. In one embodiment, the KRas G12C-associated cancer is lung cancer. In one embodiment, the KRAS G12C-associated cancer is colorectal cancer.

In one embodiment, the therapeutically effective amount of the combination of a PD-1/PD-L1 inhibitor or a pharmaceutical composition thereof and a KRas G12C inhibitor compound of Formula (I), Formula I-A, or Formula I-B, or a pharmaceutically acceptable salt or a pharmaceutical composition thereof, results in an increased duration of overall survival ("OS") in subjects relative to treatment with only the KRas G12C inhibitor. In one embodiment, the increased duration of overall survival ("OS") in subjects relative to treatment with KRas G12C inhibitor monotherapy is for the remaining life time of the subject. In one embodiment, the therapeutically effective amount of the combination of a PD-1/PD-L1 inhibitor or a pharmaceutical composition thereof and a KRas G12C inhibitor compound of Formula (I), Formula I-A, or Formula I-B, or a pharmaceutically acceptable salt or a pharmaceutical composition thereof, results in an increased duration of progression-free survival ("PFS") in subjects relative to treatment with only the KRas G12C inhibitor. In one embodiment, the therapeutically effective amount of the combination of a PD-1/PD-L1 inhibitor or a pharmaceutical composition thereof and a KRas G12C inhibitor compound of Formula (I), Formula I-A, or Formula I-B, or a pharmaceutically acceptable salt or a pharmaceutical composition thereof, results in increased tumor regression in subjects relative to treatment with only the KRas G12C inhibitor. In one embodiment, the therapeutically effective amount of the combination of a PD-1/PD-L1 inhibitor or a pharmaceutical composition thereof and a KRas G12C inhibitor compound of Formula (I), Formula I-A, or Formula I-B, or a pharmaceutically acceptable salt or a pharmaceutical composition thereof, results in increased tumor growth inhibition in subjects relative to treatment with only the KRas G12C inhibitor. In one embodiment, the therapeutically effective amount of the combination of a PD-1/PD-L1 inhibitor or a pharmaceutical composition thereof and a KRas G12C inhibitor compound of Formula (I), Formula I-A, or Formula I-B, or a pharmaceutically acceptable salt or a pharmaceutical composition thereof, results in an improvement in the duration of stable disease in subjects compared to treatment with only the KRas G12C inhibitor. In one embodiment, the KRas G12C inhibitor is a compound selected from compound Nos. 1-678 (as numbered in WO2019099524), or a pharmaceutically acceptable salt thereof (e.g., Example No. 234, 359, 478 or 507 or a pharmaceutically acceptable salt thereof). In one embodiment, the PD-1/PD-L1 inhibitor is selected from nivolumab, pembrolizumab, cemiplimab, tislelizumab, atezolizumab, avelumab, and durvalumab. In one embodiment, the therapeutic combination comprises therapeutically effective amounts of Example No. 234 and nivolumab. In one embodiment, the therapeutic combination comprises therapeutically effective amounts of Example No. 234 and pembrolizumab. In one embodiment, the therapeutic combination comprises therapeutically effective amounts of Example No. 234 and cemiplimab. In one embodiment, the therapeutic combination comprises therapeutically effective amounts of Example No. 234 and tislelizumab. In one embodiment, the therapeutic combination comprises therapeutically effective amounts of Example No. 234 and atezolizumab. In one embodiment, the therapeutic combination comprises therapeutically effective amounts of Example No. 234 and avelumab. In one embodiment, the therapeutic combination comprises therapeutically effective amounts of Example No. 234 and durvalumab. In one embodiment, the therapeutic combination comprises therapeutically effective amounts of Example No. 359 and nivolumab. In one embodiment, the therapeutic combination comprises therapeutically effective amounts of Example No. 359 and pembrolizumab. In one embodiment, the therapeutic combination comprises therapeutically effective amounts of Example No. 359 and cemiplimab. In one embodiment, the therapeutic combination comprises therapeutically effective amounts of Example No. 359 and tislelizumab. In one embodiment, the therapeutic combination comprises therapeutically effective amounts of Example No. 359 and atezolizumab. In one embodiment, the therapeutic combination comprises therapeutically effective amounts of Example No. 359 and avelumab. In one embodiment, the therapeutic combination comprises therapeutically effective amounts of Example No. 359 and durvalumab. In one embodiment, the therapeutic combination comprises therapeutically effective amounts of Example No. 478 and nivolumab. In one embodiment, the therapeutic combination comprises therapeutically effective amounts of Example No. 478 and pembrolizumab. In one embodiment, the therapeutic combination comprises therapeutically effective amounts of Example No. 478 and cemiplimab. In one embodiment, the therapeutic combination comprises therapeutically effective amounts of Example No. 478 and tislelizumab. In one embodiment, the therapeutic combination comprises therapeutically effective amounts of Example No. 478 and atezolizumab. In one embodiment, the therapeutic combination comprises therapeutically effective amounts of Example No. 478 and avelumab. In one embodiment, the therapeutic combination comprises therapeutically effective amounts of Example No. 478 and durvalumab. In one embodiment, the therapeutic combination comprises therapeutically effective amounts of Example No. 507 and nivolumab. In one embodiment, the therapeutic combination comprises therapeutically effective amounts of Example No. 507 and pembrolizumab. In one embodiment, the therapeutic combination comprises therapeutically effective amounts of Example No. 507 and cemiplimab. In one embodiment, the therapeutic combination comprises therapeutically effective amounts of Example No. 507 and tislelizumab. In one embodiment, the therapeutic combination comprises therapeutically effective amounts of Example No. 507 and atezolizumab. In one embodiment, the therapeutic combination comprises therapeutically effective amounts of Example No. 507 and avelumab. In one embodiment, the therapeutic combination comprises therapeutically effective amounts of Example No. 507 and durvalumab.

In another embodiment, the PD-1/PD-L1 inhibitor is administered in combination with the KRas G12C inhibitor once disease progression has been observed for KRas G12C monotherapy, in which the combination therapy results in enhanced clinical benefit for the patient by increasing OS, PFS, tumor regression, tumor growth inhibition or the duration of stable disease in the patient. In one embodiment, the KRas G12C inhibitor is a compound selected from compound Nos. 1-678 (as numbered in WO2019099524), or a pharmaceutically acceptable salt thereof (e.g., Example No. 234, 359, 478 or 507 or a pharmaceutically acceptable salt thereof). In one embodiment, the PD-1/PD-L1 inhibitor is selected from nivolumab, pembrolizumab, cemiplimab, tislelizumab, atezolizumab, avelumab, and durvalumab. In one embodiment, the therapeutic combination comprises therapeutically effective amounts of Example No. 234 and nivolumab. In one embodiment, the therapeutic combination comprises therapeutically effective amounts of Example No. 234 and pembrolizumab. In one embodiment, the therapeutic combination comprises therapeutically effective amounts of Example No. 234 and cemiplimab. In one embodiment, the therapeutic combination comprises therapeutically effective amounts of Example No. 234 and tislelizumab. In one embodiment, the therapeutic combination comprises therapeutically effective amounts of Example No. 234 and atezolizumab. In one embodiment, the therapeutic combination comprises therapeutically effective amounts of Example No. 234 and avelumab. In one embodiment, the therapeutic combination comprises therapeutically effective amounts of Example No. 234 and durvalumab. In one embodiment, the therapeutic combination comprises therapeutically effective amounts of Example No. 359 and nivolumab. In one embodiment, the therapeutic combination comprises therapeutically effective amounts of Example No. 359 and pembrolizumab. In one embodiment, the therapeutic combination comprises therapeutically effective amounts of Example No. 359 and cemiplimab. In one embodiment, the therapeutic combination comprises therapeutically effective amounts of Example No. 359 and tislelizumab. In one embodiment, the therapeutic combination comprises therapeutically effective amounts of Example No. 359 and atezolizumab. In one embodiment, the therapeutic combination comprises therapeutically effective amounts of Example No. 359 and avelumab. In one embodiment, the therapeutic combination comprises therapeutically effective amounts of Example No. 359 and durvalumab. In one embodiment, the therapeutic combination comprises therapeutically effective amounts of Example No. 478 and nivolumab. In one embodiment, the therapeutic combination comprises therapeutically effective amounts of Example No. 478 and pembrolizumab. In one embodiment, the therapeutic combination comprises therapeutically effective amounts of Example No. 478 and cemiplimab. In one embodiment, the therapeutic combination comprises therapeutically effective amounts of Example No. 478 and tislelizumab. In one embodiment, the therapeutic combination comprises therapeutically effective amounts of Example No. 478 and atezolizumab. In one embodiment, the therapeutic combination comprises therapeutically effective amounts of Example No. 478 and avelumab. In one embodiment, the therapeutic combination comprises therapeutically effective amounts of Example No. 478 and durvalumab. In one embodiment, the therapeutic combination comprises therapeutically effective amounts of Example No. 507 and avelumab. In one embodiment, the therapeutic combination comprises therapeutically effective amounts of Example No. 507 and pembrolizumab. In one embodiment, the therapeutic combination comprises therapeutically effective amounts of Example No. 507 and cemiplimab. In one embodiment, the therapeutic combination comprises therapeutically effective amounts of Example No. 507 and tislelizumab. In one embodiment, the therapeutic combination comprises therapeutically effective amounts of Example No. 507 and atezolizumab. In one embodiment, the therapeutic combination comprises therapeutically effective amounts of Example No. 507 and avelumab. In one embodiment, the therapeutic combination comprises therapeutically effective amounts of Example No. 507 and durvalumab.

The compositions and methods provided herein may be used for the treatment of a wide variety of cancers including tumors such as lung, colorectal, pancreas, prostate, breast, brain, skin, cervical carcinomas, testicular carcinomas, etc. More particularly, cancers that may be treated by the compositions and methods of the invention include, but are not limited to, tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer. In one embodiment, the KRas G12C-associated cancer is colorectal cancer.

Also provided herein is a method for treating cancer in a subject in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of a combination of a PD-1/PD-L1 inhibitor and a KRas G12C inhibitor compound of Formula I, Formula I-A, Formula 1-B, or a pharmaceutically acceptable salt or pharmaceutical composition thereof, wherein the PD-1/PD-L1 inhibitor synergistically increases the sensitivity of the KRas G12C-associated cancer to the KRas G12C inhibitor.

The combinations and methods provided herein also may be used for the treatment of a KRas G12C-associated cancer in a subject in need thereof, wherein the KRas G12C-associated cancer is resistant to treatment with a PD-1/PD-L1 inhibitor, comprising administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof.

In one embodiment, the combinations and methods provided herein are used for the treatment of a KRas G12C-associated cancer and determined to have previously developed resistance to treatment with a PD-1/PD-L1 inhibitor that include administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof.

Also the combinations and methods provided herein also may be used for suppressing resistance to treatment with a PD-1/PD-L1 inhibitor in a subject having a KRas G12C-associated cancer that include administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof.

In one embodiment, the invention provides methods of treating a subject identified or diagnosed as having a KRAS G12C-associated cancer that include (a) detecting resistance of the KRas G12C-associated cancer in the subject to treatment with a PD-1/PD-L1 inhibitor that was previously administered to the patient; and (b) after (a), administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof.

The combinations and methods provided herein also may be used for the treatment of a subject identified or diagnosed as having a KRas G12C-associated cancer and determined to have previously developed resistance to treatment with a KRAS G12C inhibitor that include administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof.

In one embodiment, the invention provides methods of treating a subject identified or diagnosed as having a KRas G12C-associated cancer, comprising (a) administering a KRAS G12C inhibitor as monotherapy until disease progression, and (b) after (a), administering to the subject a therapeutically effective amount of a combination of a PD-1/PD-L1 inhibitor, or a pharmaceutical composition thereof, and a KRAS G12C inhibitor of Formula (I), Formula I-A or Formula I-B, or a pharmaceutically acceptable salt or a pharmaceutical composition thereof.

In one embodiment, the KRas G12C inhibitor used for treating the KRas G12C-associated cancers in any of the foregoing methods is a compound selected from compound Nos. 1-678 (as numbered in WO2019099524), or a pharmaceutically acceptable salt thereof (e.g., Example No. 234, 359, 478 or 507 or a pharmaceutically acceptable salt thereof). In one embodiment, the PD-1/PD-L1 inhibitor is selected from nivolumab, pembrolizumab, cemiplimab, tislelizumab, atezolizumab, avelumab, and durvalumab. In one embodiment, the therapeutic combination comprises therapeutically effective amounts of Example No. 234 and nivolumab. In one embodiment, the therapeutic combination comprises therapeutically effective amounts of Example No. 234 and pembrolizumab. In one embodiment, the therapeutic combination comprises therapeutically effective amounts of Example No. 234 and cemiplimab. In one embodiment, the therapeutic combination comprises therapeutically effective amounts of Example No. 234 and tislelizumab. In one embodiment, the therapeutic combination comprises therapeutically effective amounts of Example No. 234 and atezolizumab. In one embodiment, the therapeutic combination comprises therapeutically effective amounts of Example No. 234 and avelumab. In one embodiment, the therapeutic combination comprises therapeutically effective amounts of Example No. 234 and durvalumab. In one embodiment, the therapeutic combination comprises therapeutically effective amounts of Example No. 359 and nivolumab. In one embodiment, the therapeutic combination comprises therapeutically effective amounts of Example No. 359 and pembrolizumab. In one embodiment, the therapeutic combination comprises therapeutically effective amounts of Example No. 359 and cemiplimab. In one embodiment, the therapeutic combination comprises therapeutically effective amounts of Example No. 359 and tislelizumab. In one embodiment, the therapeutic combination comprises therapeutically effective amounts of Example No. 359 and atezolizumab. In one embodiment, the therapeutic combination comprises therapeutically effective amounts of Example No. 359 and avelumab. In one embodiment, the therapeutic combination comprises therapeutically effective amounts of Example No. 359 and durvalumab. In one embodiment, the therapeutic combination comprises therapeutically effective amounts of Example No. 478 and nivolumab. In one embodiment, the therapeutic combination comprises therapeutically effective amounts of Example No. 478 and pembrolizumab. In one embodiment, the therapeutic combination comprises therapeutically effective amounts of Example No. 478 and cemiplimab. In one embodiment, the therapeutic combination comprises therapeutically effective amounts of Example No. 478 and tislelizumab. In one embodiment, the therapeutic combination comprises therapeutically effective amounts of Example No. 478 and atezolizumab. In one embodiment, the therapeutic combination comprises therapeutically effective amounts of Example No. 478 and avelumab. In one embodiment, the therapeutic combination comprises therapeutically effective amounts of Example No. 478 and durvalumab. In one embodiment, the therapeutic combination comprises therapeutically effective amounts of Example No. 507 and nivolumab. In one embodiment, the therapeutic combination comprises therapeutically effective amounts of Example No. 507 and pembrolizumab. In one embodiment, the therapeutic combination comprises therapeutically effective amounts of Example No. 507 and cemiplimab. In one embodiment, the therapeutic combination comprises therapeutically effective amounts of Example No. 507 and tislelizumab. In one embodiment, the therapeutic combination comprises therapeutically effective amounts of Example No. 507 and atezolizumab. In one embodiment, the therapeutic combination comprises therapeutically effective amounts of Example No. 507 and avelumab. In one embodiment, the therapeutic combination comprises therapeutically effective amounts of Example No. 507 and durvalumab.

In one embodiment, a compound of Formula I, Formula I-A, Formula 1-B, or a pharmaceutically acceptable salt or pharmaceutical composition thereof is administered as a tablet or capsule. In one embodiment, a tablet or capsule formulation of a compound of Formula I comprises about 10 mg to about 100 mg (e.g., about 10 mg to about 95 mg, about 10 mg to about 90 mg, about 10 mg to about 85 mg, about 10 mg to about 80 mg, about 10 mg to about 75 mg, about 10 mg to about 70 mg, about 10 mg to about 65 mg, about 10 mg to about 60 mg, about 10 mg to about 55 mg, about 10 mg to about 50 mg, about 10 mg to about 45 mg, about 10 mg to about 40 mg, about 10 mg to about 35 mg, about 10 mg to about 30 mg, about 10 mg to about 25 mg, about 10 mg to about 20 mg, about 10 mg to about 15 mg, about 15 mg to about 100 mg, about 15 mg to about 95 mg, about 15 mg to about 90 mg, about 15 mg to about 85 mg, about 15 mg to about 80 mg, about 15 mg to about 75 mg, about 15 mg to about 70 mg, about 15 mg to about 65 mg, about 15 mg to about 60 mg, about 15 mg to about 55 mg, about 15 mg to about 50 mg, about 15 mg to about 45 mg, about 15 mg to about 40 mg, about 15 mg to about 35 mg, about 15 mg to about 30 mg, about 15 mg to about 25 mg, about 15 mg to about 20 mg, about 20 mg to about 100 mg, about 20 mg to about 95 mg, about 20 mg to about 90 mg, about 20 mg to about 85 mg, about 20 mg to about 80 mg, about 20 mg to about 75 mg, about 20 mg to about 70 mg, about 20 mg to about 65 mg, about 20 mg to about 60 mg, about 20 mg to about 55 mg, about 20 mg to about 50 mg, about 20 mg to about 45 mg, about 20 mg to about 40 mg, about 20 mg to about 35 mg, about 20 mg to about 30 mg, about 20 mg to about 25 mg, about 25 mg to about 100 mg, about 25 mg to about 95 mg, about 25 mg to about 90 mg, about 25 mg to about 85 mg, about 25 mg to about 80 mg, about 25 mg to about 75 mg, about 25 mg to about 70 mg, about 25 mg to about 65 mg, about 25 mg to about 60 mg, about 25 mg to about 55 mg, about 25 mg to about 50 mg, about 25 mg to about 45 mg, about 25 mg to about 40 mg, about 25 mg to about 35 mg, about 25 mg to about 30 mg, about 30 mg to about 100 mg, about 30 mg to about 95 mg, about 30 mg to about 90 mg, about 30 mg to about 85 mg, about 30 mg to about 80 mg, about 30 mg to about 75 mg, about 30 mg to about 70 mg, about 30 mg to about 65 mg, about 30 mg to about 60 mg, about 30 mg to about 55 mg, about 30 mg to about 50 mg, about 30 mg to about 45 mg, about 30 mg to about 40 mg, about 30 mg to about 35 mg, about 35 mg to about 100 mg, about 35 mg to about 95 mg, about 35 mg to about 90 mg, about 35 mg to about 85 mg, about 35 mg to about 80 mg, about 35 mg to about 75 mg, about 35 mg to about 70 mg, about 35 mg to about 65 mg, about 35 mg to about 60 mg, about 35 mg to about 55 mg, about 35 mg to about 50 mg, about 35 mg to about 45 mg, about 35 mg to about 40 mg, about 40 mg to about 100 mg, about 40 mg to about 95 mg, about 40 mg to about 90 mg, about 40 mg to about 85 mg, about 40 mg to about 80 mg, about 40 mg to about 75 mg, about 40 mg to about 70 mg, about 40 mg to about 65 mg, about 40 mg to about 60 mg, about 40 mg to about 55 mg, about 40 mg to about 50 mg, about 40 mg to about 45 mg, about 45 mg to about 100 mg, about 45 mg to about 95 mg, about 45 mg to about 90 mg, about 45 mg to about 85 mg, about 45 mg to about 80 mg, about 45 mg to about 75 mg, about 45 mg to about 70 mg, about 45 mg to about 65 mg, about 45 mg to about 60 mg, about 45 mg to about 55 mg, about 45 mg to about 50 mg, about 50 mg to about 100 mg, about 50 mg to about 95 mg, about 50 mg to about 90 mg, about 50 mg to about 85 mg, about 50 mg to about 80 mg, about 50 mg to about 75 mg, about 50 mg to about 70 mg, about 50 mg to about 65 mg, about 50 mg to about 60 mg, about 50 mg to about 55 mg, about 55 mg to about 100 mg, about 55 mg to about 95 mg, about 55 mg to about 90 mg, about 55 mg to about 85 mg, about 55 mg to about 80 mg, about 55 mg to about 75 mg, about 55 mg to about 70 mg, about 55 mg to about 65 mg, about 55 mg to about 60 mg, about 60 mg to about 100 mg, about 60 mg to about 95 mg, about 60 mg to about 90 mg, about 60 mg to about 85 mg, about 60 mg to about 80 mg, about 60 mg to about 75 mg, about 60 mg to about 70 mg, about 60 mg to about 65 mg, about 65 mg to about 100 mg, about 65 mg to about 95 mg, about 65 mg to about 90 mg, about 65 mg to about 85 mg, about 65 mg to about 80 mg, about 65 mg to about 75 mg, about 65 mg to about 70 mg, about 70 mg to about 100 mg, about 70 mg to about 95 mg, about 70 mg to about 90 mg, about 70 mg to about 85 mg, about 70 mg to about 80 mg, about 70 mg to about 75 mg, about 75 mg to about 100 mg, about 75 mg to about 95 mg, about 75 mg to about 90 mg, about 75 mg to about 85 mg, about 75 mg to about 80 mg, about 80 mg to about 100 mg, about 80 mg to about 95 mg, about 80 mg to about 90 mg, about 80 mg to about 85 mg, about 85 mg to about 100 mg, about 85 mg to about 95 mg, about 85 mg to about 90 mg, about 90 mg to about 100 mg, about 90 mg to about 95 mg, about 95 mg to about 100 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg) of a compound of Formula Nos. 1-678 (as numbered in WO2019099524), or a pharmaceutically acceptable salt thereof (e.g., Example No. 234, 359, 478 or 507 or a pharmaceutically acceptable salt thereof). In one embodiment, a compound of Formula I is orally administered once a day (QD) on a daily basis during a period of time. In one embodiment, a compound of Formula I is orally administered twice a day (BID) on a daily basis during a period of time. In one embodiment, a compound of Formula I is orally administered in the amount of about 20 mg to about 500 mg (e.g., about 20 mg to about 480 mg, about 20 mg to about 460 mg, about 20 mg to about 440 mg, about 20 mg to about 420 mg, about 20 mg to about 400 mg, about 20 mg to about 380 mg, about 20 mg to about 360 mg, about 20 mg to about 340 mg, about 20 mg to about 320 mg, about 20 mg to about 300 mg, about 20 mg to about 280 mg, about 20 mg to about 260 mg, about 20 mg to about 240 mg, about 20 mg to about 220 mg, about 20 mg to about 200 mg, about 20 mg to about 180 mg, about 20 mg to about 160 mg, about 20 mg to about 140 mg, about 20 mg to about 120 mg, about 20 mg to about 100 mg, about 20 mg to about 80 mg, about 20 mg to about 60 mg, about 20 mg to about 40 mg, about 40 mg to about 500 mg, about 40 mg to about 480 mg, about 40 mg to about 460 mg, about 40 mg to about 440 mg, about 40 mg to about 420 mg, about 40 mg to about 400 mg, about 40 mg to about 380 mg, about 40 mg to about 360 mg, about 40 mg to about 340 mg, about 40 mg to about 320 mg, about 40 mg to about 300 mg, about 40 mg to about 280 mg, about 40 mg to about 260 mg, about 40 mg to about 240 mg, about 40 mg to about 220 mg, about 40 mg to about 200 mg, about 40 mg to about 180 mg, about 40 mg to about 160 mg, about 40 mg to about 140 mg, about 40 mg to about 120 mg, about 40 mg to about 100 mg, about 40 mg to about 80 mg, about 40 mg to about 60 mg, about 60 mg to about 500 mg, about 60 mg to about 480 mg, about 60 mg to about 460 mg, about 60 mg to about 440 mg, about 60 mg to about 420 mg, about 60 mg to about 400 mg, about 60 mg to about 380 mg, about 60 mg to about 360 mg, about 60 mg to about 340 mg, about 60 mg to about 320 mg, about 60 mg to about 300 mg, about 60 mg to about 280 mg, about 60 mg to about 260 mg, about 60 mg to about 240 mg, about 60 mg to about 220 mg, about 60 mg to about 200 mg, about 60 mg to about 180 mg, about 60 mg to about 160 mg, about 60 mg to about 140 mg, about 60 mg to about 120 mg, about 60 mg to about 100 mg, about 60 mg to about 80 mg, about 80 mg to about 500 mg, about 80 mg to about 480 mg, about 80 mg to about 460 mg, about 80 mg to about 440 mg, about 80 mg to about 420 mg, about 80 mg to about 400 mg, about 80 mg to about 380 mg, about 80 mg to about 360 mg, about 80 mg to about 340 mg, about 80 mg to about 320 mg, about 80 mg to about 300 mg, about 80 mg to about 280 mg, about 80 mg to about 260 mg, about 80 mg to about 240 mg, about 80 mg to about 220 mg, about 80 mg to about 200 mg, about 80 mg to about 180 mg, about 80 mg to about 160 mg, about 80 mg to about 140 mg, about 80 mg to about 120 mg, about 80 mg to about 100 mg, about 100 mg to about 500 mg, about 100 mg to about 480 mg, about 100 mg to about 460 mg, about 100 mg to about 440 mg, about 100 mg to about 420 mg, about 100 mg to about 400 mg, about 100 mg to about 380 mg, about 100 mg to about 360 mg, about 100 mg to about 340 mg, about 100 mg to about 320 mg, about 100 mg to about 300 mg, about 100 mg to about 280 mg, about 100 mg to about 260 mg, about 100 mg to about 240 mg, about 100 mg to about 220 mg, about 100 mg to about 200 mg, about 100 mg to about 180 mg, about 100 mg to about 160 mg, about 100 mg to about 140 mg, about 100 mg to about 120 mg, about 120 mg to about 500 mg, about 120 mg to about 480 mg, about 120 mg to about 460 mg, about 120 mg to about 440 mg, about 120 mg to about 420 mg, about 120 mg to about 400 mg, about 120 mg to about 380 mg, about 120 mg to about 360 mg, about 120 mg to about 340 mg, about 120 mg to about 320 mg, about 120 mg to about 300 mg, about 120 mg to about 280 mg, about 120 mg to about 260 mg, about 120 mg to about 240 mg, about 120 mg to about 220 mg, about 120 mg to about 200 mg, about 120 mg to about 180 mg, about 120 mg to about 160 mg, about 120 mg to about 140 mg, about 140 mg to about 500 mg, about 140 mg to about 480 mg, about 140 mg to about 460 mg, about 140 mg to about 440 mg, about 140 mg to about 420 mg, about 140 mg to about 400 mg, about 140 mg to about 380 mg, about 140 mg to about 360 mg, about 140 mg to about 340 mg, about 140 mg to about 320 mg, about 140 mg to about 300 mg, about 140 mg to about 280 mg, about 140 mg to about 260 mg, about 140 mg to about 240 mg, about 140 mg to about 220 mg, about 140 mg to about 200 mg, about 140 mg to about 180 mg, about 140 mg to about 160 mg, about 160 mg to about 500 mg, about 160 mg to about 480 mg, about 160 mg to about 460 mg, about 160 mg to about 440 mg, about 160 mg to about 420 mg, about 160 mg to about 400 mg, about 160 mg to about 380 mg, about 160 mg to about 360 mg, about 160 mg to about 340 mg, about 160 mg to about 320 mg, about 160 mg to about 300 mg, about 160 mg to about 280 mg, about 160 mg to about 260 mg, about 160 mg to about 240 mg, about 160 mg to about 220 mg, about 160 mg to about 200 mg, about 160 mg to about 180 mg, about 180 mg to about 500 mg, about 180 mg to about 480 mg, about 180 mg to about 460 mg, about 180 mg to about 440 mg, about 180 mg to about 420 mg, about 180 mg to about 400 mg, about 180 mg to about 380 mg, about 180 mg to about 360 mg, about 180 mg to about 340 mg, about 180 mg to about 320 mg, about 180 mg to about 300 mg, about 180 mg to about 280 mg, about 180 mg to about 260 mg, about 180 mg to about 240 mg, about 180 mg to about 220 mg, about 180 mg to about 200 mg, about 200 mg to about 500 mg, about 200 mg to about 480 mg, about 200 mg to about 460 mg, about 200 mg to about 440 mg, about 200 mg to about 420 mg, about 200 mg to about 400 mg, about 200 mg to about 380 mg, about 200 mg to about 360 mg, about 200 mg to about 340 mg, about 200 mg to about 320 mg, about 200 mg to about 300 mg, about 200 mg to about 280 mg, about 200 mg to about 260 mg, about 200 mg to about 240 mg, about 200 mg to about 220 mg, about 220 mg to about 500 mg, about 220 mg to about 480 mg, about 220 mg to about 460 mg, about 220 mg to about 440 mg, about 220 mg to about 420 mg, about 220 mg to about 400 mg, about 220 mg to about 380 mg, about 220 mg to about 360 mg, about 220 mg to about 340 mg, about 220 mg to about 320 mg, about 220 mg to about 300 mg, about 220 mg to about 280 mg, about 220 mg to about 260 mg, about 220 mg to about 240 mg, about 240 mg to about 500 mg, about 240 mg to about 480 mg, about 240 mg to about 460 mg, about 240 mg to about 440 mg, about 240 mg to about 420 mg, about 240 mg to about 400 mg, about 240 mg to about 380 mg, about 240 mg to about 360 mg, about 240 mg to about 340 mg, about 240 mg to about 320 mg, about 240 mg to about 300 mg, about 240 mg to about 280 mg, about 240 mg to about 260 mg, about 260 mg to about 500 mg, about 260 mg to about 480 mg, about 260 mg to about 460 mg, about 260 mg to about 440 mg, about 260 mg to about 420 mg, about 260 mg to about 400 mg, about 260 mg to about 380 mg, about 260 mg to about 360 mg, about 260 mg to about 340 mg, about 260 mg to about 320 mg, about 260 mg to about 300 mg, about 260 mg to about 280 mg, about 280 mg to about 500 mg, about 280 mg to about 480 mg, about 280 mg to about 460 mg, about 280 mg to about 440 mg, about 280 mg to about 420 mg, about 280 mg to about 400 mg, about 280 mg to about 380 mg, about 280 mg to about 360 mg, about 280 mg to about 340 mg, about 280 mg to about 320 mg, about 280 mg to about 300 mg, about 300 mg to about 500 mg, about 300 mg to about 480 mg, about 300 mg to about 460 mg, about 300 mg to about 440 mg, about 300 mg to about 420 mg, about 300 mg to about 400 mg, about 300 mg to about 380 mg, about 300 mg to about 360 mg, about 300 mg to about 340 mg, about 300 mg to about 320 mg, about 320 mg to about 500 mg, about 320 mg to about 480 mg, about 320 mg to about 460 mg, about 320 mg to about 440 mg, about 320 mg to about 420 mg, about 320 mg to about 400 mg, about 320 mg to about 380 mg, about 320 mg to about 360 mg, about 320 mg to about 340 mg, about 340 mg to about 500 mg, about 340 mg to about 480 mg, about 340 mg to about 460 mg, about 340 mg to about 440 mg, about 340 mg to about 420 mg, about 340 mg to about 400 mg, about 340 mg to about 380 mg, about 340 mg to about 360 mg, about 360 mg to about 500 mg, about 360 mg to about 480 mg, about 360 mg to about 460 mg, about 360 mg to about 440 mg, about 360 mg to about 420 mg, about 360 mg to about 400 mg, about 360 mg to about 380 mg, about 380 mg to about 500 mg, about 380 mg to about 480 mg, about 380 mg to about 460 mg, about 380 mg to about 440 mg, about 380 mg to about 420 mg, about 380 mg to about 400 mg, about 400 mg to about 500 mg, about 400 mg to about 480 mg, about 400 mg to about 460 mg, about 400 mg to about 440 mg, about 400 mg to about 420 mg, about 420 mg to about 500 mg, about 420 mg to about 480 mg, about 420 mg to about 460 mg, about 420 mg to about 440 mg, about 440 mg to about 500 mg, about 440 mg to about 480 mg, about 440 mg to about 460 mg, about 460 mg to about 500 mg, about 460 mg to about 480 mg, about 480 mg to about 500 mg, about 25, about 50, about 75, about 100, about 150, about 200, about 250, about 300, about 350, about 400, about 450, or about 500 mg), during a period of time.

In one embodiment, the combination therapy comprises oral administration of a compound of Formula I once or twice a day on a daily basis (during a period of time), e.g., in an amount of about 10 mg to about 400 mg (e.g., about 10 mg to about 380 mg, about 10 mg to about 360 mg, about 10 mg to about 340 mg, about 10 mg to about 320 mg, about 10 mg to about 300 mg, about 10 mg to about 280 mg, about 10 mg to about 260 mg, about 10 mg to about 240 mg, about 10 mg to about 220 mg, about 10 mg to about 200 mg, about 10 mg to about 180 mg, about 10 mg to about 160 mg, about 10 mg to about 140 mg, about 10 mg to about 120 mg, about 10 mg to about 100 mg, about 10 mg to about 80 mg, about 10 mg to about 60 mg, about 10 mg to about 40 mg, about 10 mg to about 20 mg, about 20 mg to about 400 mg, about 20 mg to about 380 mg, about 20 mg to about 360 mg, about 20 mg to about 340 mg, about 20 mg to about 320 mg, about 20 mg to about 300 mg, about 20 mg to about 280 mg, about 20 mg to about 260 mg, about 20 mg to about 240 mg, about 20 mg to about 220 mg, about 20 mg to about 200 mg, about 20 mg to about 180 mg, about 20 mg to about 160 mg, about 20 mg to about 140 mg, about 20 mg to about 120 mg, about 20 mg to about 100 mg, about 20 mg to about 80 mg, about 20 mg to about 60 mg, about 20 mg to about 40 mg, about 40 mg to about 400 mg, about 40 mg to about 380 mg, about 40 mg to about 360 mg, about 40 mg to about 340 mg, about 40 mg to about 320 mg, about 40 mg to about 300 mg, about 40 mg to about 280 mg, about 40 mg to about 260 mg, about 40 mg to about 240 mg, about 40 mg to about 220 mg, about 40 mg to about 200 mg, about 40 mg to about 180 mg, about 40 mg to about 160 mg, about 40 mg to about 140 mg, about 40 mg to about 120 mg, about 40 mg to about 100 mg, about 40 mg to about 80 mg, about 40 mg to about 60 mg, about 60 mg to about 400 mg, about 60 mg to about 380 mg, about 60 mg to about 360 mg, about 60 mg to about 340 mg, about 60 mg to about 320 mg, about 60 mg to about 300 mg, about 60 mg to about 280 mg, about 60 mg to about 260 mg, about 60 mg to about 240 mg, about 60 mg to about 220 mg, about 60 mg to about 200 mg, about 60 mg to about 180 mg, about 60 mg to about 160 mg, about 60 mg to about 140 mg, about 60 mg to about 120 mg, about 60 mg to about 100 mg, about 60 mg to about 80 mg, about 80 mg to about 400 mg, about 80 mg to about 380 mg, about 80 mg to about 360 mg, about 80 mg to about 340 mg, about 80 mg to about 320 mg, about 80 mg to about 300 mg, about 80 mg to about 280 mg, about 80 mg to about 260 mg, about 80 mg to about 240 mg, about 80 mg to about 220 mg, about 80 mg to about 200 mg, about 80 mg to about 180 mg, about 80 mg to about 160 mg, about 80 mg to about 140 mg, about 80 mg to about 120 mg, about 80 mg to about 100 mg, about 100 mg to about 400 mg, about 100 mg to about 380 mg, about 100 mg to about 360 mg, about 100 mg to about 340 mg, about 100 mg to about 320 mg, about 100 mg to about 300 mg, about 100 mg to about 280 mg, about 100 mg to about 260 mg, about 100 mg to about 240 mg, about 100 mg to about 220 mg, about 100 mg to about 200 mg, about 100 mg to about 180 mg, about 100 mg to about 160 mg, about 100 mg to about 140 mg, about 100 mg to about 120 mg, about 120 mg to about 400 mg, about 120 mg to about 380 mg, about 120 mg to about 360 mg, about 120 mg to about 340 mg, about 120 mg to about 320 mg, about 120 mg to about 300 mg, about 120 mg to about 280 mg, about 120 mg to about 260 mg, about 120 mg to about 240 mg, about 120 mg to about 220 mg, about 120 mg to about 200 mg, about 120 mg to about 180 mg, about 120 mg to about 160 mg, about 120 mg to about 140 mg, about 140 mg to about 400 mg, about 140 mg to about 380 mg, about 140 mg to about 360 mg, about 140 mg to about 340 mg, about 140 mg to about 320 mg, about 140 mg to about 300 mg, about 140 mg to about 280 mg, about 140 mg to about 260 mg, about 140 mg to about 240 mg, about 140 mg to about 220 mg, about 140 mg to about 200 mg, about 140 mg to about 180 mg, about 140 mg to about 160 mg, about 160 mg to about 400 mg, about 160 mg to about 380 mg, about 160 mg to about 360 mg, about 160 mg to about 360 mg, about 160 mg to about 340 mg, about 160 mg to about 320 mg, about 160 mg to about 300 mg, about 160 mg to about 280 mg, about 160 mg to about 260 mg, about 160 mg to about 240 mg, about 160 mg to about 220 mg, about 160 mg to about 200 mg, about 160 mg to about 180 mg, about 180 mg to about 400 mg, about 180 mg to about 380 mg, about 180 mg to about 360 mg, about 180 mg to about 340 mg, about 180 mg to about 320 mg, about 180 mg to about 300 mg, about 180 mg to about 280 mg, about 180 mg to about 260 mg, about 180 mg to about 240 mg, about 180 mg to about 220 mg, about 180 mg to about 200 mg, about 200 mg to about 400 mg, about 200 mg to about 380 mg, about 200 mg to about 360 mg, about 200 mg to about 340 mg, about 200 mg to about 320 mg, about 200 mg to about 300 mg, about 200 mg to about 280 mg, about 200 mg to about 260 mg, about 200 mg to about 240 mg, about 200 mg to about 220 mg, about 220 mg to about 400 mg, about 220 mg to about 380 mg, about 220 mg to about 360 mg, about 220 mg to about 340 mg, about 220 mg to about 320 mg, about 220 mg to about 300 mg, about 220 mg to about 280 mg, about 220 mg to about 260 mg, about 220 mg to about 240 mg, about 240 mg to about 400 mg, about 240 mg to about 380 mg, about 240 mg to about 360 mg, about 240 mg to about 340 mg, about 240 mg to about 320 mg, about 240 mg to about 300 mg, about 240 mg to about 280 mg, about 240 mg to about 260 mg, about 260 mg to about 400 mg, about 260 mg to about 380 mg, about 260 mg to about 360 mg, about 260 mg to about 340 mg, about 260 mg to about 320 mg, about 260 mg to about 300 mg, about 260 mg to about 280 mg, about 280 mg to about 400 mg, about 280 mg to about 380 mg, about 280 mg to about 360 mg, about 280 mg to about 340 mg, about 280 mg to about 320 mg, about 280 mg to about 300 mg, about 300 mg to about 400 mg, about 300 mg to about 380 mg, about 300 mg to about 360 mg, about 300 mg to about 340 mg, about 300 mg to about 320 mg, about 320 mg to about 400 mg, about 320 mg to about 380 mg, about 320 mg to about 360 mg, about 340 mg to about 360 mg, about 340 mg to about 400 mg, about 340 mg to about 380 mg, about 340 mg to about 360 mg, about 360 mg to about 400 mg, about 360 mg to about 380 mg, about 380 mg to about 400 mg, about 100 mg, about 200 mg, about 300 mg, or about 400 mg), and i.v. administration of a PD-1/PD-L1 inhibitor which is administered, for example, once a week, once every two weeks, once every three weeks, or once every four weeks, depending on the dosage. In one embodiment, the KRas G12C inhibitor is orally administered once daily. In one embodiment, the KRas G12C inhibitor is orally administered twice daily.

In one embodiment, the PD-L1 inhibitor is avelumab or a biosimilar thereof. In one embodiment, avelumab or a biosimilar thereof is administered intravenously in the amount of about 800 mg every 2 weeks (Q2W) or about 10 mg/kg every 2 weeks (Q2W). In one embodiment, avelumab or a biosimilar thereof is administered intravenously over 60 minutes.

In one embodiment, the PD-L1 inhibitor is atezolizumab or a biosimilar thereof. In one embodiment, atezolizumab or a biosimilar thereof is administered at a dose of 1200 mg intravenously once every 3 weeks (Q3W) or at a dose of 840 mg intravenously two weeks apart. In one embodiment, atezolizumab or a biosimilar thereof is administered intravenously over 60 minutes.

In one embodiment, the PD-L1 inhibitor is durvalumab or a biosimilar thereof. In one embodiment, durvalumab or a biosimilar thereof is administered at a dose of 10 mg/kg intravenously once every 2 weeks (Q2W). In one embodiment, durvalumab or a biosimilar thereof is administered intravenously over 60 minutes.

In one embodiment, the PD-1 inhibitor is nivolumab or a biosimilar thereof. In one embodiment, nivolumab or a biosimilar thereof is administered at a dose of 240 mg intravenously once every 2 weeks (Q2W). In one embodiment, nivolumab or a biosimilar thereof is administered at a dose of 480 mg intravenously once every 4 weeks (Q4W). In one embodiment, nivolumab or a biosimilar thereof is administered intravenously over 30 minutes.

In one embodiment, the PD-1 inhibitor is pembrolizumab or a biosimilar thereof. In one embodiment, pembrolizumab is administered at a dose of 200 mg intravenously once every 3 weeks (Q3W). In one embodiment, pembrolizumab or a biosimilar thereof is administered intravenously over 60 minutes.

In one embodiment, the PD-1 inhibitor is cemiplimab or a biosimilar thereof. In one embodiment, cemiplimab or a biosimilar thereof is administered at a dose of 350 mg intravenously once every 3 weeks (Q3W). In one embodiment, cemiplimab or a biosimilar thereof is administered intravenously over 30 minutes.

In one embodiment, the PD-1 inhibitor is tislelizumab or a biosimilar thereof. In one embodiment, tislelizumab or a biosimilar thereof is administered at a dose of 200 mg intravenously once every 3 weeks (Q3W).

One skilled in the art will recognize that, both in vivo and in vitro trials using suitable, known and generally accepted cell and/or animal models are predictive of the ability of a test compound of the combination or the combination to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

In some embodiments, the methods provided herein can result in a 1% to 99% (e.g., 1% to 98%, 1% to 95%, 1% to 90%, 1 to 85%, 1 to 80%, 1% to 75%, 1% to 70%, 1% to 65%, 1% to 60%, 1% to 55%, 1% to 50%, 1% to 45%, 1% to 40%, 1% to 35%, 1% to 30%, 1% to 25%, 1% to 20%, 1% to 15%, 1% to 10%, 1% to 5%, 2% to 99%, 2% to 90%, 2% to 85%, 2% to 80%, 2% to 75%, 2% to 70%, 2% to 65%, 2% to 60%, 2% to 55%, 2% to 50%, 2% to 45%, 2% to 40%, 2% to 35%, 2% to 30%, 2% to 25%, 2% to 20%, 2% to 15%, 2% to 10%, 2% to 5%, 4% to 99%, 4% to 95%, 4% to 90%, 4% to 85%, 4% to 80%, 4% to 75%, 4% to 70%, 4% to 65%, 4% to 60%, 4% to 55%, 4% to 50%, 4% to 45%, 4% to 40%, 4% to 35%, 4% to 30%, 4% to 25%, 4% to 20%, 4% to 15%, 4% to 10%, 6% to 99%, 6% to 95%, 6% to 90%, 6% to 85%, 6% to 80%, 6% to 75%, 6% to 70%, 6% to 65%, 6% to 60%, 6% to 55%, 6% to 50%, 6% to 45%, 6% to 40%, 6% to 35%, 6% to 30%, 6% to 25%, 6% to 20%, 6% to 15%, 6% to 10%, 8% to 99%, 8% to 95%, 8% to 90%, 8% to 85%, 8% to 80%, 8% to 75%, 8% to 70%, 8% to 65%, 8% to 60%, 8% to 55%, 8% to 50%, 8% to 45%, 8% to 40%, 8% to 35%, 8% to 30%, 8% to 25%, 8% to 20%, 8% to 15%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, 10% to 40%, 10% to 35%, 10% to 30%, 10% to 25%, 10% to 20%, 10% to 15%, 15% to 99%, 15% to 95%, 15% to 90%, 15% to 85%, 15% to 80%, 15% to 75%, 15% to 70%, 15% to 65%, 15% to 60%, 15% to 55%, 15% to 50%, 15% to 55%, 15% to 50%, 15% to 45%, 15% to 40%, 15% to 35%, 15% to 30%, 15% to 25%, 15% to 20%, 20% to 99%, 20% to 95%, 20% to 90%, 20% to 85%, 20% to 80%, 20% to 75%, 20% to 70%, 20% to 65%, 20% to 60%, 20% to 55%, 20% to 50%, 20% to 45%, 20% to 40%, 20% to 35%, 20% to 30%, 20% to 25%, 25% to 99%, 25% to 95%, 25% to 90%, 25% to 85%, 25% to 80%, 25% to 75%, 25% to 70%, 25% to 65%, 25% to 60%, 25% to 55%, 25% to 50%, 25% to 45%, 25% to 40%, 25% to 35%, 25% to 30%, 30% to 99%, 30% to 95%, 30% to 90%, 30% to 85%, 30% to 80%, 30% to 75%, 30% to 70%, 30% to 65%, 30% to 60%, 30% to 55%, 30% to 50%, 30% to 45%, 30% to 40%, 30% to 35%, 35% to 99%, 35% to 95%, 35% to 90%, 35% to 85%, 35% to 80%, 35% to 75%, 35% to 70%, 35% to 65%, 35% to 60%, 35% to 55%, 35% to 50%, 35% to 45%, 35% to 40%, 40% to 99%, 40% to 95%, 40% to 90%, 40% to 85%, 40% to 80%, 40% to 75%, 40% to 70%, 40% to 65%, 40% to 60%, 40% to 55%, 40% to 60%, 40% to 55%, 40% to 50%, 40% to 45%, 45% to 99%, 45% to 95%, 45% to 95%, 45% to 90%, 45% to 85%, 45% to 80%, 45% to 75%, 45% to 70%, 45% to 65%, 45% to 60%, 45% to 55%, 45% to 50%, 50% to 99%, 50% to 95%, 50% to 90%, 50% to 85%, 50% to 80%, 50% to 75%, 50% to 70%, 50% to 65%, 50% to 60%, 50% to 55%, 55% to 99%, 55% to 95%, 55% to 90%, 55% to 85%, 55% to 80%, 55% to 75%, 55% to 70%, 55% to 65%, 55% to 60%, 60% to 99%, 60% to 95%, 60% to 90%, 60% to 85%, 60% to 80%, 60% to 75%, 60% to 70%, 60% to 65%, 65% to 99%, 60% to 95%, 60% to 90%, 60% to 85%, 60% to 80%, 60% to 75%, 60% to 70%, 60% to 65%, 70% to 99%, 70% to 95%, 70% to 90%, 70% to 85%, 70% to 80%, 70% to 75%, 75% to 99%, 75% to 95%, 75% to 90%, 75% to 85%, 75% to 80%, 80% to 99%, 80% to 95%, 80% to 90%, 80% to 85%, 85% to 99%, 85% to 95%, 85% to 90%, 90% to 99%, 90% to 95%, or 95% to 100%) reduction in the volume of one or more solid tumors in a patient following treatment with the combination therapy for a period of time between 1 day and 2 years (e.g., between 1 day and 22 months, between 1 day and 20 months, between 1 day and 18 months, between 1 day and 16 months, between 1 day and 14 months, between 1 day and 12 months, between 1 day and 10 months, between 1 day and 9 months, between 1 day and 8 months, between 1 day and 7 months, between 1 day and 6 months, between 1 day and 5 months, between 1 day and 4 months, between 1 day and 3 months, between 1 day and 2 months, between 1 day and 1 month, between one week and 2 years, between 1 week and 22 months, between 1 week and 20 months, between 1 week and 18 months, between 1 week and 16 months, between 1 week and 14 months, between 1 week and 12 months, between 1 week and 10 months, between 1 week and 9 months, between 1 week and 8 months, between 1 week and 7 months, between 1 week and 6 months, between 1 week and 5 months, between 1 week and 4 months, between 1 week and 3 months, between 1 week and 2 months, between 1 week and 1 month, between 2 weeks and 2 years, between 2 weeks and 22 months, between 2 weeks and 20 months, between 2 weeks and 18 months, between 2 weeks and 16 months, between 2 weeks and 14 months, between 2 weeks and 12 months, between 2 weeks and 10 months, between 2 weeks and 9 months, between 2 weeks and 8 months, between 2 weeks and 7 months, between 2 weeks and 6 months, between 2 weeks and 5 months, between 2 weeks and 4 months, between 2 weeks and 3 months, between 2 weeks and 2 months, between 2 weeks and 1 month, between 1 month and 2 years, between 1 month and 22 months, between 1 month and 20 months, between 1 month and 18 months, between 1 month and 16 months, between 1 month and 14 months, between 1 month and 12 months, between 1 month and 10 months, between 1 month and 9 months, between 1 month and 8 months, between 1 month and 7 months, between 1 month and 6 months, between 1 month and 6 months, between 1 month and 5 months, between 1 month and 4 months, between 1 month and 3 months, between 1 month and 2 months, between 2 months and 2 years, between 2 months and 22 months, between 2 months and 20 months, between 2 months and 18 months, between 2 months and 16 months, between 2 months and 14 months, between 2 months and 12 months, between 2 months and 10 months, between 2 months and 9 months, between 2 months and 8 months, between 2 months and 7 months, between 2 months and 6 months, or between 2 months and 5 months, between 2 months and 4 months, between 3 months and 2 years, between 3 months and 22 months, between 3 months and 20 months, between 3 months and 18 months, between 3 months and 16 months, between 3 months and 14 months, between 3 months and 12 months, between 3 months and 10 months, between 3 months and 8 months, between 3 months and 6 months, between 4 months and 2 years, between 4 months and 22 months, between 4 months and 20 months, between 4 months and 18 months, between 4 months and 16 months, between 4 months and 14 months, between 4 months and 12 months, between 4 months and 10 months, between 4 months and 8 months, between 4 months and 6 months, between 6 months and 2 years, between 6 months and 22 months, between 6 months and 20 months, between 6 months and 18 months, between 6 months and 16 months, between 6 months and 14 months, between 6 months and 12 months, between 6 months and 10 months, or between 6 months and 8 months) (e.g., as compared to the size of the one or more solid tumors in the patient prior to treatment).

The phrase "time of survival" means the length of time between the identification or diagnosis of cancer (e.g., any of the cancers described herein) in a mammal by a medical professional and the time of death of the mammal (caused by the cancer). Methods of increasing the time of survival in a mammal having a cancer are described herein.

In some embodiments, any of the methods described herein can result in an increase (e.g., a 1% to 400%, 1% to 380%, 1% to 360%, 1% to 340%, 1% to 320%, 1% to 300%, 1% to 280%, 1% to 260%, 1% to 240%, 1% to 220%, 1% to 200%, 1% to 180%, 1% to 160%, 1% to 140%, 1% to 120%, 1% to 100%, 1% to 95%, 1% to 90%, 1% to 85%, 1% to 80%, 1% to 75%, 1% to 70%, 1% to 65%, 1% to 60%, 1% to 55%, 1% to 50%, 1% to 45%, 1% to 40%, 1% to 35%, 1% to 30%, 1% to 25%, 1% to 20%, 1% to 15%, 1% to 10%, 1% to 5%, 5% to 400%, 5% to 380%, 5% to 360%, 5% to 340%, 5% to 320%, 5% to 300%, 5% to 280%, 5% to 260%, 5% to 240%, 5% to 220%, 5% to 200%, 5% to 180%, 5% to 160%, 5% to 140%, 5% to 120%, 5% to 100%, 5% to 90%, 5% to 80%, 5% to 70%, 5% to 60%, 5% to 50%, 5% to 40%, 5% to 30%, 5% to 20%, 5% to 10%, 10% to 400%, 10% to 380%, 10% to 360%, 10% to 340%, 10% to 320%, 10% to 300%, 10% to 280%, 10% to 260%, 10% to 240%, 10% to 220%, 10% to 200%, 10% to 180%, 10% to 160%, 10% to 140%, 10% to 120%, 10% to 100%, 10% to 90%, 10% to 80%, 10% to 70%, 10% to 60%, 10% to 50%, 10% to 40%, 10% to 30%, 10% to 20%, 20% to 400%, 20% to 380%, 20% to 360%, 20% to 340%, 20% to 320%, 20% to 300%, 20% to 280%, 20% to 260%, 20% to 240%, 20% to 220%, 20% to 200%, 20% to 180%, 20% to 160%, 20% to 140%, 20% to 120%, 20% to 100%, 20% to 90%, 20% to 80%, 20% to 70%, 20% to 60%, 20% to 50%, 20% to 40%, 20% to 30%, 30% to 400%, 30% to 380%, 30% to 360%, 30% to 340%, 30% to 320%, 30% to 300%, 30% to 280%, 30% to 260%, 30% to 240%, 30% to 220%, 30% to 200%, 30% to 180%, 30% to 160%, 30% to 140%, 30% to 120%, 30% to 100%, 30% to 90%, 30% to 80%, 30% to 70%, 30% to 60%, 30% to 50%, 30% to 40%, 40% to 400%, 40% to 380%, 40% to 360%, 40% to 340%, 40% to 320%, 40% to 300%, 40% to 280%, 40% to 260%, 40% to 240%, 40% to 220%, 40% to 200%, 40% to 180%, 40% to 160%, 40% to 140%, 40% to 120%, 40% to 100%, 40% to 90%, 40% to 80%, 40% to 70%, 40% to 60%, 40% to 50%, 50% to 400%, 50% to 380%, 50% to 360%, 50% to 340%, 50% to 320%, 50% to 300%, 50% to 280%, 50% to 260%, 50% to 240%, 50% to 220%, 50% to 200%, 50% to 180%, 50% to 160%, 50% to 140%, 50% to 140%, 50% to 120%, 50% to 100%, 50% to 90%, 50% to 80%, 50% to 70%, 50% to 60%, 60% to 400%, 60% to 380%, 60% to 360%, 60% to 340%, 60% to 320%, 60% to 300%, 60% to 280%, 60% to 260%, 60% to 240%, 60% to 220%, 60% to 200%, 60% to 180%, 60% to 160%, 60% to 140%, 60% to 120%, 60% to 100%, 60% to 90%, 60% to 80%, 60% to 70%, 70% to 400%, 70% to 380%, 70% to 360%, 70% to 340%, 70% to 320%, 70% to 300%, 70% to 280%, 70% to 260%, 70% to 240%, 70% to 220%, 70% to 200%, 70% to 180%, 70% to 160%, 70% to 140%, 70% to 120%, to 100%, 70% to 90%, 70% to 80%, 80% to 400%, 80% to 380%, 80% to 360%, 80% to 340%, 80% to 320%, 80% to 300%, 80% to 280%, 80% to 260%, 80% to 240%, 80% to 220%, 80% to 200%, 80% to 180%, 80% to 160%, 80% to 140%, 80% to 120%, 80% to 100%, 80% to 90%, 90% to 400%, 90% to 380%, 90% to 360%, 90% to 340%, 90% to 320%, 90% to 300%, 90% to 280%, 90% to 260%, 90% to 240%, 90% to 220%, 90% to 200%, 90% to 180%, 90% to 160%, 90% to 140%, 90% to 120%, 90% to 100%, 100% to 400%, 100% to 380%, 100% to 360%, 100% to 340%, 100% to 320%, 100% to 300%, 100% to 280%, 100% to 260%, 100% to 240%, 100% to 220%, 100% to 200%, 100% to 180%, 100% to 160%, 100% to 140%, 100% to 120%, 120% to 400%, 120% to 380%, 120% to 360%, 120% to 340%, 120% to 320%, 120% to 300%, 120% to 280%, 120% to 260%, 120% to 240%, 120% to 220%, 120% to 200%, 120% to 180%, 120% to 160%, 120% to 140%, 140% to 400%, 140% to 380%, 140% to 360%, 140% to 340%, 140% to 320%, 140% to 300%, 140% to 280%, 140% to 260%, 140% to 240%, 140% to 220%, 140% to 200%, 140% to 180%, 140% to 160%, 160% to 400%, 160% to 380%, 160% to 360%, 160% to 340%, 160% to 320%, 160% to 300%, 160% to 280%, 160% to 260%, 160% to 240%, 160% to 220%, 160% to 200%, 160% to 180%, 180% to 400%, 180% to 380%, 180% to 360%, 180% to 340%, 180% to 320%, 180% to 300%, 180% to 280%, 180% to 260%, 180% to 240%, 180% to 220%, 180% to 200%, 200% to 400%, 200% to 380%, 200% to 360%, 200% to 340%, 200% to 320%, 200% to 300%, 200% to 280%, 200% to 260%, 200% to 240%, 200% to 220%, 220% to 400%, 220% to 380%, 220% to 360%, 220% to 340%, 220% to 320%, 220% to 300%, 220% to 280%, 220% to 260%, 220% to 240%, 240% to 400%, 240% to 380%, 240% to 360%, 240% to 340%, 240% to 320%, 240% to 300%, 240% to 280%, 240% to 260%, 260% to 400%, 260% to 380%, 260% to 360%, 260% to 340%, 260% to 320%, 260% to 300%, 260% to 280%, 280% to 400%, 280% to 380%, 280% to 360%, 280% to 340%, 280% to 320%, 280% to 300%, 300% to 400%, 300% to 380%, 300% to 360%, 300% to 340%, or 300% to 320%) in the time of survival of the patient (e.g., as compared to a patient having a similar cancer and administered a different treatment or not receiving a treatment), or for the remaining life time of the treated patient.

In some embodiments of any of the methods described herein, before treatment with the compositions or methods of the invention, the patient was treated with one or more of a chemotherapy, a targeted anticancer agent, radiation therapy, and surgery, and optionally, the prior treatment was unsuccessful; and/or the patient has been administered surgery and optionally, the surgery was unsuccessful; and/or the patient has been treated with a platinum-based chemotherapeutic agent, and optionally, the patient has been previously determined to be non-responsive to treatment with the platinum-based chemotherapeutic agent; and/or the patient has been treated with a kinase inhibitor, and optionally, the prior treatment with the kinase inhibitor was unsuccessful; and/or the patient was treated with one or more other therapeutic agent(s).

Kits

The present invention also relates to a kit comprising a PD-1/PD-L1 inhibitor or a pharmaceutical composition thereof and a KRas G12C inhibitor compound of Formula (I), Formula I-A or Formula I-B, or a pharmaceutically acceptable salt or a pharmaceutical composition thereof. Also provided is a kit comprising a PD-1/PD-L1 inhibitor or a pharmaceutical composition thereof and a KRas G12C inhibitor compound of Formula (I), Formula I-A or Formula I-B, or a pharmaceutically acceptable salt or a pharmaceutical composition thereof, for use in treating a hematological cancer.

In a related aspect, the invention provides a kit containing a dose of a PD-1/PD-L1 inhibitor or a pharmaceutical composition thereof and a dose of a KRas G12C inhibitor compound of Formula (I), Formula I-A or Formula I-B, or a pharmaceutically acceptable salt or a pharmaceutical composition thereof in an amount effective to inhibit proliferation of cancer cells, particularly KRas G12C-expressing cancer cells, in a subject. The kit in some cases includes an insert with instructions for administration of the PD-1/PD-L1 inhibitor or a pharmaceutical composition thereof and a KRas G12C inhibitor compound of Formula (I), Formula I-A or Formula I-B, or a pharmaceutically acceptable salt or a pharmaceutical composition thereof. The insert may provide a user with one set of instructions for using the PD-1/PD-L1 inhibitor or a pharmaceutical composition thereof in combination with a KRas G12C inhibitor compound of Formula (I), Formula I-A or Formula I-B, or a pharmaceutically acceptable salt or a pharmaceutical composition thereof.

Example A

Engineering of Colon Cancer Cell Line CT26.WT to Express KRas G12C

This Example illustrates that the colon cancer cell line CT26.WT (ATCC CRL-2638) was genetically modified to express KRas G12C rending these cells susceptible to target therapy using the KRas G12C inhibitors of the present invention.

CT26.WT cell line is triallelic for the KRas gene (NCBI Ref: NM_021284) and each allele harbors a mutation at codon 12 that changes a glycine residue (G) to an aspartic acid residue (D). In order to create a CT26.WT cell line derivative harboring a KRas G12C mutation, the G12D codon was changed to a G12C codon using a CRISPR/CAS9 system (Synthego, Redwood City, CA) in the following manner.

Briefly, a synthetically modified guide RNA (sgRNA) targeting the region near the KRas 12 codon was designed and synthesized based on high specificity and propensity to create double strand breaks when complexed with the CAS9 DNA endonuclease. A single-stranded donor oligonucleotide (ssODN) was designed to enable homologous donor repair at the site of the sgRNA cut site and introduce the desired cysteine codon (GAT; D to TGT: C) at position 12 while also introducing silent mutations to prevent recutting.

Cas9/sgRNA riboprotein complexes and ssODN were transfected into CT26.WT cells. Single cell CT26.WT clones were isolated and their genotypes were screened by Sanger DNA sequencing to identify homozygous G12C targeted clones.

One particular clone, KRas G12C CT26.WT E3 clone was selected for further analysis.

Example B

Inhibition of KRas G12C-Dependent Cell Growth

This Example illustrates that exemplary compounds of the present invention inhibit the growth of engineered CT26.WT KRas G12C E3 clone that expresses KRas G12C with a greater potency than the parental CT26.WT wild type cell line.

The cellular inhibition of KRAs G12C by exemplary compounds of the present invention was determined by measuring the amount of intracellular ATP.

CT26.WT wild type cells and CT26.WT G12C E3 clone expressing KRas G12C were cultured in RPMI medium supplemented with 10% fetal bovine serum and 1% penicillin/1% streptomycin and plated at a density of 1000 cells/90μl/well in 96 well white assay plates. A dose response curve for compounds of the present invention was determined by adding a 10 μl aliquot of stock solutions of varying concentrations of compounds to the same medium in each well, over a concentration range of 10 μM using 3-fold dilutions to a final concentration of 1.5 nM. The plates were incubated at 37° C. for 3 days and the viability of the cells was measured using a CTG assay kit (Cell Titre Glo; Promega cat. no G7573) on Day 3 in accordance with the manufacturer's instructions.

The $IC_{50}$ values for each cell line at Day 3 were calculated using Graph pad PRISM software and the results are shown in Table 1.

TABLE 1

| Cell Line | IC50 (nM) |
|---|---|
| CT26.WT KRas Wild Type | 3239 |
| CT26.WT KRas G12C | 455.3 |

As shown in Table 1, the CT26.WT cell line expressing KRas G12C was about 7-fold more sensitive to inhibition by Example 478 compared to the syngeneic parent wild type KRas cell line thereby demonstrating the enhanced sensitivity and specificity of this cell line to KRas G12C inhibitors of the present invention.

Example C

In Vivo Models for Examining KRas G12C Inhibitor—Immune Cell Modulation

This Example illustrates that the in vivo administration of a KRas G12C inhibitor alone or in combination with an anti-PD-1 antibody to CT26.WT KRas G12C E3 clone-bearing animals results in intra-tumoral modulation of key immune cell populations.

BALBc mice were inoculated in the right hind flank with 1×10$^6$ CT26.WT KRas G12C E3 cells harboring the KRas G12C mutation. When tumor volumes reach between 200-400 mm$^3$ in size (Day 0), the mice were divided into two sets of three groups of 5 mice each. The first group was daily administered vehicle (10% Captisol in 50 mM citrate buffer pH 5.0), the second group was administered a 100 mg/kg oral dose of the KRas G12C inhibitor Example 478 daily for four days (Day 4), the third group was administered 10 mg/kg of murine anti-PD-1 antibody IP on Days 1, 4 and 7. and the fourth group was administered a combination of a 100 mg/kg oral dose of the KRas G12C inhibitor Example 478 daily for four days and 10 mg/kg of murine anti-PD-1 antibody IP on Days 1, 4 and 7

Approximately three hours after the final Day 4 dose, the mice were euthanized and tumor were harvested for FACS analysis (MI Bioresearch, Ann Arbor, MI). Individual tumors were homogenized and live tumor cells were isolated from the homogenized tumors using a 7-AAD Viability dye. Isolated live cells were separated from cell debris by centrifugation, washed, and resuspended in ice cold DPBS medium. An aliquot of 1×10$^6$ cells was transferred to pre-defined wells in a deep well 96 well plates containing specific fluorescein-tagged antibodies to specific immune cell extracellular and intracellular markers.

One plate was designed to quantitate the percentage of CD45+CD3+ T-cells including CD4+ and CD8+ T-cells, CD69 & PD-1 expressing CD8+ T-cells, KI-67+CD8+ T-cells, natural killer (NK) T-cells and regulatory T-cells (T-regs). The percentages of the cells were determined using an Attune NxT Acoustic Focusing Cytometer. The results are shown in Table 2.

TABLE 2

Immune Cell Populations Post-treatment using a KRas G12C inhibitor or a KRas G12C inhibitor + PD-1/PD-L1 Inhibitor Combination

| Treatment | CD45+# | % CD3+ T-Cells* | % CD4+ T-Cells* | % CD8+ T-Cells* | % T-Regs | % CD69+ CD8+‡ | % PD-1 CD8+‡ | % KI167+ CD8+ T | % KI167+ CD8+ | % NK* | % NK-T* |
|---|---|---|---|---|---|---|---|---|---|---|---|
| Vehicle | 28.8 ± 6.1 | 18.5 ± 4.0 | 6.3 ± 1.9 | 10.2 ± 2.9 | 2.8 ± 0.5 | 3.4 ± 1.4 | 87.4 ± 8.3 | 4869 ± 395 | 3088 ± 943 | 11.2 ± 3.6 | 2.3 ± 0.5 |
| Ex 478 | 57.6 ± 7.0 | 32.5 ± 5.2 | 13.5 ± 3.6 | 15.4 ± 3.6 | 5.8 ± 0.5 | 7.2 ± 3.8 | 83.0 ± 8.3 | 4061 ± 786 | 2834 ± 883 | 11.6 ± 3.1 | 5.2 ± 0.6 |
| Anti-PD-1 | 31.6 ± 5.3 | 24.6 ± 6.4 | 6.6 ± 1.1 | 14.3 ± 4.9 | 3.6 ± 0.9 | 2.8 ± 0.4 | 1.3 ± 0.3 | 5507 ± 605 | 4800 ± 770 | 11.9 ± 2.1 | 2.2 ± 0.3 |
| Combination | 70.0 ± 6.3 | 34.9 ± 2.3 | 15.8 ± 1.6 | 15.3 ± 4.6 | 8.4 ± 0.8 | 6.1 ± 1.7 | 2.0 ± 0.6 | 4382 ± 699 | 3878 ± 765 | 14.6 ± 3.5 | 6.5 ± 1.3 | percentage of live cells
*remaining values percentage of CD45+ cells
‡ percentage of CD8+ T-cells A second plate was designed to quantitate the percentage of CD45+CD11+ cells including myeloid-derived suppressor cells (G-MDSC and M-MDSC), M1 & M2 macrophages and dendritic cells (DC). The percentages of the cells were determined using an Attune NxT Acoustic Focusing Cytometer. Positive and negative control samples were processed in parallel. The results are shown in Table 3.

TABLE 3

Immune Cell Populations Post-treatment using a KRas G12C inhibitor or a KRas G12C inhibitor + anti-PD-1/anti-PD-L1 Combination

| Treatment | % CD45+# | % CD19+* | % CD11b+ | % MAC | % M1 | % M2 | % G-MDSC | % M-MDSC | % DC |
|---|---|---|---|---|---|---|---|---|---|
| Vehicle | 30 ± 6.4 | 2.0 ± 1.3 | 66 ± 4.5 | 33 ± 5.5 | 1.2 ± 0.2 | 31.9 ± 5.6 | 4.0 ± 3.8 | 15.1 ± 1.8 | 3.4 ± 0.5 |
| Ex 478 | 61 ± 6.6 | 3.2 ± 1.7 | 56 ± 2.8 | 35 ± 3.8 | 2.6 ± 0.8 | 32.3 ± 3.0 | 1.2 ± 0.4 | 6.0 ± 1.8 | 5.5 ± 1.7 |
| Anti-PD-1 | 35 ± 4.4 | 1.6 ± 0.6 | 67 ± 2.6 | 31 ± 0.9 | 1.6 ± 0.3 | 29.7 ± 1.0 | 2.7 ± 2.1 | 16.3 ± 0.9 | 2.4 ± 1.1 |
| Combination | 73 ± 6.1 | 2.1 ± 0.9 | 56 ± 2.1 | 31 ± 2.8 | 3.2 ± 0.5 | 28.0 ± 2.4 | 0.8 ± 0.3 | 7.8 ± 1.1 | 5.1 ± 1.6 | percentage of live cells
*remaining values percentage of CD45+ cell

After four days of dosing of Example 478 at 100 mg/kg, numerous differences in the immune cell populations in the tumor microenvironment were observed. For instance, intra-tumoral CD45+ cells increased as a percentage of live cells. This increase is indicative of an active immune tumor microenvironment (TME), as it is not only a marker for hematopoietic cells, but also an essential regulator of T and B cell antigen receptor-mediated activation (e.g., see Perrick N. CD45. PathologyOutlines.com website. http://www.pathologyoutlines.com/topic/cdmarkerscd45.html). Additional increases were observed in the CD4 and CD4 Helper T cell populations. These immune cell types are paramount in stimulating killer T cells, macrophages and B cells to mount an immune response. The observed increase in CD8 positive immune cells, cytotoxic T cells, leads to effect killing of target cells. In the presence of an antigen, CD8+ T cells progress through 3 phases initiated by proliferation, then contraction and ultimately differentiation to a long-lived memory T cell. This increase in CD8 positive immune cells may also represent an early hallmark for CD8 positive immune cell clonal expansion and thus provide a mechanism for efficient recognition and killing of cancer cells in the present and future (e.g., see Clambey et al., (2005) Immun Rev 205:170-189). Consistent with T cell increases, Example 478 treatment in the tumor caused an increase in CD19 positive cells. This marker, a common B cell marker, represents a cell type that regulates B cell development, activation and differentiation (e.g., see Otero & Ricket (2003) J. Immunol. 171:5921-5930). Thus, this B cell increase is capable of eliciting a high-affinity response to pathogens and may provide the host with protective long-lived humoral immunity.

Furthermore, M1 macrophages represent the first responders in intracellular pathogens and exhibit a high level of phagocytic activity. The observed increase of M1 provides a rationale for increased proinflammatory cytokine signaling and a hallmark for an acute inflammatory response (Atri et al., (2018) Int J Mol Sci 19:1801). MDSC accumulate significantly during pathologic conditions and have been detected in almost all studied tumor models and tested cancer patients (e.g., see Youn & Gabrilovich (2010) Euro J Immunol 40:2969-2975) These conditions not only cause the expansion MDSC cells, but also may lead to their activation, which in turn up-regulates many intermediates with potential immune suppressive activity, such as ROS, iNOS, COX2, and arginase (Youn & Gabrilovich (2010) Euro J Immunol 40:2969-2975).

A large majority of the increased CD8+ T-cell population post-treatment with Example 478 single agent expressed PD-1 (83%) and remain susceptible to inhibition by PD-L1 thereby blocking activation of these T-cells; however, after four days of combination therapy, PD-1 surface protein expression in the CD8+ T-cells had been blocked by binding of the PD-1 inhibitor (only 1.2% express PD-1) thereby preventing these T-cells from being suppressed by PD-L1 and allowing for these cells to become activated and to mount an adaptive anti-tumor response resulting in a durable complete response in animal models.

Collectively, treatment with a KRas G12C inhibitor of the present invention results in the modulation of key immune cell subtypes in the tumor that may contribute to the overall mechanism of tumor reduction in this model. The noteworthy contribution from treatment with a PD-1 inhibitor was the dramatic decrease in PD-1 positive CD8 immune cells in the tumor. This modulation suggests, in an already immunologically hot tumor microenvironment as described with KRas G12C inhibitor treatment alone, decreasing this population of immune cells would lead to additional anti-tumor activity by removing an existing inhibition dictated by the PD-1/PD-L1 axis signaling pathway.

Example D

In Vivo Models for Examining KRas G12C Inhibitor+PD-1/PD-L1 Inhibitor Combinations BALBc mice were inoculated in the right hind flank with $1 \times 10^6$ CT26.WT KRas G12C E3 cells harboring the KRas G12C mutation, and tumor volumes were measured using a caliper every two-three days and tumor volumes were calculated by the formula: 0.5×(Length×Width).

When tumor volumes reached between 200-400 mm$^3$ in size (Study Day 0), the mice were divided into four groups of 5 mice each. The first group was daily administered vehicle (10% Captisol in 50 mM citrate buffer pH 5.0) through Study Day 15 and also administered i.p. vehicle (BioXcel diluent) on Study Days 1, 4 and 7. The second group was daily administered a 10 mg/kg i.p. dose of the murine anti-PD-1 antibody (F26, BioXcel) at Days 1, 4 and 7. The third group was administered a 100 mg/kg dose of the KRas G12C inhibitor Example 478 through Study Day 29. The fourth group was daily administered a 100 mg/kg dose of the KRas G12C inhibitor Example 478 through Study Day 29 in combination with a 10 mg/kg i.p. dose of the F26 murine anti-PD-1 antibody at Study Days 1, 4 and 7.

At Study Day 29, administration of 100 mg/kg dose of the KRas G12C inhibitor Example 478 was stopped in the single agent and combination groups.

At Study Day 39, four tumor-free mice from the combination group were rechallenged $1 \times 10^6$ CT26.WT KRas G12C E3 cells in the opposite left flank and mice were monitored for tumor growth for a period of twenty four days to determine whether a durable, adaptive immune response was observed.

Table 4

Tumor Volumes (Mm$^3$) of CT26.WT KRas G12C E3 Clone Tumor Bearing Mice Treated with Single Agents and in Combination

TABLE 4A

| Group 1: Vehicle | | | | | |
|---|---|---|---|---|---|
| Study Day | M1 | M2 | M3 | M4 | M5 |
| 0 | 132 | 251 | 157 | 339 | 261 |
| 3 | 306 | 644 | 357 | 520 | 319 |
| 7 | 713 | 1164 | 943 | 829 | 630 |
| 9 | 885 | 1583 | 1269 | 1024 | 591 |
| 11 | 1389 | 1936 | 1723 | 1178 | 892 |
| 14 | 2034 | 2633 | 2394 | 1541 | 1501 |

TABLE 4B

| Group 2: 10 mg/kg i.p. F26 murine anti-PD-1 antibody | | | | | |
|---|---|---|---|---|---|
| Study Day | M1 | M2 | M3 | M4 | M5 |
| 0 | 229 | 312 | 104 | 232 | 273 |
| 3 | 403 | 484 | 183 | 367 | 469 |
| 7 | 529 | 522 | 568 | 728 | 779 |
| 9 | 805 | 840 | 725 | 875 | 1164 |
| 11 | 1073 | 968 | 1206 | 1254 | 1518 |
| 14 | 1760 | 1091 | 1604 | 1784 | 2088 |

TABLE 4C

| Group 3: 100 mg/kg KRas G12C Inhibitor Example 478 | | | | | |
|---|---|---|---|---|---|
| Study Day | M1 | M2 | M3 | M4 | M5 |
| 0 | 194 | 314 | 242 | 110 | 268 |
| 3 | 32 | 173 | 131 | 69 | 130 |
| 7 | 0 | 4 | 14 | 14 | 4 |
| 9 | 0 | 0 | 0 | 0 | 0 |
| 11 | 0 | 0 | 0 | 0 | 0 |
| 14 | 0 | 0 | 0 | 0 | 0 |
| 17 | 0 | 0 | 32 | 0 | 0 |
| 21 | 0 | 63 | 160 | 0 | 0 |
| 23 | 0 | 198 | 400 | 0 | 0 |
| 25 | 0 | 360 | 804 | 0 | 106 |
| 28 | 0 | 501 | | 0 | 319 |
| 30 | 0 | | | 0 | 496 |

TABLE 4C-continued

Group 3: 100 mg/kg KRas G12C Inhibitor Example 478

| Study Day | M1 | M2 | M3 | M4 | M5 |
|---|---|---|---|---|---|
| 32 | 0 | | | 0 | 772 |
| 35 | 0 | | | 0 | 1243 |
| 38 | 0 | | | 0 | |
| 44 | 0 | | | 32 | |
| 46 | 68 | | | 142 | |
| 49 | 259 | | | 336 | |
| 51 | 391 | | | 349 | |
| 53 | 691 | | | 656 | |
| 56 | 1265 | | | 1006 | |
| 60 | 1787 | | | 1295 | |
| 63 | 2412 | | | 2163 | |

TABLE 4D

Group 4: 100 mg/kg KRas G12C Inhibitor Example 478 + 10 mg/kg i.p. F26 murine anti-PD-1 antibody[‡]

| Study Day | M1 | M2 | M3 | M4 | M5 |
|---|---|---|---|---|---|
| 0 | 285 | 231 | 98 | 277 | 230 |
| 3 | 121 | 160 | 14 | 123 | 151 |
| 7 | 77 | 32 | 0 | 4 | 32 |
| 9 | 14 | 0 | 0 | 0 | 0 |
| 11 | 4 | 0 | 0 | 0 | 0 |
| 14 | 0 | 0 | 0 | 0 | 0 |
| 17 | 0 | 0 | 0 | 0 | 0 |
| 21 | 0 | 0 | 0 | 0 | 0 |
| 23 | 0 | 0 | 0 | 0 | 0 |
| 25 | 0 | 0 | 0 | 0 | 0 |
| 28 | 0 | 0 | 0 | 0 | 0 |
| 30 | 0 | 0 | 0 | 0 | 0 |
| 32 | 0 | 0 | 0 | 0 | 0 |
| 35 | 0 | 0 | 0 | 0 | 0 |
| 38 | 0 | 0 | 0 | 0 | 0 |
| 44 | 0R 0L | 230 | 0R 0L | 0R 0L | 0R 0L |
| 46 | 0R 0L | 313 | 0R 0L | 0R 0L | 0R 0L |
| 49 | 0R 0L | 447 | 0R 0L | 0R 0L | 0R 0L |
| 51 | 0R 0L | 706 | 0R 0L | 0R 0L | 0R 0L |
| 53 | 0R 0L | 825 | 0R 0L | 0R 0L | 0R 0L |
| 56 | 0R 0L | 1357 | 0R 0L | 0R 0L | 0R 0L |
| 60 | 0R 0L | 1710 | 0R 0L | 0R 0L | 0R 0L |
| 63 | 0R 0L | 2262 | 0R 0L | 0R 0L | 0R 0L |
| 65 | 0R 0L | | 0R 0L | 0R 0L | 0R 0L |
| 67 | 0R 0L | | 0R 0L | 0R 0L | 0R 0L |
| 70 | 0R 0L | | 0R 0L | 0R 0L | 0R 0L |
| 72 | 0R 0L | | 0R 0L | 0R 0L | 0R 0L |
| 74 | 0R 0L | | 0R 0L | 0R 0L | 0R 0L |
| 77 | 0R 0L | | 0R 0L | 0R 0L | 0R 0L |
| 79 | 0R 0L | | 0R 0L | 0R 0L | 0R 0L |
| 84 | 0R 0L | | 0R 0L | 0R 0L | 0R 0L |
| 86 | 0R 0L | | 0R 0L | 0R 0L | 0R 0L |
| 88 | 0R 0L | | 0R 0L | 0R 0L | 0R 0L |
| 91 | 0R 0L | | 0R 0L | 0R 0L | 0R 0L |
| 93 | 0R 0L | | 0R 0L | 0R 0L | 0R 0L |
| 95 | 0R 0L | | 0R 0L | 0R 0L | 0R 0L |
| 98 | 0R 0L | | 0R 0L | 0R 0L | 0R 0L |
| 100 | 0R 0L | | 0R 0L | 0R 0L | 0R 0L |
| 102 | 0R 0L | | 0R 0L | 0R 0L | 0R 0L |
| 115 | 0R 0L | | 0R 0L | 0R 0L | 0R 0L |
| 120 | 0R 0L | | 0R 0L | 0R 0L | 0R 0L |

[‡]"R" refers to the site of the original implantation in the right limb and "L" refers to the site of re-challenge in the left limb As shown in Table 4B, the administration of anti-PD-1 F26 antibody as a single agent exhibited only a minimal 19.8% tumor growth inhibition at Day 14 compared to vehicle-treated mice.

As shown in Table 4C, the administration of KRas G12C inhibitor Example 478 as a single agent exhibited a robust anti-tumor response with all five treated mice achieving a complete response after nine days of administration (Study Day 9). All five mice remained without a detectable tumor for at least five days; however, eventually tumor growth was detected at the original site of implantation in all five mice mice either while still receiving Example 478 daily (three mice, Study Days 17, 21 & 25) or after administration was stopped at Study Day 29 (two mice, Study Days 44 & 46).

As shown in Table 4D, the co-administration of the combination of the anti-PD-1 F26 antibody and KRas G12C inhibitor Example 478 similarly exhibited a robust anti-tumor response with all five treated mice (M1-M5) achieving a complete response after fourteen days of administration (Study Day 14). Four of the five mice (M1 & M3-M5) remained without a detectable tumor for at least ninety one days after administration of Example 478 was stopped (Study Day 120). Tumor growth was detected in a single mouse (M2) starting at Study Day 44, fifteen days after administration of Example 478 was stopped.

Four of the five mice (M1 & M3-M5) remained without a detectable tumor at Study Day 39 and were rechallenged with CT26.WT KRas G12C E3 cells in the opposite left flank. No detectable tumor growth was observed at the original implantation site (R) or at the second reimplantation site (L) whereas, in contrast, implantation of the same cells into naïve mice resulted in tumor formation (data not shown). These results demonstrate that combination treated animals exhibited an anti-tumor immunological memory that resulted in a durable complete response for at least forty nine days demonstrating the superiority of the combination therapy at treating and potentially preventing the re-occurrence of KRas G12C-associated cancers.

Tables 5A-5D represent a repeat of the study shown in 4A-4D. In the second study the number of treated mice was increased from 5 animals per group to 10 animals per group. When tumor volumes reach between 200-400 mm$^3$ in size (Study Day 0), the mice were divided into four groups of 10 mice each. The first group was daily administered vehicle (10% Captisol in 50 mM citrate buffer pH 5.0) through Study Day 10 and also administered i.p. vehicle (BioXcel diluent) on Study Days 1, 4 and 7. The second group was daily administered a 10 mg/kg i.p. dose of the murine anti-PD-1 antibody (F26, BioXcel) at Days 1, 4 and 7. The third group was administered a 100 mg/kg dose of the KRas G12C inhibitor Example 478 through Study Day 25. The fourth group was daily administered a 100 mg/kg dose of the KRas G12C inhibitor Example 478 through Study Day 25 in combination with a 10 mg/kg i.p. dose of the F26 murine anti-PD-1 antibody at Study Days 1, 4 and 7.

At Study Day 25, administration of 100 mg/kg dose of the KRas G12C inhibitor Example 478 was stopped in the single agent and combination groups.

At Study Day 32, seven tumor-free mice from the combination group were rechallenged 1×10$^6$ CT26.WT KRas G12C E3 cells in the opposite left flank and mice were monitored for tumor growth for a period of fifty days to determine whether a durable, adaptive immune response was observed.

Table 5

Tumor Volumes (Mm$^3$) of Repeat of CT26.WT KRas G12C E3 Clone Tumor Bearing Mice Treated with Single Agents and in Combination

TABLE 5A

| | Group 1: Vehicle | | | | | | | | | |
|---|---|---|---|---|---|---|---|---|---|---|
| Study Day | M1 | M2 | M3 | M4 | M5 | M6 | M7 | M8 | M9 | M10 |
| 0 | 203 | 182 | 257 | 200 | 181 | 255 | 222 | 157 | 225 | 332 |
| 3 | 519 | 355 | 634 | 416 | 486 | 754 | 426 | 310 | 571 | 1024 |
| 5 | 780 | 632 | 747 | 953 | 643 | 1311 | 571 | 516 | 916 | 1256 |
| 7 | 1096 | 981 | 1172 | 1303 | 981 | 1678 | 841 | 857 | 1452 | 1617 |
| 10 | 1967 | 1690 | 2192 | 2286 | 1848 | 2658 | 1582 | 1740 | 2453 | 2552 |

TABLE 5B

| | Group 2: 10 mg/kg i.p. F26 murine anti-PD-1 antibody | | | | | | | | | |
|---|---|---|---|---|---|---|---|---|---|---|
| Study Day | M1 | M2 | M3 | M4 | M5 | M6 | M7 | M8 | M9 | M10 |
| 0 | 198 | 171 | 304 | 206 | 270 | 213 | 186 | 230 | 252 | 165 |
| 3 | 450 | 224 | 735 | 547 | | 515 | 250 | 503 | 618 | 420 |
| 5 | 545 | 391 | 1058 | 795 | | 929 | 470 | 584 | 778 | 606 |
| 7 | 796 | 617 | 1755 | 1175 | | 1549 | 915 | 937 | 1033 | 1304 |
| 10 | 1132 | 1023 | 2258 | 1695 | | 2150 | 1509 | 1554 | 1576 | 1626 |

TABLE 5C

| | Group 3: 100 mg/kg KRas G12C Inhibitor Example 47 8‡ | | | | | | | | | |
|---|---|---|---|---|---|---|---|---|---|---|
| Study Day | M1 | M2 | M3 | M4 | M5 | M6 | M7 | M8 | M9 | M10 |
| 0 | 158 | 330 | 221 | 255 | 269 | 229 | 184 | 175 | 206 | 198 |
| 3 | 32 | 102 | 143 | 133 | 181 | 140 | 63 | 93 | 59 | 32 |
| 5 | 0 | 0 | 14 | 14 | 63 | 0 | 0 | 4 | 0 | 4 |
| 7 | 0 | 0 | 4 | 4 | 32 | 0 | 0 | 0 | 0 | 0 |
| 10 | 0 | 0 | 0 | 0 | 0 | 0 | 0 | 0 | 0 | 0 |
| 14 | 0 | 4 | 0 | 0 | 0 | 0 | 0 | 0 | 0 | 0 |
| 17 | 0 | 212 | 0 | 32 | 0 | 0 | 0 | 0 | 0 | 0 |
| 19 | 51 | 875 | 32 | 371 | 0 | 63 | 0 | 0 | 0 | 0 |
| 21 | 268 | 1320 | 139 | 762 | 0 | 274 | 0 | 0 | 0 | 0 |
| 24 | 877 | 2470 | 588 | 1498 | 0 | 291 | 0 | 0 | 0 | 0 |
| 26 | 1237 | | 923 | 1699 | 14 | | 0 | 0 | 0 | 0 |
| 28 | 1371 | | 1056 | 2035 | 14 | | 0 | 0 | 0 | 0 |
| 31 | 2334 | | 2113 | | 161 | | 0R 0L | 0R 0L | 0R 0L | 0R 0L |
| 33 | | | | | 289 | | 63R 0L | 32R 0L | 4R 0L | 0R 0L |
| 38 | | | | | 425 | | 318R 0L | 124R 0L | 63R 0L | 0R 0L |
| 40 | | | | | | | 464R 0L | 511R 0L | 326R 0L | 0R 0L |
| 42 | | | | | | | 550R 0L | 868R 0L | 704R 0L | 0R 0L |
| 45 | | | | | | | 1447R 0L | 2052R 0L | 196R 0L | 0R 0L |
| 47 | | | | | | | 1947R 0L | | | 0R 0L |
| 49 | | | | | | | | | | 0R 0L |
| 52 | | | | | | | | | | 0R 0L |
| 56 | | | | | | | | | | 0R 0L |
| 69 | | | | | | | | | | 0R 0L |
| 74 | | | | | | | | | | 0R 0L |

‡"R" refers to the site of the original implantation in the right flank and "L" refers to the site of re-challenge in the left flank

TABLE 5D

Group 4: 100 mg/kg KRas G12C Inhibitor Example 478 + 10 mg/kg i.p. F26 murine anti-PD-1 antibody[‡]

| Study Day | M1 | M2 | M3 | M4 | M5 | M6 | M7 | M8 | M9 | M10 |
|---|---|---|---|---|---|---|---|---|---|---|
| 0 | 276 | 191 | 245 | 210 | 195 | 168 | 246 | 212 | 166 | 288 |
| 3 | 32 | 98 | 156 | 140 | 14 | 32 | 116 | 112 | 104 | 135 |
| 5 | 0 | 32 | 63 | 63 | 0 | 4 | 0 | 77 | 4 | 32 |
| 7 | 0 | 0 | 32 | 14 | 0 | 0 | 0 | 4 | 4 | 0 |
| 10 | 0 | 0 | 4 | 0 | 0 | 0 | 0 | 0 | 0 | 0 |
| 14 | 0 | 0 | 4 | 0 | 0 | 0 | 0 | 0 | 0 | 0 |
| 17 | 0 | 0 | 4 | 0 | 0 | 0 | 0 | 0 | 0 | 0 |
| 19 | 0 | 0 | 4 | 0 | 0 | 0 | 0 | 0 | 0 | 0 |
| 21 | 0 | 14 | 4 | 0 | 0 | 0 | 0 | 0 | 0 | 0 |
| 24 | 0 | 203 | 97 | 0 | 0 | 0 | 14 | 0 | 0 | 0 |
| 26 | 0 | 1006 | 136 | 0 | 0 | 0 | 84 | 0 | 0 | 0 |
| 28 | 0 | 1312 | 133 | 0 | 0 | 0 | 164 | 0 | 0 | 0 |
| 31 | 0R 0L | 1893 | 177 | 0R 0L | 0R 0L | 0R 0L | 312 | 0R 0L | 0R 0L | 0R 0L |
| 33 | 0R 0L | 1935 | 221 | 0R 0L | 0R 0L | 0R 0L | | 0R 0L | 0R 0L | 0R 0L |
| 38 | 0R 0L | 2332 | 490 | 0R 0L | 0R 0L | 0R 0L | | 0R 0L | 0R 0L | 0R 0L |
| 40 | 0R 0L | | 507 | 0R 0L | 0R 0L | 0R 0L | | 0R 0L | 0R 0L | 0R 0L |
| 42 | 0R 0L | | 581 | 0R 0L | 0R 0L | 0R 0L | | 0R 0L | 0R 0L | 0R 0L |
| 45 | 0R 0L | | 873 | 0R 0L | 0R 0L | 0R 0L | | 0R 0L | 0R 0L | 0R 0L |
| 47 | 0R 0L | | 923 | 0R 0L | 0R 0L | 0R 0L | | 0R 0L | 0R 0L | 0R 0L |
| 49 | 0R 0L | | 1195 | 0R 0L | 0R 0L | 0R 0L | | 0R 0L | 0R 0L | 0R 0L |
| 52 | 0R 0L | | 1517 | 0R 0L | 32R 0L | 0R 0L | | 0R 0L | 0R 0L | 0R 0L |
| 54 | 0R 0L | | 1577 | 0R 0L | 282R 0L | 0R 0L | | 0R 0L | 0R 0L | 0R 0L |
| 56 | 0R 0L | | 1631 | 0R 0L | 754R 0L | 0R 0L | | 0R 0L | 0R 0L | 0R 0L |
| 69 | 0R 0L | | | 0R 0L | | 0R 0L | | 0R 0L | 0R 0L | 0R 0L |
| 75 | | | | 0R 0L | | 0R 0L | | 0R 0L | 0R 0L | 0R 0L |

[‡]"R" refers to the site of the original implantation in the right flank and "L" refers to the site of re-challenge in the left flankAs shown in Table 5B, the administration of anti-PD-1 F26 antibody as a single agent exhibited only a minimal 25.6% tumor growth inhibition at Day 10 compared to vehicle-treated mice.

As shown in Table 5C, the administration of KRas G12C inhibitor Example 478 as a single agent exhibited a robust anti-tumor response with all ten treated mice achieving a complete response in all mice after ten days of administration (Study Day 10). 9 of the 10 mice remained without a detectable tumor for at least four days after achieving a complete response; however, eventually tumor growth was detected in 6 out of 9 mice at the original site of implantation while still receiving Example 478 daily (five mice, Study Days 14 (M2), 17 (M4) & 19 (M1, M3 & M6)) or after administration was stopped at Study Day 25 (one mouse (M6) Study Day 26). Three mice (M7-M9) remained tumor free for six days after Example 478 daily administration was stopped (Day 31) and one mouse (M10) remained tumor free for at least forty nine days.

As shown in Table 5D, the co-administration of the combination of the anti-PD-1 F26 antibody and KRas G12C inhibitor Example 478 similarly exhibited a robust anti-tumor response with nine out of ten treated mice achieving a complete response after ten days of administration (Study Day 10). Eight mice remained without a detectable tumor for at least twenty four days after administration of Example 478 was stopped (Study Day 49). Tumor growth was detected in a one of the eight mice (M3) starting at Study Day 52.

Seven of the ten mice (M1, M4, M5, M6, M8, M9 and M10) remained without a detectable tumor at Study Day 32 and were rechallenged with CT26.WT KRas G12C E3 cells in the opposite left flank. No detectable tumor growth was observed at the original implantation site (R) or at the second reimplantation site (L) in six out of seven mice whereas, in contrast, implantation of the same cells into naïve mice resulted in tumor formation (data not shown). Tumor formation was detected in a single mouse at the original implantation site at Study Day 52 (M3); however, no tumor formation was detected at the site of rechallenge. These results demonstrate that combination treated animals exhibited an anti-tumor immunological memory that resulted in a durable complete response for at least fifty days demonstrating the superiority of the combination therapy at treating and potentially preventing the re-occurrence of KRas G12C-associated cancers.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of treating a KRas G12C-associated cancer in a subject in need thereof, comprising administering to the subject a therapeutically effective amount of a combination of a PD-1/PD-L1 inhibitor selected from the group consisting of nivolumab, pembrolizumab, cemiplimab, tislelizumab, atezolizumab, avelumab, and durvalumab, and a compound of formula:

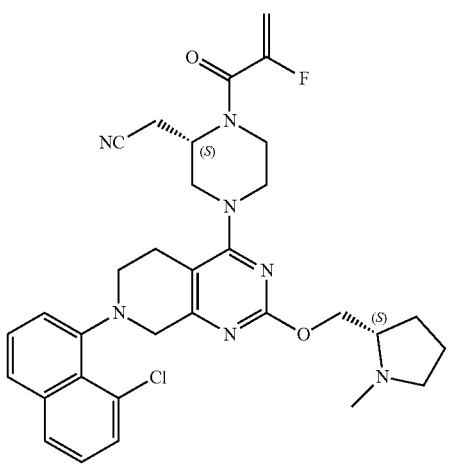

or a pharmaceutically acceptable salt thereof.

2. The method according to claim 1, wherein the PD-1/PD-L1 inhibitor is a PD-1 inhibitor.

3. The method of claim 2, wherein the PD-1 inhibitor is selected from the group consisting of nivolumab, pembrolizumab, cemiplimab, and tislelizumab.

4. The method of claim 3, wherein the PD-1 inhibitor is nivolumab.

5. The method of claim 4, wherein the therapeutically effective amount of nivolumab in the combination is about 240 mg administered every two weeks.

6. The method of claim 4, wherein the therapeutically effective amount of nivolumab in the combination is about 480 mg administered every four weeks.

7. The method of claim 3, wherein the PD-1 inhibitor is pembrolizumab.

8. The method of claim 7, wherein the therapeutically effective amount of pembrolizumab in the combination is about 200 mg administered every three weeks.

9. The method of claim 7, wherein the KRas G12C-associated cancer is non-small cell lung cancer (NSCLC).

10. The method of claim 3, wherein the wherein the PD-1 inhibitor is cemiplimab.

11. The method of claim 10, wherein the therapeutically effective amount of pembrolizumab in the combination is about 350 mg administered every three weeks.

12. The method of claim 3, wherein the PD-1 inhibitor is tislelizumab.

13. The method of claim 12, wherein the therapeutically effective amount of tislelizumab in the combination is about 200 mg administered every three weeks.

14. The method according to claim 1, wherein the PD-1/PD-L1 inhibitor is a PD-L1 inhibitor.

15. The method of claim 14, wherein the PD-L1 inhibitor is selected from the group consisting of atezolizumab, avelumab, and durvalumab.

16. The method of claim 15, wherein the PD-L1 inhibitor is atezolizumab.

17. The method of claim 16, wherein the therapeutically effective amount of atezolizumab in the combination is about 1200 mg administered every three weeks.

18. The method of claim 15, wherein the PD-L1 inhibitor is avelumab.

19. The method of claim 18, wherein the therapeutically effective amount of avelumab in the combination is about 10 mg/kg administered every two weeks or 800 mg every two weeks.

20. The method of claim 15, wherein the PD-L1 inhibitor is durvalumab.

21. The method of claim 20, wherein the therapeutically effective amount of durvalumab in the combination is about 10 mg/kg administered every two weeks.

22. The method according to claim 1, wherein the PD-1/PD-L1 inhibitor and the compound of formula:

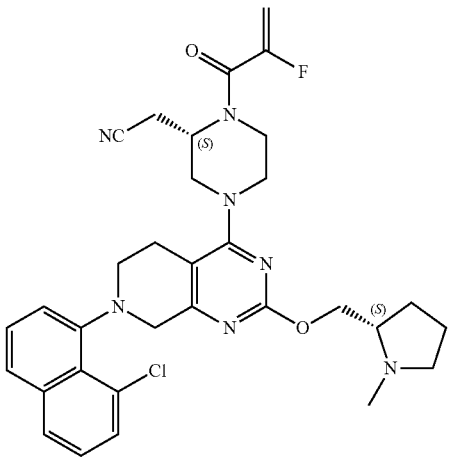

or a pharmaceutically acceptable salt thereof are administered on the same day.

23. The method according to claim 1, wherein the PD-1/PD-L1 inhibitor and the compound of formula:

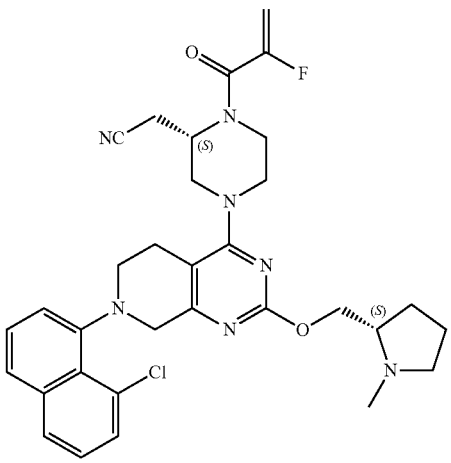

or a pharmaceutically acceptable salt thereof are administered on different days.

24. The method according to claim 1, wherein the compound of formula:

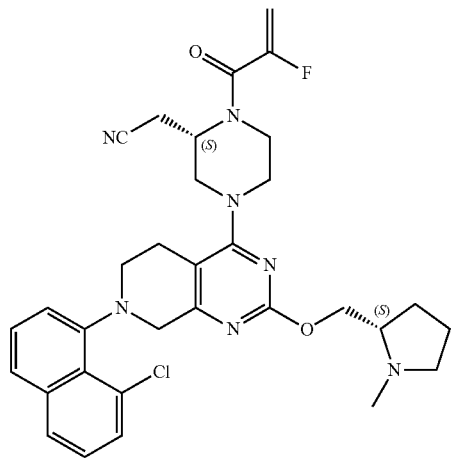

or a pharmaceutically acceptable salt thereof is administered at a maximum tolerated dose.

25. The method according to claim 1, wherein the PD-1/PD-L1 inhibitor and the compound of formula:

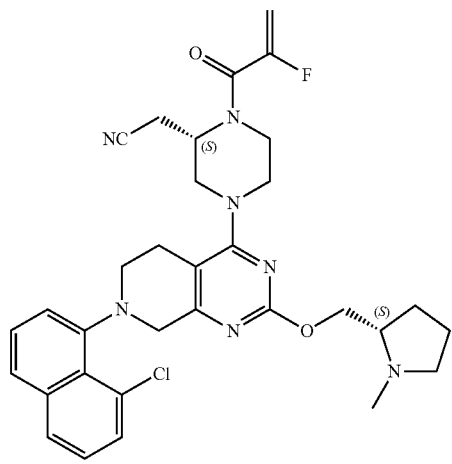

or a pharmaceutically acceptable salt thereof are each administered at a maximum tolerated dose.

26. The method of according to claim 1, wherein the therapeutically effective amount of the combination of the PD-1/PD-L1 inhibitor and the compound of formula:

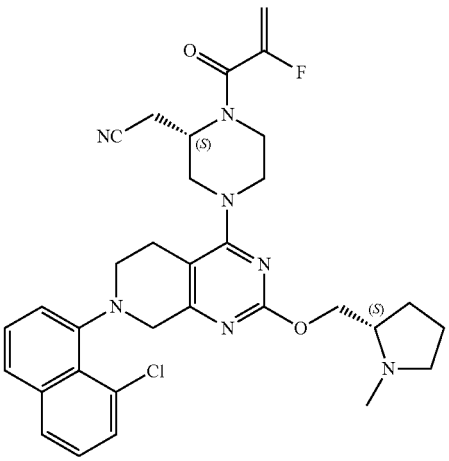

or a pharmaceutically acceptable salt thereof results in an increased duration of overall survival, an increased duration of progression free survival, an increase in tumor growth regression, an increase in tumor growth inhibition or an increased duration of stable disease in the subjects relative to treatment with only the compound of formula:

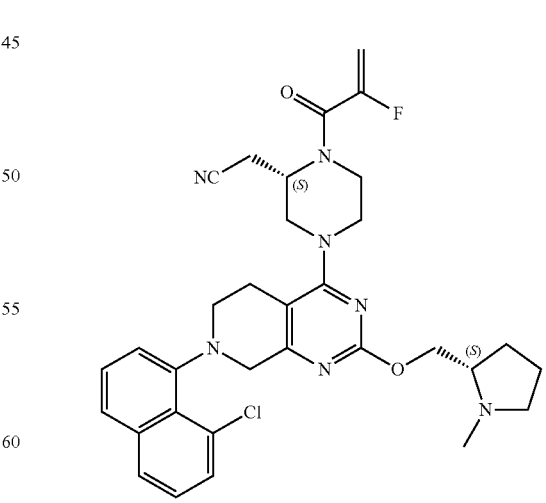

or a pharmaceutically acceptable salt thereof.

27. The method according to claim 1, wherein the therapeutically effective amount of the combination of the PD-1/PD-L1 inhibitor and the compound of formula:

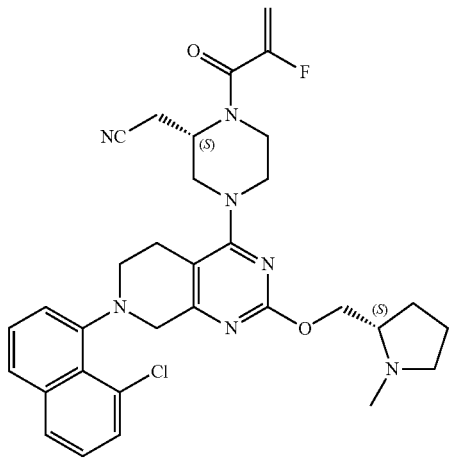

or a pharmaceutically acceptable salt thereof results in a durable complete response.

28. A pharmaceutical composition comprising a therapeutically effective amount of a PD-1/PD-L1 inhibitor selected from the group consisting of nivolumab, pembrolizumab, cemiplimab, tislelizumab, atezolizumab, avelumab, and durvalumab and a compound of formula:

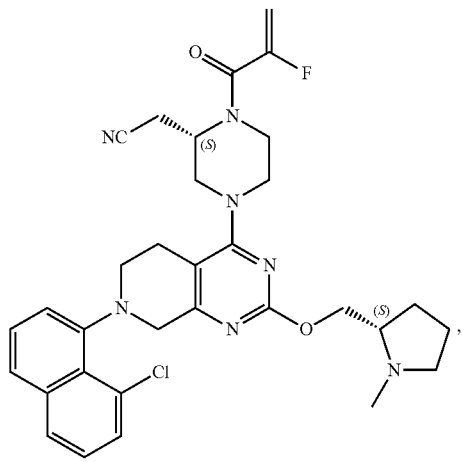

or a pharmaceutically acceptable salt thereof, and a pharmaceutically acceptable excipient.

29. The method according to claim 1, wherein the method incudes a durable complete response in the subject having a KRas G12C-associated cancer.

30. A method of treating a KRas G12C-associated cancer in a subject in need thereof, wherein the KRas G12C-associated cancer is resistant to treatment with a PD-1/PD-L1 inhibitor, comprising administering to the subject a therapeutically effective amount of a combination of a PD-1/PD-L1 inhibitor selected from the group consisting of nivolumab, pembrolizumab, cemiplimab, tislelizumab, atezolizumab, avelumab, and durvalumab or a pharmaceutical composition thereof, and a compound of formula:

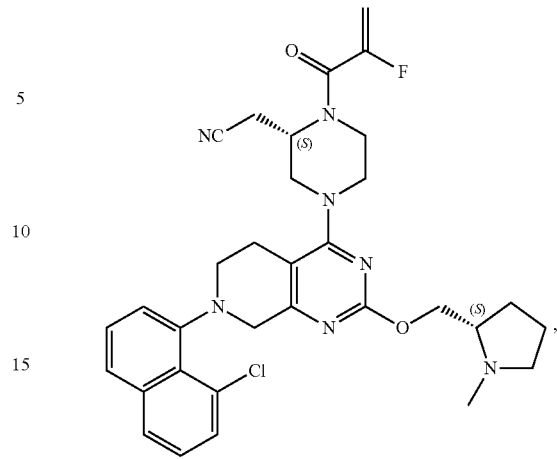

or a pharmaceutically acceptable salt thereof, or a pharmaceutical composition thereof.

31. A method for treating a KRas G12C-associated cancer and determined to have previously developed resistance to treatment with a PD-1/PD-L1 inhibitor that include administering to the subject a therapeutically effective amount of a combination of a PD-1/PD-L1 inhibitor selected from the group consisting of nivolumab, pembrolizumab, cemiplimab, tislelizumab, atezolizumab, avelumab, and durvalumab or a pharmaceutical composition thereof, and a compound of formula:

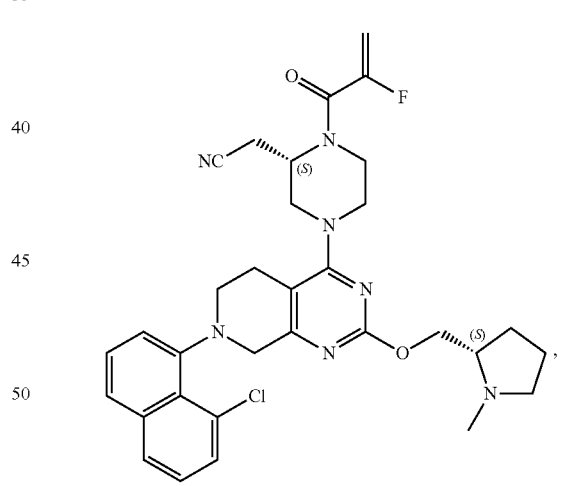

or a pharmaceutically acceptable salt thereof, or a pharmaceutical composition thereof.

32. A method for suppressing resistance to treatment with a PD-1/PD-L1 inhibitor in a subject having a KRas G12C-associated cancer that include administering to the subject a therapeutically effective amount of a combination of a PD-1/PD-L1 inhibitor selected from the group consisting of nivolumab, pembrolizumab, cemiplimab, tislelizumab, atezolizumab, avelumab, and durvalumab, or a pharmaceutical composition thereof, and a compound of formula:

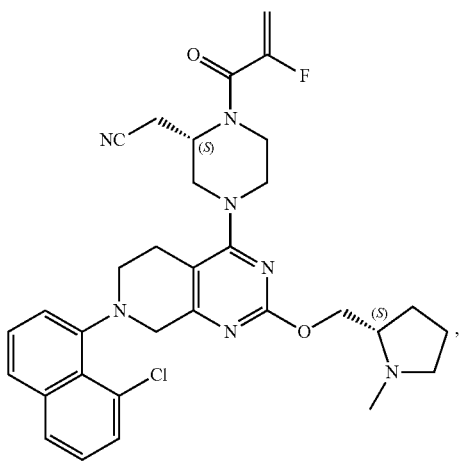

or a pharmaceutically acceptable salt thereof, or a pharmaceutical composition thereof.

33. A method of treating a subject identified or diagnosed as having a KRAS G12C-associated cancer that include (a) detecting resistance of the KRas G12C-associated cancer in the subject to treatment with a PD-1/PD-L1 inhibitor that was previously administered to the patient; and (b) after (a), administering to the subject a therapeutically effective amount of a combination of a PD-1/PD-L1 inhibitor selected from the group consisting of nivolumab, pembrolizumab, cemiplimab, tislelizumab, atezolizumab, avelumab, and durvalumab, or a pharmaceutical composition thereof, and a compound of formula:

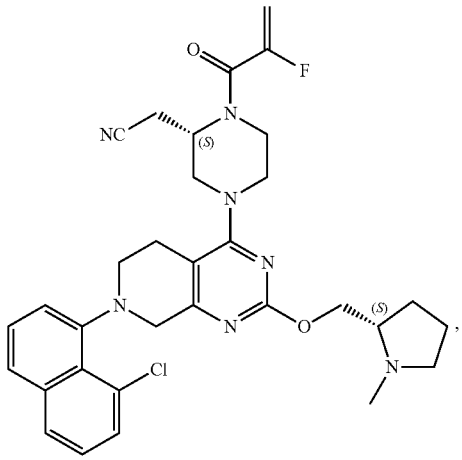

or a pharmaceutically acceptable salt thereof, or a pharmaceutical composition thereof.

34. A method of treating a subject identified or diagnosed as having a KRas G12C-associated cancer and determined to have previously developed resistance to treatment with a KRAS G12C inhibitor that include administering to the subject a therapeutically effective amount of a combination of a PD-1/PD-L1 inhibitor selected from the group consisting of nivolumab, pembrolizumab, cemiplimab, tislelizumab, atezolizumab, avelumab, and durvalumab, or a pharmaceutical composition thereof, and a compound of formula:

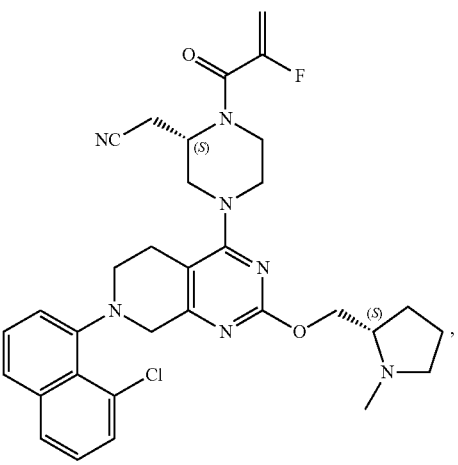

or a pharmaceutically acceptable salt thereof, or a pharmaceutical composition thereof.

35. A method of treating a subject identified or diagnosed as having a KRas G12C-associated cancer, comprising (a) administering a KRAS G12C inhibitor as monotherapy until disease progression, and (b) after (a), administering to the subject a therapeutically effective amount of a combination of a PD-1/PD-L1 inhibitor selected from the group consisting of nivolumab, pembrolizumab, cemiplimab, tislelizumab, atezolizumab, avelumab, and durvalumab, or a pharmaceutical composition thereof, and a compound of formula:

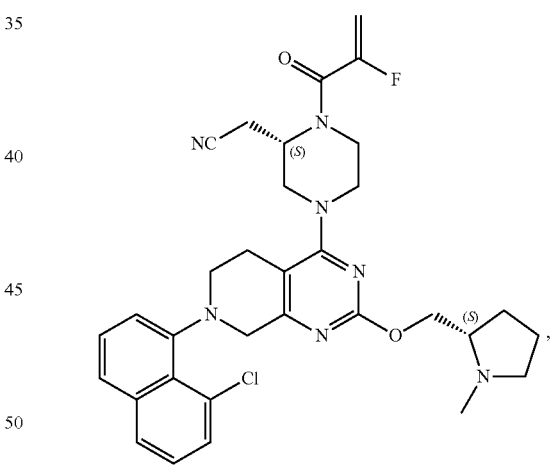

or a pharmaceutically acceptable salt thereof, or a pharmaceutical composition thereof.

36. The method according to claim 1, wherein the therapeutically effective amount of the KRas G12C inhibitor is between about 0.01 to 100 mg/kg per day.

37. The method of claim 36, wherein the therapeutically effective amount of the KRas G12C inhibitor is between about 0.1 to 50 mg/kg per day.

38. The method according to claim 1, wherein the KRas G12C-associated cancer is selected from the group consisting of
   Cardiac: sarcoma selected from angiosarcoma, fibrosarcoma, rhabdomyosarcoma, and liposarcoma, myxoma, rhabdomyoma, fibroma, lipoma and teratoma;

Lung: bronchogenic carcinoma selected from squamous cell, undifferentiated small cell, undifferentiated large cell, and adenocarcinoma, alveolar carcinoma, bronchiolar carcinoma, bronchial adenoma, sarcoma, lymphoma, chondromatous hamartoma, mesothelioma, and non-small cell lung cancer;

Gastrointestinal: esophagus selected from squamous cell carcinoma, adenocarcinoma, leiomyosarcoma, and lymphoma, stomach selected from carcinoma, lymphoma, and leiomyosarcoma, pancreas selected from ductal adenocarcinoma, insulinoma, glucagonoma, gastrinoma, carcinoid tumors, and vipoma, small bowel selected from adenocarcinoma, lymphoma, carcinoid tumors, Kaposi's sarcoma, leiomyoma, hemangioma, lipoma, neurofibroma, and fibroma, large bowel selected from adenocarcinoma, tubular adenoma, villous adenoma, hamartoma, and leiomyoma;

Genitourinary tract: kidney selected from adenocarcinoma, Wilm's tumor (nephroblastoma), lymphoma, and leukemia, bladder and urethra selected from squamous cell carcinoma, transitional cell carcinoma, and adenocarcinoma, prostate selected from adenocarcinoma and sarcoma, testis selected from seminoma, teratoma, embryonal carcinoma, teratocarcinoma, choriocarcinoma, sarcoma, interstitial cell carcinoma, fibroma, fibroadenoma, adenomatoid tumors, and lipoma;

Liver: hepatoma selected from hepatocellular carcinoma, cholangiocarcinoma, hepatoblastoma, angiosarcoma, hepatocellular adenoma, and hemangioma;

Biliary tract: gall bladder carcinoma, ampullary carcinoma, and cholangiocarcinoma;

Bone: osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors;

Nervous system: skull selected from osteoma, hemangioma, granuloma, xanthoma, and osteitis deformans, meninges selected from meningioma, meningiosarcoma, and gliomatosis, brain selected from astrocytoma, medulloblastoma, glioma, ependymoma, germinoma, glioblastoma multiform, oligodendroglioma, schwannoma, retinoblastoma, congenital tumors, and spinal cord neurofibroma;

Gynecological: uterus selected from endometrial carcinoma, granulosa-thecal cell tumors, Sertoli-Leydig cell tumors, dysgerminoma, and malignant teratoma, vulva selected from squamous cell carcinoma, intraepithelial carcinoma, adenocarcinoma, fibrosarcoma, and melanoma, vagina selected from clear cell carcinoma, squamous cell carcinoma, botryoid sarcoma, and fallopian tubes;

Hematologic: selected from blood selected from myeloid leukemia, acute lymphoblastic leukemia, chronic lymphocytic leukemia, myeloproliferative diseases, multiple myeloma, and myelodysplastic syndrome, Hodgkin's disease, and non-Hodgkin's lymphoma;

Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

39. The method according to claim 38, wherein the cancer is non-small cell lung cancer.

40. The method according to claim 38, wherein the cancer is colorectal cancer.

41. The method according to claim 38, wherein the cancer is pancreatic cancer.

42. A kit comprising the pharmaceutical composition of claim 27 for treating a KRas G12C cancer in a subject.

43. A kit comprising: a) a pharmaceutical composition comprising a PD-1/PD-L1 inhibitor selected from the group consisting of nivolumab, pembrolizumab, cemiplimab, tislelizumab, atezolizumab, avelumab, and durvalumab, and b) a pharmaceutical composition comprising a compound of formula:

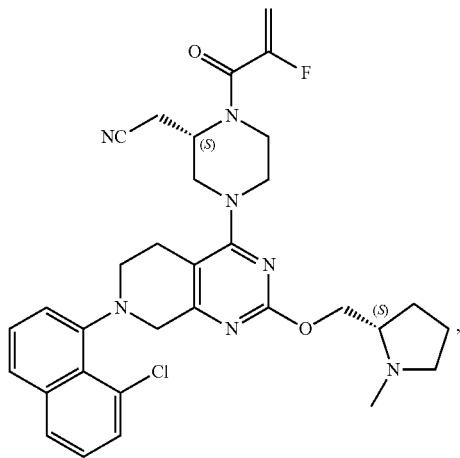

or a pharmaceutically acceptable salt thereof, for treating a KRas G12C cancer in a subject.

* * * * *